US012571052B2

(12) United States Patent
Minn et al.

(10) Patent No.: US 12,571,052 B2
(45) Date of Patent: Mar. 10, 2026

(54) IMMUNOMODULATORY RNA

(71) Applicant: THE TRUSTEES OF THE UNIVERSITY OF PENNSYLVANIA, Philadelphia, PA (US)

(72) Inventors: Andy J. Minn, Philadelphia, PA (US); Barzin Y. Nabet, Menlo Park, CA (US); Lexus R. Johnson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 354 days.

(21) Appl. No.: 17/749,039

(22) Filed: May 19, 2022

(65) Prior Publication Data

US 2023/0121917 A1     Apr. 20, 2023

Related U.S. Application Data

(63) Continuation of application No. 17/476,342, filed on Sep. 15, 2021, now abandoned, which is a continuation of application No. 15/947,526, filed on Apr. 6, 2018, now abandoned.

(60) Provisional application No. 62/614,610, filed on Jan. 8, 2018, provisional application No. 62/483,082, filed on Apr. 7, 2017.

(51) Int. Cl.
| | |
|---|---|
| *C12Q 1/6886* | (2018.01) |
| *A61K 31/7105* | (2006.01) |
| *A61K 45/06* | (2006.01) |
| *A61P 35/00* | (2006.01) |
| *C12N 15/117* | (2010.01) |

(52) U.S. Cl.
CPC ........ *C12Q 1/6886* (2013.01); *A61K 31/7105* (2013.01); *A61K 45/06* (2013.01); *A61P 35/00* (2018.01); *C12N 15/117* (2013.01); *C12N 2310/14* (2013.01); *C12N 2310/17* (2013.01); *C12N 2310/20* (2017.05); *C12N 2330/10* (2013.01); *C12Q 2600/118* (2013.01); *C12Q 2600/158* (2013.01)

(58) Field of Classification Search
CPC .. C12Q 1/6886; A61K 31/7105; A61K 45/06; A61P 35/00; C12N 15/117; C12N 2310/17; C12N 2310/14; C12N 2310/20
See application file for complete search history.

(56) References Cited

PUBLICATIONS

Wang et al. ("Targeting the CSF1/CSF1R signaling pathway: an innovative strategy for ultrasound combined with macrophage exhaustion in pancreatic cancer therapy." Frontiers in Immunology 15 (2024): 1481247).*

Wong et al. ("Messaging with naked RNA." Science Signaling 10.490 (2017)).*

Nabet B. Y. et al. (Exosome RNA unshielding couples stromal activation to pattern recognition receptor signaling in cancer. Cell 170, 352-366.e13 (2017)).*

Peyraud et al. ("CSF-1R inhibitor development: current clinical status." Current Oncology Reports 19.11 (2017): 70).*

Hao et al. ("Efficacy and safety of anti-PD-1 and anti-PD-1 combined with anti-CTLA-4 immunotherapy to advanced melanoma: A systematic review and meta-analysis of randomized controlled trials." Medicine 96.26 (2017)).*

Boelens , et al., "Exosome Transfer From Stromal to Breast Cancer Cells Regulates Therapy Resistance Pathways", Cell 159(3), Oct. 2014, 499-513.

Eckwahl , et al., "Analysis of the Human Immunodeficiency virus-1 RNA Packageome", RNA. 22(8), Aug. 2016, 1228-1238.

Garcia , et al., "Packaging of Host mY RNAs by Murine Leukemia Virus May Occur Early in Y RNA Biogenesis", J Virol. 83(23), Dec. 2009, 12526-12534.

Hegde , et al., "Combinational Targeting Offsets Antigen Escape and Enhances Effector Functions of Adoptively Transferred T Cells in Glioblastoma", Mol Ther. 22(5), May 2014, 1063.

Onafuwa-Nuga , et al., "7SL RNA, but Not the 54-kd Signal Recognition Particle Protein, Is an Abundant Component of Both Infectious HIV-1 and Minimal Virus-Like Particles", RNA 12(4), Apr. 2006, 542-546.

Roybal , et al., "Precision Tumor Recognition by T Cells With Combinatorial Antigen Sensing Circuits", Cell. 164(4), Feb. 2016, 770-779.

Wang , et al., "dsRNA sensors and plasmacytold dendritic cells in host defense and autoimmunity", Immunol Rev. 243(1), Sep. 2011, 74-90.

Weichselbaum , et al., "An Interferon-Related Gene Signature for DNA Damage Resistance Is a Predictive Marker for Chemotherapy and Radiation for Breast Cancer", Proc Natl Acad Sci U S A. 105(47), Nov. 2008, 18490-18495.

White , "Transcription by RNA Polymerase III: More Complex Than We Thought", Nat Rev Genet. 12(7), May 2011, 459-463 (abstract).

Wong, Wei , "Messaging with naked RNA", Science Signaling, vol. 10, Issue 490 (Aug. 2017), eaao5132 DOI: 10.1126/scisignal. aao5132.

* cited by examiner

Primary Examiner — Kimberly Chong
(74) Attorney, Agent, or Firm — Saul Ewing LLP; Kathryn Doyle; Justin Crotty

(57) ABSTRACT

The present invention includes methods for detecting cancer in a subject and measuring the effectiveness of a cancer treatment. In certain embodiments, the invention includes assessing the level of unshielded RN7SL1 RNA in a sample from a subject.

5 Claims, 88 Drawing Sheets

Specification includes a Sequence Listing.

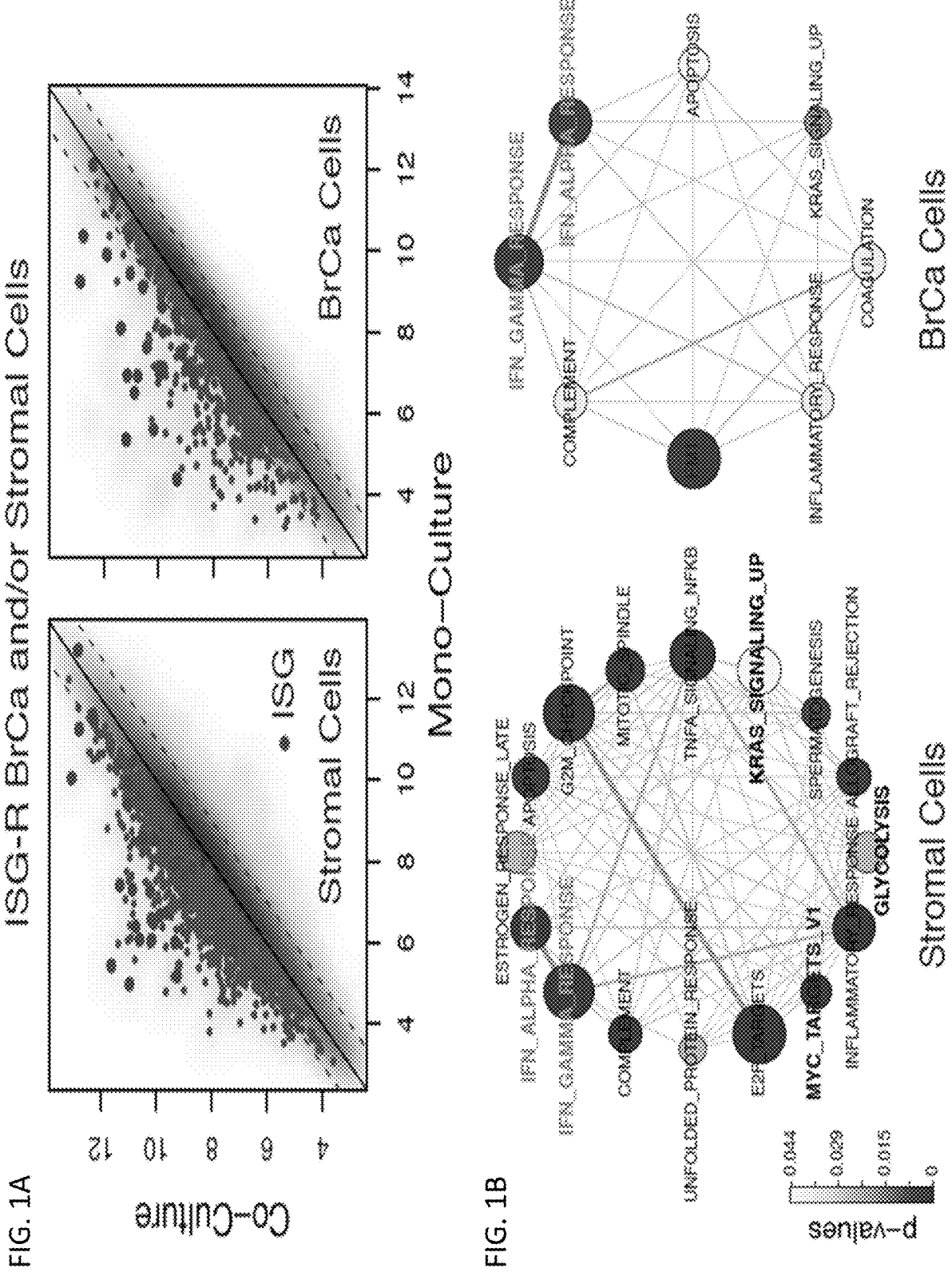

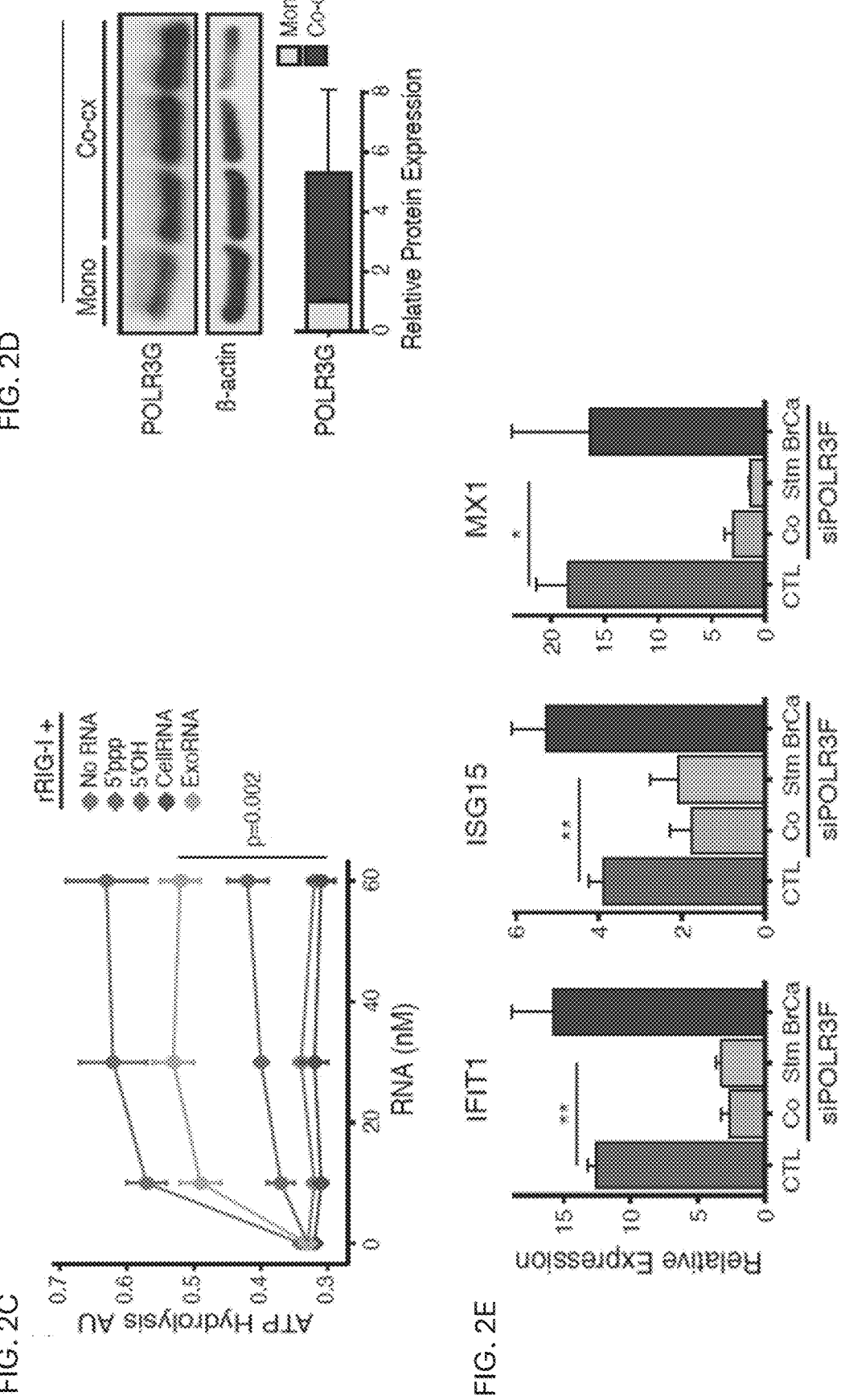

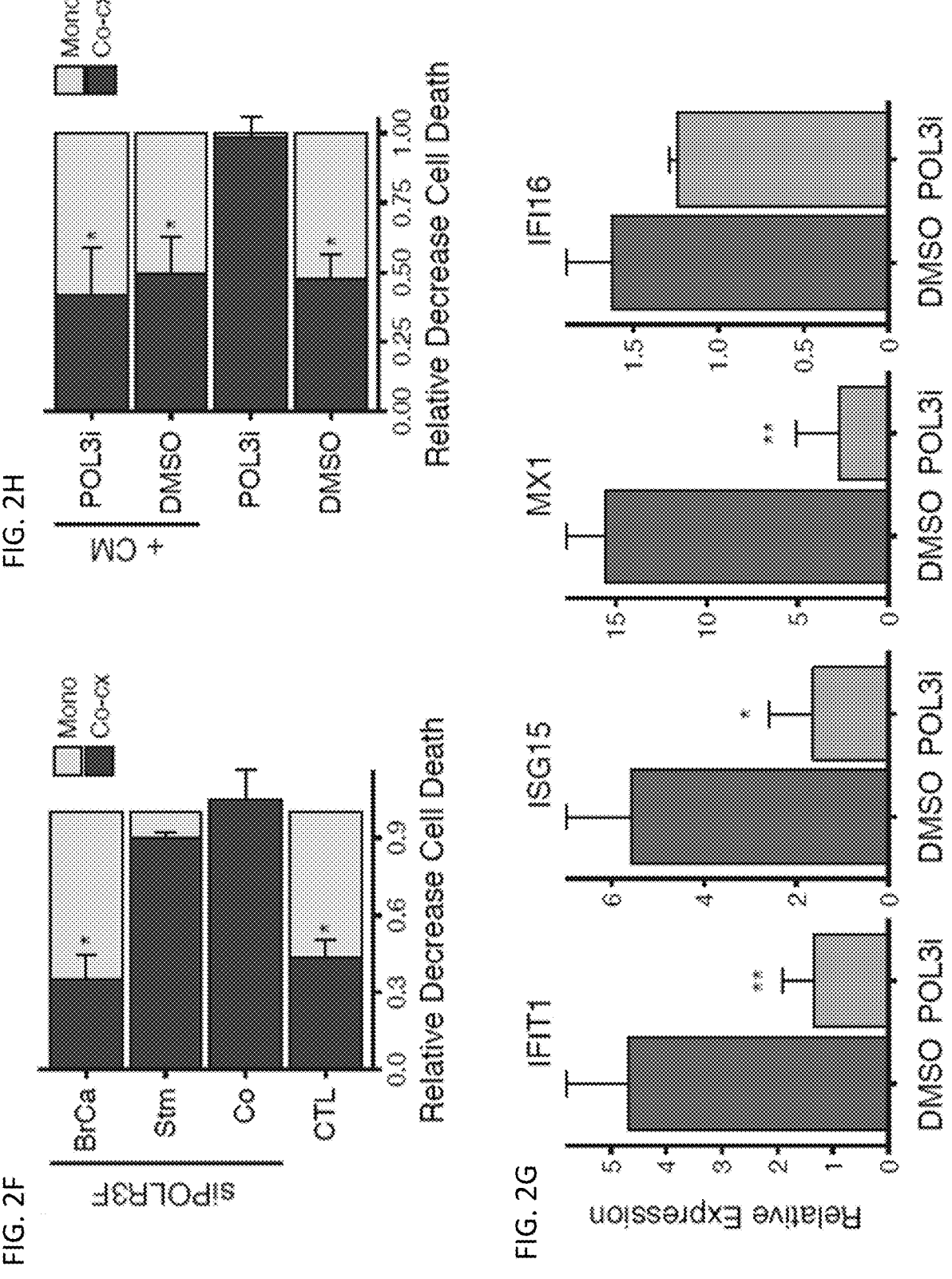

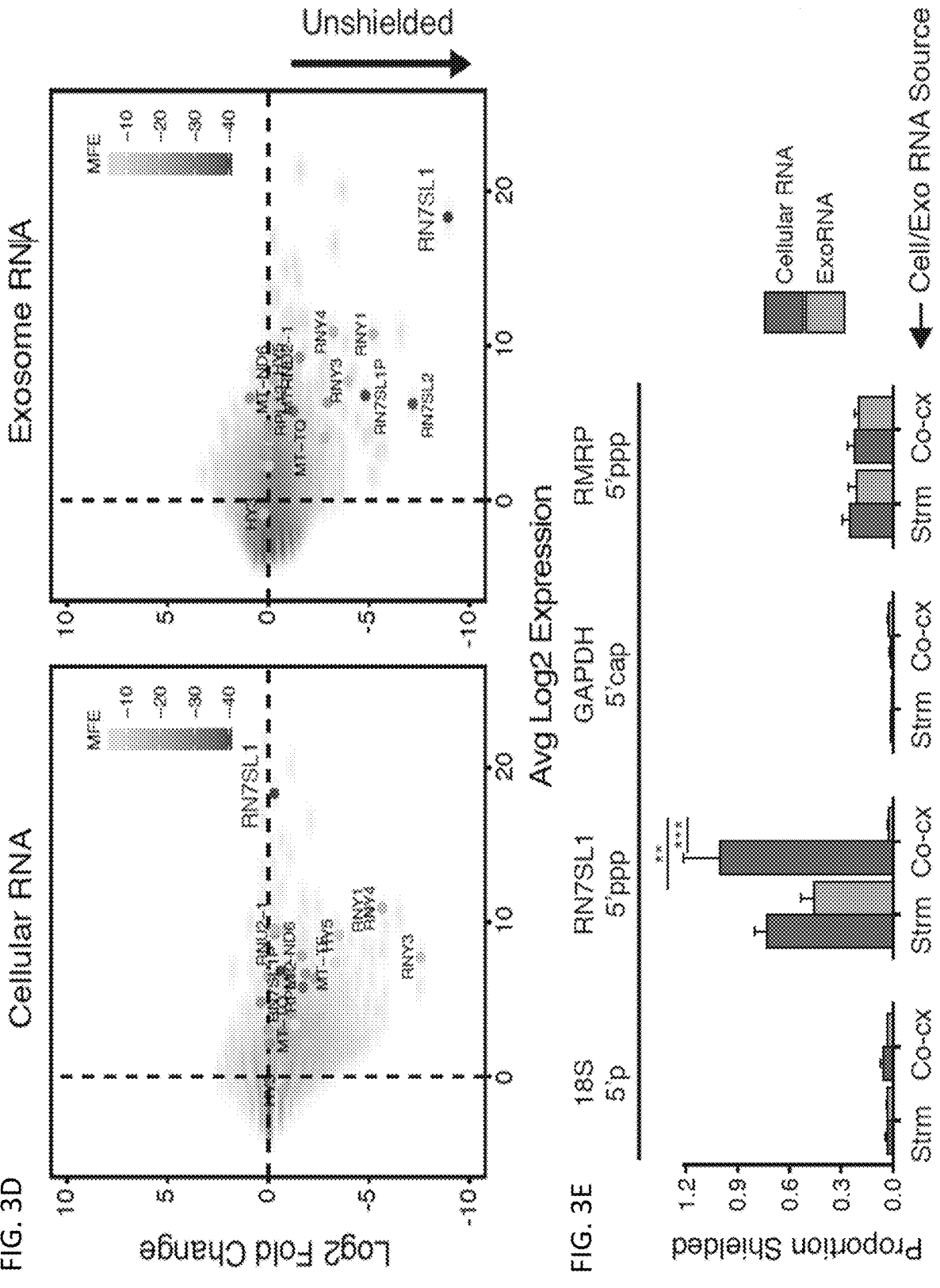

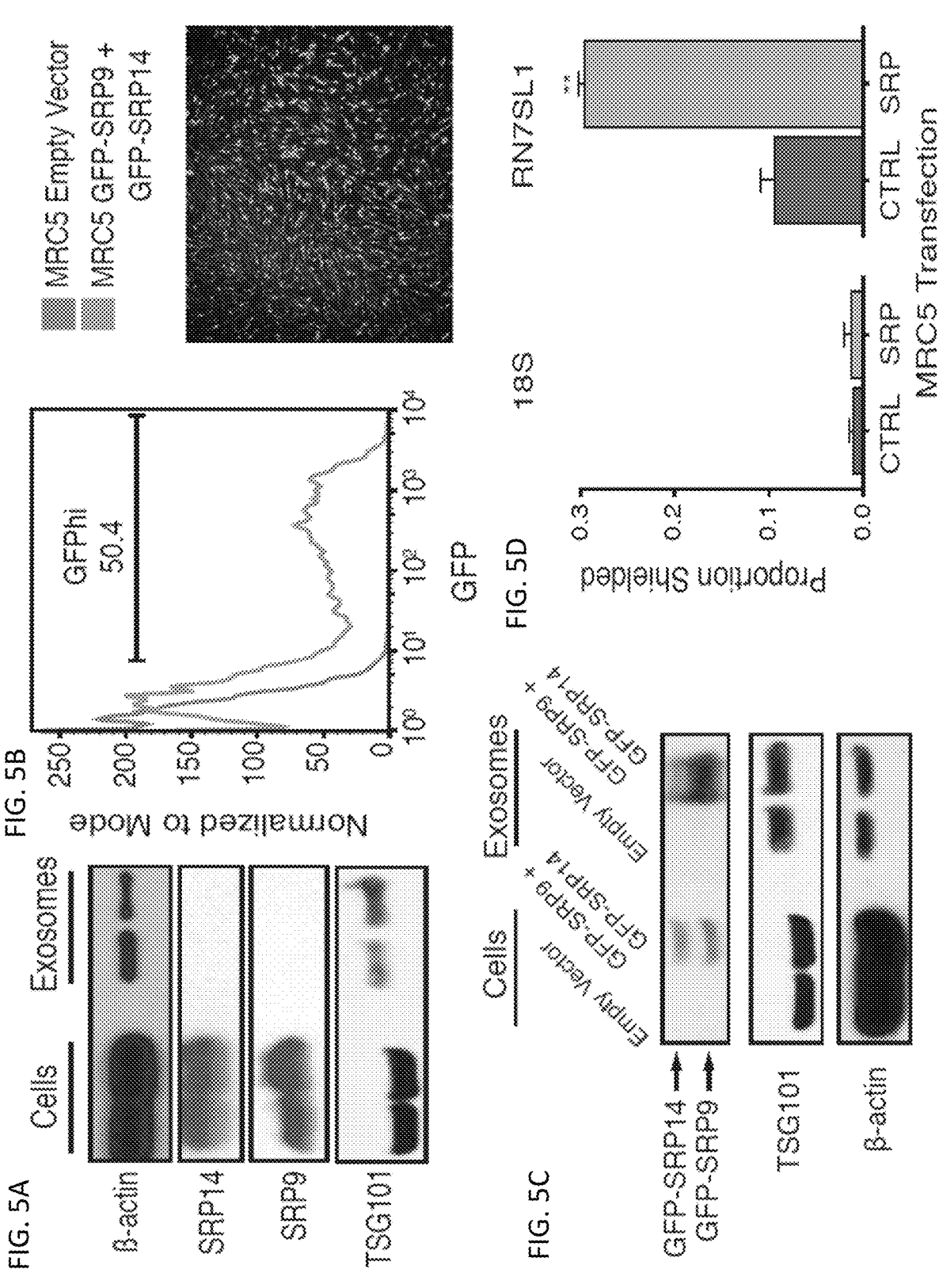

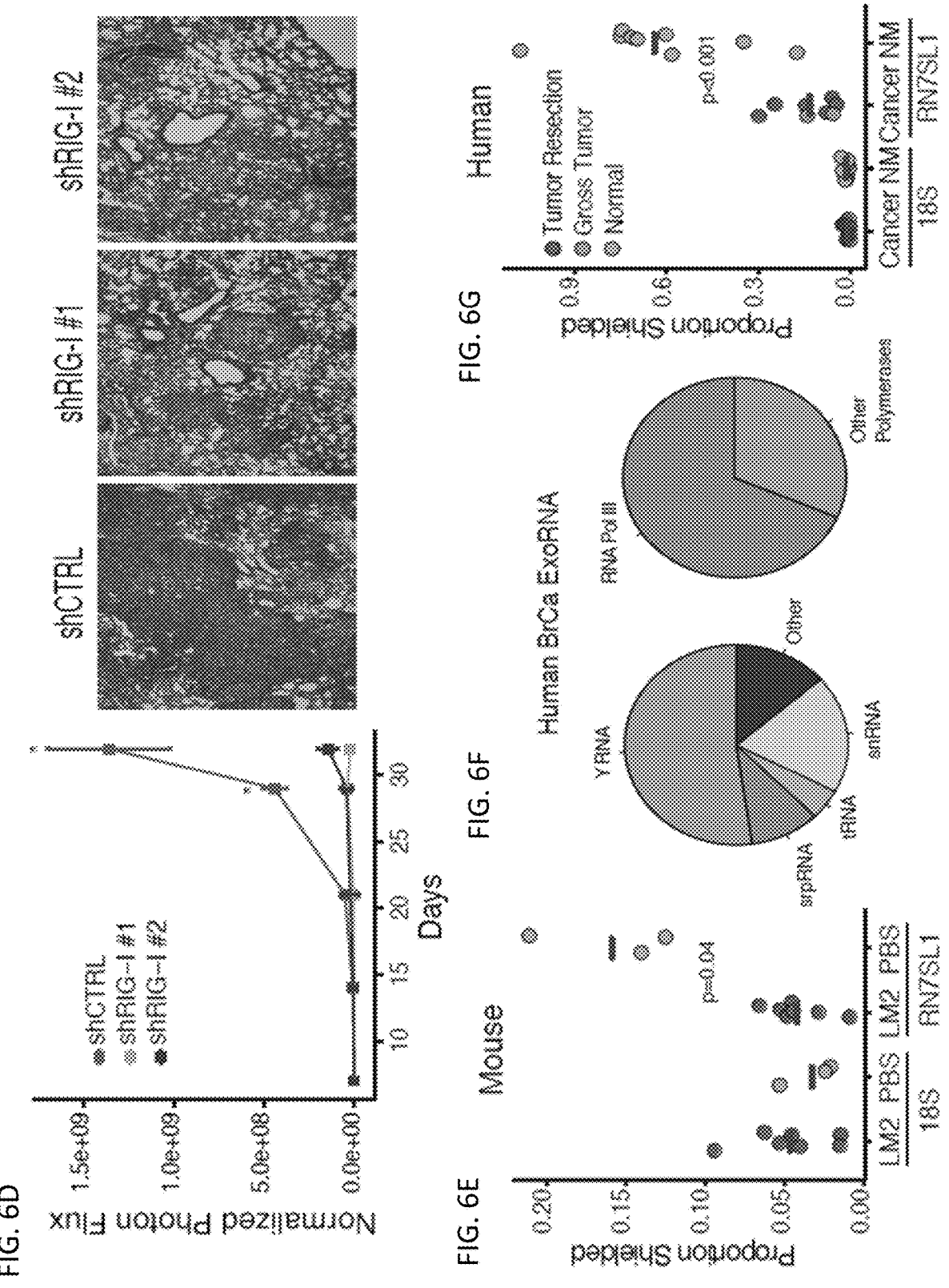

FIG. 8A

ISG-NR Breast Cancer and/or Stromal Cells

FIG. 8B

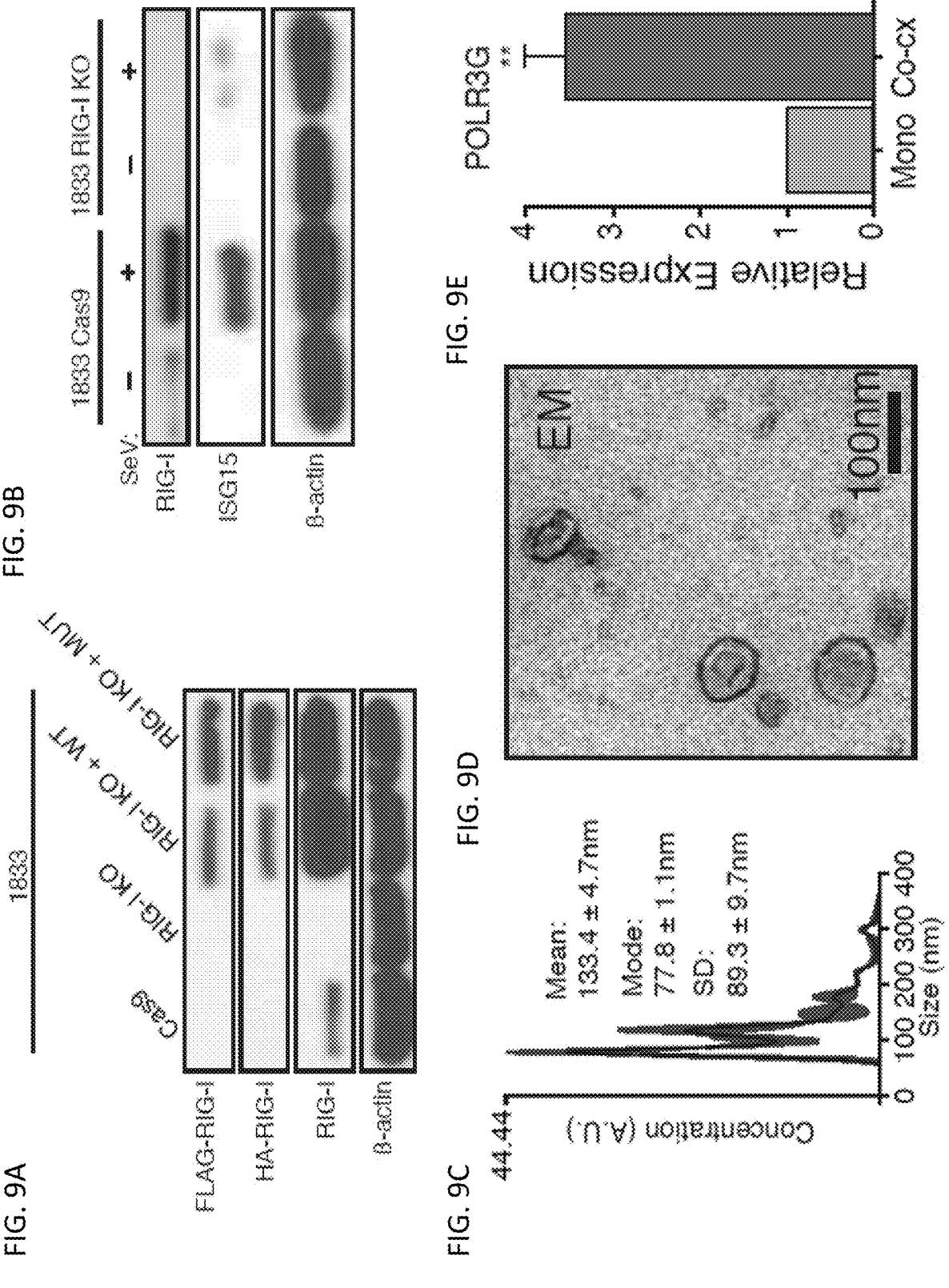

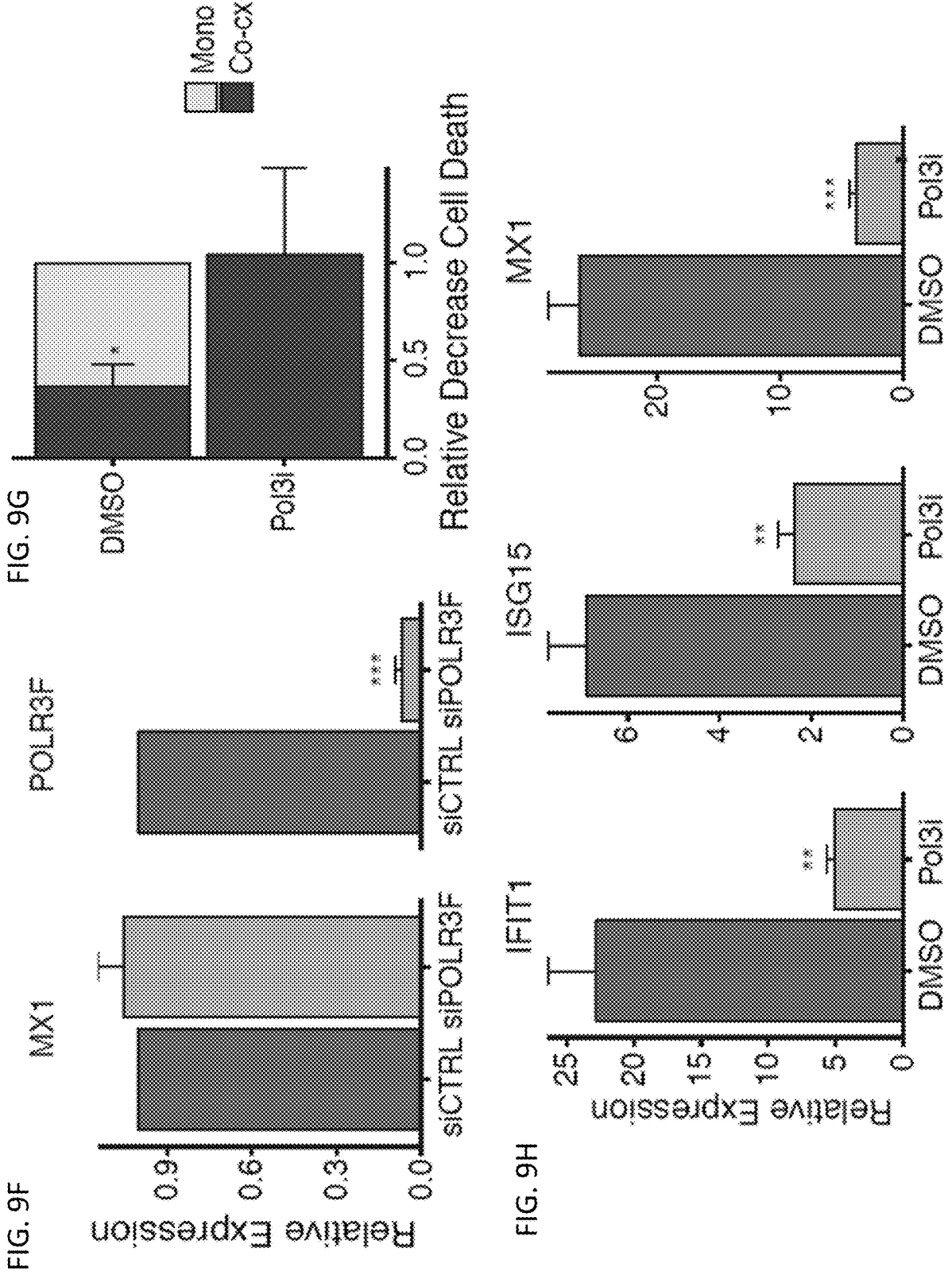

FIG. 91

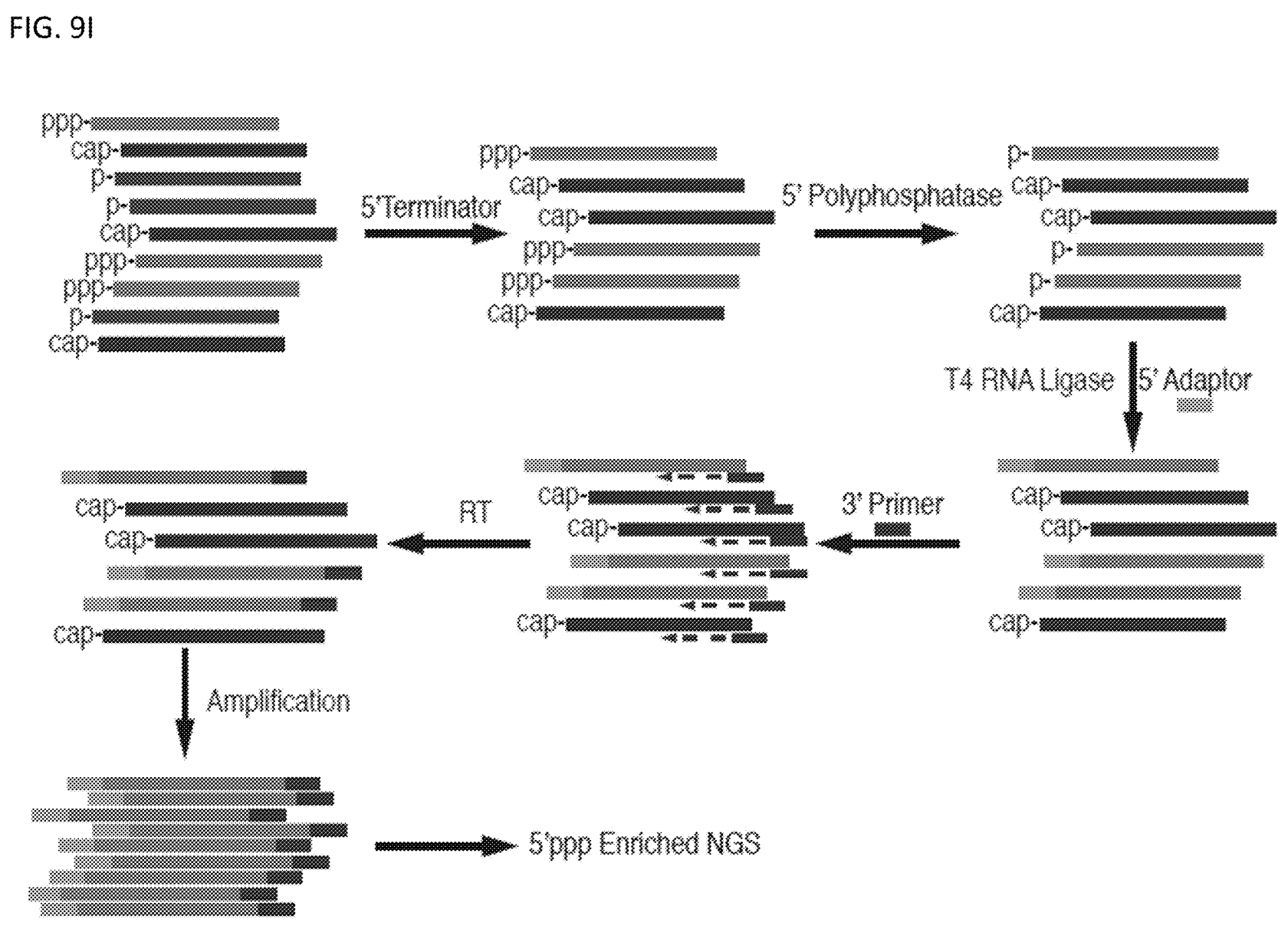

FIG. 12C
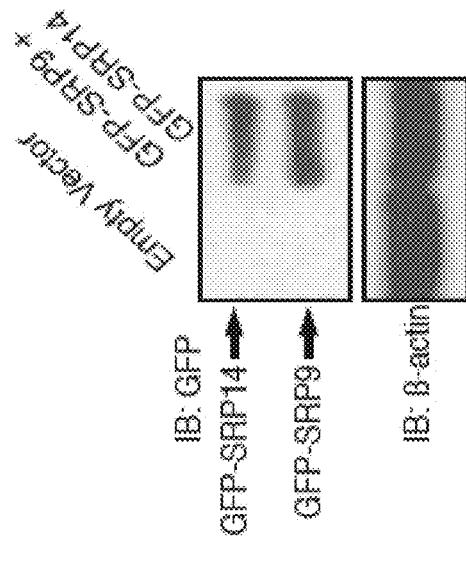
FIG. 12B
FIG. 12A
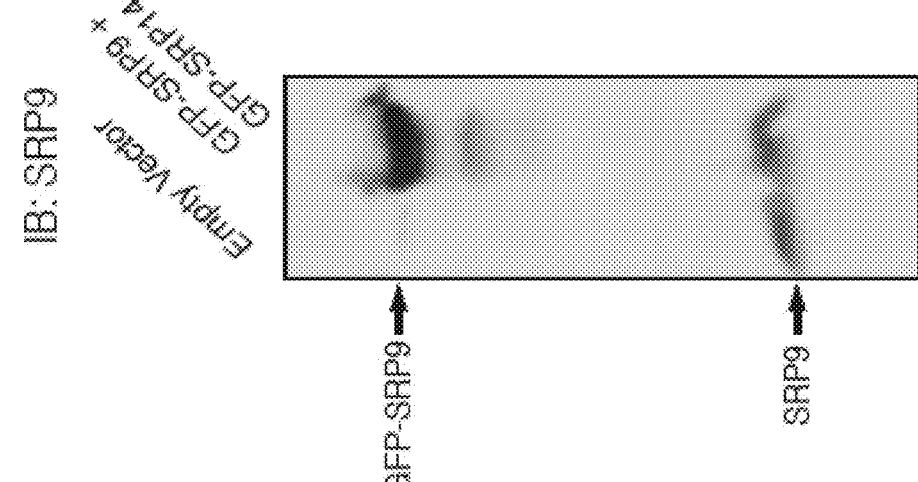

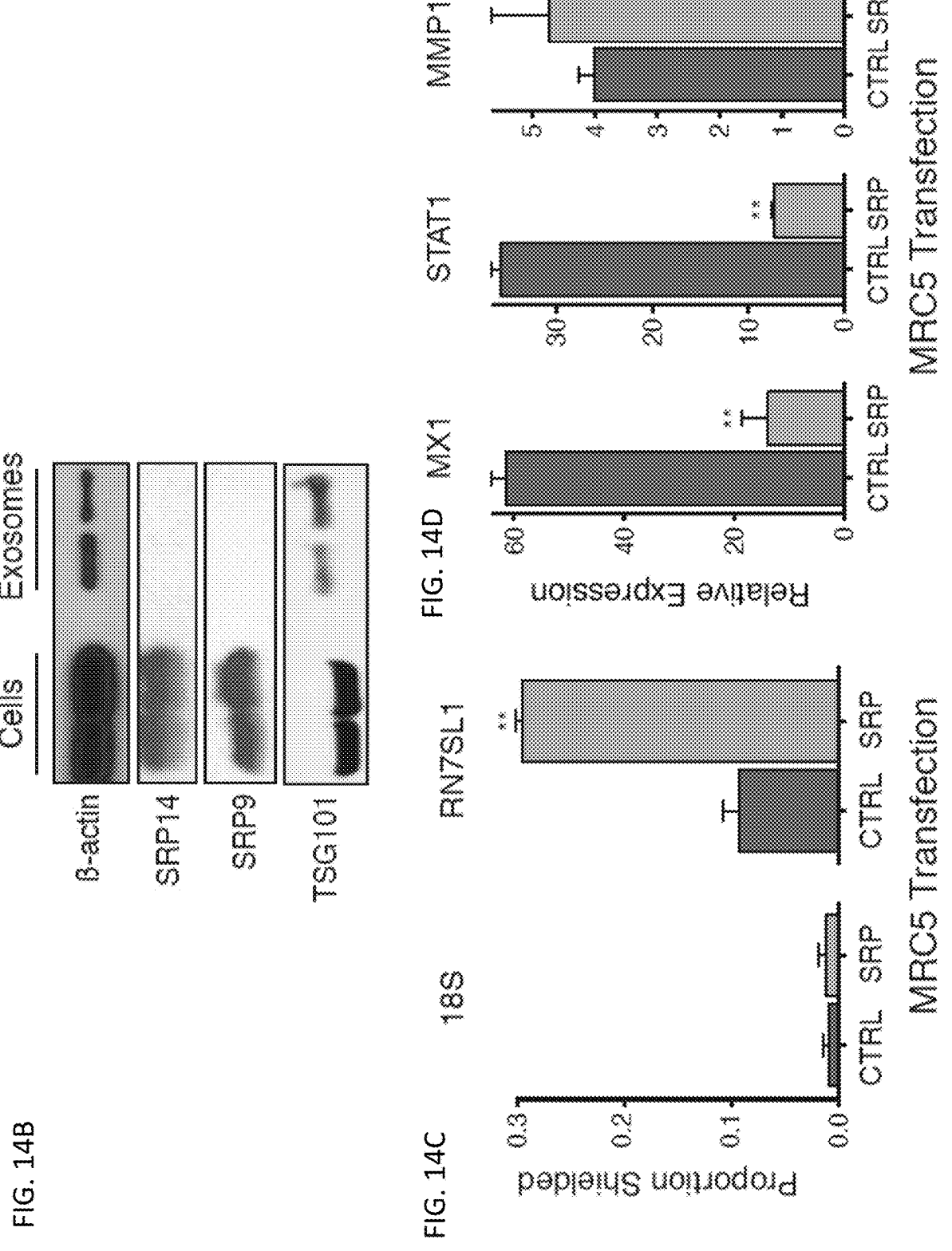

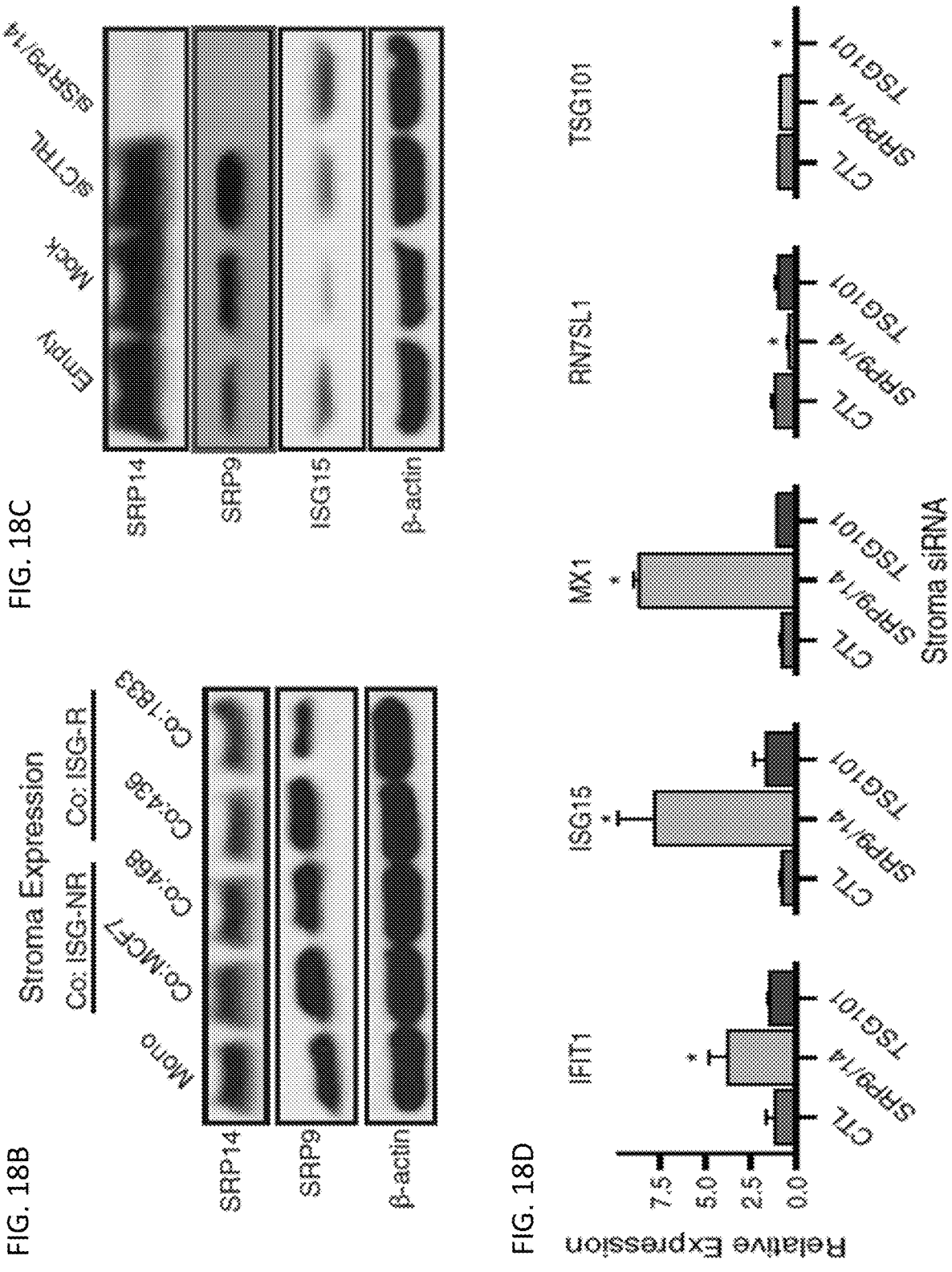

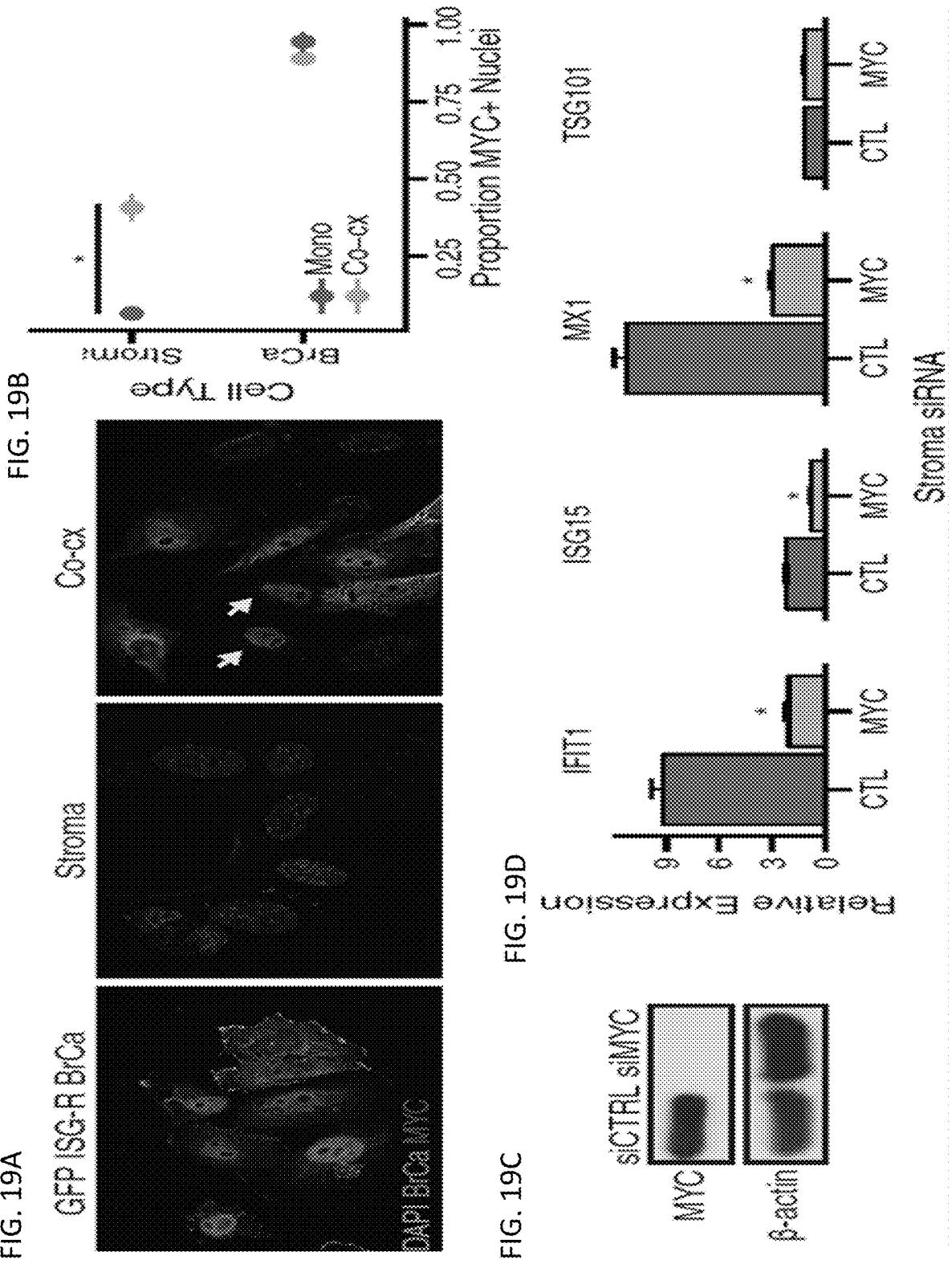

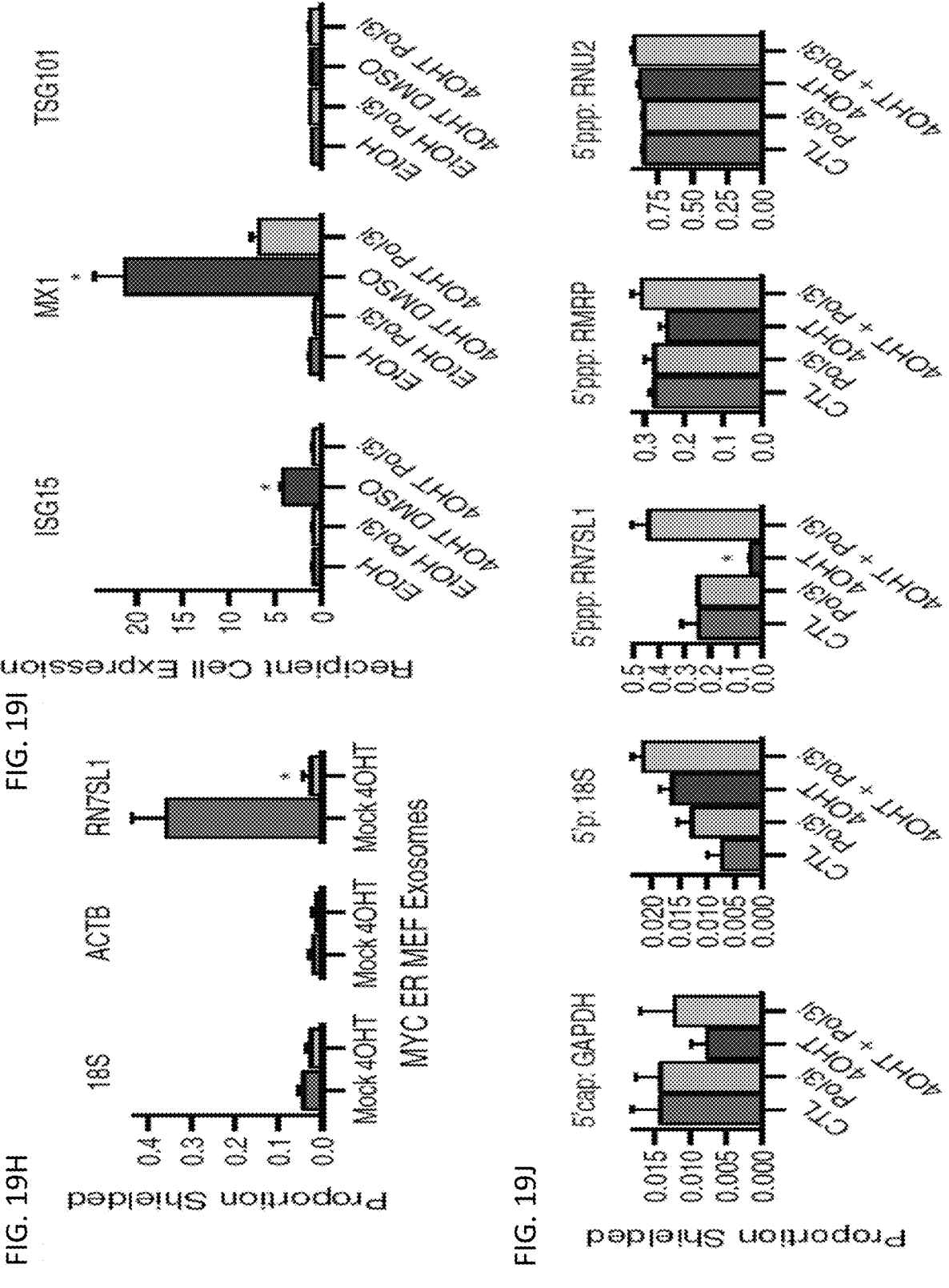

Human:

| SEQ ID NOs: | | Forward | Reverse | SEQ ID NOs: |
|---|---|---|---|---|
| 18 | GAPDH | GCTCAGACACCATGGGGAAGG | TTCCCGTTCTCAGCCTTGAC | 19 |
| 20 | 18S | GTTCAGGCCACCCGAGATTGA | CCCATCACGAATGGGGTTCA | 21 |
| 22 | ACTB | GCCCTGAGGCACTCTTCCA | CGGATGTCCACGTCACACTTC | 23 |
| 24 | IFIT1 | GGCTGCCTAATTTACAGCAACC | GGCATTTCATCGTCATCAATGG | 25 |
| 26 | MX1 | CGACACGAGTTCCACAAATG | AAGCCTGGCAGCTCTCTACC | 27 |
| 28 | ISG15 | GAGAGGCAGCGAACTCATCT | CTTCAGCTCTGACACCGACA | 29 |
| 30 | RIG-I | CACCTCAGTTGCTGATGAAGGC | GTCAGAAGGAAGCACTTGCTACC | 31 |
| 32 | POLR3G | GATGACGATGATGCCGCAGA | GGTTGCCTCATCCATGTTGT | 33 |
| 34 | POLR3F | AGGCTCCACCAGTCACAGAC | TGCCATTAACAGAAATCAACAAA | 35 |
| 36 | STAT1 | TTACTCCAGGCCAAAGGCAAG | TTCAGCTTGTGATGGCGATAG | 37 |
| 38 | 7SK | GGGTTGATTCGGCTGATCT | GGGGATGGTGTCGTCCTCTT | 39 |
| 40 | RN7SL1 | GTGTCCGCACTAAGTTCGG | TATTCACAGGCGCGGATCC | 41 |
| 42 | hsRN7SL1 | GCTACTCGGGGAGGCTGAGGCT | TATTCACAGGCGCGGATCC | 43 |
| 44 | RMRP | AAAGTCCGCCAAGAAGCGTA | CTGCCCTGCCTAACTAGAGGG | 45 |
| 46 | RPPH1 | AGCTTGGAACAGACTCACGG | AATGGGGCGGGAGGAGAGTAGT | 47 |
| 48 | RNU2 | CGTCCTCTATCCGAGGACAAT | CGGAGCAAGCTCCTATTCCA | 49 |
| 50 | TSG101 | AGAAGGGGCGTGATAGACCT | CACTGAGACCGGCAGTCTTT | 51 |
| 52 | MMP1 | TGTGGTGTCTCACAGCTTCC | TTTTCAACTTGCCTCCCATC | 53 |

FIG. 21A

Mouse:

| SEQ ID NOs: | | Forward | Reverse | SEQ ID NOs: |
|---|---|---|---|---|
| 54 | GAPDH | AGGTCGGTGTGAACGGATTTG | TGTAGACCATGTAGTTGAGGTCA | 55 |
| 56 | 18S | CCCCATGAACGAGGGAATT | GGGACTTAATCAACGCAAGCTT | 57 |
| 58 | STAT1 | ACAACATGCTGGTGACAGAGCC | TGAAAACTGCCAACTCAACACCTC | 59 |
| 60 | ISG15 | CCAGTCTCTGACTGTGAGAGC | GCATCACTGTGCTGCTGGGAC | 61 |
| 62 | MX1 | GACCATAGGGGTCTTGACCAA | AGACTTGCTCTTTCTGAAAAGCC | 63 |
| 64 | mmRN7SL1 | GCTACTCGGGAGGCTGAGACA | TATTCACAGGCGCGATCC | 65 |

Spike-In Controls:

| SEQ ID NOs: | | Forward | Reverse | SEQ ID NOs: |
|---|---|---|---|---|
| 66 | DVG396 | ACTGGGGTCATTCCCTGACCA | CCCTCAGGTTCCTGATCTCAC | 67 |
| 68 | ERCC04 | TGGGGCGAGTATTCCCAATG | TGGGGAAATTTGGGAAGCAGT | 69 |
| 70 | ERCC95 | CTTGCCTGCTGCCATGTTGTG | GAGCGATAGCGGTTAAGCCA | 71 |
| 72 | ERCC108 | GCGGCTGTTGCGTAAATCAA | AGCCGACTGCTCGTCATATC | 73 |
| 74 | ERCC130 | GTACTGACCAGCGTCACACA | GCGTGCGGTCAATCATCTTC | 75 |

FIG. 21B

| GeneID | baseMean | log2FoldChange | lfcSE | stat | pvalue | padj | Chr | Start | End |
|---|---|---|---|---|---|---|---|---|---|
| ENSG00000197658 | 6.24922245 | -0.99099727 | 0.85536469 | -1.15856696 | 0.24663274 | 0.99951929 | chr9 | 1.27E+08 | 1.27E+08 |
| ENSG00000198695 | 11.2427723 | -0.050443096 | 0.69441388 | -0.07264126 | 0.9420916 | 0.99951929 | chrM | 14149 | 14673 |
| ENSG00000200090 | 0.44248194 | 0.238632644 | 1.02885914 | 0.231939082 | 0.81658533 | NA | chr11 | 47726894 | 47726992 |
| ENSG00000201098 | 1864.66515 | -0.904999318 | 0.25961934 | -3.4858702 | 0.00049054 | 0.3322584 | chr7 | 1.49E+08 | 1.49E+08 |
| ENSG00000202354 | 191.942026 | -0.788798711 | 0.33781515 | -2.33500096 | 0.01954337 | 0.99951929 | chr7 | 1.49E+08 | 1.49E+08 |
| ENSG00000210107 | 2.575527 | 0.567573134 | 1.0284317 | 0.551882184 | 0.58102908 | 0.99951929 | chrM | 4329 | 4400 |
| ENSG00000210194 | 2.64801422 | 0.788711237 | 1.0355084 | 0.763108313 | 0.4453988 | 0.99951929 | chrM | 14674 | 14742 |
| ENSG00000252216 | 3089.86193 | -0.713159963 | 0.29268918 | -2.43657784 | 0.01482698 | 0.99951929 | chr7 | 1.49E+08 | 1.49E+08 |
| ENSG00000274012 | 537.830543 | 5.766305089 | 0.35886225 | 16.06829669 | 4.26E-58 | 6.49E-54 | chr14 | 49862550 | 49862849 |
| ENSG00000274585 | 69.4733793 | 1.473067514 | 0.402918 | 3.655998236 | 0.00025618 | 0.19045028 | chr17 | 43233787 | 43233977 |
| ENSG00000278771 | 164.916614 | 6.36343356 | 0.53874544 | 11.81157763 | 3.40E-32 | 1.30E-28 | chr14 | 49853616 | 49853914 |

FROM FIG. 22A-1

| Strand | Symbol | Family | Class | Description |
|---|---|---|---|---|
| - | RPL12 | protein_coding | coding | ribosomal protein L12 [Source:HGNC Symbol;Acc:HGNC:10302] KNOWN |
| - | MT-ND6 | protein_coding | coding | mitochondrially encoded NADH:ubiquinone oxidoreductase core subunit 6 [Source:HGNC Symbol;Acc:HGNC:7462] KNOWN |
| - | | misc_RNA | small_ncRNA | Y RNA [Source:RFAM;Acc:RF00019] NOVEL |
| - | RNY1 | misc_RNA | small_ncRNA | RNA, Ro-associated Y1 [Source:HGNC Symbol;Acc:HGNC:10242] KNOWN |
| + | RNY3 | misc_RNA | small_ncRNA | RNA, Ro-associated Y3 [Source:HGNC Symbol;Acc:HGNC:10243] KNOWN |
| - | MT-TQ | Mt_tRNA | small_ncRNA | mitochondrially encoded tRNA glutamine [Source:HGNC Symbol;Acc:HGNC:7495] KNOWN |
| - | MT-TE | Mt_tRNA | small_ncRNA | mitochondrially encoded tRNA glutamic acid [Source:HGNC Symbol;Acc:HGNC:7479] KNOWN |
| + | RNY4 | misc_RNA | small_ncRNA | RNA, Ro-associated Y4 [Source:HGNC Symbol;Acc:HGNC:10244] KNOWN |
| - | | misc_RNA | small_ncRNA | Metazoan signal recognition particle RNA [Source:RFAM;Acc:RF00017] KNOWN |
| - | RNU2-1 | snRNA | small_ncRNA | RNA, U2 small nuclear 1 [Source:HGNC Symbol;Acc:HGNC:10142] KNOWN |
| - | | misc_RNA | small_ncRNA | Metazoan signal recognition particle RNA [Source:RFAM;Acc:RF00017] NOVEL |

FROM FIG. 22A-1

| RNA7SL | 1362889.48 | 5.954339049 | 0.02545977 | 233.872443 | 0 | 0 | RN7SL1 | 1 | 299 |
|---|---|---|---|---|---|---|---|---|---|
| RMSK0254000 | 242.35257 | -1.138725411 | 0.63128694 | -1.80381587 | 0.07126018 | 0.9995192 | chr1 | 1.46E+08 | 1.46E+08 |
| RMSK0284470 | 2.7754918 | -1.272011565 | 1.0664373 | -1.19277115 | 0.23295901 | 0.9995192 | chr1 | 1.61E+08 | 1.61E+08 |
| RMSK0284494 | 62.7646692 | -0.711842908 | 0.47397976 | -1.50184241 | 0.13313781 | 0.9995192 | chr1 | 1.61E+08 | 1.61E+08 |
| RMSK0444065 | 1494.97116 | -0.907348767 | 0.30166415 | -3.00781106 | 0.00263137 | 0.9995192 | chr1 | 2.49E+08 | 2.49E+08 |
| RMSK1848200 | 2.93925883 | -0.75997998 | 1.02648171 | -0.74037362 | 0.45907332 | 0.9995192 | chr5 | 1.81E+08 | 1.81E+08 |
| RMSK1848423 | 2.68430756 | -0.289504941 | 1.04341312 | -0.27745956 | 0.78142726 | 0.9995192 | chr5 | 1.81E+08 | 1.81E+08 |
| RMSK1898352 | 14.0521361 | -0.786930354 | 0.6636876 | -1.18563392 | 0.2357432 | 0.9995192 | chr6 | 26556546 | 26556619 |
| RMSK1899770 | 43.5179255 | -1.260921498 | 0.53061588 | -2.37633668 | 0.0174855 | 0.9995192 | chr6 | 27280270 | 27280342 |
| RMSK1900244 | 946.850226 | -0.844448884 | 0.27379573 | -3.0842296 | 0.0020408 | 0.9995192 | chr6 | 27503744 | 27503815 |
| RMSK1900901 | 1.18621733 | -1.07772496 | 1.09126123 | -0.98759572 | 0.32335068 | NA | chr6 | 27753400 | 27753472 |
| RMSK1903167 | 8.53056844 | -0.647165683 | 0.76755607 | -0.84315102 | 0.39914399 | 0.9995192 | chr6 | 28896222 | 28896328 |
| RMSK2406652 | 52.4481908 | -1.081991716 | 0.44985777 | -2.40518624 | 0.01616423 | 0.9995192 | chr7 | 1.49E+08 | 1.49E+08 |
| RMSK2705056 | 78.9814499 | -1.377096393 | 1.01782356 | -1.35298145 | 0.17606156 | 0.9995192 | chr9 | 14433940 | 14434011 |
| RMSK2896852 | 0.37687212 | -0.451640769 | 1.03215777 | -0.43758951 | 0.66169838 | NA | chr9 | 1.33E+08 | 1.33E+08 |
| RMSK3556856 | 70.791057 | -1.065156761 | 0.40599969 | -2.62354082 | 0.0087021 | 0.9995192 | chr11 | 59550986 | 59551059 |
| RMSK3874632 | 191.942816 | -0.960878858 | 0.33304937 | -2.88509433 | 0.00391296 | 0.9995192 | chr12 | 98503500 | 98503574 |
| RMSK4003721 | 739.593924 | -1.078693607 | 0.84721423 | -1.27322414 | 0.20293852 | 0.9995192 | chr13 | 44917926 | 44917998 |
| RMSK4094422 | 1.99565811 | -0.543342632 | 1.11798403 | -0.48600214 | 0.62696565 | NA | chr13 | 99536321 | 99536396 |
| RMSK4442186 | 182.751153 | -1.254216659 | 0.41042181 | -3.05592108 | 0.0022437 | 0.9995192 | chr16 | 3175691 | 3175763 |
| RMSK4489775 | 3.92237991 | -0.399615749 | 0.95482219 | -0.41852373 | 0.67555424 | 0.9995192 | chr16 | 22195710 | 22195792 |
| RMSK4629380 | 5.14114463 | -1.153250435 | 0.9321286 | -1.23722244 | 0.2160451 | 0.9995192 | chr17 | 8119155 | 8119230 |
| RMSK5186324 | 26.7019261 | -1.787469268 | 0.96042015 | -1.86113252 | 0.06272545 | 0.9995192 | chr21 | 17454786 | 17454859 |

FROM FIG. 22A-2

| + | RNA7SL | 7SL | small_ncRNA | abundant |
|---|---|---|---|---|
| + | tRNA-Glu-GAG_ | tRNA | tRNA | 1:72:3 |
| + | tRNA-Leu-CTG | tRNA | tRNA | 1:83:3 |
| - | tRNA-Glu-GAG_ | tRNA | tRNA | -3:72:1 |
| + | tRNA-Glu-GAG_ | tRNA | tRNA | 1:72:3 |
| + | tRNA-Leu-CTY | tRNA | tRNA | 1:82:3 |
| - | tRNA-Val-GTY | tRNA | tRNA | -3:73:1 |
| + | tRNA-Lys-AAG | tRNA | tRNA | 1:74:2 |
| - | tRNA-Val-GTG | tRNA | tRNA | -3:73:1 |
| + | tRNA-Asp-GAY | tRNA | tRNA | 1:72:3 |
| - | tRNA-Val-GTY | tRNA | tRNA | -3:73:1 |
| - | tRNA-Leu-TTG | tRNA | tRNA | -2:84:1 |
| + | HY5 | scRNA | scRNA | 0:1 |
| - | tRNA-His-CAY_ | tRNA | tRNA | -3:72:1 |
| + | tRNA-Gly-GGA | tRNA | tRNA | 1:38:37 |
| - | tRNA-Val-GTA | tRNA | tRNA | -2:74:1 |
| + | tRNA-Asp-GAY | tRNA | tRNA | 1:72:3 |
| - | tRNA-Glu-GAG_ | tRNA | tRNA | -2:73:1 |
| - | HY3 | scRNA | scRNA | -1:100:1 |
| + | tRNA-Lys-AAG | tRNA | tRNA | 1:73:3 |
| - | tRNA-Leu-CTA | tRNA | tRNA | -2:83:1 |
| + | tRNA-Lys-AAA | tRNA | tRNA | 0.094444444 |
| - | tRNA-Gly-GGY | tRNA | tRNA | 0.051400463 |

FROM FIG. 22A-3

FIG. 22A-4

| GeneID | baseMean | log2FoldChange | lfcSE | stat |
|---|---|---|---|---|
| ENSG00000202354 | 213.851281 | -7.55166408 | 0.733268856 | -10.29862923 |
| ENSG00000252316 | 1897.900988 | -5.652718821 | 0.282248468 | -20.02745618 |
| ENSG00000201098 | 1748.988174 | -5.021029124 | 0.248122469 | -20.23609201 |
| RMSK2406652 | 560.0749163 | -3.508335854 | 0.30389105 | -11.54471596 |
| ENSG00000210194 | 163.5949397 | -3.27878428 | 0.406801309 | -8.059915763 |
| RMSK1900901 | 4.660837415 | -2.711521961 | 1.42100595 | -1.90817073 |
| RMSK1S18423 | 14.31581345 | -2.533881312 | 0.852449187 | -2.972471967 |
| RMSK4442186 | 81.18317387 | -2.296389763 | 0.440933656 | -5.20801652 |
| RMSK0284376 | 4.586025236 | -1.866745797 | 1.414296336 | -1.319911358 |
| RMSK1903167 | 99.38408977 | -1.838929128 | 0.424703117 | -4.329916724 |
| ENSG00000197958 | 55.07686176 | -1.698370645 | 0.490353793 | -3.463561758 |
| ENSG00000198695 | 224.7102352 | -1.645613466 | 0.268916855 | -6.119413618 |
| ENSG00000210107 | 10.44446317 | -1.306040743 | 0.888969005 | -1.469163419 |
| RMSK4489775 | 17.13747112 | -1.126875418 | 0.80511134 | -1.399651653 |
| RMSK2705056 | 16.36323769 | -1.014741941 | 0.800183697 | -1.268136235 |
| RMSK1899770 | 89.40455336 | -0.990214654 | 0.424225008 | -2.334173225 |
| ENSG00000278771 | 75.92669217 | -0.917411598 | 0.571614882 | -1.604947013 |
| RMSK4629380 | 4.922476046 | -0.85099014 | 1.258085796 | -0.676416619 |
| RMSK0284494 | 72.90677656 | -0.785367399 | 0.421189603 | -1.864640989 |
| RMSK0444065 | 720.5290218 | -0.75118771 | 0.768076296 | -0.978011839 |
| RMSK0284470 | 7.248270743 | -0.72043246 | 1.204960582 | -0.59788882 |
| RMSK4094422 | 0.541223191 | -0.670246869 | 1.802658666 | -0.371810194 |
| ENSG00000274012 | 111.8280877 | -0.589628629 | 0.368999083 | -1.597913534 |
| RMSK3556856 | 66.15875945 | -0.477247483 | 0.417346498 | -1.143528183 |
| RMSK4003721 | 734.1446404 | -0.318067499 | 0.31312372 | -1.015788581 |
| ENSG00000274585 | 609.9006579 | -0.303825167 | 0.254423052 | -1.194173107 |
| RNA7SL | 327546.4579 | -0.283969148 | 0.190992366 | -1.486808894 |
| RMSK1900244 | 726.8474926 | -0.275331041 | 0.29872492 | -0.921687554 |
| RMSK0254000 | 84.05747772 | -0.071865542 | 0.476332816 | -0.150872541 |
| RMSK1848200 | 4.48357604 | -0.062522422 | 1.309852053 | -0.04773243 |
| RMSK1898352 | 8.319887325 | -0.010277352 | 1.024567648 | -0.010030916 |
| RMSK3874632 | 95.73762968 | 0.045724591 | 0.443940382 | 0.102997142 |
| RMSK5186324 | 28.24019394 | 0.376033889 | 0.596185549 | 0.630732982 |

FIG. 22B-1

| pvalue | padj | Chr | Start | End | Strand |
|---|---|---|---|---|---|
| 7.15E-25 | 4.31E-21 | chr7 | 148983755 | 148983856 | + |
| 3.17E-89 | 1.53E-84 | chr7 | 148963315 | 148963410 | + |
| 4.71E-91 | 3.41E-86 | chr7 | 148987136 | 148987248 | - |
| 7.85E-31 | 5.98E-27 | chr7 | 148941488 | 148941571 | + |
| 7.63E-16 | 2.70E-12 | chrM | 14674 | 14742 | - |
| 0.056369153 | 1 | chr6 | 27753400 | 27753472 | - |
| 0.002954122 | 0.543524639 | chr5 | 181188416 | 181188488 | - |
| 1.91E-07 | 0.000177165 | chr16 | 3175691 | 3175763 | + |
| 0.186864615 | 1 | chr1 | 161399700 | 161399772 | - |
| 1.49E-05 | 0.007882865 | chr6 | 28896222 | 28896328 | - |
| 0.000533074 | 0.1607039 | chr9 | 127447674 | 127451405 | - |
| 9.39E-10 | 1.39E-06 | chrM | 14149 | 14673 | - |
| 0.14178847 | 1 | chrM | 4329 | 4400 | - |
| 0.161617658 | 1 | chr16 | 22195710 | 22195792 | - |
| 0.204749303 | 1 | chr9 | 14433940 | 14434011 | - |
| 0.019586653 | 1 | chr6 | 27280270 | 27280342 | - |
| 0.108505466 | 1 | chr14 | 49853616 | 49853914 | - |
| 0.498776169 | 1 | chr17 | 8119155 | 8119230 | + |
| 0.062231743 | 1 | chr1 | 161454608 | 161454679 | - |
| 0.328068469 | 1 | chr1 | 248874248 | 248874319 | + |
| 0.54991412 | 1 | chr1 | 161441533 | 161441615 | + |
| 0.710034173 | 1 | chr13 | 99536321 | 99536396 | - |
| 0.110062222 | 1 | chr14 | 49862550 | 49862849 | - |
| 0.25281936 | 1 | chr11 | 59550986 | 59551059 | - |
| 0.309730075 | 1 | chr13 | 44917926 | 44917998 | - |
| 0.232410261 | 1 | chr17 | 43233787 | 43233977 | - |
| 0.137065292 | 1 | RN7SL1 | 1 | 299 | + |
| 0.356691574 | 1 | chr6 | 27503744 | 27503815 | + |
| 0.880076262 | 1 | chr1 | 146035692 | 146035763 | + |
| 0.961929488 | 1 | chr5 | 181101840 | 181101921 | + |
| 0.991996621 | 1 | chr6 | 26556619 | 26556619 | + |
| 0.917965239 | 1 | chr12 | 98503503 | 98503574 | + |
| 0.52821513 | 1 | chr21 | 17454786 | 17454859 | - |

FROM FIG. 22B-1

Figure 22B-3:
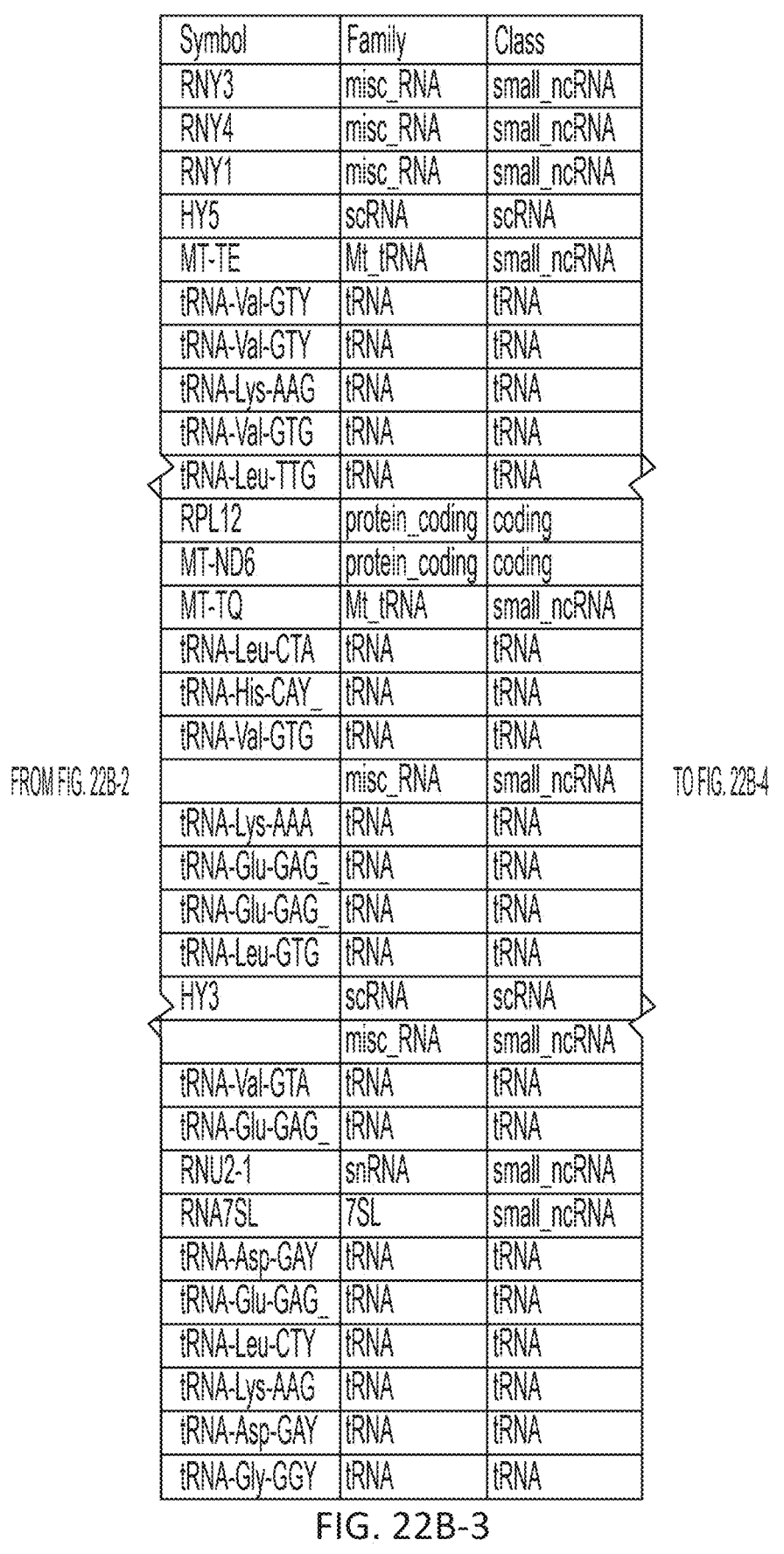

| Symbol | Family | Class |
|---|---|---|
| RNY3 | misc_RNA | small_ncRNA |
| RNY4 | misc_RNA | small_ncRNA |
| RNY1 | misc_RNA | small_ncRNA |
| HY5 | scRNA | scRNA |
| MT-TE | Mt_tRNA | small_ncRNA |
| tRNA-Val-GTY | tRNA | tRNA |
| tRNA-Val-GTY | tRNA | tRNA |
| tRNA-Lys-AAG | tRNA | tRNA |
| tRNA-Val-GTG | tRNA | tRNA |
| tRNA-Leu-TTG | tRNA | tRNA |
| RPL12 | protein_coding | coding |
| MT-ND6 | protein_coding | coding |
| MT-TQ | Mt_tRNA | small_ncRNA |
| tRNA-Leu-CTA | tRNA | tRNA |
| tRNA-His-CAY_ | tRNA | tRNA |
| tRNA-Val-GTG | tRNA | tRNA |
|  | misc_RNA | small_ncRNA |
| tRNA-Lys-AAA | tRNA | tRNA |
| tRNA-Glu-GAG_ | tRNA | tRNA |
| tRNA-Glu-GAG_ | tRNA | tRNA |
| tRNA-Leu-GTG | tRNA | tRNA |
| HY3 | scRNA | scRNA |
|  | misc_RNA | small_ncRNA |
| tRNA-Val-GTA | tRNA | tRNA |
| tRNA-Glu-GAG_ | tRNA | tRNA |
| RNU2-1 | snRNA | small_ncRNA |
| RNA7SL | 7SL | small_ncRNA |
| tRNA-Asp-GAY | tRNA | tRNA |
| tRNA-Glu-GAG_ | tRNA | tRNA |
| tRNA-Leu-CTY | tRNA | tRNA |
| tRNA-Lys-AAG | tRNA | tRNA |
| tRNA-Asp-GAY | tRNA | tRNA |
| tRNA-Gly-GGY | tRNA | tRNA |

FROM FIG. 22B-2

| Description | MFE | MFEden |
|---|---|---|
| RNA, Ro-associated Y3 [Source:HGNC Symbol;Acc:HGNC:10243] KNOWN | -29.3 | -13.75212766 |
| RNA, Ro-associated Y4 [Source:HGNC Symbol;Acc:HGNC:10244] KNOWN | -31.2 | -16.84886364 |
| RNA, Ro-associated Y1 [Source:HGNC Symbol;Acc:HGNC:10242] KNOWN | -34.4 | -17.16857143 |
| 0.1 | -25.3 | -11.74605263 |
| mitochondrially encoded tRNA glutamic acid [Source:HGNC | -19.6 | -5.290163934 |
| -3:73:1 | -25.4 | -13.88769231 |
| -3:73:1 | -25.4 | -13.88769231 |
| 1:73:-3 | -30.4 | -21.58 |
| -3:73:1 | -25.4 | -13.88769231 |
| -2:84:1 | -41 | -24.87575758 |
| ribosomal protein L12 [Source:HGNC Symbol;Acc:HGNC:10302] KNOWN | -1388.1 | NA |
| mitochondrially encoded NADH:ubiquinone oxidoreductase core | -117 | -19.46363636 |
| mitochondrially encoded tRNA glutamine [Source:HGNC | -19.3 | -4.5734375 |
| -2:83:1 | -33 | -22.16933333 |
| -3:72:1 | -26.9 | -16.4484375 |
| -3:73:1 | -26.3 | -15.27230769 |
| Metazoan signal recognition particle RNA [Source:RFAM;Acc:RF00017] | -130.8 | -39.32199313 |
| 0.094444444 | -29.6 | -19.45147059 |
| -3:72:1 | -26.9 | -16.4484375 |
| 1:72:-3 | -23.6 | -11.2921875 |
| 1:83:-3 | -37.2 | -27.76933333 |
| -1:100:1 | -29.2 | -18.86323529 |
| Metazoan signal recognition particle RNA [Source:RFAM;Acc:RF00017] | -135 | -40.62568493 |
| -2:74:1 | -24.5 | -12.31363636 |
| -2:73:1 | -26.7 | -15.88769231 |
| RNA, U2 small nuclear 1 [Source:HGNC Symbol;Acc:HGNC:10142] | -63.5 | -25.75245902 |
| abundant | -136 | -41.10893471 |
| 1:72:-3 | -27 | -16.6046875 |
| 1:72:-3 | -26.9 | -16.4484375 |
| 1:82:-3 | -36 | -26.52297297 |
| 1:74:-2 | -30.4 | -21.2530303 |
| 1:72:-3 | -26.7 | -16.1359375 |
| 0.051400463 | -32.8 | -24.88939394 |

FROM FIG. 22B-3

FIG. 22B-4

| GeneID | baseMean | log2FoldChange | lfcSE | stat | pvalue | padj | Chr |
|---|---|---|---|---|---|---|---|
| RNA7SL | 327546.4579 | -8.912860314 | 0.191712 | -46.4908 | 0 | 0 | RN7SL1 |
| ENSG00000278771 | 75.92669217 | -7.170128496 | 0.705714 | -10.1601 | 2.99E-24 | 6.31E-20 | chr14 |
| ENSGC0000201098 | 1748.988174 | -5.209348437 | 0.268056 | -19.4338 | 3.99E-84 | 2.81E-79 | chr7 |
| ENSGG0000274012 | 111.8280877 | -4.824720789 | 0.452796 | -10.6554 | 1.65E-26 | 3.86E-22 | chr14 |
| ENSGG0000202354 | 213.851281 | -3.944824098 | 0.582972 | -6.76675 | 1.32E-11 | 2.14E-07 | chr7 |
| ENSG00000252316 | 1897.900988 | -3.214754322 | 0.296694 | -10.8353 | 2.34E-27 | 6.18E-23 | chr7 |
| RMSK4442186 | 81.18317387 | -2.942231457 | 1.253117 | -2.34793 | 0.018878 | 1 | chr16 |
| RMSK2705056 | 16.36323769 | -2.774860866 | 1.372169 | -2.02224 | 0.043151 | 1 | chr9 |
| ENSG00000210107 | 10.44446317 | -2.193383233 | 1.276074 | -1.71885 | 0.085641 | 1 | chrM |
| ENSG00000274585 | 609.9006579 | -1.543663909 | 0.953416 | -1.61909 | 0.105428 | 1 | chr17 |
| ENSG00000210194 | 163.5949397 | -1.515709086 | 1.153941 | -1.31351 | 0.189012 | 1 | chrM |
| RMSK0284376 | 4.586025236 | -1.425626346 | 1.681349 | -0.84791 | 0.39649 | 1 | chr1 |
| ENSG00000197958 | 55.07686176 | -1.221303614 | 0.845393 | -1.44466 | 0.148554 | 1 | chr9 |
| RMSK2406652 | 560.0749163 | -1.113111492 | 1.170961 | -0.9506 | 0.341809 | 1 | chr7 |
| RMSK1900244 | 726.8474926 | -0.827956855 | 0.482785 | -1.71496 | 0.086352 | 1 | chr6 |
| RMSK1899770 | 89.40455336 | -0.612955938 | 1.028927 | -0.59572 | 0.55136 | 1 | chr6 |
| RMSK4003721 | 734.1446404 | -0.598195333 | 0.416605 | -1.43588 | 0.151036 | 1 | chr13 |
| RMSK0444065 | 720.5290218 | -0.531124104 | 0.851391 | -0.62383 | 0.532738 | 1 | chr1 |
| ENSG00000198695 | 224.7102352 | -0.258453387 | 0.376958 | -0.68563 | 0.492947 | 1 | chrM |
| RMSK3874632 | 95.73762968 | -0.200937977 | 0.907229 | -0.22149 | 0.824714 | 1 | chr12 |
| RMSK3556856 | 66.15875945 | -0.013876655 | 0.957805 | -0.01449 | 0.988441 | 1 | chr11 |
| RMSK1898352 | 8.319887325 | -0.007559956 | 1.441999 | -0.00524 | 0.995817 | 1 | chr6 |
| RMSK0284470 | 7.248270743 | 0 | 1.694662 | 0 | 1 | 1 | chr1 |
| RMSK1848200 | 4.48357604 | 0 | 1.719782 | 0 | 1 | 1 | chr5 |
| RMSK1848423 | 14.31581345 | 0 | 1.619806 | 0 | 1 | 1 | chr5 |
| RMSK1900901 | 4.660837415 | 0 | 1.711348 | 0 | 1 | 1 | chr6 |
| RMSK4489775 | 17.13747112 | 0 | 1.616778 | 0 | 1 | 1 | chr16 |
| RMSK5186324 | 28.24019394 | 0 | 1.584244 | 0 | 1 | 1 | chr21 |
| RMSK0284494 | 72.90677656 | 0.224999241 | 0.858231 | 0.262166 | 0.793193 | 1 | chr1 |
| RMSK4094422 | 0.541223191 | 0.238454208 | 1.806039 | 0.132032 | 0.894959 | 1 | chr13 |
| RMSK0254000 | 84.05747772 | 0.351689871 | 1.464692 | 0.240112 | 0.810244 | 1 | chr1 |
| RMSK4629380 | 4.922476046 | 0.449817609 | 1.648934 | 0.272793 | 0.785012 | 1 | chr17 |
| RMSK1903167 | 99.38408977 | 0.930655922 | 1.396286 | 0.666523 | 0.505077 | 1 | chr6 |

FIG. 22C-1

| Start | End | Strand | Symbol | Family | Class | Description | MFE | MFEden |
|---|---|---|---|---|---|---|---|---|
| 1 | 299 | + | RNA7SL | 7SL | small_ncRNA | abundant | -136 | -41.1089 |
| 49853616 | 49853914 | - | | misc_RNA | small_ncRNA | Metazoan signal re | -130.8 | -39.322 |
| 1.49E+08 | 1.49E+08 | - | RNY1 | misc_RNA | small_ncRNA | RNA, Ro-associate | -34.4 | -17.1686 |
| 49862550 | 49862849 | - | | misc_RNA | small_ncRNA | Metazoan signal re | -135 | -40.6257 |
| 1.49E+08 | 1.49E+08 | + | RNY3 | misc_RNA | small_ncRNA | RNA, Ro-associate | -29.3 | -13.7521 |
| 1.49E+08 | 1.49E+08 | + | RNY4 | misc_RNA | small_ncRNA | RNA, Ro-associate | -31.2 | -16.8489 |
| 3175691 | 3175763 | + | tRNA-Lys- | tRNA | tRNA | 1:73:-3 | -30.4 | -21.58 |
| 14433940 | 14434011 | - | tRNA-His- | tRNA | tRNA | -3:72:1 | -26.9 | -16.4484 |
| 4329 | 4400 | - | MT-TQ | Mt_tRNA | small_ncRNA | mitochondrially e | -19.3 | -4.57344 |
| 43233787 | 43233977 | - | RNU2-1 | snRNA | small_ncRNA | RNA, U2 small nuc | -63.5 | -25.7525 |
| 14674 | 14742 | - | MT-TE | Mt_tRNA | small_ncRNA | mitochondrially e | -19.6 | -5.29016 |
| 1.61E+08 | 1.61E+08 | - | tRNA-Val- | tRNA | tRNA | -3:73:1 | -25.4 | -13.8877 |
| 1.27E_08 | 1.27E_08 | - | RPL12 | protein_cod | coding | ribosomal protein | -1388.1 | NA |
| 1.49E+08 | 1.49E+08 | + | HY5 | scRNA | scRNA | 0.1 | -25.3 | -11.7461 |
| 27503744 | 27503815 | + | tRNA-Asp | tRNA | tRNA | 1:72:-3 | -27 | -16.6047 |
| 27280270 | 27280342 | - | tRNA-Val- | tRNA | tRNA | -3:73:1 | -26.3 | -15.2723 |
| 44917926 | 44917998 | - | tRNA-Glu- | tRNA | tRNA | -2:73:1 | -26.7 | -15.8877 |
| 2.49E+08 | 2.49E+08 | + | tRNA-Glu- | tRNA | tRNA | 1:72:-3 | -23.6 | -11.2922 |
| 14149 | 14673 | - | MT-ND6 | protein_cod | coding | mitochondrially e | -117 | -19.4636 |
| 98503503 | 98503574 | + | tRNA-Asp- | tRNA | tRNA | 1:72:-3 | -26.7 | -16.1359 |
| 59550986 | 59551059 | - | tRNA-Val- | tRNA | tRNA | -2:74:1 | -24.5 | -12.3136 |
| 26556546 | 26556619 | + | tRNA-Lys- | tRNA | tRNA | 1:74:-2 | -30.4 | -21.253 |
| 1.61E+08 | 1.61E+08 | + | tRNA-Leu- | tRNA | tRNA | 1:83:-3 | -37.2 | -27.7693 |
| 1.61E+08 | 1.81E+08 | + | tRNA-Leu- | tRNA | tRNA | 1:82:-3 | -36 | -26.523 |
| 1.81E+08 | 1.81E+08 | - | tRNA-Val- | tRNA | tRNA | -3:73:1 | -25.4 | -13.8877 |
| 27753400 | 27753472 | - | tRNA-Val- | tRNA | tRNA | -3:73:1 | -25.4 | -13.8877 |
| 22195710 | 22195792 | - | tRNA-Leu- | tRNA | tRNA | -2:83:1 | -33 | -22.1693 |
| 17454786 | 17454859 | - | tRNA-Gly- | tRNA | tRNA | 0.051400463 | -32.8 | -24.8894 |
| 1.61E+08 | 1.61E+08 | - | tRNA-Glu- | tRNA | tRNA | -3:72:1 | -26.9 | -16.4484 |
| 99536321 | 99536396 | - | HY3 | scRNA | scRNA | -1:100:1 | -29.2 | -18.8632 |
| 1.46E+08 | 1.46E+08 | + | tRNA-Glu- | tRNA | tRNA | 1:72:-3 | -26.9 | -16.4484 |
| 8119155 | 8119230 | + | tRNA-Lys- | tRNA | tRNA | 0.094444444 | -29.6 | -19.4515 |
| 288896222 | 28896328 | - | tRNA-Leu- | tRNA | tRNA | -2:84:1 | -41 | -24.8758 |

| ID | Sex | Status | Age | Cancer Type | Resection |
|----|-----|--------|-----|-------------|-----------|
| H1 | Female | Healthy | 42 | None | N/A |
| H2 | Female | Healthy | 77 | None | N/A |
| H3 | Female | Healthy | 24 | None | N/A |
| H4 | Female | Healthy | 52 | None | N/A |
| H5 | Female | Healthy | 27 | None | N/A |
| H6 | Male | Healthy | 27 | None | N/A |
| H7 | Male | Healthy | 27 | None | N/A |
| H8 | Male | Healthy | 44 | None | N/A |
| H9 | Male | Healthy | 49 | None | N/A |
| H10 | Male | Healthy | 57 | None | N/A |
| C1 | Female | Cancer | 52 | Breast | Yes |
| C2 | Female | Cancer | 49 | Breast | Yes |
| C3 | Female | Cancer | 49 | Breast | Yes |
| C4 | Female | Cancer | 72 | Breast | Yes |
| C5 | Female | Cancer | 55 | Breast | Yes |
| C6 | Female | Cancer | 49 | Breast | Yes |
| C7 | Male | Cancer | 82 | Pleomorphic undifferentiated sarcoma | No |
| C8 | Female | Cancer | 33 | Cervical squamous cell carcinoma | No |

GO Terms Enriched:
Inflammation
Apoptosis
Degredation of ECM

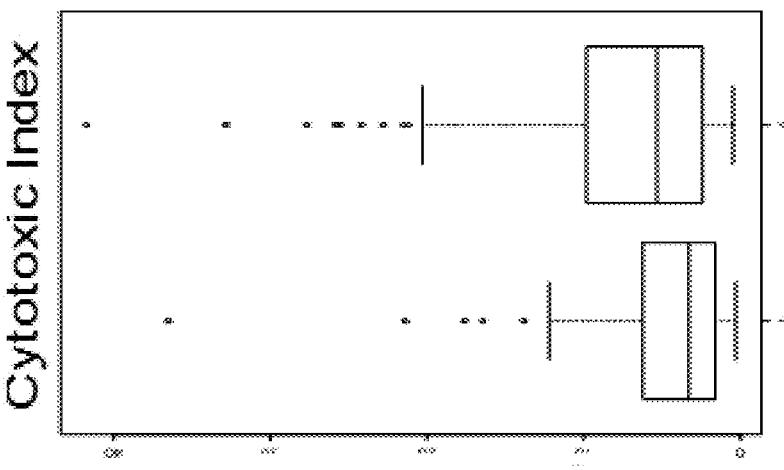
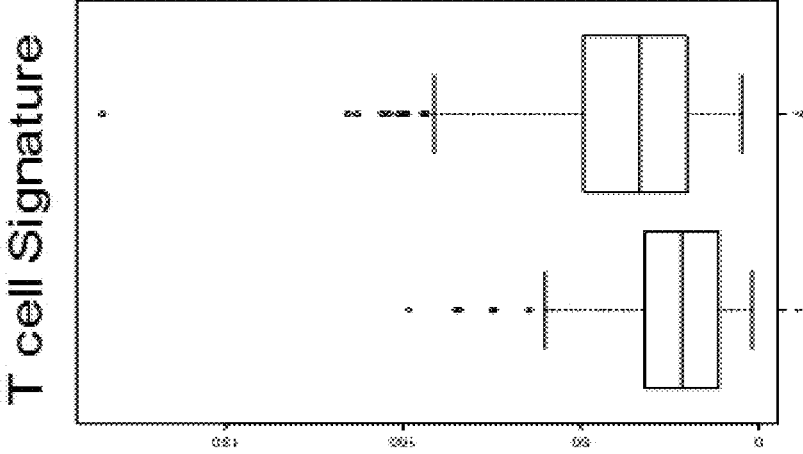
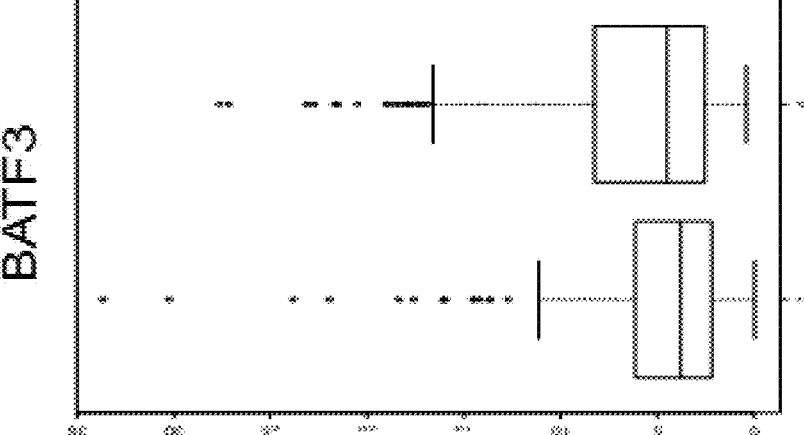
FIG. 30

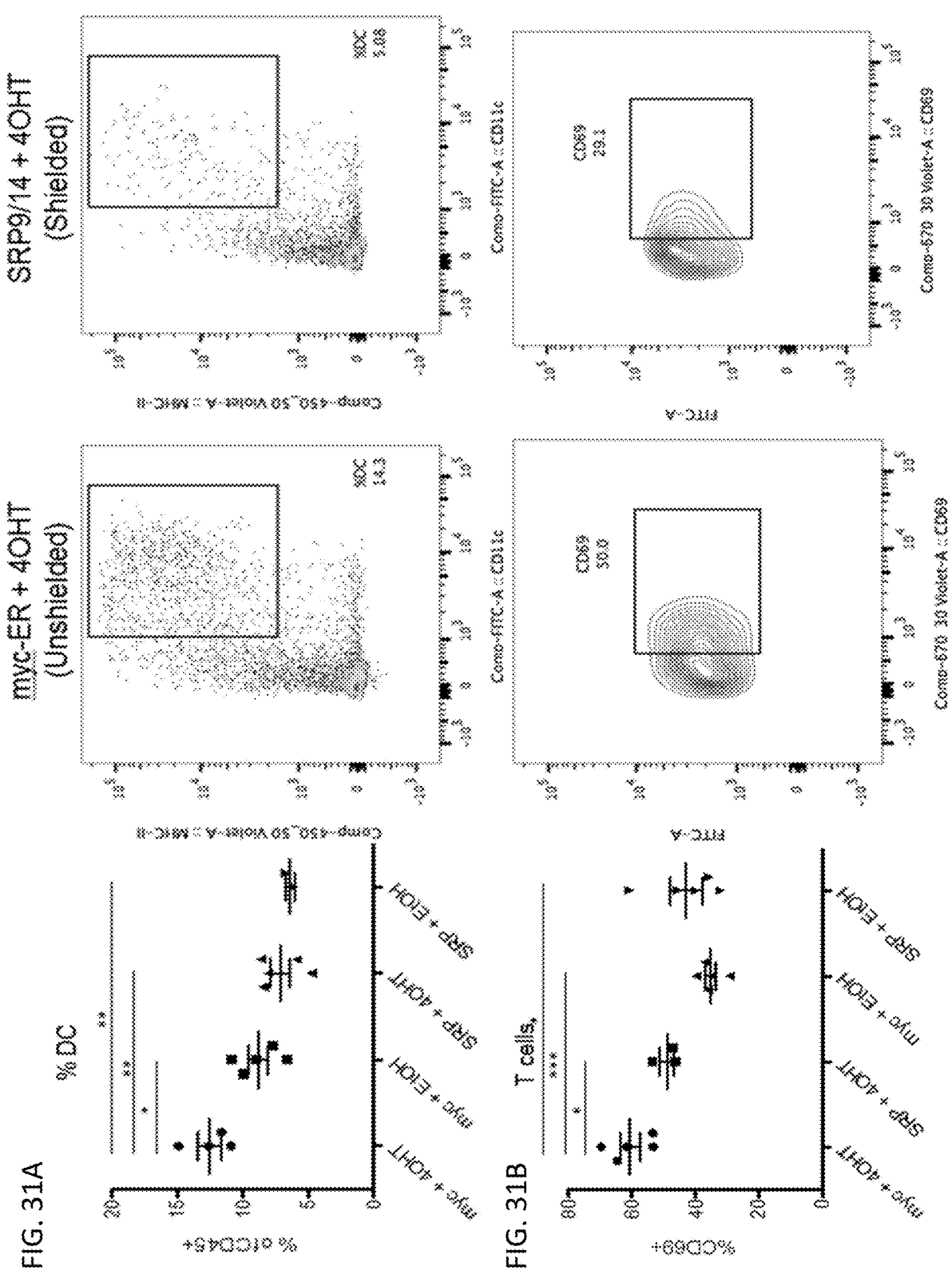

FIG. 31C
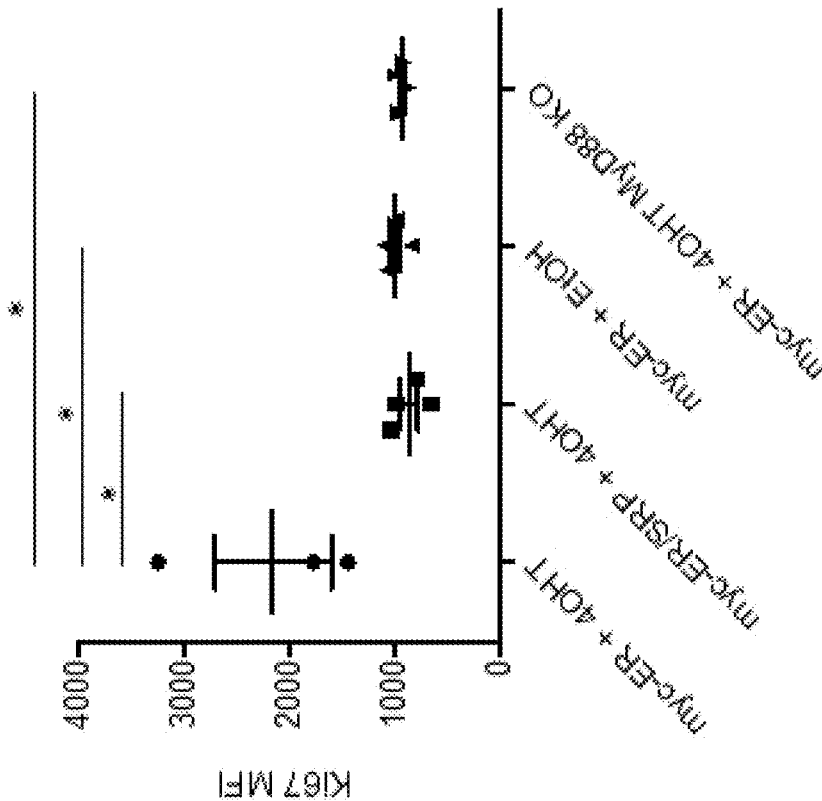
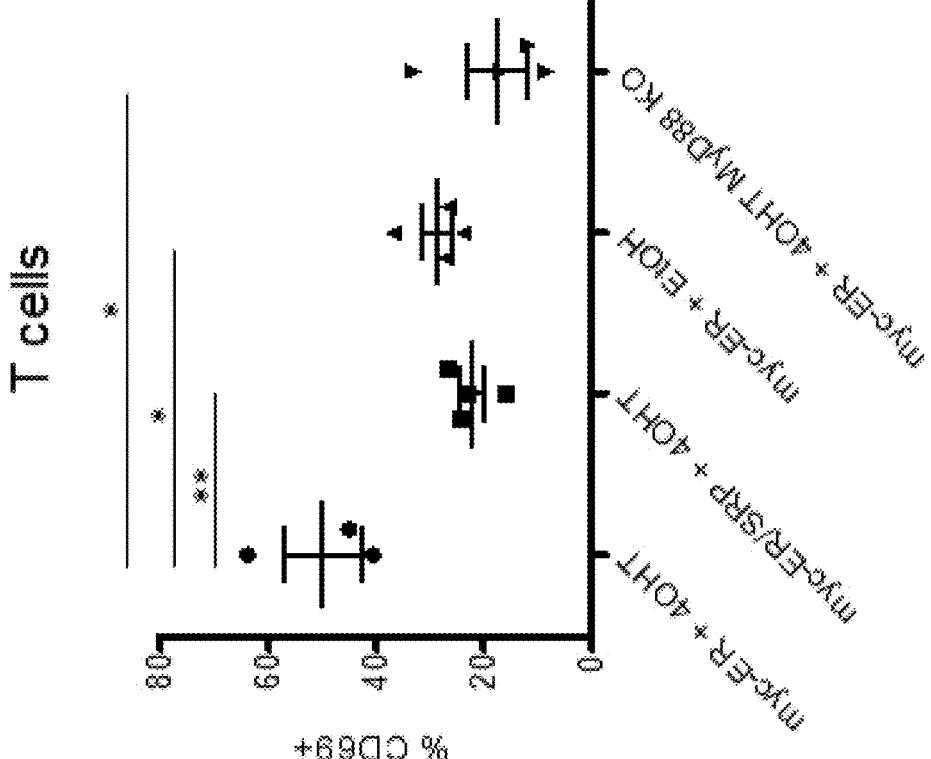

SEQ ID NO: 77

7SL1 Secondary Structure

SEQ ID NO: 76

HP Structure

Human SRP RNA large (S) domain

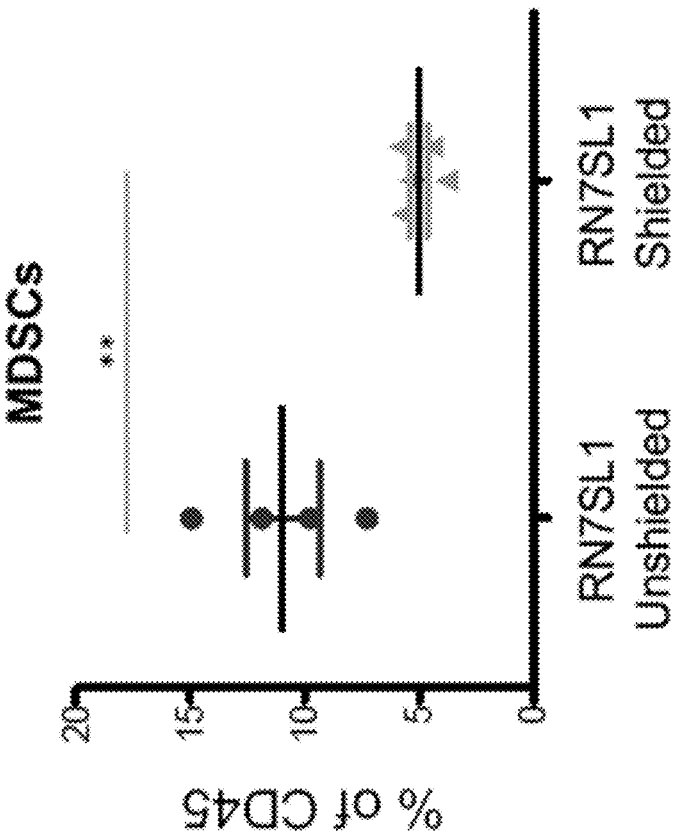
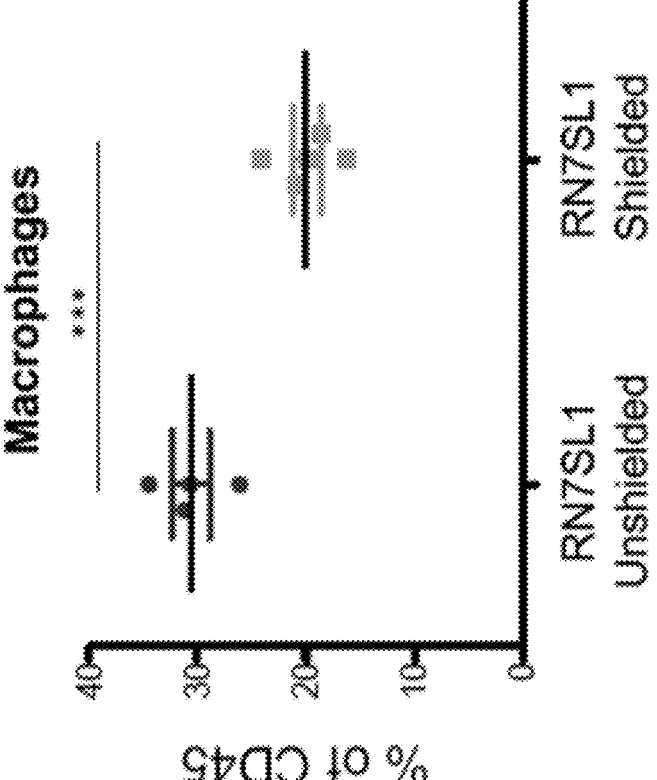
FIG. 36A

IMMUNOMODULATORY RNA

CROSS-REFERENCE TO RELATED APPLICATIONS

This present application is a continuation of U.S. patent application Ser. No. 17/476,342, filed Sep. 15, 2021, which is a continuation of U.S. patent application Ser. No. 15/947, 526, filed Apr. 6, 2018, which is entitled to priority under 35 U.S.C. § 119 (e) to U.S. Provisional Patent Application No. 62/483,082, filed Apr. 7, 2017, and U.S. Provisional Patent Application No. 62/614,610, filed Jan. 8, 2018, which are hereby incorporated by reference in their entireties herein.

STATEMENT REGARDING FEDERALLY SPONSORED RESEARCH OR DEVELOPMENT

This invention was made with government support under W81XWH-14-1-0450 awarded by the Department of Defense. The government has certain rights in the invention.

SEQUENCE LISTING

The ASCII text file named "046483_7158US3_ST25.txt" created on Mar. 24, 2025, comprising 16,799 bytes, is hereby incorporated by reference in its entirety.

BACKGROUND OF THE INVENTION

The dynamic interaction and co-regulation of critical signaling pathways between cancer cells and stromal cells of the tumor microenvironment can significantly influence tumor progression and therapy response. Through reciprocal signaling between these heterotypic cell types, cancer cell proliferation, cell death, and metabolism can be altered. Paracrine and juxtacrine signaling components that can be employed between cancer and stromal cells include RAS, WNT, NOTCH, STAT, and several others. The importance of these tumor-stromal signaling cascades may be to help amplify critical oncogenic pathways in cancer cells to promote tumor progression, metastasis, and resistance. However, the mechanisms that govern how cancer and stromal cells interact to accomplish these events are not well understood.

Another pathological condition that favors effective cell-cell communication to amplify critical signaling pathways is viral infection. Upon infection, cells induce an anti-viral response that includes the upregulation of interferon-stimulated genes (ISGs). This response is driven by the recognition of viral RNA by pattern recognition receptors (PRRs), such as RIG-I. Recent evidence reveals that in addition to cell intrinsic anti-viral responses that occur after viral infection, mechanisms exist to propagate an anti-viral response from infected to uninfected cells. For example, viral RNAs can be packaged into exosomes, small extracellular vesicles that originate in multivesicular bodies and are also implicated in a myriad of processes related to cancer progression. Secretion and transfer of exosomes to bystander cells can then result in recognition of exosome-transferred viral RNA by PRRs. This culminates in ISG induction within uninfected cells and tissue-level amplification of the antiviral response.

Across many common human cancers, a large proportion of patients have tumors that unexpectedly express high levels of ISGs. A subset of breast cancer cells, which are denoted as ISG responders (ISG-Rs), can induce ISGs through cell-cell contact with stromal fibroblasts and the subsequent secretion of exosomes. These exosomes contain RNA (exoRNA) that is enriched in non-coding transcripts. Upon transfer to ISG-R breast cancer cells, the exoRNA stimulates RIG-I, resulting in ISG induction and STAT1 activation. STAT1 amplifies the NOTCH3 transcriptional response, resulting in expansion of tumor-initiating cells and therapy resistance. Consistent with these experimental findings, patients with tumors expressing high levels of ISGs are more likely to relapse after chemotherapy or radiation therapy. Thus, a subset of breast cancer cells can amplify oncogenic pathways through anti-viral signaling resulting from stromal cell contact. Activation of breast cancer RIG-I by exoRNA after encountering stromal cells is reminiscent of how viral infection of one cell population can propagate anti-viral responses to neighboring cells. Similar examples of PRRs recognizing exoRNA in the tumor microenvironment have been reported to influence cancer progression. However, such potential examples of virus mimicry within a tumor raises questions on the similarities between cancer-associated antiviral signaling and virus-mediated signaling. Moreover, given that cancer-associated anti-viral signaling is occurring in a sterile microenvironment, the nature of the endogenous RNA and how it activates RIG-I are unanswered questions.

There are multiple properties that RIG-I utilizes to distinguish self from non-self RNA. Typically, RIG-I recognizes cytoplasmic double-stranded RNA that is 5' triphosphorylated, generally short (<300 bp), and has a blunt 5' end. For viral RNAs, polyuridine motifs can favor recognition, while RNA modifications such as 2-O-methylation can critically prevent RIG-I binding to 5' capped cellular RNAs. However, much of the RNA features and requirements for optimal RIG-I activation are based on synthetic and/or artificial RNAs in vitro. Emerging evidence indicates that endogenous RNA can function as a damage-associated molecular pattern (DAMP) to activate PRRs under a variety of pathological conditions, such as chemotherapy, radiation, and autoimmunity. How endogenous RNAs can function as DAMPs to activate PRRs while avoiding recognition under non-pathological conditions is not well understood.

A need exists for compositions and methods to detect and treat cancer. The current invention satisfies this need.

SUMMARY OF THE INVENTION

One aspect of the invention includes a method of detecting and treating a cancer in a subject. The method comprises assessing the level of unshielded RN7SL1 RNA in a sample from the subject. The level of unshielded RN7SL1 RNA from the subject is compared to a reference sample which is an otherwise identical non-cancerous sample from a subject. When the level of unshielded RN7SL1 RNA from the subject is higher than the control sample, the subject has cancer, and treatment of the cancer in the subject is recommended.

Another aspect of the invention includes a method of detecting and treating a cancer in a subject. The method comprises assessing the level of unshielded RN7SL1 RNA in a sample from the subject and assessing the level of shielded RN7SL1 RNA in the sample from the subject. The level of unshielded RN7SL1 RNA is compared to the level of shielded RN7SL1 RNA. When the level of unshielded RN7SL1 RNA from the subject is higher than the level of shielded RN7SL1 RNA, the subject has cancer, and treatment of the cancer in the subject is recommended.

Yet another aspect of the invention includes a method of treating a cancer in a subject in need thereof. The method comprises administering to the subject a therapeutically effective amount of an unshielded RN7SL1 RNA.

Still another aspect of the invention includes a method of treating a subject having cancer comprising assessing the aggressiveness of the cancer. The method comprises assessing the level of unshielded RN7SL1 RNA in a sample from the subject and comparing the level of unshielded RN7SL1 RNA from the subject to a reference sample. The reference is an otherwise identical non-cancerous sample from a subject. When the level of unshielded RN7SL1 RNA from the subject is higher than the control sample, the cancer is aggressive, and the subject is treated with an aggressive cancer therapy.

Another aspect of the invention includes a method of treating a subject having cancer comprising assessing the aggressiveness of the cancer. The method comprises assessing the level of unshielded RN7SL1 RNA in a sample from the subject, assessing the level of shielded RN7SL1 RNA in the sample from the subject, and comparing the level of unshielded RN7SL1 RNA to the level of shielded RN7SL1 RNA. When the level of unshielded RN7SL1 RNA from the subject is higher than the shielded RN7SL1 RNA, the cancer is aggressive, and the subject is treated with an aggressive cancer therapy.

Yet another aspect of the invention includes a method of determining whether treatment in a subject should be altered because the subject is resistant to a therapy. is selected from the group consisting of chemotherapy, radiation, and targeted therapy. The method comprises assessing the level of unshielded RN7SL1 RNA in a sample from the subject and comparing the level of unshielded RN7SL1 RNA from the subject to a reference sample. The reference is an otherwise identical non-cancerous sample from a subject. When the level of unshielded RN7SL1 RNA from the subject is higher than the control sample, the subject is resistant to the therapy, and the subject's treatment is altered so as to provide benefit to the subject.

Still another aspect of the invention includes a method of treating a subject having cancer comprising predicting whether a subject will respond to an immunotherapy treatment. The method comprises assessing the level of unshielded RN7SL1 RNA in a sample from the subject and comparing the level of unshielded RN7SL1 RNA from the subject to a reference sample. The reference is an otherwise identical non-cancerous sample from a subject. When the level of unshielded RN7SL1 RNA from the subject is higher than the control sample, the subject is predicted to respond to immunotherapy, and the subject is treated with the immunotherapy.

Another aspect of the invention includes a method of treating a subject having cancer comprising measuring the effectiveness of an immunotherapy treatment in the subject. The method comprises administering to the subject an immunotherapy treatment and assessing the level of unshielded RN7SL1 RNA in a sample from the subject. The level of unshielded RN7SL1 RNA from the subject is compared to a reference sample. The reference is an otherwise identical non-cancerous sample from a subject. When the level of unshielded RN7SL1 RNA from the subject is higher than the control sample, the immunotherapy treatment is deemed effective, and immunotherapy treatment is continued in the subject.

In various embodiments of the above aspects or any other aspect of the invention delineated herein, the subject is a human. In one embodiment, the sample is selected from the group consisting of blood, serum, plasma, biopsy, or tumor. In one embodiment, the cancer comprises breast cancer.

In one embodiment, assessing the RNA levels comprises a method selected from the group consisting of RNA sequencing, microarray, and qRT-PCR.

In one embodiment, treatment comprises surgery, chemotherapy, immunotherapy, targeted therapy, immune checkpoint blockade (ICB) therapy, or radiotherapy. In one embodiment, the treatment comprises administering at least one therapeutic agent selected from the group consisting of an anti-PD-1 antibody, an anti-PD-L1 antibody, an anti-CTLA-4 antibody, a CSF1R inhibitor, an anti-CSF1R antibody, a small molecule inhibitor of CSF1R, e.g., BLZ945, anti-TIM-3 antibody molecule, or an anti-LAG-3 molecule an IL-13 inhibitor, an IL-4 inhibitor, an IL-13Rα1 inhibitor, an IL-4Rα inhibitor, an IL-10 inhibitor, a CSF-1 inhibitor, a TGF beta inhibitor, a JAK2 inhibitor, a cell surface molecule, an iron oxide, a small molecule inhibitor, a PI3K inhibitor, an HDAC inhibitor, an inhibitor of the glycolytic pathway, a mitochondria-targeted antioxidant, a clodronate liposome, a Flt3 ligand polypeptide, or any combination thereof.

In one embodiment, the invention further comprises administering an additional treatment to the subject, wherein the additional treatment is selected from the group consisting of surgery, chemotherapy, immunotherapy, targeted therapy, immune checkpoint blockade (ICB) therapy, or radiotherapy. In one embodiment, the additional treatment comprises administering at least one therapeutic agent selected from the group consisting of an anti-PD-1 antibody, an anti-PD-L1 antibody, an anti-CTLA-4 antibody, a CSF1R inhibitor, an anti-CSF1R antibody, a small molecule inhibitor of CSF1R, e.g., BLZ945, anti-TIM-3 antibody molecule, or an anti-LAG-3 molecule an IL-13 inhibitor, an IL-4 inhibitor, an IL-13Rα1 inhibitor, an IL-4Rα inhibitor, an IL-10 inhibitor, a CSF-1 inhibitor, a TGF beta inhibitor, a JAK2 inhibitor, a cell surface molecule, an iron oxide, a small molecule inhibitor, a PI3K inhibitor, an HDAC inhibitor, an inhibitor of the glycolytic pathway, a mitochondria-targeted antioxidant, a clodronate liposome, a Flt3 ligand polypeptide, or any combination thereof.

In one embodiment, the unshielded RN7SL1 RNA is administered to the tumor microenvironment of the subject. In one embodiment, the RN7SL1 RNA comprises SEQ ID NO: 2

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

Figures 1C, 1D:
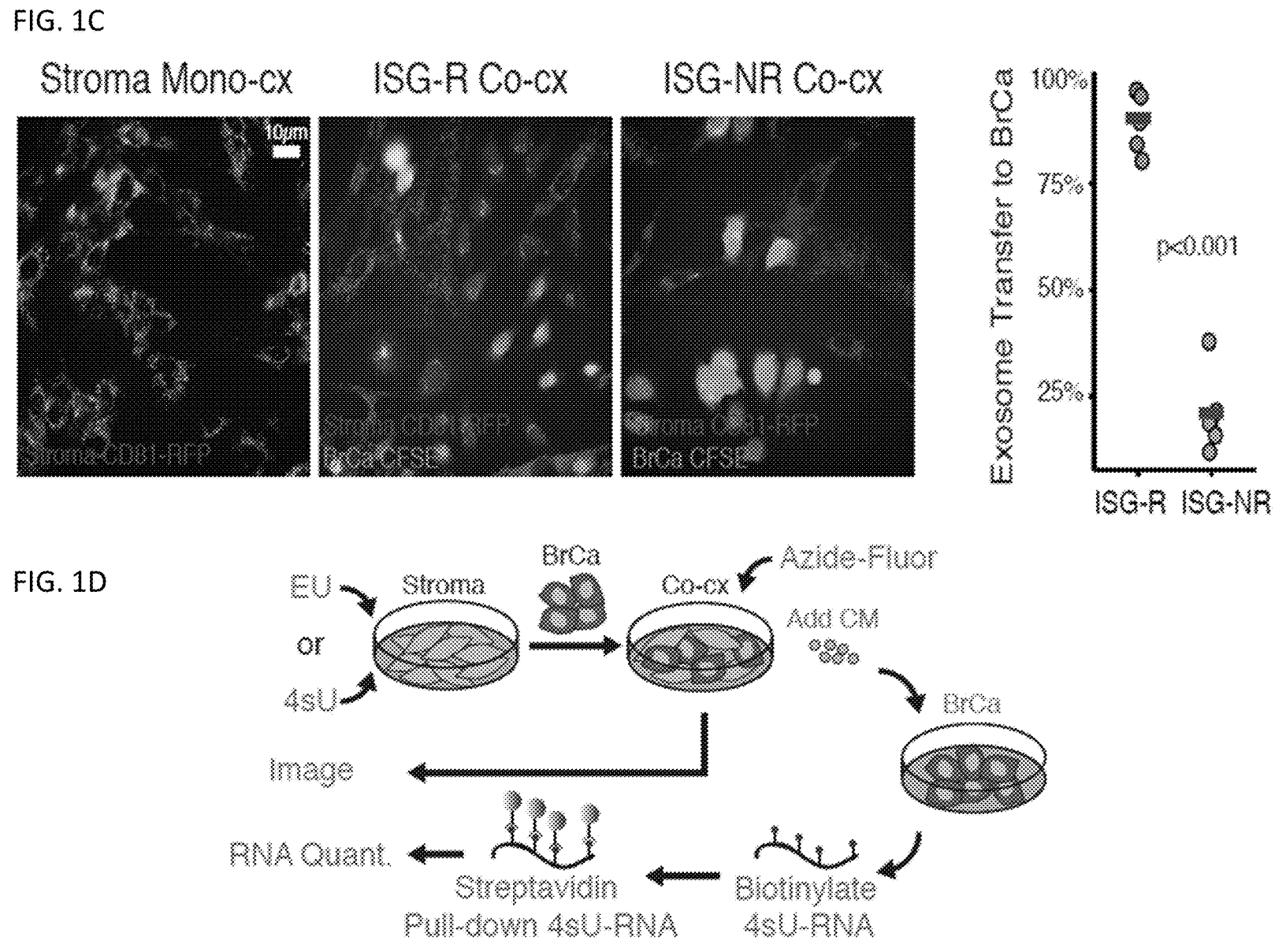

FIGS. 1A-1H are a series of plots and images illustrating stromal cell activation and ISG induction occurs upon breast cancer cell interaction and results in stromal RNA transfer via exosomes. FIG. 1A shows gene expression of MRC5 fibroblasts (Stromal Cells) and ISG-R 1833 breast cancer cells (BrCa Cells) after co-culture versus mono-culture. Genes indicated in red are cancer-associated ISGs. Genes in blue are significantly upregulated either in stromal cells (left panel) or ISG-R breast cancer cells (right panel) after co-culture. FIG. 1B is a gene set analysis showing significantly enriched hallmark gene sets after co-culture versus mono-culture in fibroblasts and ISG-R breast cancer cells. Size of circles is proportional to number of genes, and circles are color-coded by FDR-adjusted p-value as indicated in the legend. Thickness of lines is proportional to genes shared between sets. Anti-viral response pathways (blue) and select stromal activation pathways (bold) are highlighted. FIG. 1C shows MRC5 fibroblasts transduced with CD81-RFP to track exosome transfer co-cultured with CFSE-labeled ISG-R 1833 or ISG-NR MCF7 breast cancer cells. Exosome transfer to breast cancer was quantified as percentage of breast cancer cells with RFP foci (right panel). FIG. 1D is a schematic for measuring RNA transfer from stromal to breast cancer cells utilizing the uridine analog EU for fluorescence microscopy (green) or 4sU for streptavidin pull-down (orange). FIG. 1E shows MRC5 fibroblasts labeled with EU and co-cultured with DiD lipid-labeled 1833 breast cancer cells. Shown are representative images, with yellow arrows indicating EU-positive 1833 cells, and quantitation. FIG. 1F shows conditioned media (CM) from 4sU-labeled MRC5 fibroblasts grown in monoculture (Stroma, orange) or co-cultured with 1833 breast cancer cells (Co-cx, blue) was isolated. Shown is relative 4sU RNA transfer to mono-cultured 1833 breast cancer cells after addition of CM or exosome depleted CM (Co-cx Exo(–) CM) (n=5). Comparisons are made to DMSO control.

FIG. 1G shows the same as in (FIG. 1F) except CM was isolated from MRC5 or BJ 4sU-labeled fibroblasts left in mono-culture or co-cultured with indicated ISG-R or ISG-NR breast cancer cells. Shown is relative 4sU RNA transfer after CM addition to each of the mono-cultured breast cancer cells (n=3). FIG. 1H displays allelic frequency of exoRNA SNPs from exosomes isolated from 1833 breast cancer (BrCa), MRC5 fibroblasts (Stroma), or from co-culture of both cell types (Co-cx). Analysis is based on SNPs present in exoRNA from breast cancer cells and not present in fibroblasts. Unless indicated, error bars are SEM of biological replicates and *p<0.05,  p<0.01, * p<0.001.

FIGS. 2A-2K are a series of plots and images illustrating stromal POL3-derived exoRNA activates breast cancer RIG-I in a 5'triphosphate-dependent manner. FIG. 2A shows the distribution of RNA classes found in cellular RNA and exosome RNA by RNA-seq after co-culture of 1833 breast cancer cells with MRC5 stromal cells. Ribosomal RNA counts were removed. FIG. 2B shows ISG expression after transfection of co-culture exoRNA or co-culture cellular RNA into 1833 control cells (WT), RIG-I knockout 1833 cells (KO), or RIG-I KO 1833 cells restored with either wild-type (KO+WT) or RIG-I$^{K858/861A}$ 5'ppp binding mutant (KO+MUT) (n=5). Baseline was established by mock transfection. FIG. 2C shows ATP hydrolysis assay for RIG-I activation in response to increasing amounts of the indicated RNA. ExoRNA and cellular RNA are from co-culture of 1833 and MRC5 cells. 5'OH is a negative control and 5'ppp is a positive control (n=3). FIG. 2D depicts immunoblots for RPC32 (POLR3G) and P-actin in sorted MRC5 fibroblasts after mono- or co-culture (top). Quantification of POLR3G protein expression relative to P-actin after co-culture (bottom panel). FIG. 2E shows expression of ISGs in sorted 1833 cells. FIG. 2F shows RT-mediated cell death in 1833 cells after co-culture with MRC5 cells (CTL) or after siRNA knockdown of POLR3F in 1833 (BrCa), MRC5 (Stm), or both cell types (Co). Gene expression values are relative to sorted 1833 cells grown in mono-culture, and cell death was assessed 4 days after 10 Gy RT (n=3). FIG. 2G shows ISG expression in 1833 cells after addition of CM from DMSO or POL3 inhibitor (POL3i) treated co-cultures. Values are relative to 1833 cells grown in mono-culture (n=3). FIG. 2H shows RT-mediated cell death of 1833 cells in mono-culture (Mono) or co-culture with MRC5 cells (Co-cx). Cells were grown in the presence of DMSO or POL3i and with (+CM) or without rescue using co-culture CM (n=3). FIG. 2I shows ATP hydrolysis assay for RIG-I activation as shown in (FIG. 2C) except exoRNA from POL3i-treated co-cultures was additionally assessed (n=3). FIG. 2J shows abundance (Log 10) of RNA classes in 5'ppp-seq compared to exoRNA-seq. RNA classes depleted in 5'ppp-seq by approximately 10-fold or greater are shown on the left (n=4). FIG. 2K shows relative RNA polymerase III transcript levels in exosomes harvested from DMSO or POL3i-treated co-cultures (n=3). Unless indicated, error bars are SEM of biological replicates and *p<0.05, ** p<0.01.

FIGS. 3A-3F are a series of plots and images illustrating 5'ppp RN7SL1 exoRNA generated by tumor-stromal interaction is unshielded. FIG. 3A shows ISG expression in 1833 breast cancer cells after addition of exosomes from MRC5 stromal cell mono-culture (Strm) or co-culture of 1833 and MRC5 cells (Co-cx) (n=3). Values are relative to mock control. FIG. 3B depicts exoRNA and 5'ppp exoRNA enriched in co-culture exosomes. Shown is average expression (Log 2) by exoRNA-seq in co-culture versus fold-change in co-culture compared to MRC5 stromal cell mono-culture (n=2). Transcripts identified by 5'ppp-seq are shown in red. ExoRNA was rRNA-depleted. FIG. 3C depicts differentially expressed exoRNA from MRC5 mono-culture (Stroma) compared to co-culture of 1833 and MRC5 cells (Co-cx) (n=2). FIG. 3D shows expression of co-culture cellular RNA (left panel) or co-culture exoRNA (right panel) versus degree of RNA binding protein (RBP) unshielding. RBP unshielding (y-axis) is determined by fold change in RNA expression after MNase treatment with or without detergent (n=2). Smaller y-axis values indicate more unshielding. Transcripts identified by 5'ppp-seq are denoted by solid circles and color-coded based on normalized minimum free energy (MFE) to predict extent of double stranded RNA folding (lower MFE indicates more extensive double-stranded folding). FIG. 3E displays the extent of RBP-shielding of 5'ppp RN7SL1 in cells (Cellular RNA) or exosomes (ExoRNA) isolated from either MRC5 stromal mono-culture (Strm) or co-culture of 1833 and MRC5 cells (Co-cx). Proportion shielded is determined by MNase treatment with and without detergent followed by qRT-PCR (MNase-qRT-PCR) (n=3). Also shown are other RNAs with the indicated 5' modification. FIG. 3F displays the extent of RBP-shielding for cellular RNA (Cell) or exoRNA (Exo) isolated from co-cultures of the indicated ISG-R and ISG-NR breast cancer cells (labeled on right) with MRC5 fibroblasts. Proportion shielded is determined by MNase-qRT-PCR (n=3). Unless indicated, error bars are SEM of biological replicates and *p<0.05,  p<0.01, * p<0.001.

FIG. 4A illustrates conditioned media (CM) from 4sU-labeled MRC5 fibroblasts co-cultured with either ISG-R (orange) or ISG-NR (blue) breast cancer cells. Shown is relative 4sU RNA transfer to breast cancer cells in mono-culture after addition of CM (n=3). FIG. 4B shows ISG expression in 1833 breast cancer cells after transfection of co-culture exoRNA, cellular RNA, or RN7SL1 RNA. RIG-I status of 1833 cells was wild type (WT), knocked out (KO), or knocked out and restored with either wild-type RIG-I (KO+WT) or RIG-I$^{K858/861A}$ (KO+MUT) (n=3). Values are relative to mock control. FIG. 4C shows ATP hydrolysis assay for RIG-I activation by RN7SL1. Shown are increasing concentrations of RN7SL1 or the indicated RNA ligands. 5'ppp and DVG396 are positive controls. 5'OH and GAPDH300 are negative controls (n=3). FIG. 4D is a schematic to measure 4sU-labeled stromal RNA bound to breast cancer RIG-I after co-culture (Cell, top schema) or after addition of co-culture conditioned media (CM bottom schema). FIG. 4E shows representative immunoprecipitation of FLAG-RIG-I. FIG. 4F depicts quantitation of indicated 4sU-labeled MRC5 stromal RNA transferred and then bound to 1833 breast cancer RIG-I. Shown is relative binding to reconstituted wild type RIG-I (KO+WT, blue) or RIG-I$^{K858/861A}$ (KO+ MUT, orange) after co-culture (Cell) or addition of co-culture CM (CM). Binding of 5'cap mRNAs are shown on the left and 5'ppp RNAs on the right (n=3). Unless indicated, error bars are SEM of biological replicates and *p<0.05, ** p<0.01.

FIGS. 5A-5F are a series of plots and images illustrating stromal SRP9 and SRP14 regulate RN7SL1 shielding and activation of breast cancer RIG-I. FIG. 5A shows immunoblots for the indicated proteins in co-culture cells and exosomes. Lysates used were normalized to absolute levels of RN7SL1 RNA. FIG. 5B shows flow cytometry (left panel) and fluorescence microscopy (right panel) for GFP expression after transfection of GFP-SRP9 and GFP-SRP14 in MRC5 fibroblasts. FIG. 5C shows immunoblots for the indicated proteins in co-culture cells and exosomes after GFP-SRP9 and GFP-SRP14 transfection in MRC5 fibroblasts. FIG. 5D illustrates the extent of RBP-shielding for the indicated exoRNAs isolated from 1833 breast cancer cells co-cultured with control (CTRL) or GFP-SRP9 and GFP-SRP14 (SRP) transfected MRC5 fibroblasts. Proportion shielded is determined by MNase-qRT-PCR (n=3). FIG. 5E shows relative expression of ISGs in sorted 1833 cells after co-culture with MRC5 cells transfected with GFP-SRP9 and GFP-SRP14 (n=3). TSG101 and MMP1 are non-ISGs not expected to change. FIG. 5F shows an immunoblot for SRP9 pre-cleavage (lane 2) and post-cleavage (lane 1) of the GST tag with TEV protease. RN7SL1 binding to RIG-I was measured by ATP hydrolysis assay with or without addition of equimolar amounts of recombinant SRP9 (n=3). 5'ppp and DVG396 are positive controls. 5'OH is a negative control. Unless indicated, error bars are SEM of biological replicates and *p<0.05, ** p<0.01.

FIGS. 6A-6G are a series of plots and images illustrating unshielded stromal RN7SL1 exoRNA promotes breast cancer progression and is present in the serum of cancer patients. FIG. 6A depicts 1833 breast cancer cells were xenografted subcutaneously into athymic mice and 10 μg of exosomes from MRC5 stromal cell mono-culture or 1833 and MRC5 co-culture were injected intratumorally 3 times a week (n=5 per group). Shown are tumor growth curves. FIG. 6B depicts 1833 breast cancer cells with (RIG-I KO) or without (RIG-I WT) knockout of RIG-I were xenografted subcutaneously into athymic mice and 50 ng of the indicated liposome-encapsulated RNA was injected intratumorally 3 times a week (n=5 per group). Shown are tumor growth curves. FIG. 6C shows expression of ISGs measured by qRT-PCR with human specific primers from the indicated tumors from (FIG. 6B). TSG101 and MMP1 are non-ISGs not expected to change (n=5). FIG. 6D shows normalized photon flux from the lungs of athymic mice (left plot) tail-vein injected with luciferase-labeled 4175 ISG-R breast cancer cells (LM2) engineered with one of two independent shRNAs to RIG-I or a control shRNA (n=5 per group). Hematoxylin and eosin stain of mouse lung sections at experimental endpoint (right panels). FIG. 6E shows the extent of RBP-shielding of mouse RN7SL1 or 18S rRNA from serum exosomes 2 weeks after mice were tail-vein injected for lung metastasis induction with 4175 breast cancer cells (LM2) or injected with PBS. Proportion shielded is determined by MNase-qRT-PCR. Mouse-specific primers were validated for specificity. FIG. 6F displays the average distribution of exoRNA in each RNA class (left pie chart) or by POL3 regulation (right pie chart) from serum exosomes of breast cancer patients (n=2). Only the top 200 highest expressed non-ribosomal RNA transcripts were considered. FIG. 6G shows the extent of RBP-shielding of RN7SL1 or 18S rRNA from serum exosomes of cancer patients or normal volunteers without cancer (NM). Legend indicates samples from normal volunteers and cancer patients with or without tumor resection. Proportion shielded is determined by MNase-qRT-PCR. Unless indicated, error bars are SEM of biological replicates and *p<0.05, ** p<0.01.

FIGS. 8A-8B are a series of plots and images illustrating stromal cell activation and ISG induction occurs upon breast cancer cell interaction and results in stromal RNA transfer via exosomes. FIG. 8A is a set of graphs depicting gene expression of MRC5 fibroblasts (Stromal Cells) and ISG-NR breast cancer cells (BrCa Cells) after co-culture versus mono-culture. Genes indicated in red are ISGs. Genes color-coded blue are significantly upregulated in stromal cells after interaction with ISG-NR breast cancer cells. FIG. 8B is a plot showing the percentage of 4sU-labeled RNA in indicated fibroblasts after 24 hours compared to total RNA (n=3). Error bars are SEM of biological replicates.

FIGS. 9A-9I are a series of plots and images illustrating stromal POL3-derived exoRNA activates breast cancer RIG-I in a 5'triphosphate-dependent manner. FIG. 9A is an immunoblot confirmation of Cas9 control (WT), RIG-I knockout (KO), and RIG-I KO 1833 cells restored with either wild-type (KO+WT) or RIG-I$^{K858/861A}$ 5'ppp binding mutant (KO+MUT). FIG. 9B is an immunoblot confirmation of RIG-I KO in ISG-R 1833 breast cancer cell line. RIG-I pathway activation was stimulated by Sendai virus (SeV) and assessed by ISG15 induction. FIG. 9C depicts nanosight quantification of size and quantity of a representative exosome purification. FIG. 9D depicts purified exosome confirmation by electron microscopy negative staining. FIG. 9E shows gene expression of sorted MRC5 fibroblast RNA polymerase III subunit POLR3G after co-culture with ISG-R 1833 breast cancer. Values are relative to sorted MRC5 cells grown in mono-culture (n=3). FIG. 9F shows gene expression after indicated siRNA transfected in MRC5 cells (n=3). FIG. 9G illustrates RT-mediated cell death in 1833 cells in mono-culture (Mono) or co-culture with MRC5 cells (Co-cx). Cells were grown in the presence of DMSO or POL3 inhibitor (Pol3i), and cell death was assessed 4 days after 10 Gy RT (n=3). FIG. 9H ISG expression in sorted 1833 after co-culture with MRC5 cells in the presence of DMSO or POL3i. Gene expression values are relative to sorted 1833 cells grown in mono-culture (n=7). FIG. 9I is a schematic for 5'triphosphate enriched RNA-seq (5'ppp-seq). Unless indicated, error bars are SEM of biological replicates and  p<0.01, * p<0.001.

FIG. 10A shows relative expression of transcripts identified by 5'ppp-seq in exosomes from MRC5 mono-culture (Stroma) or MRC5 and 1833 co-culture (Co-cx). Values are relative to exoRNA from MRC5 mono-culture (n=3). FIG. 10B ISG expression in 1833 cells after transfection of exoRNA or cellular RNA from MRC5 mono-culture (Strm) or co-culture of 1833 and MRC5 cells (Co-cx) (n=3). Values are relative to mock transfection. FIG. 10C Schema for MNase-seq or MNase-qRT-PCR to analyze degree of RNA binding protein (RBP) shielding. FIG. 10D Extent of RBP-shielding of 5'ppp RN7SL1 in cells (Cell) or exosomes (Exo) isolated from co-culture of 1833 and MRC5 cells. Proportion shielded is determined by MNase treatment with and without detergent followed by qRT-PCR (MNase-qRT-PCR) (n=3). Also shown are other RNAs with the indicated 5' modification. FIG. 10E Exosome transfer to ISG-R K14cre;p53$^{F/F}$;Brca1$^{F/F}$ (KB1P) mouse breast cancer cells by differential lipid labeling of two populations of KB1P cells (Mono) or co-culture with primary mouse adult lung fibroblasts (ALFs) (Co-cx) (n=3). FIG. 10F ISG expression in sorted ISG-R KB1P cells after co-culture with ALFs. Gene expression values are relative to sorted KB1P cells grown in mono-culture (n=3). FIG. 10G RT-mediated cell death in KB1P cells in mono-culture (Mono) or co-culture with ALFs (Co-cx). Cell death was assessed 4 days after 10 Gy RT (n=3). FIG. 10H Extent of RBP-shielding of cellular RNA (Cell) or exoRNA (Exo) isolated from co-culture of KB1P cells and ALFs. Proportion shielded is determined by MNase-qRT-PCR (n=3). Unless indicated, error bars are SEM of biological replicates and *p<0.05,  p<0.01, * p<0.001.

FIGS. 12A-12C are a series images illustrating stromal SRP9 and SRP14 regulate RN7SL1 shielding and activation of breast cancer RIG-I. Shown are immunoblots for SRP9 (FIG. 12A), SRP14 (FIG. 12B), or GFP (FIG. 12C) after transfection of GFP-SRP9 and GFP-SRP14 in MRC5 fibroblasts.

FIGS. 14A-14D are a series of plots and images illustrating unshielded RN7SL1 in exosomes. FIG. 14A illustrates the unshielded RN7SL1 in exosomes vs cellular RNA. FIG. 14B shows how its RBP SRP9 and SRP14 are absent in exosomes but present in the ctyoplasm of cells. FIGS. 14C-14D show how over expression of SRP9/14 in the stromal cells to drive it into the exosomes can increase shielding of RN7SL1 in exosomes (FIG. 14C; 18S is a control) and interfere with exosomes produced from these stromal cells to stimulate anti-viral activity (FIG. 14D, MX1 and STAT1; MMP1 is negative control).

FIG. 15A shows nuclear translocation of MYC after activation. FIG. 15B shows this unshielded RN7SL1 in exosomes. FIG. 15C shows how these exosomes when injected into mice can then increase intratumoral dendritic cells known to present tumor antigen and activated intratumoral T cells (B16 is melanoma model, and PDA is pancreatic cancer model).

FIG. 16A shows how MYC target genes in stromal cells correlated with myeloid and lymphoid genes (surrogate for the immune cells themselves) in the tumor of breast cancer patients.

FIG. 16B shows that unshielded RN7SL1 is detected in serum exosomes from patients and how it associates with triple negative breast cancer (TNBC), which are known to have higher immune infiltration and more likely respond to immune checkpoint blockade therapy (n=4 each group). RMRP and RNU2 are MYC regulated as well but are not unshielded because they are not regulated by the RBP SRP9/14.

FIGS. 18A-18F are a series of plots and images illustrating disruption of the RBP (i.e. SRP9/14) for RN7SL1 in unactivated (mono-cultured) stromal cells (FIG. 18C). This leads to increase in stimulatory activity of exosomes (FIG. 18D) and unshielding of RN7SL1 in exosomes (FIG. 18F).

FIGS. 19A-19J are a series of plots and images illustrating how MYC is activated in stromal cells after breast cancer cell interaction (FIGS. 19A-19C) and is necessary to regulate RN7SL1 unshielding in exosomes (FIG. 19E) and subsequent stimulatory activity (FIG. 19D). Conversely, over-expression of MYC in stromal cells (FIG. 19F) is sufficient to unshielded RN7SL1 in exosomes (FIG. 19H) and promote its stimulatory activity (FIG. 19G). This is dependent on RNA POL3 (FIGS. 19I-19J).

FIGS. 21A-21B are a series of tables listing the primers used for qRT-PCR in the study (SEQ ID NOs: 18-75).

FIGS. 22A-22C are a series of tables showing differential expression of 5'ppp-seq identified transcripts. FIG. 22A shows differential expression of 5'ppp-seq identified transcripts in co-cx exoRNA-seq vs. stroma exoRNA-seq. FIG. 22B shows differential expression of 5'ppp-seq identified transcripts in cellular MNase-seq. FIG. 22C displays shows differential expression of 5'ppp-seq identified transcripts in exosomal MNase-seq.

FIG. 23 is a table showing characteristics of patients analyzed for exosome RN7SL1 shielding.

FIG. 24A is a graph comparing expression profiles of listed genes between the samples of the first quartile for the 7SL/SRP ratio and the samples of the fourth quartile for the 7SL/SRP ratio. FIGS. 24B and 24C are graphs showing the expression level of STAT1 and RAB7A, respectively, for the samples of the first quartile or the fourth quartile for the 7SL/SRP ratio. The 7SL/SRP ratio equals to RN7SL1 Reads/(SRP9+SRP14 Reads). The first quartile is the lower quartile, and the fourth quartile is the highest quartile.

FIG. 25A shows percent survival and FIG. 26B shows tumor volume (cm$^3$), for each of the indicated time points.

FIGS. 26A-26E are a series of plots illustrating unshielded 7SL drives myeloid infiltration into the tumor microenvironment. Mice were implanted with tumors as described in FIGS. 25A-25B. Tumors were harvested 13 days later and assessed for infiltration of macrophages or myeloid derived suppressor cells (MDSCs). Macrophages are considered Lin−, F4/80+, CD11b+ cells, MDSCs were considered Lin−, F4/80−, CD11c−, CD11b+, Ly6C+. Tumors were treated with aCTLA4 blocking antibody as described in FIGS. 25A-25B, and harvested at d15 to measure M2 polarization of macrophages as marked by CD206. 7SL Unshielded=myc-ER+4OHT, 7SL Shielded=myc-ER/SRP+4OHT. MEFs (referred to as "myc" in FIGS. 26A and 26B) or MEFs co-expressing SRP9/14 (referred to as "SRP" in FIGS. 26A and 26B) were treated with 4OHT or EtOH. EtOH treatment and SRP overexpression were used as a negative controls. FIG. 26A is a graph showing the percent of macrophages in CD45+ cells for each group tested. FIG. 26B is a graph showing the percent of MDSCs in CD45+ cells for each group tested. FIG. 26C is a panel of graphs showing flow cytometry plots for macrophages (upper panels) and MDSCs (lower panels) for the myc+4OHT treatment group ("7SL Unshielded") and the SRP+4OHT treatment group ("7SL Shielded"). FIG. 26D is a graph showing % CD206+ macrophages for the myc+4OHT+anti-CTLA-4 treatment group ("7SL Unshielded") and the myc+EtOH+anti-CTLA-4 treatment group ("7SL Unactivated"). FIG. 26E shows mice were implanted with the same tumors and subsequently treated with CSF1R inhibitor BLZ945. Polarization of macrophages and frequency of CD103+DCs are shown.

FIG. 30 is a series of graphs illustrating data from RNA-Seq analysis from TCGA lung adenocarcinoma samples were separated by level of unshielded 7SL1 RNA into quartiles and expression of indicated genes was graphed.

FIGS. 31A-31C are a series of plots illustrating unshielded 7SL increases DC infiltration and intratumoral T cell activation, dependent upon host MyD88 signaling. MEFs transduced to express a 4OHT-inducible myc protein were activated using 4OHT and implanted at a 1:1 ratio with B16-F10 melanoma cells into mice. Tumors were isolated 13 days later and assessed by flow cytometry to determine frequency of DCs (FIG. 31A) and activation of T cells (FIG. 31B. The same experiment was done in mice deficient for the signaling adapter protein MyD88 and T cell activation was assessed (FIG. 31C).

FIG. 32C shows results from mice implanted with tumors and treated with aCTLA4+/−CSF1Ri. Tumors were harvested 13 days later and immune populations were assessed using an unbiased clustering of flow cytometry data. Activated CD4+ is emphasized.

FIG. 35A is a schematic representation of the MEF system for identifying the relevance of 7SL RNA by SRP9/14. FIG. 35B is a schematic illustrating tumor/MEF co-implantation setup for assessing the influence of unshielded 7SL on immune infiltration and activation in vivo. FIG. 35C is a series of plots illustrating the relative frequency of indicated pro-inflammatory immune populations in tumors following tumor harvest ~2 weeks post-injection.

FIGS. 36A-36B are a series of plots illustrating unshielded RN7SL1 in the tumor microenvironment increases tumor-associated macrophages (TAMs) and myeloid derived suppressor cells (MDSCs). FIG. 36A shows the relative frequency of indicated immunosuppressive populations in tumors following tumor harvest ~2 weeks post-injection. FIG. 36B shows representative flow cytometry plots of populations in FIG. 36A.

FIG. 37A is a schematic illustrating inhibition of M2 polarization reveals the immunostimulatory effect of unshielded RN7SL1. FIG. 37B is a graph showing percent survival in mice treated with an anti-PD1 antibody and an anti-CTLA-4 antibody in the presence of unshielded or shielded RN7SL1. FIG. 37C is a graph showing percent survival in mice treated with an anti-PD1 antibody, an anti-CTLA-4 antibody, and a colony-stimulating factor 1 receptor (CSF1R) inhibitor in the presence of unshielded or shielded RN7SL1.

DETAILED DESCRIPTION

Definitions

Figures 1E, 1F:
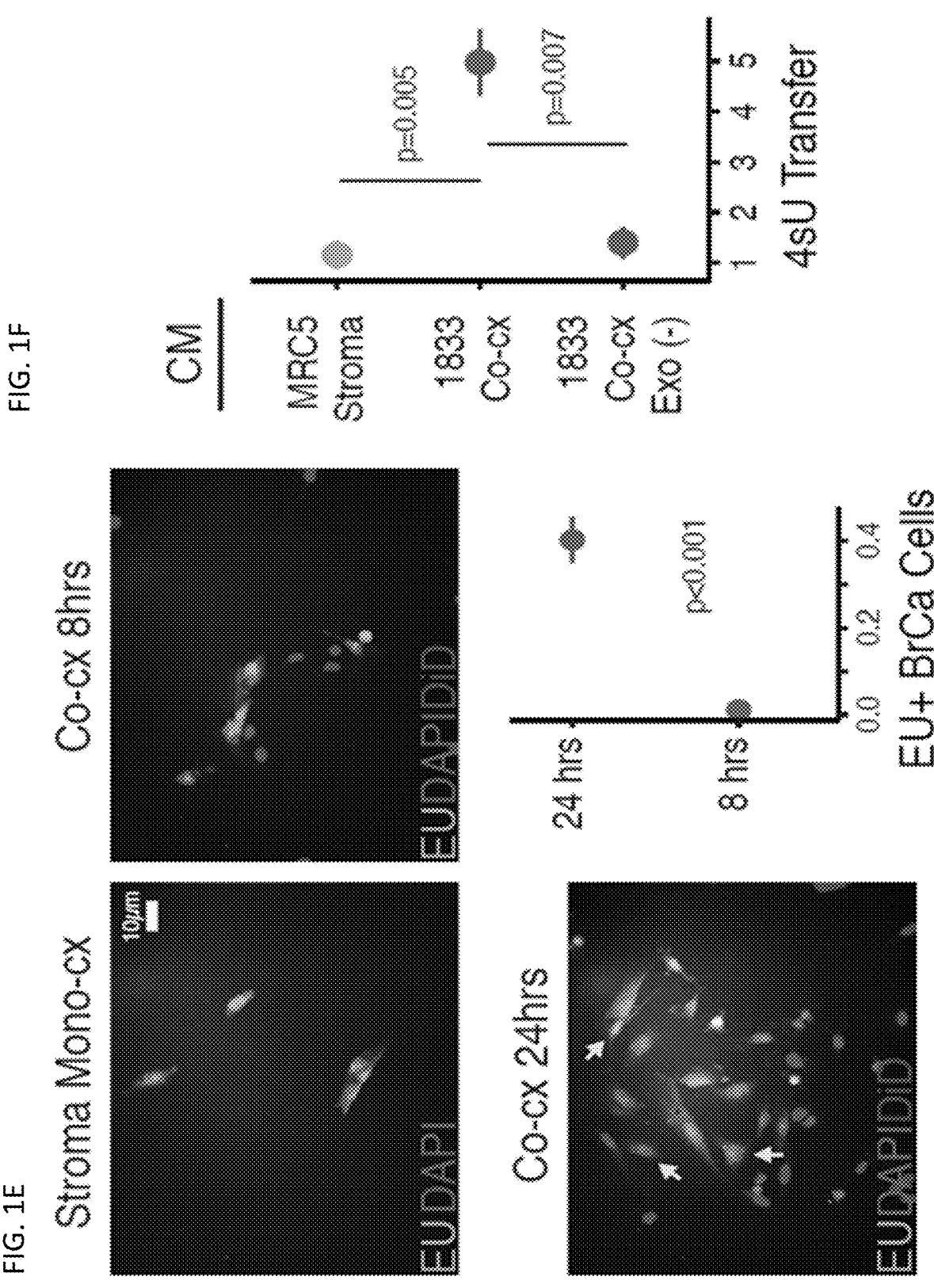

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, a cancer is "aggressive" if it displays characteristics of spreading (metastasizing) to other sites of the body, and/or is highly invasive and/or is difficult to treat.

As used herein, the term "autologous" is meant to refer to any material derived from the same individual to which it is later to be re-introduced into the individual.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide "Parenteral" administration of an immunogenic composition includes, e.g., subcutaneous (s.c.), intravenous (i.v.), intramuscular (i.m.), or intrasternal injection, or infusion techniques.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

The term "therapeutic" as used herein means a treatment and/or prophylaxis. A therapeutic effect is obtained by suppression, remission, or eradication of a disease state.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention features compositions and methods for the detection or diagnosis of cancer in a subject.

In one embodiment, the invention features diagnostic assessment of unshielded RN7SL1 RNA levels as a measurement for the presence, progression, and/or treatment efficacy of cancer.

In cancer, endogenous RNAs can act as damage-associated molecular patterns (DAMPs) to stimulate viral RNA receptors like RIG-I. How endogenous RNA DAMPs are deployed without being recognized under non-pathological conditions was previously unknown. This process is examined herein in the context of virus mimicry whereby breast cancer (BrCa) cells induced an anti-viral response in stromal cells. This was accompanied by stromal activation, upregulation of RNA polymerase III, and subsequent increase in stromal 5'triphosphate RN7SL1, an srpRNA, in exosomes. Unlike cytoplasmic RN7SL1 that is shielded by RNA binding proteins (RBPs), RN7SL1 in exosomes produced after BrCa cell interaction lacked RBPs like SRP9/14. Consequently, unshielded stromal RN7SL1 in exosomes, which is also found in cancer patients, was transferred to BrCa cells to activate RIG-I. This enhances tumor growth, metastasis, and therapy resistance. Thus, RBPs shielded endogenous POL3-driven RNA from RIG-I, a process circumvented when BrCa cells coerced stromal cells to propagate anti-viral signaling through exosomes.

Major components of the tumor microenvironment include stromal cells and immune cells. It is well recognized that the tumor microenvironment has a critical function in cancer progression and response to therapies. The biological mechanisms utilized by the tumor microenvironment to influence cancer progression and therapy response, how to target relevant pathways that can alter this microenvironment, and assays to interrogate the status of the microenvironment have significant therapeutic potential.

Using mouse cancer models, experiments disclosed herein demonstrate that the delivery of the active form of the RNA can have local and systemic immunomodulatory effects. This includes impacting the differentiation and activation of myeloid/dendritic cells, T cells, and other immune cells. Based on these findings, the data suggest that delivery of the RNA can influence the effectiveness of cancer immunotherapies and/or other cancer therapies.

Also discovered herein were specific signaling pathways and regulatory mechanisms that control the active properties of the RNA. Some of these pathways are currently druggable (e.g., NOTCH) while others hold promise as new targets (e.g., RBPs). These results suggest that existing and novel drug targets that impact the RNA can serve as therapeutics to alter the tumor and immune microenvironment to influence the effectiveness of cancer immunotherapies and/or other cancer therapies.

The effectiveness of conventional cancer therapies (e.g., chemotherapy, radiation), targeted therapies (e.g., kinase inhibitors), and immunotherapies (e.g., immune checkpoint blockade) critically depends on the tumor microenvironment. For example, the lack of T cells predicts poor response to immunotherapies, the abundance of unfavorable myeloid populations in the tumor cause resistance to chemotherapy and radiation, and activated stromal cells drive progression and resistance to various cancer therapies. The status of the active RNA in exosomes is demonstrated herein to be associated with these properties and an assay is developed that quantitates the active RNA from blood/serum. The assay can readily be performed on human blood/serum and can serve as a biomarker.

Figure 6A:
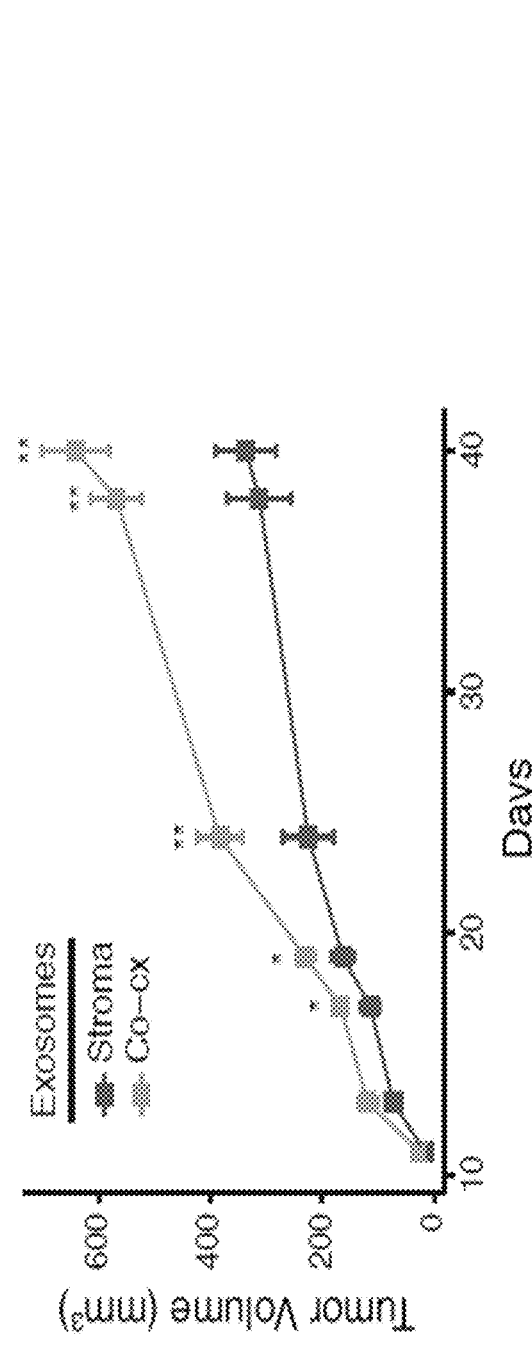
Figure 6B:
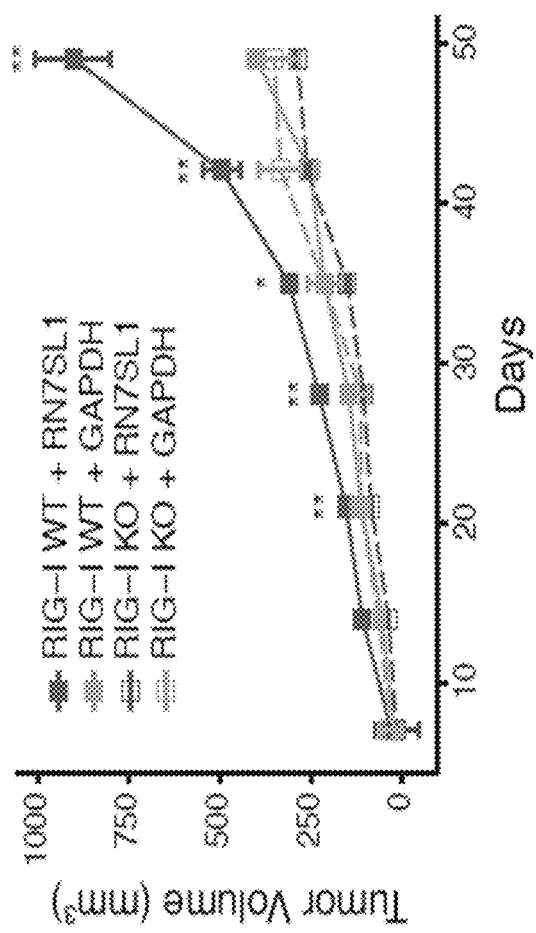

The stromal and immune cells of the tumor microenvironment can influence cancer progression and therapy resistance in complex and dichotomous ways. Many cancers are characterized by dominant immunosuppressive features that prevent an immune-mediated anti-tumor response. In this setting, rather than generating a favorable anti-tumor immune response, inflammatory factors and damage-associated molecular patterns (DAMPs), such as unshielded RN7SL1 in exosomes, can promote tumor progression and therapy resistance. Accordingly, it was shown herein that delivery of unshielded RN7SL1 or blocking its production (through genetic manipulation of its regulatory pathways) can facilitate therapy resistance and tumor progression in immunocompromised mice (FIGS. 2F-2H; FIGS. 6A-6B and 6D). However, the availability of new immunotherapies that can block major immunosuppressive mechanisms (e.g., immune checkpoint agents such as anti-PD1/PDL1 or anti-CTLA4) or directly deliver activated immune cells to the tumor (e.g., CAR T cells) may allow DAMP signals to regain their immunostimulatory function. Consistent with this concept, delivery of unshielded RN7SL1 either directly or through exosomes from MYC-activated stromal cells can promote immune cell activation in the neutral immune environment of mouse spleens (FIGS. 17A-17B), and enhance immune infiltration and expression of activation markers in multiple types of mouse tumors (FIG. 15C). Thus, these data suggest that unshielded RN7SL1 and similar unshielded RNA can be combined with immunotherapies such as immune checkpoint blockade and/or CAR T cells to enhance therapeutic response to various cancer immunotherapies.

Methods

The present invention includes methods for detecting and treating cancer in a subject. In one aspect, the method comprises assessing the level of unshielded RN7SL1 RNA in a sample from the subject and comparing it to a reference sample. The reference is an otherwise identical non-cancerous sample from a subject. When the level of unshielded RN7SL1 RNA from the subject is higher than the control sample, the subject has cancer, and a treatment is recommended to the subject.

In another aspect, the invention includes a method of measuring the effectiveness of a cancer treatment in a subject. The method comprises assessing the level of unshielded RN7SL1 RNA in a sample from the subject before the subject is given the cancer treatment, then assessing the level of unshielded RN7SL1 RNA in a sample from the subject after the subject is given the cancer treatment. The pre-treatment level of unshielded RN7SL1 RNA is compared with the post-treatment level of unshielded RN7SL1 RNA. When the post-treatment level of unshielded RN7SL1 RNA is lower than the pre-treatment level of unshielded RN7SL1 RNA, the cancer treatment is deemed to be effective. When the post-treatment level of unshielded RN7SL1 RNA is higher than the pre-treatment level of unshielded RN7SL1 RNA, the cancer treatment is deemed to be not effective. Depending on the results of the assay, an alteration or ceassation of cancer treatment may be recommended to the subject.

In another aspect the invention includes a method of treating cancer in a subject by administering a therapeutically effective amount of an unshielded RN7SL1 RNA to a subject in need thereof. In certain embodiments, the RNA is administered to the tumor microenvironment. In certain embodiments, the RN7SL1 RNA comprises SEQ ID NO: 2. The unshielded RN7SL1 RNA can be administered alone or in conjunction with another cancer treatment. For example, the unshielded RN7SL1 RNA can be administered in combination with any immunotherapy, targeted therapy, immune checkpoint blockade (ICB) therapy known to one of ordinary skill in the art.

A targeted therapy can include any therapy that targets a specific molecule. For example, a tyrosine kinase inhibitor can be used as a therapy that specifically targets a tyrosine kinase. In certain embodiments, the unshielded RN7SL1 RNA is administered in combination with at least one therapeutic agent selected from the group consisting of an anti-PD-1 antibody, an anti-PD-L1 antibody, an anti-CTLA-4 antibody, a CSF1R inhibitor, an anti-CSF1R antibody, a small molecule inhibitor of CSF1R, e.g., BLZ945, anti-TIM-3 antibody molecule, or an anti-LAG-3 molecule an IL-13 inhibitor, an IL-4 inhibitor, an IL-13Rα1 inhibitor, an IL-4Rα inhibitor, an IL-10 inhibitor, a CSF-1 inhibitor, a TGF beta inhibitor, a JAK2 inhibitor, a cell surface molecule, an iron oxide, a small molecule inhibitor, a PI3K inhibitor, an HDAC inhibitor, an inhibitor of the glycolytic pathway, a mitochondria-targeted antioxidant, a clodronate liposome, a Flt3 ligand polypeptide, or any combination thereof.

The unshielded RN7SL1 RNA can be administered in any encapsulated or modified form known to one of ordinary skill in the art.

Another aspect of the invention includes a method of detecting and treating a cancer in a subject. The method comprises assessing the level of unshielded RN7SL1 RNA in a sample from the subject and assessing the level of shielded RN7SL1 RNA in the sample from the subject. The level of unshielded RN7SL1 RNA is compared to the level of shielded RN7SL1 RNA. When the level of unshielded RN7SL1 RNA from the subject is higher than the level of shielded RN7SL1 RNA, the subject has cancer, and treatment of the cancer in the subject is recommended.

In another aspect, the invention includes a method of treating a subject having cancer comprising assessing the aggressiveness of the cancer. The method comprises assessing the level of unshielded RN7SL1 RNA in a sample from the subject and comparing the level of unshielded RN7SL1 RNA from the subject to a reference sample. The reference is an otherwise identical non-cancerous sample from a subject. When the level of unshielded RN7SL1 RNA from the subject is higher than the control sample, the cancer is aggressive, and the subject is treated with an aggressive cancer therapy.

In yet another aspect, the invention includes a method of treating a subject having cancer comprising assessing the aggressiveness of the cancer. The method comprises assessing the level of unshielded RN7SL1 RNA in a sample from the subject and assessing the level of shielded RN7SL1 RNA in the sample from the subject. The level of unshielded RN7SL1 RNA is compared to the level of shielded RN7SL1 RNA. When the level of unshielded RN7SL1 RNA from the subject is higher than the shielded RN7SL1 RNA, the cancer is aggressive, and the subject is treated with an aggressive cancer therapy.

Another aspect of the invention includes a method of determining whether treatment in a subject should be altered because the subject is resistant to a therapy. The therapy is selected from the group consisting of chemotherapy, radiation, and targeted therapy. The method comprises assessing the level of unshielded RN7SL1 RNA in a sample from the subject and comparing the level of unshielded RN7SL1 RNA from the subject to a reference sample. The reference is an otherwise identical non-cancerous sample from a subject. When the level of unshielded RN7SL1 RNA from the subject is higher than the control sample, the subject is resistant to the therapy, and subject's treatment is altered so as to provide benefit to the subject.

Yet another aspect of the invention includes a method of treating a subject having cancer comprising predicting whether a subject will respond to an immunotherapy treatment. The method comprises assessing the level of unshielded RN7SL1 RNA in a sample from the subject and comparing the level of unshielded RN7SL1 RNA from the subject to a reference sample. The reference is an otherwise identical non-cancerous sample from a subject. When the level of unshielded RN7SL1 RNA from the subject is higher than the control sample, the subject will respond to immunotherapy, and the subject is treated with the immunotherapy.

Still another aspect of the invention includes a method of treating a subject having cancer comprising measuring the effectiveness of an immunotherapy treatment in the subject. The method comprises administering to the subject an immunotherapy treatment, assessing the level of unshielded RN7SL1 RNA in a sample from the subject, and comparing the level of unshielded RN7SL1 RNA from the subject to a reference sample. The reference is an otherwise identical non-cancerous sample from a subject. When the level of unshielded RN7SL1 RNA from the subject is higher than the control sample, the immunotherapy treatment is deemed effective, and immunotherapy treatment is continued in the subject.

In certain embodiments, the subject is a human. In certain embodiments, the sample can include any type of bodily fluid, including but not limited to blood, serum, plasma, biopsy, or tumor (solid or non-solid). In other embodiments, the cancer can include any type of cancer, including but not limited to triple negative breast cancer, ovarian cancer and the like. Treatment can include any means of reducing the cancer including but not limited to pharmaceutical intervention, such as, but not limited to, kinase inhibitors, immunotherapy, surgery, chemotherapy, radiotherapy, immunotherapy, targeted therapy, or immune checkpoint blockade (ICB) therapy. Treatment can also comprise administering at least one therapeutic agent selected from the group consisting of an anti-PD-1 antibody, an anti-PD-L1 antibody, an anti-CTLA-4 antibody, a CSF1R inhibitor, an anti-CSF1R antibody, a small molecule inhibitor of CSF1R, e.g., BLZ945, anti-TIM-3 antibody molecule, or an anti-LAG-3 molecule an IL-13 inhibitor, an IL-4 inhibitor, an IL-13Rα1 inhibitor, an IL-4Rα inhibitor, an IL-10 inhibitor, a CSF-1 inhibitor, a TGF beta inhibitor, a JAK2 inhibitor, a cell surface molecule, an iron oxide, a small molecule inhibitor, a PI3K inhibitor, an HDAC inhibitor, an inhibitor of the glycolytic pathway, a mitochondria-targeted antioxidant, a clodronate liposome, a Flt3 ligand polypeptide, or any combination thereof.

RNA levels can be assessed by any method known in the art including but not limited to RNA sequencing, microarray, and qRT-PCR and other methods disclosed elsewhere herein.

Diagnostic Assays

The present invention provides a number of diagnostic assays that are useful for the identification or characterization of a disease or disorder (e.g. cancer), or a propensity to develop such a condition. In one embodiment, cancer is characterized by quantifying the level of RN7SL1 exosomal RNA. While the examples provided herein describe specific methods of detecting levels of these markers, the skilled artisan appreciates that the invention is not limited to such methods. Marker levels are quantifiable by any standard method, such methods include, but are not limited to RNA sequencing, real-time PCR, Southern blot, qRT-PCR, and/or mass spectroscopy, and other methods disclosed elsewhere herein.

The level of markers described herein defines the marker profile of a disease, disorder, or condition. The level of marker is compared to a reference. In one embodiment, the reference is the level of marker present in a control sample obtained from a patient that does not have cancer. In another embodiment, the reference is a healthy tissue or cell from the subject being tested (i.e., that is negative for cancer). In another embodiment, the reference is a baseline level of marker present in a biologic sample derived from a patient prior to, during, or after treatment for cancer. In yet another embodiment, the reference is a standardized curve. In still another embodiment, the reference is a synthetic RNA standard of a known concentration. The level of any one or more of the markers described herein (e.g. exosomal RNA) is used, alone or in combination with other standard methods, to characterize the disease, disorder, or condition (e.g. cancer).

In certain embodiments, the RNA is detected and/or quantified in a sample from the subject under examination. Any method known to those in the art can be employed for determining the level of RNAs. RNA can be isolated from the sample using any method known to those in the art. Non-limiting examples include commercial kits, such as the miRNeasy® commercially available from Qiagen (Netherlands) or the Mini Kit TRI Reagent® commercially available from Molecular Research Center, Inc. (Cincinnati, Ohio).

Generally, the isolated RNA may be amplified using methods known in the art. Amplification systems utilizing, for example, PCR or RT-PCR methodologies, are known to those skilled in the art. For a general overview of amplification technology, see, for example, Dieffenbach et al., PCR Primer: A Laboratory Manual, Cold Spring Harbor Laboratory Press, New York (1995).

An alternative method for determining the level of RNAs includes the use of molecular beacons and other labeled probes useful in, for example multiplex PCR. In a multiplex PCR assay, one PCR mixture contains primers and probes to amplify and detect multiple selected mRNAs, ncRNAs or miRNAs. Typically, different fluorochromes are used to discriminate each RNA's PCR product in the assay. The molecular beacon or probe is detected to determine the level of RNA. Molecular beacons are described, for example, by Tyagi and Kramer (Nature Biotechnology 1996; 14, 303-308) and by Andrus and Nichols (U.S. Patent Application Publication No. 20040053284).

Another accurate method for profiling RNA expression can be the use of next generation sequencing (NGS) including first, second, third as well as subsequent NGS technologies. Non-limiting examples could be the nanopore or semiconductor technologies (e.g. Oxford Nanopore Technologies, United Kingdom) or the Illumina RNA-Seq and microRNA-Seq methodologies for HiSeq or MiSeq instruments (Chu and Corey, Nucleic Acid Ther. 2012; 22 (4): 271-274; Luo, Methods Mol Biol. 2012; 822:183-8).

Detection of Biomarkers

The biomarkers of this invention can be detected by any suitable method. The methods described herein can be used individually or in combination for a more accurate detection of the biomarkers. Methods for conducting polynucleotide hybridization assays have been developed in the art. Hybridization assay procedures and conditions will vary depending on the application and are selected in accordance with the general binding methods known including those referred to in: Sambrook and Russell, Molecular Cloning: A Laboratory Manual ($3^{rd}$ Ed. Cold Spring Harbor, N.Y, 2001); Berger and Kimmel Methods in Enzymology, Vol. 152, Guide to Molecular Cloning Techniques (Academic Press, Inc., San Diego, Calif., 1987); Young and Davism, P.N.A.S, 80:1194 (1983). Methods and apparatus for carrying out repeated and controlled hybridization reactions have been described in U.S. Pat. Nos. 5,871,928, 5,874,219, 6,045,996 and 6,386, 749, 6,391,623. A data analysis algorithm (E-predict) for interpreting the hybridization results from an array is publicly available (see Urisman, 2005, Genome Biol 6:R78).

In one embodiment, the RNA is detected by detecting one or more labels attached to, or incorporated within, the sample RNA. The labels may be attached or incorporated by any of a number of means well known to those of skill in the art. In one embodiment, the label is simultaneously incorporated during the amplification step in the preparation of the sample nucleic acids. Thus, for example, PCR with labeled primers or labeled nucleotides will provide a labeled amplification product. In another embodiment, transcription amplification, as described above, using a labeled nucleotide (e.g. fluorescein-labeled UTP and/or CTP) incorporates a label into the transcribed nucleic acids. In another embodiment PCR amplification products are fragmented and labeled by terminal deoxytransferase and labeled dNTPs. Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore). In another embodiment label is added to the end of fragments using terminal deoxytransferase.

Detectable labels suitable for use in the present invention include any composition detectable by spectroscopic, photochemical, biochemical, immunochemical, electrical, optical or chemical means. Useful labels in the present invention include, but are not limited to: biotin for staining with labeled streptavidin conjugate; anti-biotin antibodies, magnetic beads (e.g., Dynabeads™.); fluorescent dyes (e.g., Cy3, Cy5, fluorescein, texas red, rhodamine, green fluorescent protein, and the like); radiolabels (e.g., $^3$H, $^{125}$I, $^{35}$S, $^4$C, or $^{32}$P); phosphorescent labels; enzymes (e.g., horse radish peroxidase, alkaline phosphatase and others commonly used in an ELISA); and colorimetric labels such as colloidal gold or colored glass or plastic (e.g., polystyrene, polypropylene, latex, etc.) beads. Patents teaching the use of such labels include U.S. Pat. Nos. 3,817,837, 3,850,752, 3,939,350, 3,996,345, 4,277,437, 4,275,149 and 4,366,241.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. Nos. 10/389, 194, 60/493,495 and in PCT Application PCT/US99/06097 (published as WO99/47964).

Detection by Microarray

In certain aspects of the invention, a sample is analyzed by means of a microarray. The nucleic acid molecules of the invention are useful as hybridizable array elements in a microarray. Microarrays generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. U.S. Pat. Nos. 5,800,992 and 6,040,138 describe methods for making arrays of nucleic acid probes that can be used to detect the presence of a nucleic acid containing a specific nucleotide sequence. Methods of forming high-density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling. For additional descriptions and methods relating to resequencing arrays see U.S. patents application Ser. Nos. 10/658,879, 60/417,190, 09/381,480, 60/409,396, and U.S. Pat. Nos. 5,861,242, 6,027,880, 5,837, 832, 6,723,503.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507). For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Kits

The invention provides a kit for the detection of a biomarker, which is indicative of the presence of cancer. The kit may be used for the diagnosis or detection of cancer. In certain embodiments, the kit comprises reagents for assessing the level of RN7SL1 exosomal RNA in a sample from a subject.

In some embodiments, the kit comprises one or more sterile containers which contain the reagents. Such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The instructions will generally include information about the use of the composition for the detection or diagnosis of cancer. The instructions may be printed directly on the container (when present), or as a label applied to the container, or as a separate sheet, pamphlet, card, or folder supplied in or with the container.

Therapy

The RNA described herein may be included in a composition for therapy. The composition may include a pharmaceutical composition and further include a pharmaceutically acceptable carrier. A therapeutically effective amount of the pharmaceutical composition comprising the RNA may be administered. In one aspect, the invention includes a method of treating a cancer in a subject in need thereof comprising administering to the subject a therapeutically effective amount of an RN7SL1 RNA. RNA of the invention can be administered in dosages and routes and at times to be determined in appropriate pre-clinical and clinical experimentation and trials. RNA may be administered multiple times at dosages within these ranges. The dosage to be administered to a subject will vary with the precise nature of the condition being treated and the recipient of the treatment. The scaling of dosages for human administration can be performed according to art-accepted practices. Administration of the RNA of the invention may be combined with other methods useful to treat the desired disease or condition as determined by those of skill in the art.

The administration of the RNA of the invention may be carried out in any convenient manner known to those of skill in the art. The RNA of the present invention may be administered to a subject by aerosol inhalation, injection, ingestion, transfusion, implantation or transplantation. The RNA described herein may be administered to a patient transarterially, subcutaneously, intradermally, intratumorally, intranodally, intramedullary, intramuscularly, by intravenous (i.v.) injection, or intraperitoneally. In other instances, the RNA of the invention is injected directly into a site of inflammation in the subject, a local disease site in the subject, a lymph node, an organ, a tumor, and the like. In one embodiment, the RNA is administered to the tumor microenvironment of the subject. Pharmaceutical compositions of the present invention may comprise an RNA as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Stimulatory RNA Molecules

In one aspect, the invention includes an RNA molecule, e.g., a stimulatory RNA molecule, e.g., an immune stimulatory RNA molecule. In some embodiments, the RNA molecule activates a pattern recognition receptor (PRR), e.g., retinoic acid-inducible gene I (RIG-I). In some embodiments, the RNA molecule activates dendritic cells (DCs), macrophages, and/or T cells.

In some embodiments, the RNA molecule is an RN7SL1 RNA molecule, e.g., a human RN7SL1 RNA molecule, or functional variant thereof. In some embodiments, the RNA molecule is an RN7SL1 RNA molecule, e.g., a human RN7SL1 RNA molecule. In some embodiments, the RNA molecule comprises the nucleotide sequence of SEQ ID NO: 2 (or a sequence at least about 85%, 90%, 95%, 99% or more identical thereto, and/or having one, two, three or more substitutions, insertions, deletions, or modifications). In some embodiments, the RNA molecule comprises an Alu domain, or functional variant thereof. In some embodiments, the RNA molecule comprises an Alu domain comprising the nucleotide sequence of SEQ ID NO: 4 or 6 (or a sequence at least about 85%, 90%, 95%, 99% or more identical thereto, and/or having one, two, three or more substitutions, insertions, deletions, or modifications). In some embodiments, the RNA molecule is an Alu-Ya5 RNA molecule, or functional variant thereof. In some embodiments, the RNA molecule is an Alu-Ya5 RNA molecule. In some embodiments, the RNA molecule comprises the nucleotide sequence of SEQ ID NO: 8 (or a sequence at least about 85%, 90%, 95%, 99% or more identical thereto, and/or having one, two, three or more substitutions, insertions, deletions, or modifications). In some embodiments, the RNA molecule is an RNA molecule that retains the immune stimulatory activity of an RN7SL1 RNA molecule or an Alu-Ya5 RNA molecule, but does not bind or does not substantially bind to SRP9 and/or SRP14. In some embodiments, the binding of the RNA molecule to SRP9 and/or SRP14 is no more than 5, 10, 15, 20, 25, 30, or 35% of the binding of an RN7SL1 RNA molecule (e.g., an RNA molecule comprising the nucleotide sequence of SEQ ID NO: 2) to SRP9 and/or SRP14. In some embodiments, the RNA molecule comprises the nucleotide sequence of SEQ ID NO: 10 (or a sequence at least about 85%, 90%, 95%, 99% or more identical thereto, and/or having one, two, three or more substitutions, insertions, deletions, or modifications). Exemplary sequences of RNA molecules and DNA molecules encoding the RNA molecules are disclosed in Table 1.

TABLE 1

Exemplary sequences of stimulatory RNAs

| SEQ ID NO | Comment | Sequence |
|---|---|---|
| SEQ ID NO: 1 | RN7SL1 | GCCGGGCGCGGTGGCGCGTGCCTGTAGTCCCAGCTACTCGGGAGGC TGAGGCTGGAGGATCGCTTGAGTCCAGGAGTTCTGGGCTGTAGTGC GCTATGCCGATCGGGTGTCCGCACTAAGTTCGGCATCAATATGGTG ACCTCCCGGGAGCGGGGGACCACCAGGTTGCCTAAGGAGGGGTGA ACCGGCCCAGGTCGGAAACGGAGCAGGTCAAAACTCCCGTGCTGAT CAGTAGTGGGATCGCGCCTGTGAATAGCCACTGCACTCCAGCCTGG GCAACATAGCGAGACCCCGTCTCT |
| SEQ ID NO: 2 | RN7SL1 RNA | GCCGGGCGCGGUGGCGCGUGCCUGUAGUCCCAGCUACUCGGGAGG CUGAGGCUGGAGGAUCGCUUGAGUCCAGGAGUUCUGGGCUGUAG UGCGCUAUGCCGAUCGGGUGUCCGCACUAAGUUCGGCAUCAAUAU GGUGACCUCCCGGGAGCGGGGGACCACCAGGUUGCCUAAGGAGGG GUGAACCGGCCCAGGUCGGAAACGGAGCAGGUCAAAACUCCCGUG CUGAUCAGUAGUGGGAUCGCGCCUGUGAAUAGCCACUGCACUCCA GCCUGGGCAACAUAGCGAGACCCCGUCUCU |
| SEQ ID NO: 3 | RN7SL1 fragment #1 | GCCGGGCGCGGTGGCGCGTGCCTGTAGTCCCAGCTACTCGGGAGGC TGAGGCTGGAGGATCGCTTGAGTC |
| SEQ ID NO: 4 | RN7SL1 fragment #1 RNA | GCCGGGCGCGGUGGCGCGUGCCUGUAGUCCCAGCUACUCGGGAGG CUGAGGCUGGAGGAUCGCUUGAGUC |
| SEQ ID NO: 5 | RN7SL1 fragment #2 | CAACATAGCGAGACCCCGTCTCT |
| SEQ ID NO: 6 | RN7SL1 fragment #2 RNA | CAACAUAGCGAGACCCCGUCUCU |
| SEQ ID NO: 7 | Alu-Ya5 followed by a poly-A tail | GCGGCCGCTCTAGAACTAGTGGATCCCCCCCCCCCGCTCCCCAAATG ACGTAACTGTCCCTGCAGCTTCTAGATAGCTTTTCGCAGCGTCTCCG ACCGGCCGGGCCGGGCGCGGTGGCTCACGCCTGTAATCCCAGCACT TTGGGAGGCCGAGGCGGGCGGATCACGAGGTCAGGAGATCGAGAC CATCCCGGCTAAAACGGTGAAACCCCGTCTCTACTAAAAATACAAA AAATTAGCCGGGCGTAGTGGCGGGCGCCTGTAGTCCCAGCTACTTG GGAGGCTGAGGCAGGAGAATGGCGTGAACCCGGGAGGCGGAGCTT GCAGTGAGCCGAGATCCCGCCACTGCACTCCAGCCTGGGCGACAGA GCGAgaCGTCTCAAATCCCCTCAAAAAAAAAAAAAAAAAAAAAAA AAAAAAAAAAAAAAAAAAAACATGGGACTCAAAGTTTCAGCATCG CGTCTCTTTTGCCGAATTCGATATCAAGCTTATCGATACC |
| SEQ ID NO: 8 | Alu-Ya5 followed by a poly-A tail RNA | GCGGCCGCUCUAGAACUAGUGGAUCCCCCCCCCCCGCUCCCCAAA UGACGUAACUGUCCCUGCAGCUUCUAGAUAGCUUUUCGCAGCGUC UCCGACCGGCCGGGCCGGGCGCGGUGGCUCACGCCUGUAAUCCCA GCACUUUGGGAGGCCGAGGCGGGCGGAUCACGAGGUCAGGAGAUC GAGACCAUCCCGGCUAAAACGGUGAAACCCCGUCUCUACUAAAAA UACAAAAAAUUAGCCGGGCGUAGUGGCGGGCGCCUGUAGUCCCAG CUACUUGGGAGGCUGAGGCAGGAGAAUGGCGUGAACCCGGGAGG CGGAGCUUGCAGUGAGCCGAGAUCCCGCCACUGCACUCCAGCCUG GGCGACAGAGCGAGACGUCUCAAAUCCCCUCAAAAAAAAAAAAAA AAAAAAAAAAAAAAAAAAAAAAAAAAAAAAAAACAUGGGACUCAAAG UUUCAGCAUCGCGUCUCUUUUGCCGAAUUCGAUAUCAAGCUUAUC GAUACC |
| SEQ ID NO: 9 | Hairpin | AGTCAGTCAGTCAGTCAGTCAGTCCCCGGGGACTGACTGACTGACT GACTGAC |
| SEQ ID NO: 10 | Hairpin RNA | AGUCAGUCAGUCAGUCAGUCAGUCCCCGGGGACUGACUGACUGAC UGACUGAC |

Chemical Modifications to RNAs

An RNA described herein may be chemically modified to enhance stability or other beneficial characteristics. Modifications include, for example, (a) end modifications, e.g., 5' end modifications (phosphorylation, conjugation, inverted linkages, etc.) or 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position, or having an acyclic sugar) or replacement of the sugar, as well as (d) backbone modifications, including modification or replacement of the phosphodiester linkages.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Modified RNAs may also contain one or more substituted sugar moieties. The RNAs can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_n O]_m CH_3$, $O(CH_2)\cdot_n OCH_3$, $O(CH_2)_n NH_2$, $O(CH_2)_n CH_3$, $O(CH_2)_n ONH_2$, and $O(CH_2)_n ON[(CH_2)_n CH_3)]_2$, where n and m are from 1 to about 10. In other embodiments, RNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $N_3$, $NH_2$, heterocycloalkyl, heterocycloalkaryl, aminoalkylamino, polyalkylamino, substituted silyl, an RNA cleaving group, a reporter group, an intercalator, and other substituents having similar properties. In some embodiments, the modification includes a 2'-methoxyethoxy (2'-O—$CH_2 CH_2 OCH_3$, also known as 2'-O-(2-methoxyethyl) or 2'-MOE) i.e., an alkoxy-alkoxy group. Another exemplary modification is 2'-dimethylaminooxyethoxy, i.e., a $O(CH_2)_2 ON(CH_3)_2$ group, also known as 2'-DMAOE, and 2'-dimethylaminoethoxyethoxy (also known as 2'-O-dimethylaminoethoxyethyl or 2'-DMAEOE), i.e., 2'-O—$CH_2$—O—$CH_2$—$N(CH_2)_2$. In some embodiments, the RNA comprises one or more acyclic nucleotides (or nucleosides). The RNA can include one or more locked nucleic acids (LNA), e.g., a nucleotide having a modified ribose moiety in which the ribose moiety comprises an extra bridge connecting, e.g., the 2' and 4' carbons.

An RNA may also include nucleobase modifications or substitutions. Unmodified or natural nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. In some embodiments, the RNA includes one or more G-clamp nucleotides (a modified cytosine analog wherein the modifications confer the ability to hydrogen bond both Watson-Crick and Hoogsteen faces of a complementary guanine within a duplex).

Stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others.

Additional chemical modifications are disclosed, e.g., in WO2015/051318 (e.g., at pages 75-83 therein), which application is herein incorporated by reference in its entirety.

RNA Conjugates, e.g., for Targeting

An RNA described herein may be conjugated to a functional moiety, e.g., to alter stability or biodistribution. In some embodiments, the RNA is conjugated to a moiety that targets cancer cells or a tumor microenvironment. For instance, the RNA may be conjugated to a targeting moiety that binds cancer cells, e.g., by binding a surface protein characteristic of cancer cells and/or of the type of tissue from which the cancer arises. The targeting moiety may be, e.g., an antibody molecule such as a single chain antibody molecule.

In some embodiments, an RNA is chemically linked to one or more ligands, moieties or conjugates, which may confer functionality, e.g., by enhancing the activity, distribution, or half-life of the RNA. Such moieties include lipid moieties such as a cholesterol moiety, cholic acid, a thioether, e.g., beryl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-phosphonate, a polyamine or a polyethylene glycol chain, or adamantane acetic acid, a palmityl moiety, or an octadecylamine or hexylamino-carbonyloxycholesterol moiety.

Ligands can also include targeting groups, e.g., a cell or tissue targeting agent, e.g., a lectin, glycoprotein, lipid or protein, e.g., an antibody molecule, that binds to a specified cell type such as a cancer cell or a cell in a tumor microenvironment. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. In some embodiments, the ligand comprises a carbohydrate, e.g., a GalNAc ligand that comprises one or more N-acetylgalactosamine (GalNAc) or a derivative thereof.

Additional conjugates are disclosed, e.g., in WO2015/051318 (e.g., at pages 91-107 therein), which application is herein incorporated by reference in its entirety.

In embodiments, the conjugate is attached to the RNA via a linker. Exemplary linkers are disclosed, e.g., in WO2015/051318 (e.g., at pages 107-116 therein), which application is herein incorporated by reference in its entirety.

RNA Delivery and Formulations

The delivery of an RNA to a subject can be achieved directly, e.g., by administering a composition comprising the RNA to a subject, or indirectly, by administering a vector that encode the RNA, e.g., administering a cell comprising the vector.

In some embodiments, the RNA can be delivered directly using a nanoparticle, a dendrimer, a polymer, liposomes, or a cationic delivery system. Cationic lipids, dendrimers, or polymers can either be bound to an RNA, or induced to form a vesicle or micelle that encases an RNA. Some non-limiting examples of drug delivery systems useful for systemic delivery of RNAs include DOTAP, Oligofectamine, solid nucleic acid lipid particles, cardiolipin, polyethyleneimine, Arg-Gly-Asp (RGD) peptides, and polyamidoamines. In some embodiments, an RNA forms a complex with cyclodextrin for systemic administration.

In some embodiments, the RNA can be delivered as a liposomal formulation. Liposomes fall into two broad classes. Cationic liposomes are positively charged liposomes which interact with the negatively charged nucleic acid molecules to form a stable complex. Liposomes which are pH-sensitive or negatively-charged, entrap nucleic acid rather than complex with it. One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol or dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol. Liposomes may also comprise lipids derivatized with one or more hydrophilic polymers such as a PEG moiety. For instance, the liposome may comprise PEG-derivatized phospholipids, e.g., DSPE-PEG. The liposome may also comprise a surfactant, e.g., a natural or synthetic surfactant. The surfactant may be, e.g., nonionic, anionic, cationic, or amphoteric.

In some embodiments, the RNA is fully encapsulated in a lipid formulation, e.g., to form a SPLP, pSPLP, SNALP, or other nucleic acid-lipid particle. In some embodiments, the RNA is formulated in a lipid nanoparticle (LNP). SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference. XTC comprising formulations are described, e.g., in International Application No. PCT/US2010/022614, filed Jan. 29, 2010, which is hereby incorporated by reference. MC3 comprising formulations are described, e.g., in International Application No. PCT/US10/28224, filed Jun. 10, 2010, which is hereby incorporated by reference. C12-200 comprising formulations are described in International Application No. PCT/US10/33777, filed May 5, 2010, which are hereby incorporated by reference.

The RNA may be administered systemically or locally e.g., by injection into a tumor or tumor microenvironment.

In some embodiments RNAs described herein can be delivered indirectly via administration of a vector (e.g., a vector within a cell) capable of directing expression of the RNA. Expression can be transient or sustained, depending upon the specific construct used and the target tissue or cell type. Transgenes can be introduced as a linear construct, a circular plasmid, or a viral vector, which can be an integrating or non-integrating vector. The transgene can also be constructed to permit it to be inherited as an extrachromosomal plasmid.

Additional RNA formulations and delivery methods are described, e.g., in WO2015/051318 (e.g., at pages 116-137 therein), which application is herein incorporated by reference in its entirety.

It should be understood that the methods and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Cell Culture and Cell Sorting. Cell culture and cell sorting were completed as previously described (Boelens et al. (2014). Cell 159, 499-513). Cell lines are listed in Table 1 and all cell lines were confirmed to be mycoplasma-free with repeated testing. All human breast cancer and stromal cell lines were cultured at 37° C. in DMEM supplemented with 10% FBS, 100 U/ml penicillin and 100 μg/ml streptomycin, and 2 mM l-glutamine. The KB1P mouse breast cancer cell lines from K14cre;p53$^{F/F}$;Brca1$^{F/F}$ mice (Liu et al. (2007). Proc. Natl. Acad. Sci. U.S.A 104, 12111-12116) were cultured in RPMI. All co-culture experiments were performed in DMEM with exosome-depleted FBS. Breast cancer cells were labeled with 7.5 μM 5-(and -6)-carboxyfluorescein diacetate, succinimidyl ester (CFSE) and mixed 1:1 with stromal cells. Cell populations with a purity of at least 98% were used for RNA or protein isolation.

TABLE 1

| Cell lines used in all studies | | | | |
| --- | --- | --- | --- | --- |
| | Human | | Mouse | |
| ISG-R | ISG-NR | Fibroblast | ISG-R | Fibroblast |
| MDA-MB-231 (1833) | MCF7 | MRC5 | KB1P | ALF |
| MDA-MB-231 (4175) | MDA-MB-468 | BJ | | |
| MDA-MB-436 | | | | |
| HCC1937 | | | | |

Cell Death Assays. Sytox cell death assays were completed as previously described (Boelens et al. (2014). Cell 159, 499-513). In brief, mono- or co-cultures were irradiated after 48 hours with 10 Gy using a Cs-137 Gammacell 40 EXACTOR. Cell death of CFSE-labeled breast cancer cells was measured at 96 hours post-radiation by flow cytometry using Sytox-Red (Invitrogen). Relative cell death was calculated by comparing mono and co-culture cell death.

Cell Culture Exosome Isolation. Cell cultures used to isolate exosomes were grown in exosome-depleted media prepared by ultracentrifugation of FBS for 3 hours at 100,000×g. Exosomes were isolated from conditioned media collected at 48-72 hours by serial high speed ultracentrifugation as previously described (Thery et al. (2006) Curr. Protoc. Cell Biol. Chapter 3, 1-29) or using 10% final concentration of polyethylene-glycol and low speed centrifugation, as previously described (Rider et al. (2016) Sci. Rep. 6, 23978). Purity was examined by electron microscopy by negative staining, protein analysis by immunoblotting, and quantified by NanoSight NS500 analysis. For exosome injection experiments, protein was quantified by Lowry method, and equivalent volume of 10 µg of exosomes were injected. For exosome depletion, conditioned media was ultracentrifuged for 8-16 hours.

Serum Exosome Collection. Serum from patients with cancer were obtained through the UPENN RadOnc Biosample Repository. Blood was collected using yellow top Vacutainer (BD) and centrifuged at 3000 rpm for 10 minutes. The samples were then frozen at −80° C. until use. Serum from healthy donors was obtained commercially (Innovative Research). For exosomes from human or mouse serum, 500 µl of serum was spun at 2000×g for 15 minutes, filtered through a 0.22 µm filter, and then purified by serial high speed ultracentrifugation.

EU Labeling and Quantification. Stromal cells were labeled with 100 µM 5-Ethynyl Uridine (EU) for 24 hours, and breast cancer cells were labeled with DiD (1:200) for 10 minutes at 37° C. Both cell types were then washed and co-cultured for 8 or 24 hours on glass coverslips. EU was then visualized by Alexa Fluor 488 azide (Alexa Fluor® 488 5-carboxamido-(6-azidohexanyl), bis(triethylammonium salt)) (Jao and Salic (2008) Proc. Natl. Acad. Sci. U.S.A 105, 15779-15784). Percentage of double positive cells that matched breast cancer cell morphology were scored as EU+ breast cancer cells.

4sU RNA Transfer Quantification. Stromal cells were labeled with 200 µM 4sU (4-Thiouracil) for 24 hours, washed, and either left in mono-culture or co-cultured with breast cancer cells. Conditioned media was isolated after 24 hours and added to mono-cultured breast cancer cells. Breast cancer cells were harvested 24 hours later and RNA extracted. 4sU-labeled RNA was specifically biotinylated with HPDP-Biotin and enriched with streptavidin-conjugated magnetic beads, as previously described (Fuchs et al. (2015) Nat. Protoc. 10, 605-618). Transfer of stromal-derived RNA was determined by quantification of total 4sU-labeled RNA in recipient breast cancer cells compared to total RNA or by qRT-PCR.

4sU-FLAG-RIP. Stromal cells were labeled with 200 µM 4sU (4-Thiouracil), washed, and co-cultured with breast cancer cells with RIG-I CRISPR KO, RIG-I KO with re-expression of FLAG-tagged RIG-I or RIG-I$^{K858/861A}$ for 48 hours. Co-cultures were harvested and 100 mg of wet cell pellet was lysed by sonication (five, one-second bursts, medium output) in RSB-200 buffer (20 mM Tris pH 7.5, 200 mM NaCl, 2.5 mM MgCl2, 0.5% NP-40, 0.1% Triton X-100, 0.2 U/uL RNase Inhibitor, and one tablet of protease inhibitors). Post-lysis, FLAG-RIG-I was immunoprecipitated with prebound and washed FLAG-M2 beads (Sigma) using 30 µL of beads per 100 mg of wet cell pellet for 2-3 hours at 4° C. Beads were then washed three times with RSB-200. RNA was extracted with TRIzol reagent utilizing linear acrylamide as a carrier. 4sU-labeled RNA was then enriched as described above.

Gene Targeting and Expression. Gene knockdown by siRNA was completed using SMARTPool siRNAs (Thermo) and transfected using 20 nM siRNA and RNAiMax (Invitrogen) transfection reagent. For stable knockdowns, shRNAs were cloned into the pGIPZ vector and transduced by virus using pCMV-VSV-G and pHR8.2AR envelope and packaging vectors in HEK293T cells. Transduced cells were selected using 1-2 ug/ml of puromycin. Wild-type and K858A/K861A binding mutant of RIG-I was cloned into the pOZ-N vector. Transduced cells were then selected with IL-2 receptor magnetic beads and expression was confirmed by Western blot for FLAG, HA, and RIG-I. RIG-I restoration was functionally confirmed by RIG-I pathway activation in response to Sendai virus infection. SRP9 and SRP14 were transiently transfected with pGFH-9 (Addgene plasmid #39538) and pGFH-14c (Addgene plasmid #39541), both gifts from Katharina Strub. Gene knockout by CRISPR was accomplished using pSp-Cas9 (BB)-2A-GFP (PX458) (Addgene plasmid #48138). RIG-I was knocked out utilizing the protocol described (Ran et al. (2013) Nat. Protoc. 8, 2281-2308). In brief, two distinct guide RNAs cloned into the pSpCas9 (BB)-2A-GFP backbone were transiently transfected into breast cancer cells. After 48 hours, single cells were sorted into 96 well single cell clones based on highest GFP expression. Clones were confirmed to have no RIG-I expression by immunoblot and pooled. RIG-I KO in the pooled clones were functionally confirmed by RIG-I pathway activation in response to Sendai virus infection.

TABLE 2

| Gene Targeting Sequences | | | |
|---|---|---|---|
| siRNA: | | | |
| | Sequence | Catalog Number | |
| CTRL | Non-Targeting #1 | D-001810-01-20 | |
| POLR3F | SMARTpool | L-019240-01-0005 | |
| shRNA: | | | |
| | Sequence | Catalog Number | SEQ ID NO: |
| CTRL | GIPZ Non-Silencing shRNA | RHS4346 | |
| RIG-1#1 | TTAAATTTGTCGCTAATCC | V2LHS-199776 | SEQ ID NO: 12 |
| RIG-I#2 | TAAAGTCCAGAATAACCTG | V2LHS 197176 | SEQ ID NO: 13 |
| CRISPR: | | | |
| | gRNA Sequence | | SEQ ID NO: |
| RIG-I#1 | GGGTCTTCCGGATATAATCC | | SEQ ID NO: 14 |
| RIG-I#2 | GGATTATATCCGGAAGACCC | | SEQ ID NO: 15 |

Recombinant Protein Production and Purification. Recombinant SRP9 was produced by subcloning the SRP9 cDNA from pGFH-9 plasmid into the pET His6 GST TEV LIC cloning vector (1G) (Addgene plasmid #29655). Recombinant protein was produced in BL21 competent *E. coli* and captured with Glutathione Sepharose beads (GE Healthcare). GST-tagged TEV Protease (Sigma) was used to cleave GST-SRP9.

In Vivo Mouse Studies. For exosome injection studies, $1 \times 10^6$ 1833 breast cancer cells were injected with Matrigel (Corning) into the flanks of 6-8 week old athymic nude mice and 10 μg of mono- or co-culture exosomes were directly injected into the tumors 3 times a week. For RNA injection studies, 50 ng of 7SL or GAPDH300 RNA encapsulated into RNAiMax liposomes were directly injected into the tumors 3 times a week. Subcutaneous tumor growth was measured by caliper. For lung colonization studies, $2 \times 10^5$ luciferase-labeled 4175 breast cancer cells were injected in the tail vein. Injections were confirmed by immediate imaging using a Xenogen IVIS 100 system. Serum was isolated from mice by cardiac puncture.

Exosome RNA Sequencing. Exosome RNA was extracted with TRIzol and library preparation was completed using the NEBNext Ultra Directional RNA Library Prep Kit for Illumina (NEB) modified so that the RNA was not fragmented prior to library preparation. ERCC controls (Invitrogen) were added into all exosome RNA samples. Libraries were sequenced on Illumina HiSeq 2500 with 100 base paired end reads.

Microarray Data Processing and Normalization. Gene expression data for ISG-R and ISG-NR breast cancer cells co-culture with MRC5 fibroblasts have been described (Boelens et al. (2014). Cell 159, 499-513) and available at the GEO (GSE60998). ISG-R cell lines included: MDA-MB-231, MDA-MB-231 (1833), and HCC1937. ISG-NR cell lines included: MCF7 and MDA-MB-468. Preprocessing, filtering, and differential gene expression analysis were performed as previously described (Boelens et al. (2014). Cell 159, 499-513). Gene set analysis was performed using the piano R package and Reactome gene sets downloaded from the Molecular Signatures Database v5.1 (softwaredof-broadinstitutedotorg/gsea/msigdb). The gene set for upregulated cancer associated ISGs has been previously described (Weichselbaum et al. (2008) Proc. Natl. Acad. Sci. U.S.A 105, 18490-18495).

MNase qRT-PCR and RNA Sequencing. Either whole cells or whole exosomes were incubated at 37° C. for 30 minutes in MNase Buffer (25 mM Tris-HCl, 2.5 mM $CaCl_2$), 50 mM NaCl, 1×PBS), with or without MNase and with or without 0.1% Triton X-100. Pre-MNase treatment, 10 ng of DVG396 RNA was spiked-in to control for differences in MNase activity with or without detergent. Post-MNase treatment, TRIzol LS reagent was used to purify RNA using linear acrylamide as a carrier, and ERCC Controls (Invitrogen) were spiked-in to account for differences in efficiency of RNA extraction. For RNA sequencing studies, libraries were prepared from purified RNA using the NEBNext Ultra Directional RNA Library Prep Kit for Illumina (NEB) without further RNA fragmentation. Libraries were sequenced on Illumina HiSeq 2500 with 100 base paired end reads. For qRT-PCR studies, percent shielded was quantified by AACt method normalizing to DVG396 spike-in and MNase without detergent.

RNA-seq data analysis. For exosome RNA-seq and MNase RNA-seq analysis, reads were trimmed first using cutadapt v1.9 (Martin (2011) EMBnet.journal 17, 10-12) with parameters-q 10-m 30-O 4. Trimmed reads were then aligned to ERCC controls, rRNAs sequences as well as RN7SL1 by using bowtie2 (Langmead and Salzberg (2012) Nat Methods 9, 357-359). The remaining reads were aligned to the GRCh38 reference genome using STAR v2.4.0k (Dobin et al. (2013) Bioinformatics 29, 15-21) with parameters—outFilterMultimapNmax 100—outFilterMismatchNmax 999—outFilterMismatchNoverLmax 0.06. Primary aligned reads were counted against GENCODE annotation v21 (Harrow et al. (2012) Genome Res. 22, 1760-1774) and RepeatMasker annotation (UCSC Genome Browser) using Subread v1.4.6 (Liao et al. (2013) Nucleic Acids Res. 41, 108-125) with parameters −s 2 −minReadOverlap 10. The DESeq2 R package version 1.10 (Love et al. (2014) Genome Biol. 15, 550-571) was used for differential gene expression analysis. ERCC controls were used for inter-sample normalization.

5' triphosphate RNA Sequencing. To enrich for 5'triphosphate RNA, 0.1-2 ug of exosomal RNA was prepared by first degrading 5'monophosphate RNA with Terminator 5'-Phosphate-Dependent Exonuclease (Epicentre), then converting 5'triphosphate to 5'p with RNA 5' Polyphosphatase (Epicentre), to allow for specific ligation of RNA adaptor P5_RNA to RNAs that originally have 5' triphosphate. Then, cDNAs were synthesized by using a primer with 5' random 9mer (P7_N9), and amplified with NEBNext PCR reagents (NEB) by using the same protocol as other RNA-seq libraries. Libraries were sequenced on Illumina HiSeq 2500 with 100 base paired end reads. Only the first reads of the paired end reads were used in data analysis. Reads were trimmed and aligned the same as RNA-seq analysis. Primary reads that matched the 5' end of annotated features were counted. Adaptors used for 5' triphosphate RNA sequencing:

```
P5 RNA (SEQ ID NO: 16):
ACACUCUUUCCCUACACGACGCUCUUCCGAUCU

P7 N9 (SEQ ID NO: 17):
GTGACTGGAGTTCAGACGTGTGCTCTTCCGATCTNNNNNNN
NNN
```

In Vitro Transcription. In vitro transcription was performed using of PCR amplified cDNA templates that contained Hepatitis Delta Virus Ribozyme to ensure homogenous 3' ends of the transcripts of interest (Avis et al. (2012) Methods Mol. Biol. 941, 83-97). In vitro transcription was completed with the MEGAshortscript T7 Transcription Kit (ThermoFisher) according to manufacturer's instructions. RNA was DNase treated and phenol/chloroform purified. After thermocycling to ensure ribozyme cleavage, correct size transcripts were gel purified.

RIG-I ATPase Assays. RIG-I ATPase assays were performed as previously described (Devarkar et al. (2016) Proc. Natl. Acad. Sci. 113, 596-601). In brief, increasing amounts of RNA (10-60 nM) were added to a constant quantity of RIG-I (5 nM) in the presence of 1 mM ATP. ATP hydrolysis was measured with the EnzChek Phosphate Assay Kit (ThermoFisher) after 60-90 minutes at 37° C. ATP hydrolysis was then measured by absorbance of 360 nm compared to background. A 19-mer 5'triphosphate dsRNA (Invivogen) and DVG396 were used as positive controls and a 19-mer 5'OH dsRNA (Invivogen) and an in vitro transcribed 300 bp ssRNA stretch of GAPDH (GAPDH300) were used as negative controls.

Protein Analysis. Protein was extracted using 2×SDS lysis buffer, separated by 4%-12% SDS-PAGE, transferred to a PVDF membrane, blocked with 5% nonfat milk in PBS-Tween (0.01%), and probed with the antibodies described herein. Protein was visualized using ECL (SuperSignal West Pico, Thermo).

qRT-PCR Gene Expression Analysis. Total RNA was isolated and purified from cells using TRIzol reagent (Invitrogen). cDNA was synthesized using the High Capacity RNA-to-cDNA kit (ABI) according to manufacturer's instructions. qRT-PCR was performed using Power SYBR Green PCR MasterMix (ABI) on the TaqMan 7900 (ABI). Relative expression levels were defined using the AACt method and normalizing to 18S rRNA, P-Actin and GAPDH.

The results of the experiments are now described.

Example 1: Stromal Activation by Breast Cancer Cell Interaction is Accompanied by an Anti-Viral Response and Stromal Exosome Transfer Previously, it was demonstrated that breast cancer interaction with stromal fibroblasts increases the production of stromal exosomes. Upon transfer to breast cancer cells, the RNA in the exosomes (exoRNA) stimulates breast cancer RIG-I to initiate an anti-viral response that subsequently promotes resistance to radiation and chemotherapy. The present study sought to more closely examine similarities between this anti-viral response initiated by tumor and stromal cell interaction with how viruses instigate an anti-viral response that spreads from infected to uninfected cells. Major transcriptomic changes resulting from heterotypic interaction between MRC5 normal lung fibroblasts and ISG-R breast cancer cells, which induce ISGs upon co-culture with stromal cells (Boelens et al. (2014). Cell 159, 499-513) were investigated. This revealed that heterotypic cell interaction leads to stromal activation characterized by a transcriptional response dominated by upregulation (FIG. 1A, left panel). Among these transcripts is an enrichment for hallmark gene sets for MYC and RAS oncogenic signaling, glycolysis, and cell cycle progression (FIG. 1B, left panel). Stromal cells additionally induce multiple ISGs, and this was also observed in ISG-R breast cancer cells (FIG. 1A). In fact, IFN signaling is among the predominant hallmark gene sets enriched after co-culture in both cell types (FIG. 1B). ISG-R breast cancer cells also show evidence for reciprocal RAS activation and enhanced expression of EMT genes expected to favor invasion, metastasis, and therapy resistance. Thus, these data suggest that besides promoting aggressive features in breast cancer cells, heterotypic interaction leads to stromal activation events accompanied by a reciprocal anti-viral response.

Figures 8A, 8B:
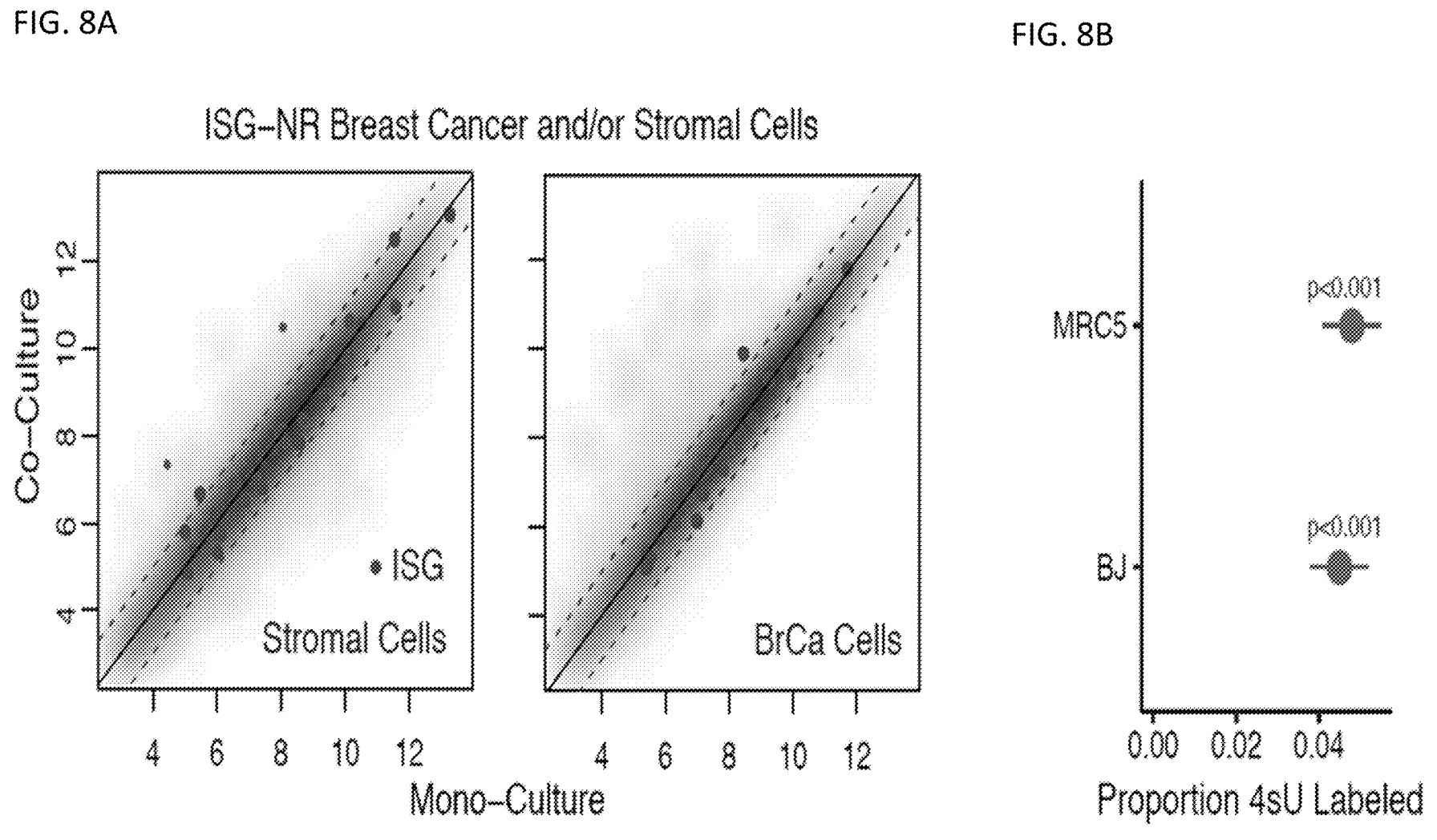

To examine if breast cancer interaction also mimics the ability of viruses to instigate exosome transfer, stromal cells were labeled with a stably expressed CD81-RFP exosome reporter (FIG. 1C). This confirmed a high level of exosome transfer from stromal cells to 1833 ISG-R breast cancer cells, which is a metastatic derivative of MDA-MB-231. In contrast, co-culture of stromal cells with breast cancer cells that fail to induce ISGs, which were previously defined as ISG non-responders (ISG-NRs), show only modest transcriptomic changes in stromal cells, no stromal ISG induction (FIG. 8A, left panel), and minimal exosome transfer to breast cancer cells (FIG. 1C). Accordingly, no anti-viral response occurs in ISG-NR breast cancer cells after co-culture (FIG. 8A, right panel). Thus, like viruses, ISG-R breast cancer cells not only can coerce an anti-viral response in stromal cells but can also promote exosome transfer to propagate anti-viral signaling.

Figures 1G, 1H:
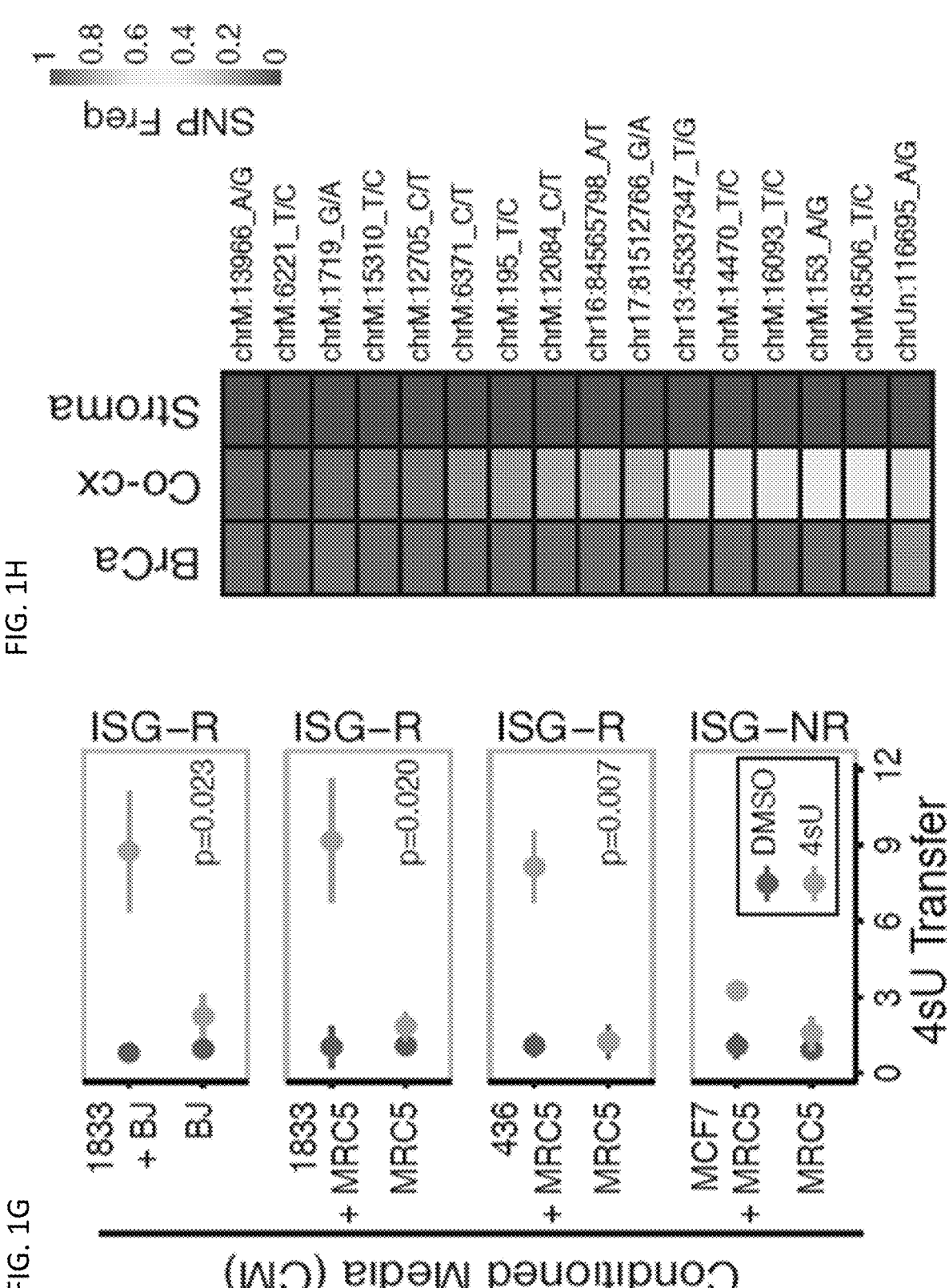

Example 2: Stromal RNA is Transferred to Breast Cancer Cells by Exosomes to Mediate an Anti-Viral Response After viral infection, viral RNA from infected cells can be packaged into exosomes for subsequent transfer to uninfected cells. To examine if RNA from stromal cells are similarly transferred to breast cancer cells by exosomes, MRC5 stromal RNA was metabolically labeled with 5-ethynyl uridine (EU) prior to co-culture with ISG-R 1833 breast cancer cells that were fluorescently marked with lipid dye (FIG. 1D). After 24 hours, over 40% of breast cancer cells acquired stromal cell RNA as measured by EU-modification by azide-linked fluorescein (FIG. 1E). To assess the role of exosomes in this transfer, stromal cell RNA was similarly labeled with 4-thiouridine (4sU) prior to co-culture with breast cancer cells (FIG. 1D and FIG. 8B). Application of the conditioned media (CM) from these co-cultures to mono-cultured breast cancer cells also resulted in stromal RNA transfer, as determined by streptavidin pull-down of biotinylated 4sU-labeled stromal RNA, but not when exosomes were depleted from the CM (FIG. 1F). Exosome-mediated transfer of MRC5 stromal RNA was also observed using another ISG-R breast cancer cell line, MDA-MB-436, and from co-cultures using BJ fibroblast cells (FIG. 1G). In contrast, markedly less stromal RNA was transferred by exosomes using CM from co-cultures with the ISG-NR breast cancer cell line MCF7 (FIG. 1G).

To corroborate the transfer of stromal RNA by exosomes, exoRNA SNP analysis was performed using exosomes from mono-cultures of either ISG-R 1833 breast cancer cells or MRC5 stromal cells and compared SNP allelic frequencies to the exoRNA from co-culture (FIG. 1H). Multiple SNPs, primarily from mitochondrial RNA, were discovered to have an allelic frequency of near one in the exoRNA from breast cancer cells but near zero in stromal exoRNA. Examination of exoRNA from co-culture revealed that most of these SNPs maintained a frequency closer to zero, consistent with the exoRNA primarily originating from stromal cells. In total, these results demonstrated that similar to transfer of viral RNA from infected to uninfected cells, cellular RNAs are transferred from stromal to breast cancer cells in an exosome-dependent manner.

Example 3: 5' Triphosphate Stromal exoRNA Activates Breast Cancer RIG-I

Figures 2A, 2B:
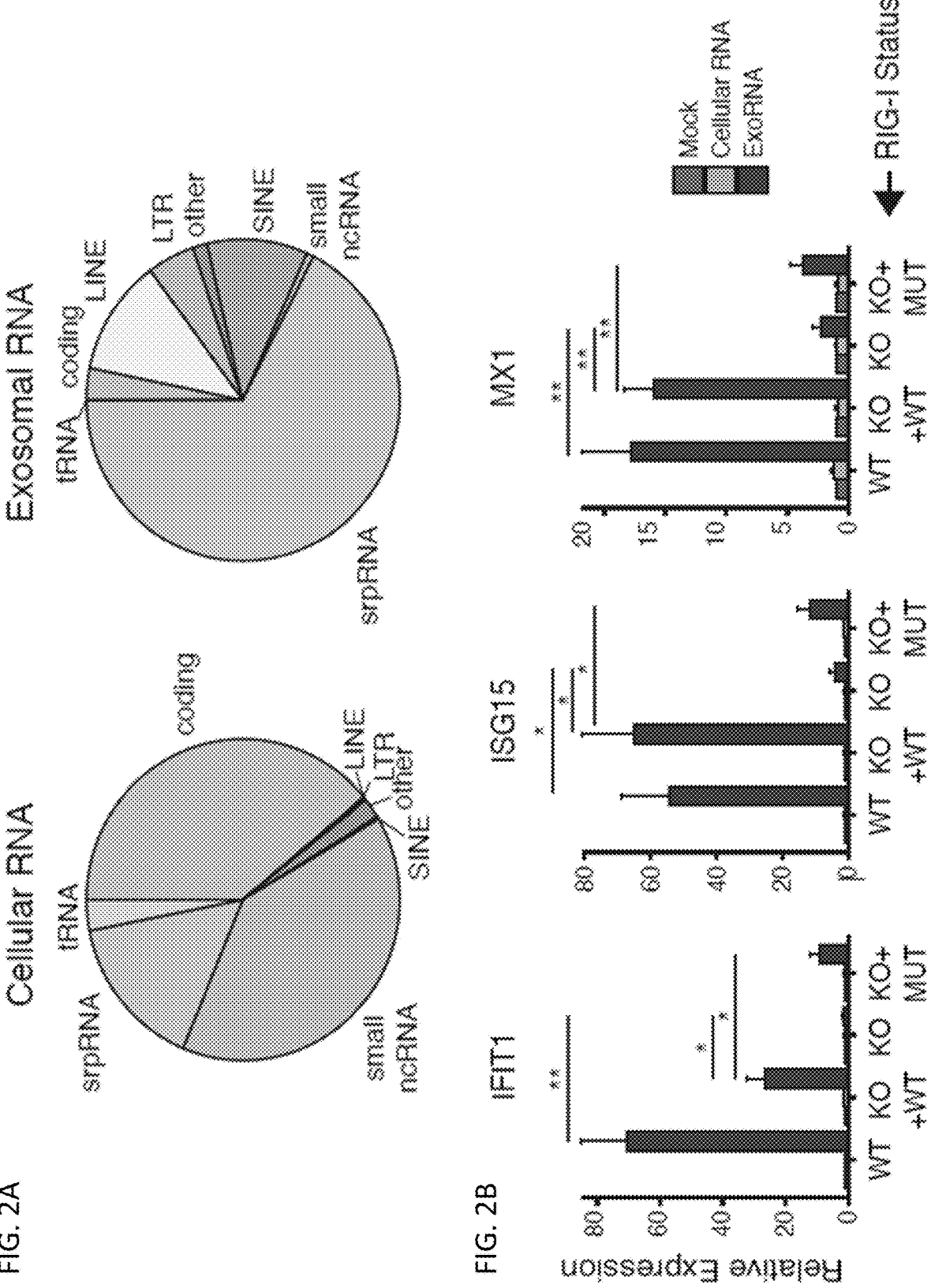

Classification of non-ribosomal exoRNA transcripts from stromal and breast cancer cell co-cultures revealed an enrichment in non-coding RNAs compared to cellular RNA (FIG. 2A). These non-coding RNAs included repeat and transposable elements, snRNA, srpRNA, and others, but no viral RNAs were detected. Previously, it was demonstrated that upon transfection this exoRNA activated the pattern recognition receptor RIG-I to induce ISGs in recipient breast cancer cells, and this activity required a 5' triphosphate (5'ppp) moiety. Thus, although the non-ribosomal portion of exoRNA demonstrated significant complexity, functional studies suggested that exoRNA ligands responsible for the breast cancer anti-viral response were 5'ppp exoRNA that binds to RIG-I. To confirm this notion, CRISPR/Cas9 was utilized to knockout RIG-I in breast cancer cells and re-expressed either wild-type (WT) RIG-I or RIG-I with alanine substitution mutations in key lysine residues (K858 and K861) that make contacts with the 5'ppp motif (RIG-I$^{K858/861A}$) (FIGS. 9A-9B). Co-culture-derived exosomes were purified (FIG. 9C-9D) and transfection of the exoRNA failed to induce ISGs in RIG-I KO breast cancer cells (FIG. 2B). Re-expression of WT RIG-I rescued this defect whereas RIG-I$^{K858/861A}$ was markedly less effective at restoring activity. In contrast, cellular RNA failed to induce ISGs regardless of RIG-I status. Consistent with these findings, addition of exoRNA but not equimolar amounts of cellular RNA to recombinant RIG-I stimulated RIG-I ATP helicase activity as measured by ATP hydrolysis (FIG. 2C). Thus, like the recognition of viral 5'ppp RNA, these results provided evidence that 5'ppp exoRNA from stromal cells can directly activate RIG-I to induce an anti-viral response.

Example 4: Stromal RNA Polymerase III Generates 5'Ppp exoRNA that Activates the Anti-Viral Response in Breast Cancer Cells In the absence of viral infection, the main source of endogenous 5'ppp RNA is from RNA polymerase III (POL3) transcription. Moreover, POL3 activity is known to be augmented by MYC activation, which appeared specifically enhanced in stromal cells after ISG-R breast cancer cell interaction (FIG. 1B, left panel). Therefore, it was sought to examine if stromal POL3 generates the exoRNA that is transferred to breast cancer cells to activate anti-viral signaling. Indeed, the POL3 subunit POLR3G was upregulated in stromal cells after co-culture with breast cancer cells (FIG. 2D and FIG. 9E). Knockdown of POL3 using an siRNA to the POLR3F subunit (FIG. 9F) revealed that inhibiting POL3 in stromal cells, but not breast cancer cells alone, significantly blunted breast cancer ISG induction (FIG. 2E).

Figures 2I, 2J, 2K:
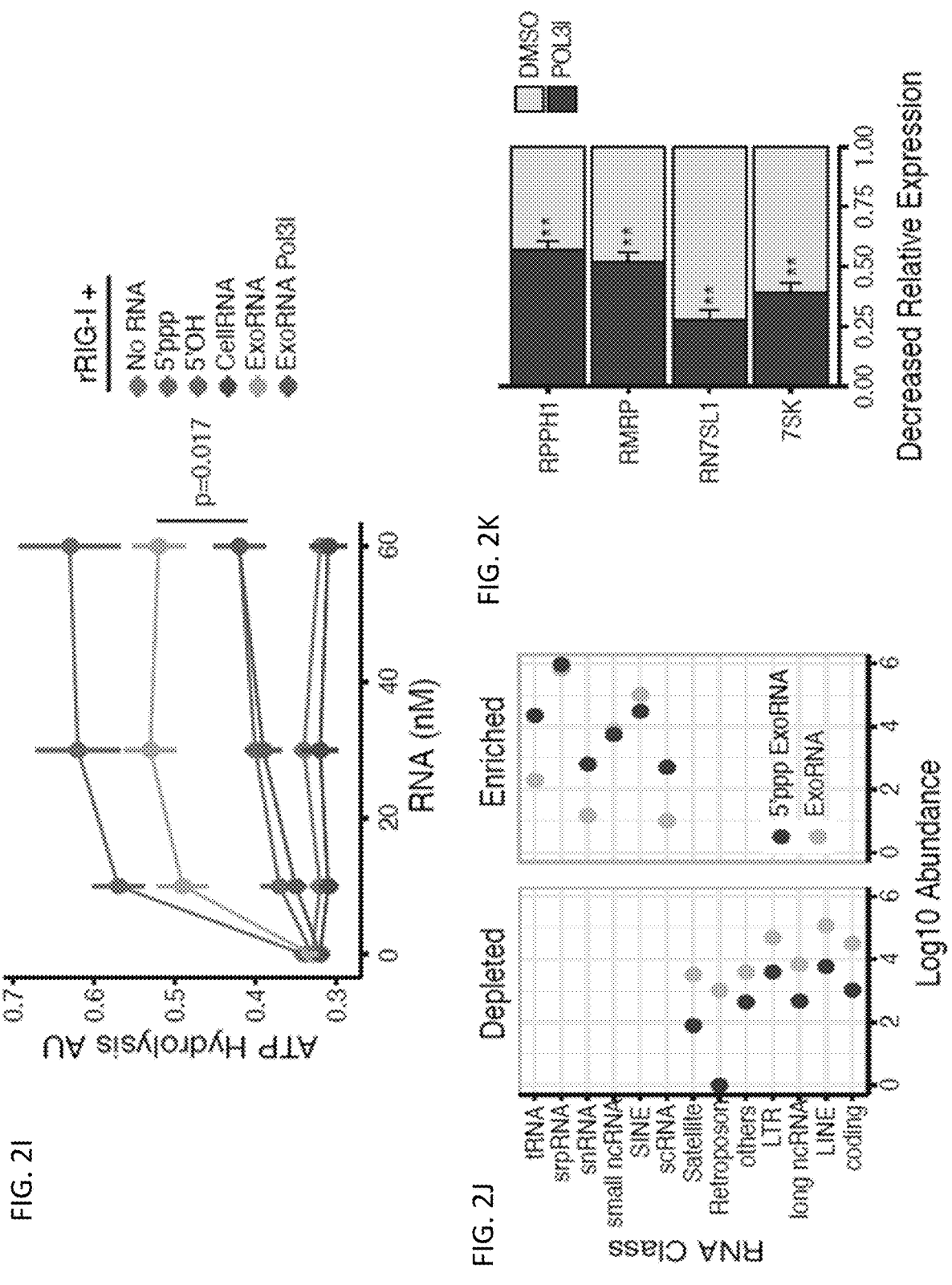

Interrogation of functional consequences revealed that the ability of stromal cells to protect breast cancer cells after radiation was impaired with stromal POL3 knockdown, but unchanged after breast cancer POL3 knockdown (FIG. 2F). Consistent with these findings, treatment with a POL3 small-molecule inhibitor also blunted stroma-mediated resistance and ISG induction in breast cancer cells after co-culture (FIGS. 9G-9H). To confirm that exoRNA was responsible for the effects resulting from inhibiting stromal POL3 RNA, CM from co-cultures treated with or without the POL3 inhibitor were isolated. CM isolated from co-cultures both induced ISGs when added to mono-cultured breast cancer cells (FIG. 2G) and re-established stroma-mediated radiation resistance that was abrogated by POL3 inhibition (FIG. 2H). In contrast, CM from co-cultures treated with POL3 inhibitor failed to induce ISGs, but expression of unrelated genes such as IFI16 was not affected (FIGS. 2G-2H). Accordingly, exoRNA from POL3 inhibitor treated co-cultures also was defective in binding to recombinant RIG-I and stimulating ATP hydrolysis activity (FIG. 2I). Thus, these results demonstrated that stromal POL3 generated exoRNA that activated breast cancer RIG-I to induce anti-viral signaling and stroma-mediated protection against DNA damage.

To characterize the exoRNA generated by stromal POL3, an approach was developed to identify 5'ppp RNA by sequencing. For this, a set of enzymatic reactions was utilized to sequentially modify the 5' end of RNA prior to library construction to deplete RNA lacking a 5'ppp modification (5'ppp-seq) (FIG. 9I). Many coding and non-coding RNAs were depleted by approximately 10-fold or greater, consistent with the absence of a 5'ppp (FIG. 2J, left panel). Examination of RNA classes that maintained or increased abundance revealed many exoRNA transcripts known to be under POL3 regulation, including tRNAs, srpRNA, Y RNA/snRNAs, and ALU/SINE RNAs (FIG. 2J, right panel). Inhibiting POL3 resulted in a decrease in the abundance of several of these 5'ppp RNA in exosomes (FIG. 2K). Thus, multiple 5'ppp exoRNAs regulated by stromal POL3 were present in exosomes and represented candidate RNA ligands for propagating an anti-viral response from stromal cells to breast cancer cells.

Figure 3A:
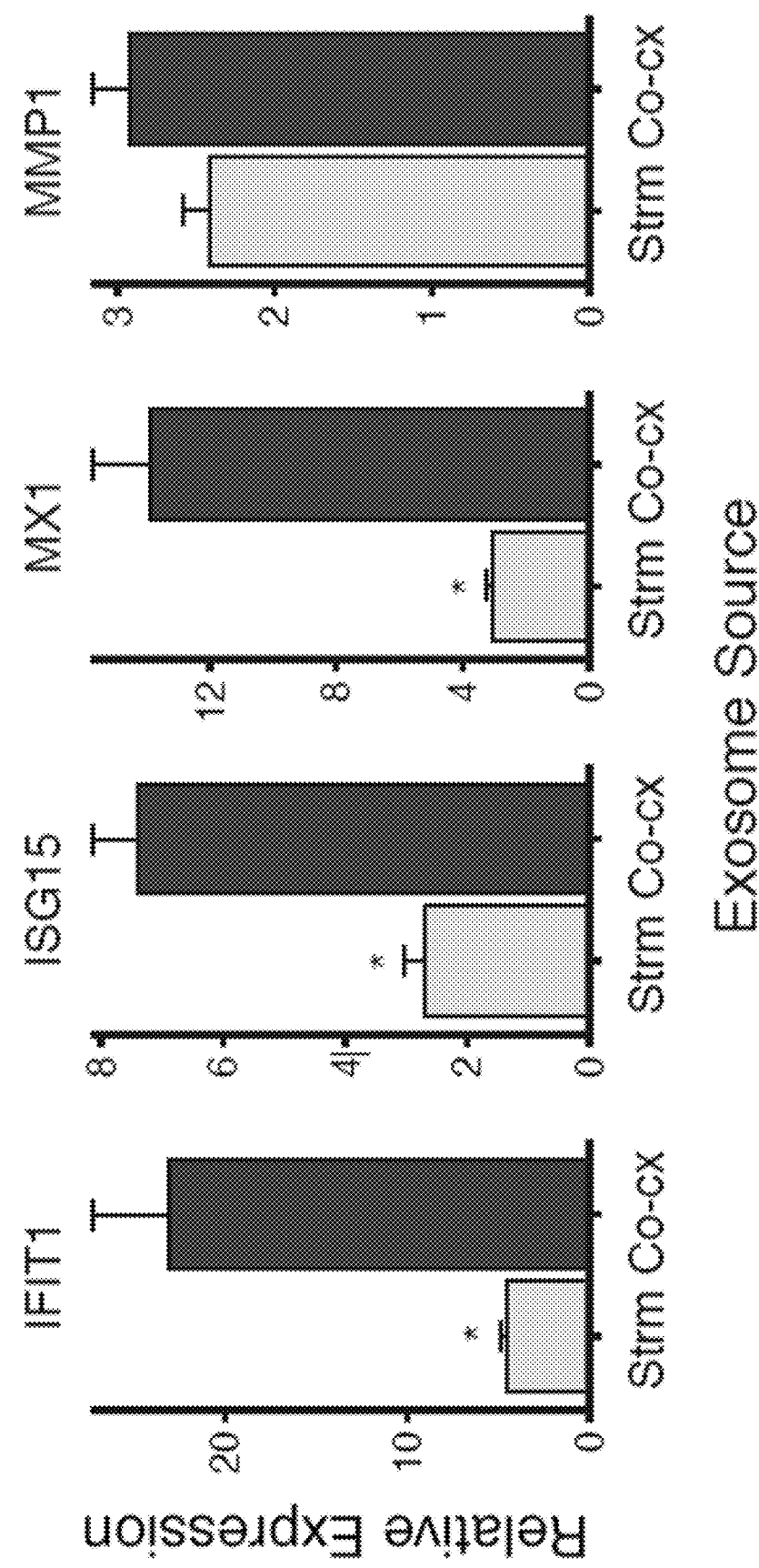
Figures 3B, 3C:
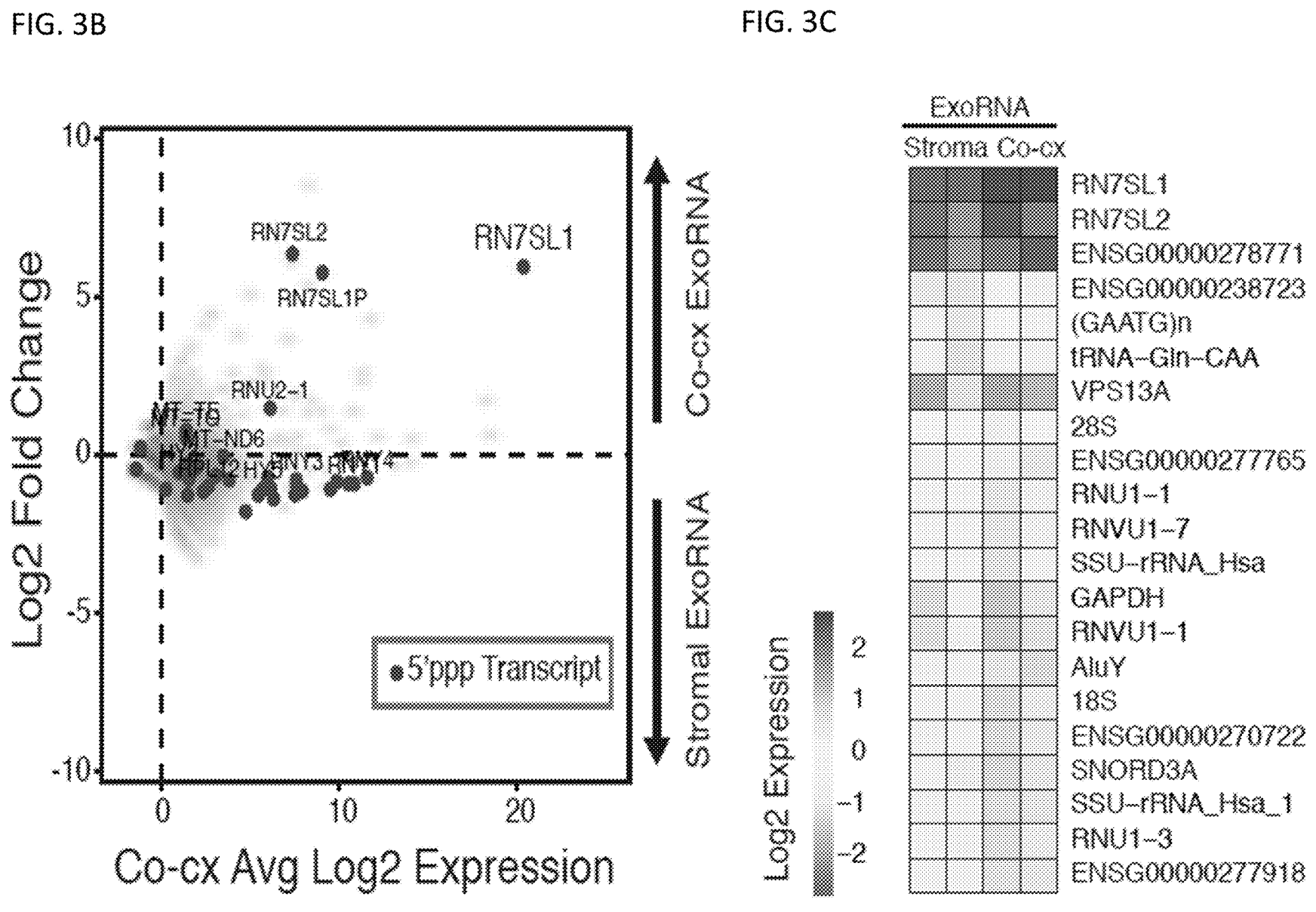
Figures 10A, 10B:
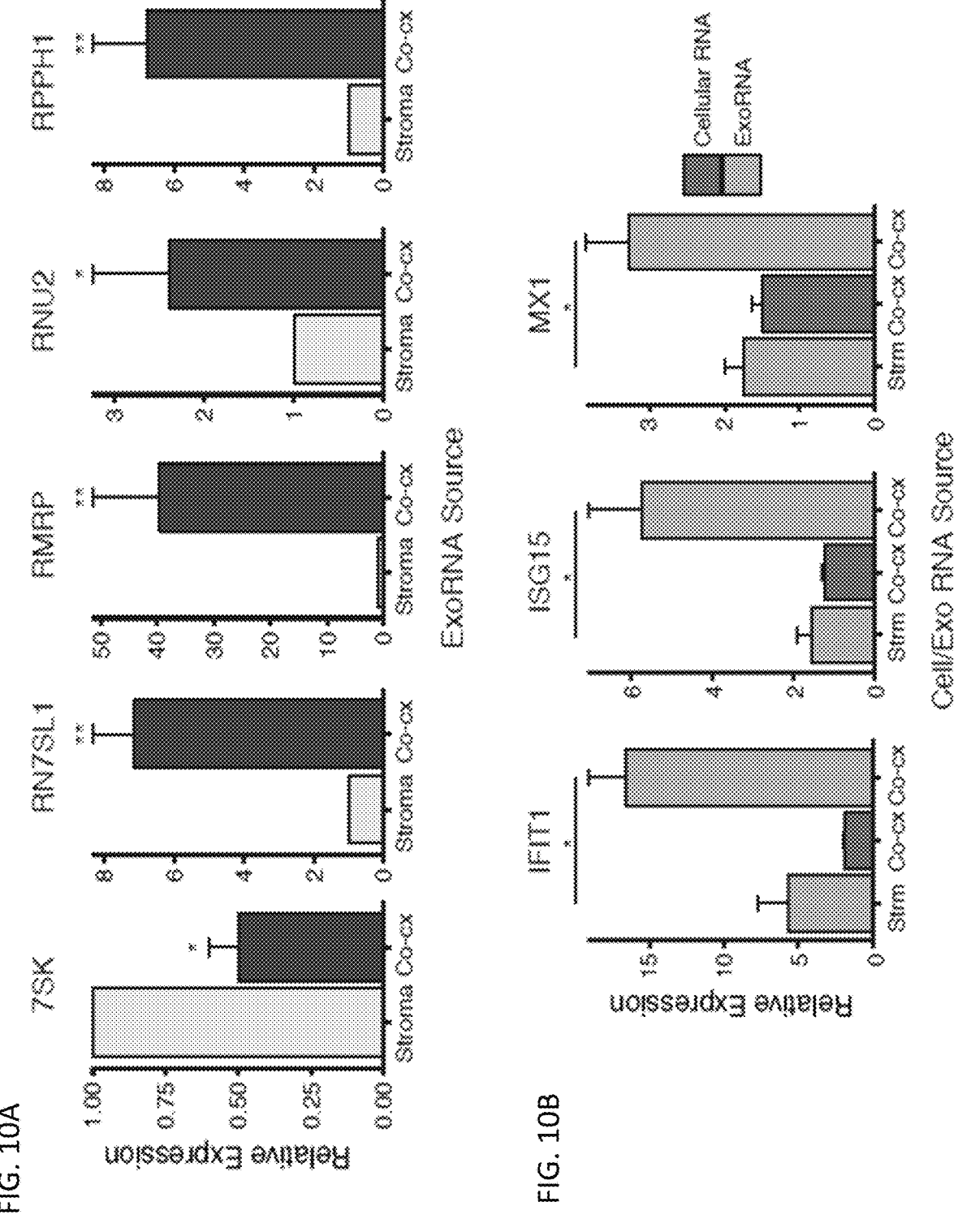
FIGS. 10A-10H are a series of plots and images illustrating 5'ppp RN7SL1 exoRNA generated by tumor-stromal interaction is unshielded.

Example 5: RN7SL1 5'Ppp exoRNA Generated from Tumor-Stromal Interaction Demonstrates Extensive Protein Unshielding As part of the strategy to identify a specific 5'ppp exoRNA from stromal cells that activates breast cancer RIG-I, differences in 5'ppp exoRNA abundance that correlated with differences in the ability of exosomes to induce anti-viral signaling were examined. Exosomes from co-culture, but not stromal cell mono-culture, induce ISGs (FIG. 3A). Because 5'ppp-seq may not be quantitative, RNA-seq was first performed from exosomes (exoRNA-seq) isolated from co-culture versus stromal mono-culture. Using these data, transcripts were specifically examined that were also identified by 5'ppp-seq. This revealed that most 5'ppp exoRNA does not or only modestly varies in abundance in exosomes from co-culture compared to stromal mono-culture (FIG. 3B). In contrast, RN7SL1, or srpRNA, and RN7SL1 pseudogenes stood out as abundant transcripts that markedly increased in exosomes from co-culture compared to stromal mono-culture (FIGS. 3B-3C, FIG. 10A, FIGS. 22A-22C). Accordingly, exoRNA derived from stromal mono-culture was less effective than co-culture exoRNA at eliciting an ISG response in breast cancer cells (FIG. 10B).

Figure 3F:
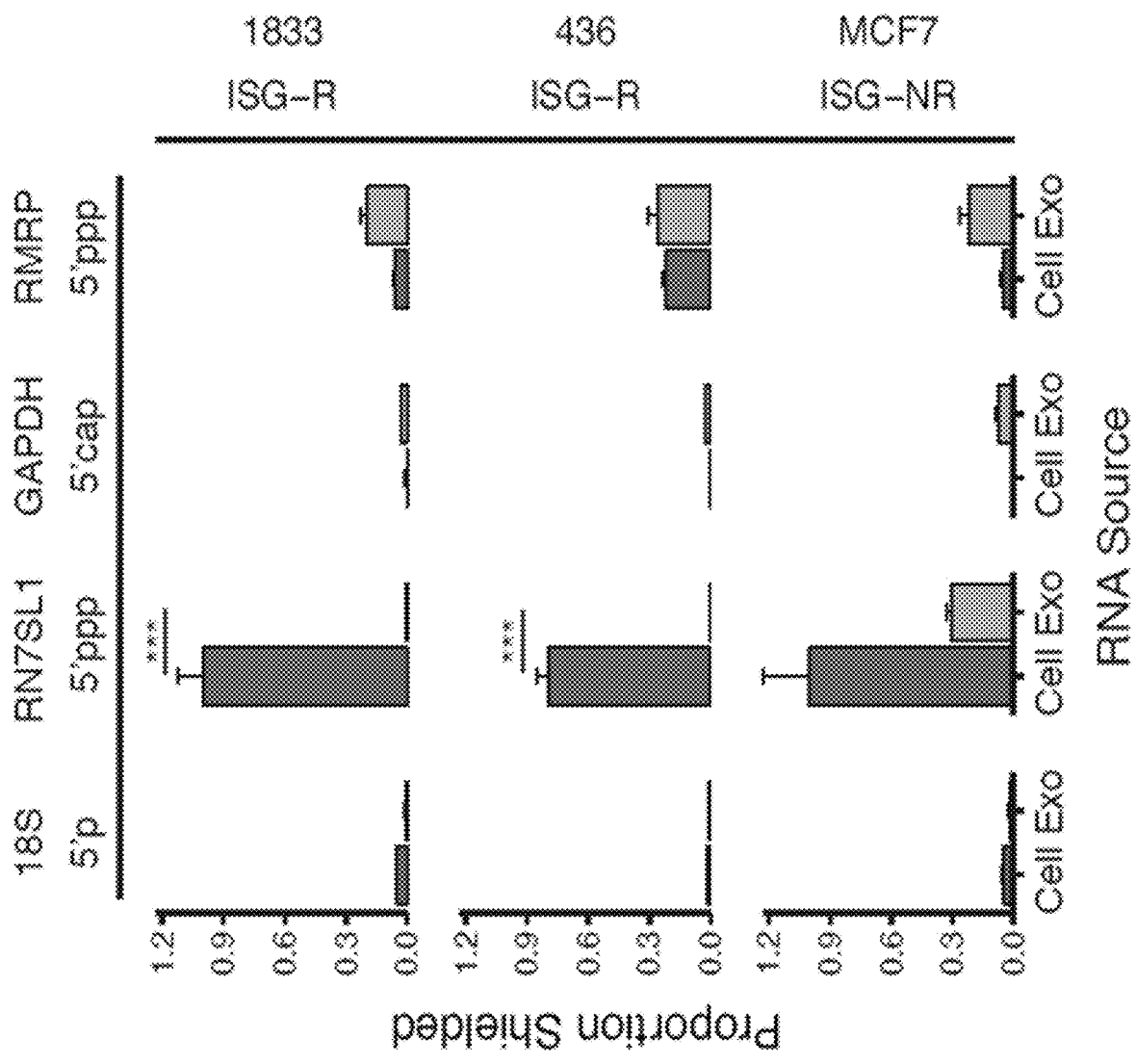
Figures 10C, 10D:
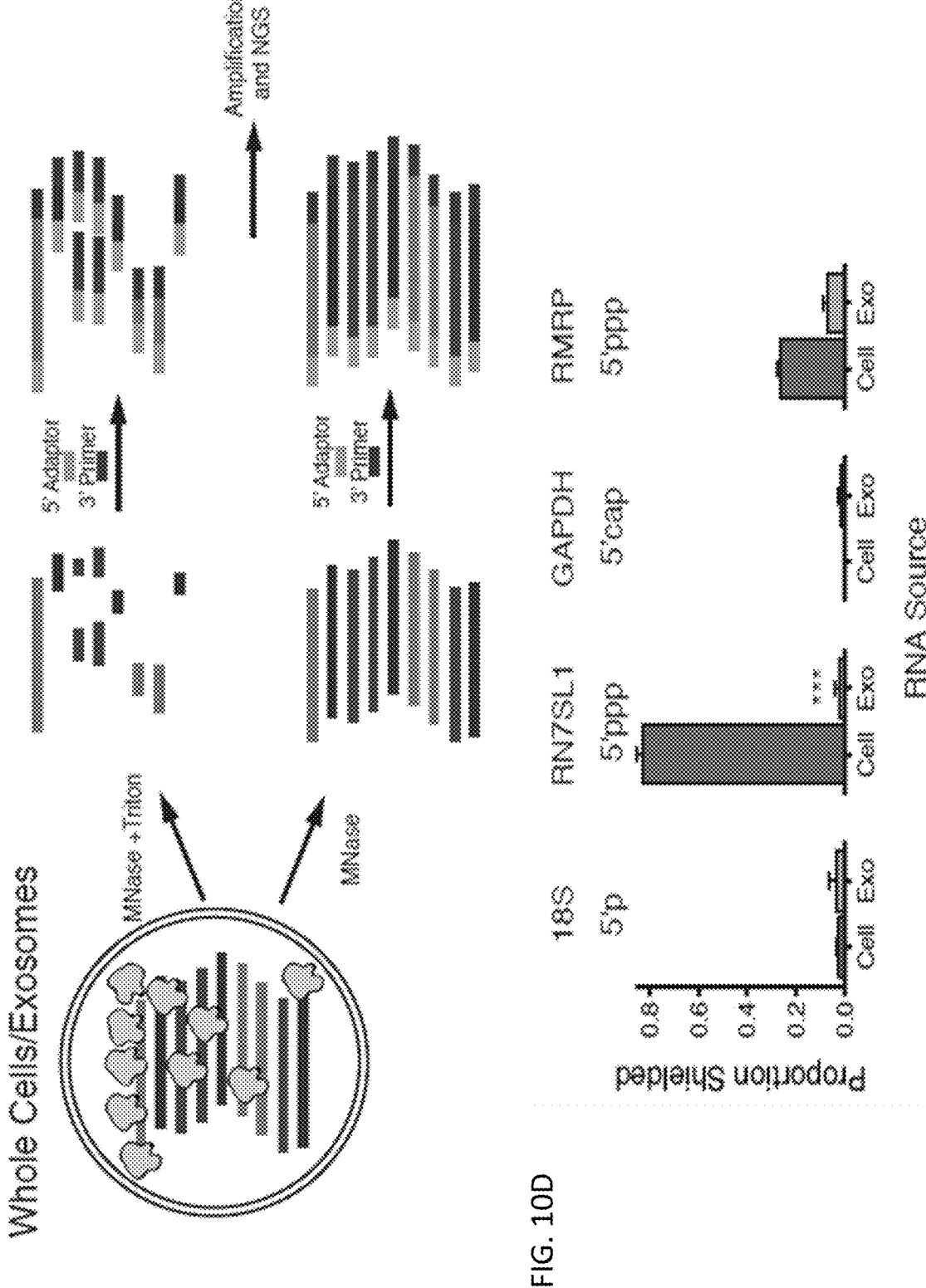
Figures 10E, 10F, 10G, 10H:
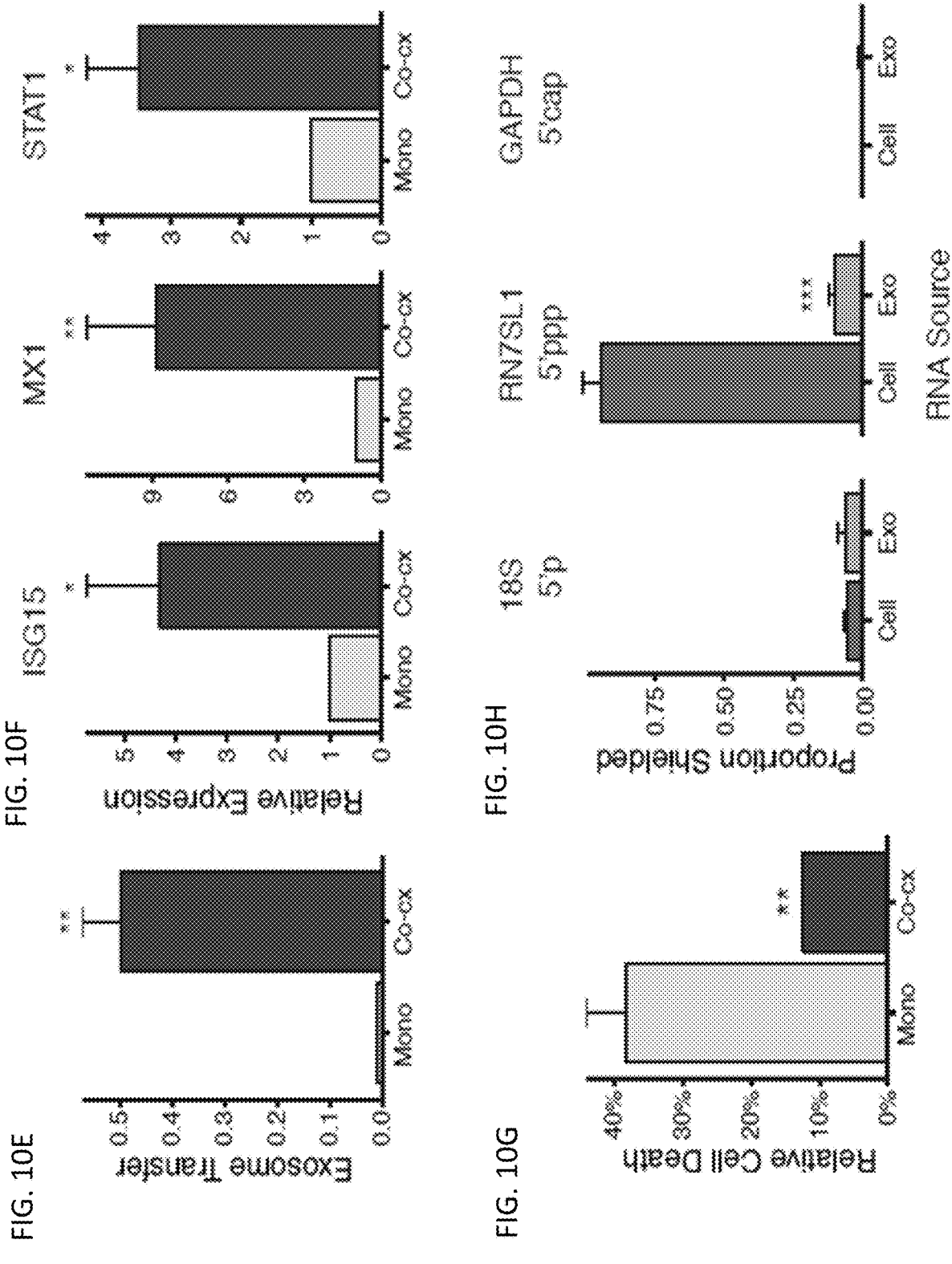

Although high levels of RN7SL1 in co-culture exosomes appeared to be a candidate RIG-I ligand based on differential expression, it was unclear why the presence of this 5'ppp RNA in the cytoplasm or in exosomes produced by stromal mono-culture would not activate RIG-I. Moreover, RN7SL1 and possibly other 5'ppp exoRNAs contain extensive double-stranded regions, an important feature given that RIG-I efficiently recognizes dsRNA. Based on these considerations, it was reasoned that alterations in binding by RNA binding proteins (RBPs) might influence the ability of endogenous RNA to activate anti-viral signaling. To examine this, cells or exosomes were treated with micrococcal nuclease (MNase) with or without membrane permeabilization prior to sequencing (MNase-seq) (FIG. 10C). This revealed that exoRNAs are generally less susceptible to MNase-dependent degradation compared to cellular RNAs, suggesting that exoRNA is relatively more "shielded" by RBPs than their cellular counterparts (FIG. 3D). However, examination of 5'ppp RNA shielding combined with predicted RNA secondary structure as measured by normalized minimum free energy (MFE), demonstrated that RN7SL1 stands out as a 5'ppp exoRNA with extensive double-stranded structure (low MFE) that is extensively shielded in cells but highly unshielded in co-culture exosomes (FIG. 3D, FIG. 10D, FIGS. 22A-22C). In contrast, most other 5'ppp exoRNA has less predicted double-stranded structure and/or is significantly more shielded in exosomes compared to RN7SL1. Other 5'ppp RNA or RNA without a 5'ppp (i.e., 5' cap mRNA and 5'-monophosphate rRNA) generally are equally unshielded in cells and exosomes (FIG. 3D and FIG. 10D), while RN7SL1 exoRNA from stromal mono-culture shows comparable shielding compared to cells (FIG. 3E). Unshielding of RN7SL1 exoRNA was also observed when other ISG-R breast cancer cells and stromal fibroblasts were co-cultured (FIG. 3F), and when primary mouse lung fibroblasts were co-cultured with K14cre;p53$^{F/F}$;Brca1$^{F/F}$ murine breast cancer cells that also have hallmarks of ISG-R breast cancers (FIGS. 10E-10H). In contrast, exosomes from co-culture of MCF7 ISG-NR breast cancer cells with stromal cells demonstrated significantly less unshielding (FIG. 3F). This, along with diminished exosome transfer (FIG. 1C), correlates with the relative inability of ISG-NR breast cancer cells to induce anti-viral signaling after co-culture. In total, these results demonstrated that after interaction with ISG-R breast cancer, stromal cells selectively deploy unshielded RN7SL1 in exosomes, an endogenous 5'ppp RNA with double-stranded structure.

Figure 4A:
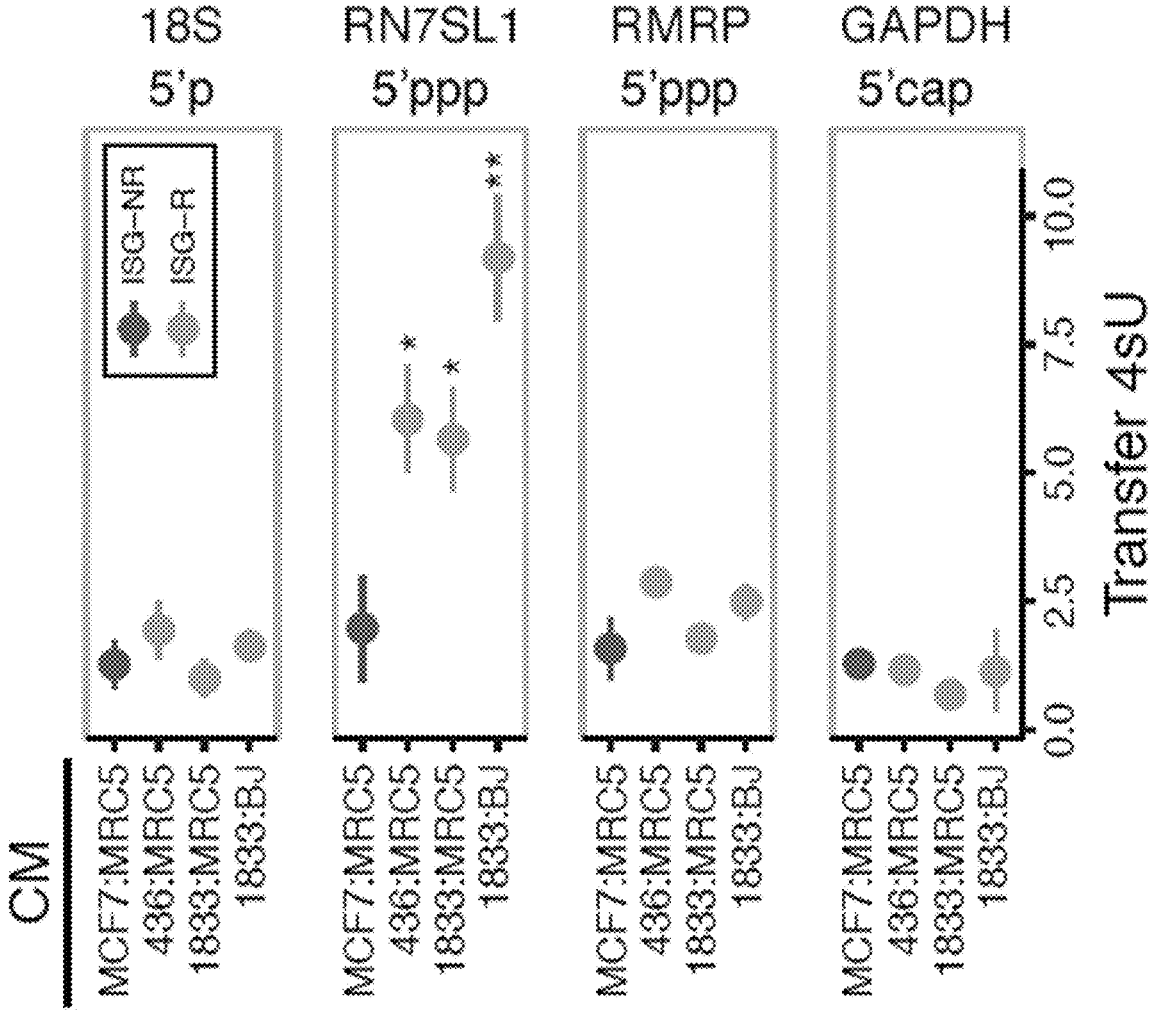
FIGS. 4A-4F are a series of plots and images illustrating unshielded RN7SL1 exoRNA is transferred by stromal cells and recognized by breast cancer RIG-I.
Figure 4B:
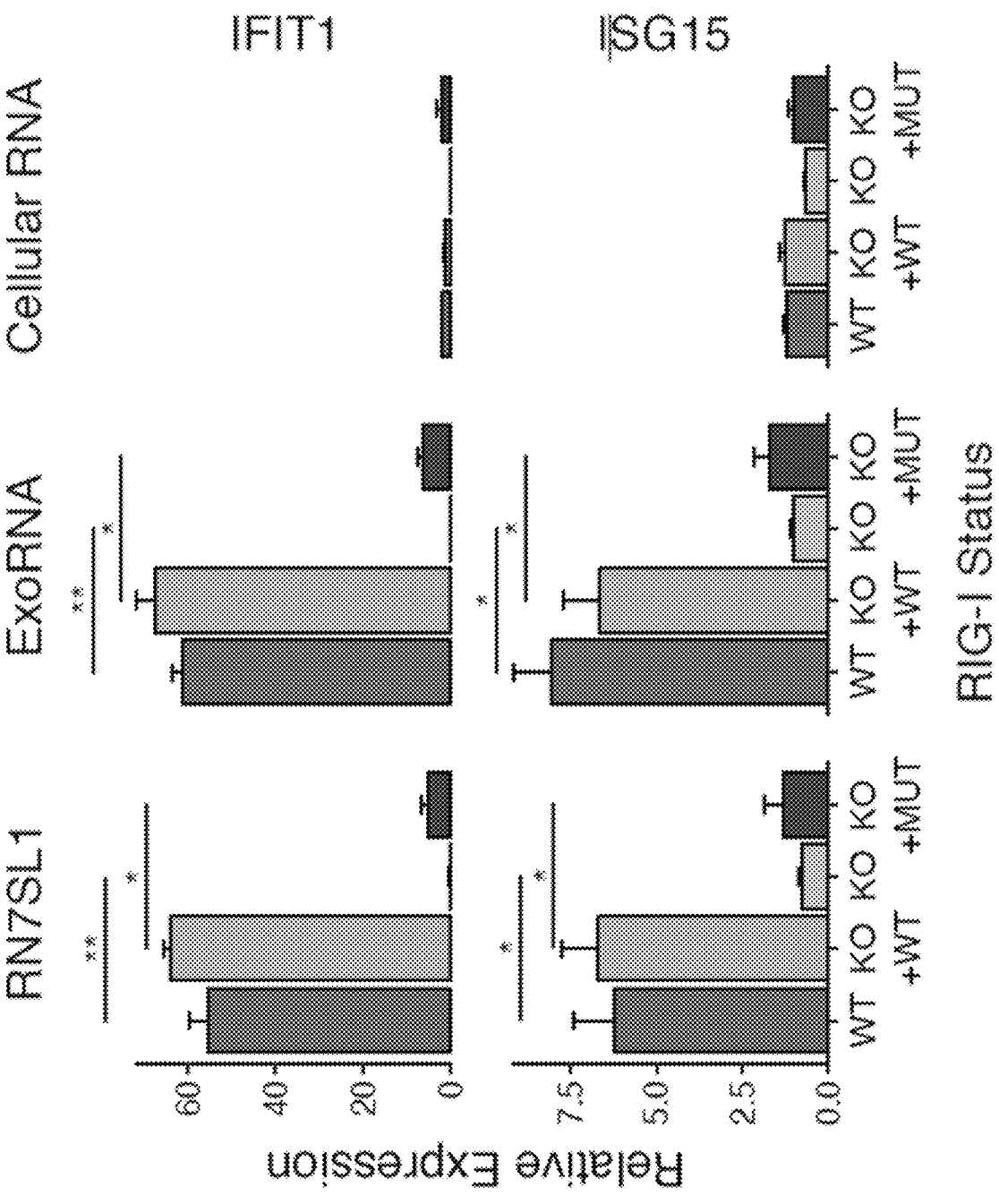
Figure 4C:
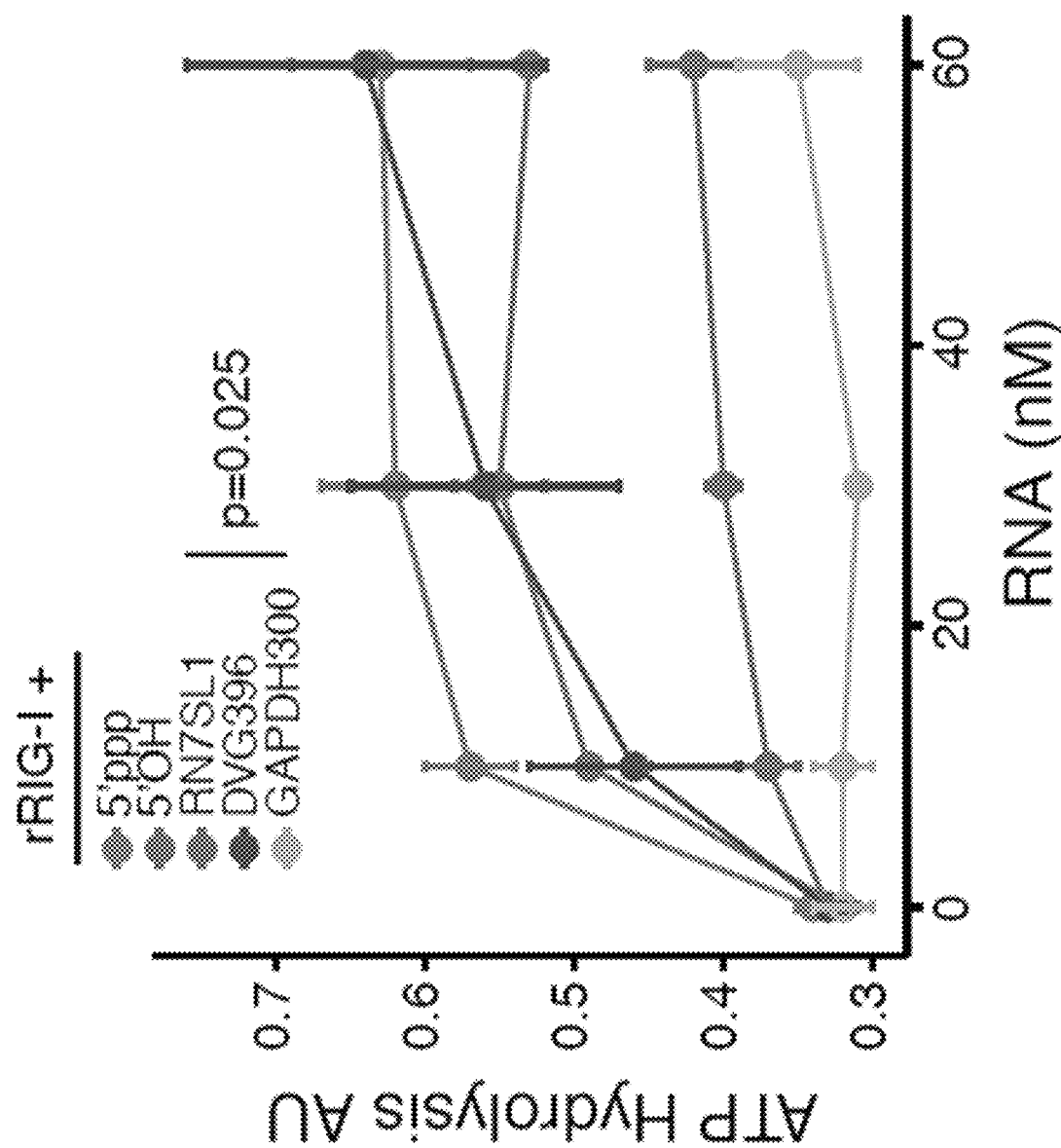
Figure 11:
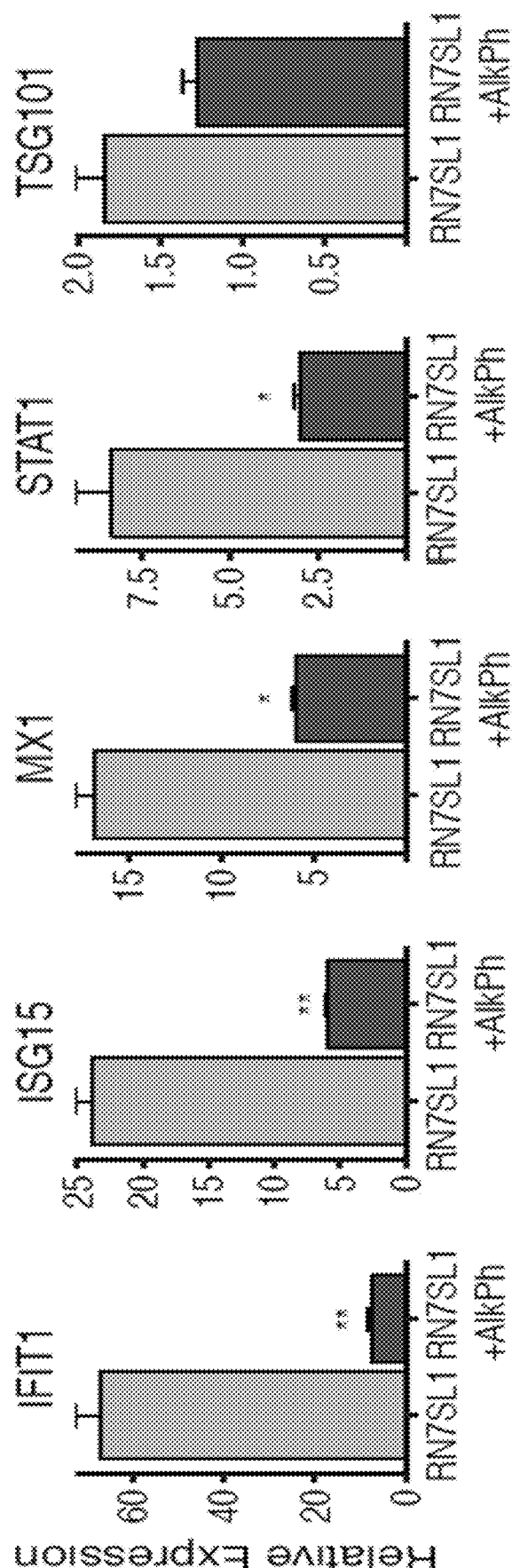
FIG. 11 is a graph showing ISG expression in 1833 breast cancer cells after transfection of in vitro transcribed RN7SL1 RNA or RN7SL1 RNA treated with alkaline phosphatase (+AlkPh) (n=3). TSG101 is a non-ISG not expected to change. Values are relative to mock control. Error bars are SEM of biological replicates and *p<0.05, ** p<0.01.

Example 6: Unshielded RN7SL1 exoRNA is Transferred by Stromal Cells and Stimulates Breast Cancer RIG-I To establish that unshielded RN7SL1 exoRNA generated by stromal cells can serve as a RIG-I ligand, stromal cell RNA was metabolically labeled with 4sU and assayed for transfer to breast cancer cells. This demonstrated that RN7SL1, but not other 5'ppp exoRNAs or exoRNA without 5'ppp, is transferred to breast cancer cells from multiple different stromal cells but only in the context of ISG-R breast cancer cell co-culture (FIG. 4A). Moreover, like exoRNA but not cellular RNA, transfection of ribozyme-cleaved in vitro transcribed RN7SL 1 induces ISGs in breast cancer cells specifically in a RIG-I-dependent manner (FIG. 4B). The ability of RN7SL1 to stimulate RIG-I requires 5'ppp. Alkaline phosphatase treatment prior to transfection abolished ISG induction (FIG. 11), and reconstitution of RIG-I KO cells with WT RIG-I but not RIG-I$^{K858/861A}$, which abolishes amino acid interactions with 5'ppp, restored antiviral signaling after RN7SL1 transfection (FIG. 4B). In vitro RIG-I ATP hydrolysis assay confirmed that RN7SL1, but not equimolar and a similarly sized GAPDH-derived RNA (GAPDH300), directly binds recombinant RIG-I (FIG. 4C). Activation of recombinant RIG-I by RN7SL1 was comparable to an equimolar amount of Sendai virus-derived RNA (DVG396). Thus, RN7SL 1 is transferred from stromal cells to ISG-R breast cancer and can directly activate RIG-I.

Figures 4D, 4E, 4F:
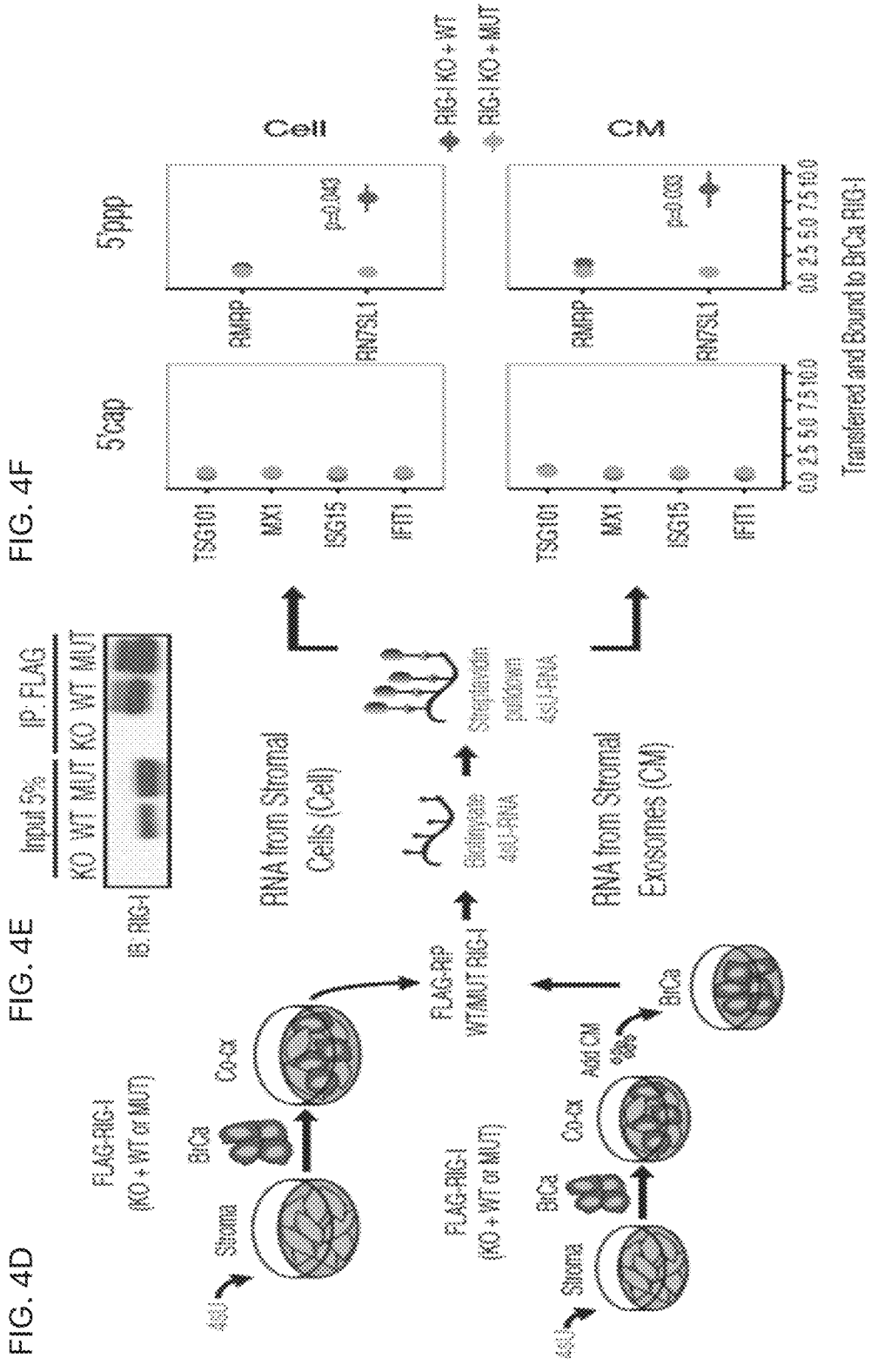

To directly examine whether stromal RN7SL1 is transferred by exosomes and binds to breast cancer RIG-I, stromal cells were labeled with 4sU prior to co-culture with breast cancer cells. This was followed by tandem pull-down of stromal RNA bound to breast cancer RIG-I by first immunoprecipitating FLAG-tagged breast cancer RIG-I and then isolating biotinylated 4sU-labeled stromal RNA with streptavidin beads (FIG. 4D, top; FIG. 4E). This sequential procedure revealed that stromal-derived RN7SL1, but not RNA without 5'ppp (i.e., capped mRNAs), specifically bound to WT RIG-I compared to RIG-I$^{K858/861A}$ (FIG. 4F, top row). Moreover, other 5'ppp RNA found in exosomes such as RMRP showed markedly less binding. To assess if this transfer of stromal RN7SL1 is mediated by exosomes, CM isolated from 4sU-labeled stromal cells co-cultured with breast cancer cells was added to breast cancer cell monocultures (FIG. 4D, bottom). Again, tandem pull-down demonstrated that stromal-derived RN7SL1, but not capped RNAs or RMRP 5'ppp RNA, specifically bound to breast cancer RIG-I when compared to RIG-I$^{K858/861A}$, consistent with exosome-mediated transfer (FIG. 4F, bottom row). Thus, after breast cancer interaction, stromal cells can transfer unshielded RN7SL1 in exosomes to directly activate RIG-I. These results show that similar to how viral RNA in exosomes can propagate an anti-viral response from infected to uninfected cells, stromal cells can disseminate an anti-viral response to breast cancer cells by deploying unshielded endogenous RN7SL1 in exosomes.

Example 7: SRP9 and SRP14 Control RN7SL1 Shielding and Anti-Viral Stimulatory Activity RN7SL 1 is an abundant cellular RNA that complexes with signal recognition particle (SRP) proteins to control co-translational protein translocation. Two SRP proteins, SRP9 and SRP14 normally bind the 5' end of RN7SL1, potentially obscuring the 5'ppp. Thus, to investigate whether SRP9 and/or SRP14 might influence recognition of RN7SL 1 by RIG-I through RBP shielding, the expression of SRP9/ 14 in exosomes was examined. In contrast to cellular extracts, which showed relatively high levels of SRP9 and SRP14, these proteins were not detectable in exosomes (FIG. 5A). GFP-tagged SRP9 and SRP14 were transiently overexpressed in stromal cells prior to co-culture to determine if this could drive these SRP proteins into exosomes and potentially partially shield exosome RN7SL1 from recognition by breast cancer RIG-I (FIG. 5B and FIGS.

Figure 5E:
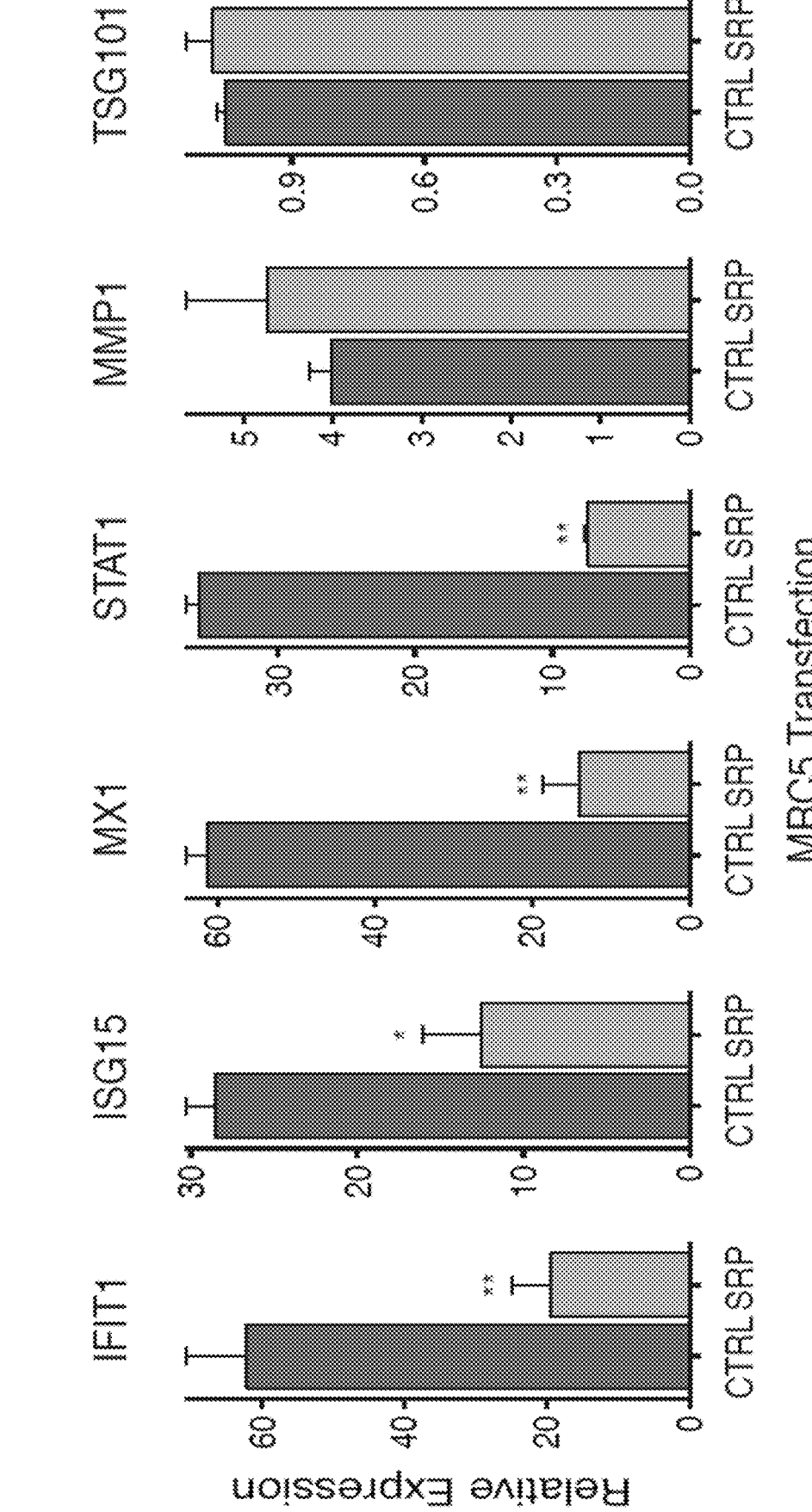
Figure 5F:
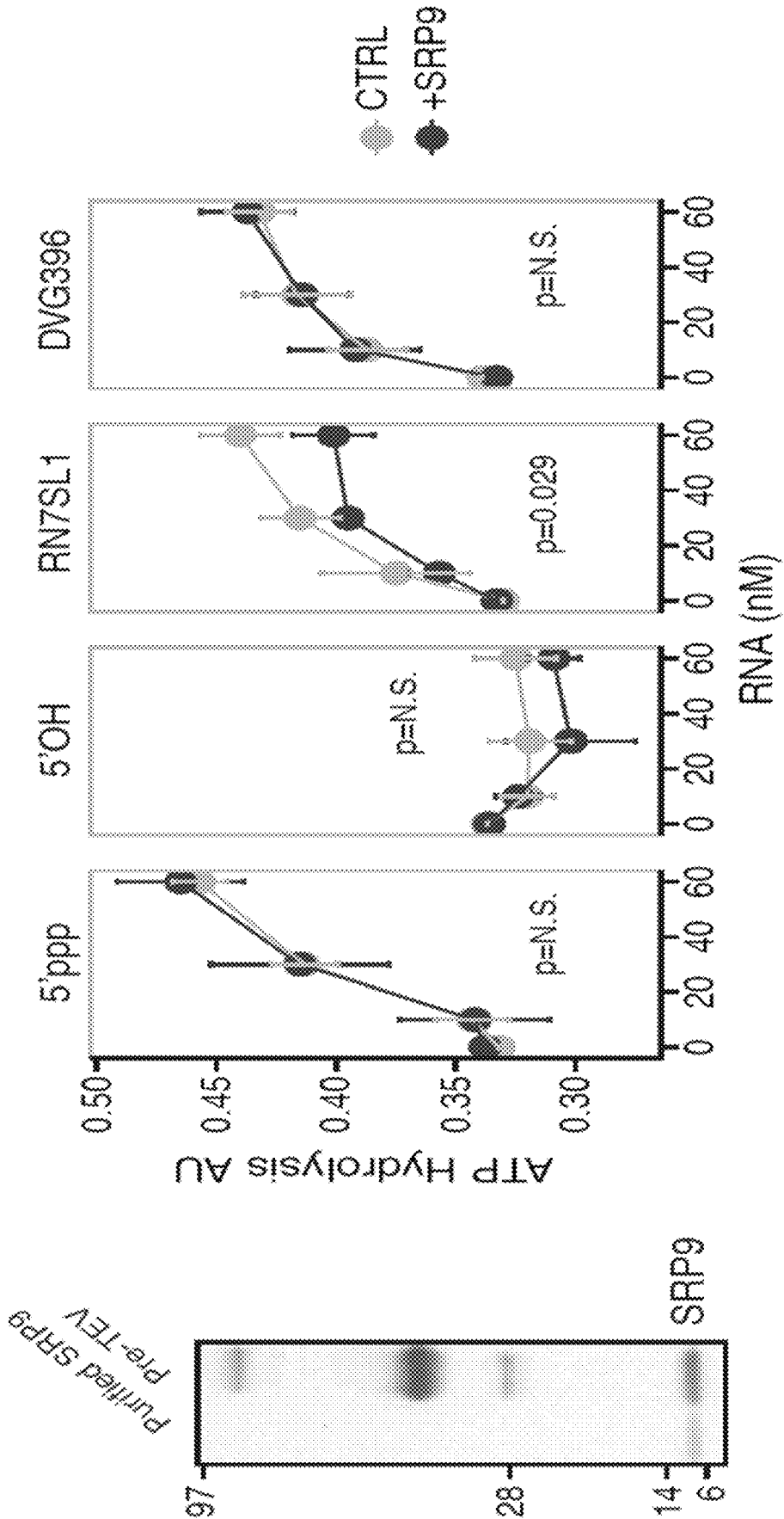

12A-12C). Indeed, transiently increasing SRP9 and SRP14 in stromal cells was sufficient to direct expression of both tagged SRP proteins into exosomes (FIG. 5C). This led to a significant increase in shielding of RN7SL1 exoRNA but not in 18S rRNA (FIG. 5D). Consequently, stroma-mediated ISG induction in breast cancer cells was reduced, while expression of non-ISGs such as MMP1 and TSG101 was not affected (FIG. 5E). Recombinant SRP9 was purified. Addition of SRP9 to in vitro transcribed RN7SL 1 partially inhibited ATP hydrolysis by recombinant RIG-I but did not influence Sendai virus-derived RNA (DVG396) or unrelated 5'ppp or 5'OH control RNAs (FIG. 5F). These results suggest that RBP shielding of cellular RN7SL1 by its SRP proteins may restrict inappropriate recognition by RIG-I in the cytoplasm. However, the absence of these RBPs in exosomes allows the transfer of unshielded RN7SL1 to neighboring cells, resulting in RIG-I activation. Thus, in a sterile tumor microenvironment, differential RBP shielding in cells versus exosomes can enable endogenous RNAs to function as DAMPs and propagate anti-viral signaling.

Figure 6C:
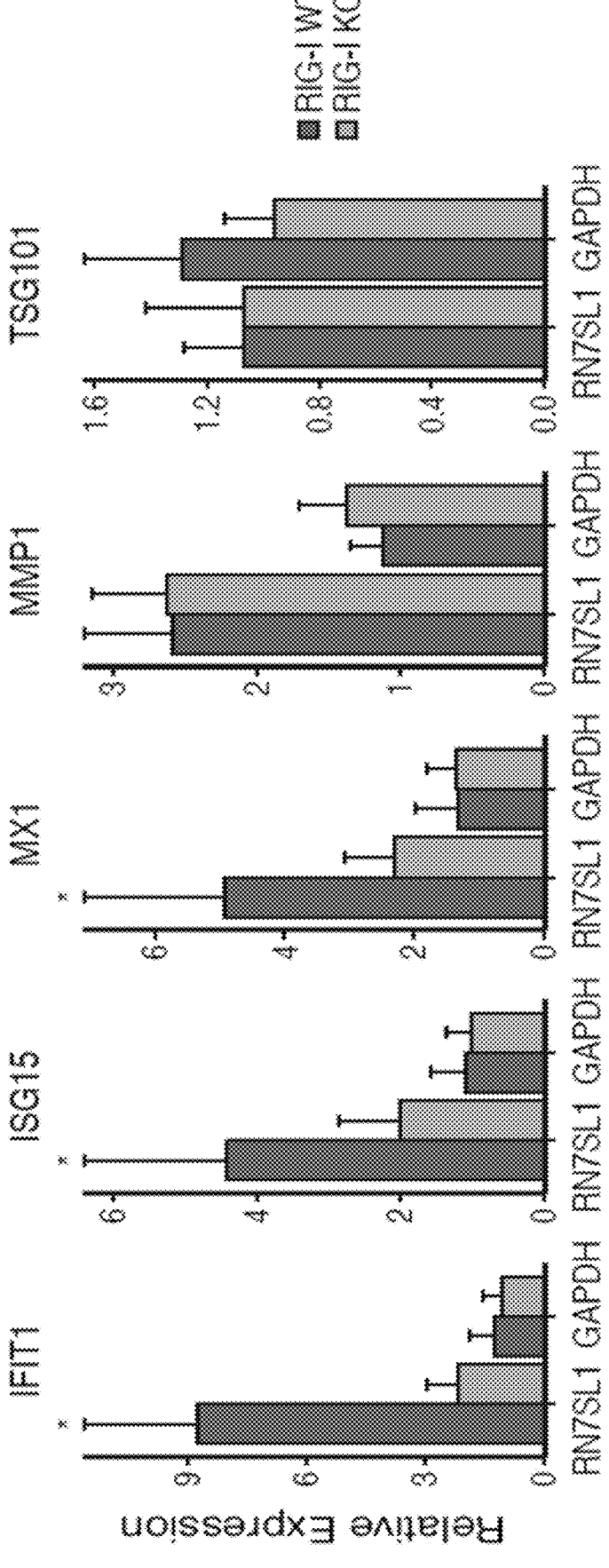

Example 8: Unshielded Stromal RN7SL1 exoRNA
Promotes Breast Cancer Progression and is Present
in the Serum of Cancer Patients A cardinal feature of stromal fibroblasts in the tumor microenvironment is the ability to promote cancer progression and metastasis. Indeed, the ability of stromal cells to induce antiviral signaling in breast cancer contributes to metastasis and/or the expansion of tumor-initiating cells, which would be expected to favor breast cancer progression. To examine whether unshielded RN7SL1 in exosomes can contribute to tumor growth, exosomes were isolated from co-culture and from stromal monoculture and direct intra-tumoral injections were performed into subcutaneous 1833 ISG-R breast cancer xenografts. Consistent with having higher levels of unshielded RN7SL1, exosomes from co-culture accelerated tumor growth compared to exosomes isolated from stromal cells alone (FIG. 6A). To directly assess if unshielded RN7SL1 can enhance tumor progression, RN7SL1 or GAPDH300 control RNA was encapsulated into liposomes and similarly delivered intratumorally. Only RN7SL1 could enhance tumor growth in a RIG-I-dependent manner as no effect was observed with RIG-I KO or with GAPDH300 control RNA (FIG. 6B). Examination of the tumor confirmed an increase in ISG expression, but not in unrelated genes like TSG101, specifically in tumors injected with RN7SL1 and expressing WT RIG-I (FIG. 6C). Thus, these results demonstrate that unshielded RN7SL1 transferred by exosomes can promote breast cancer progression.

Figure 13:
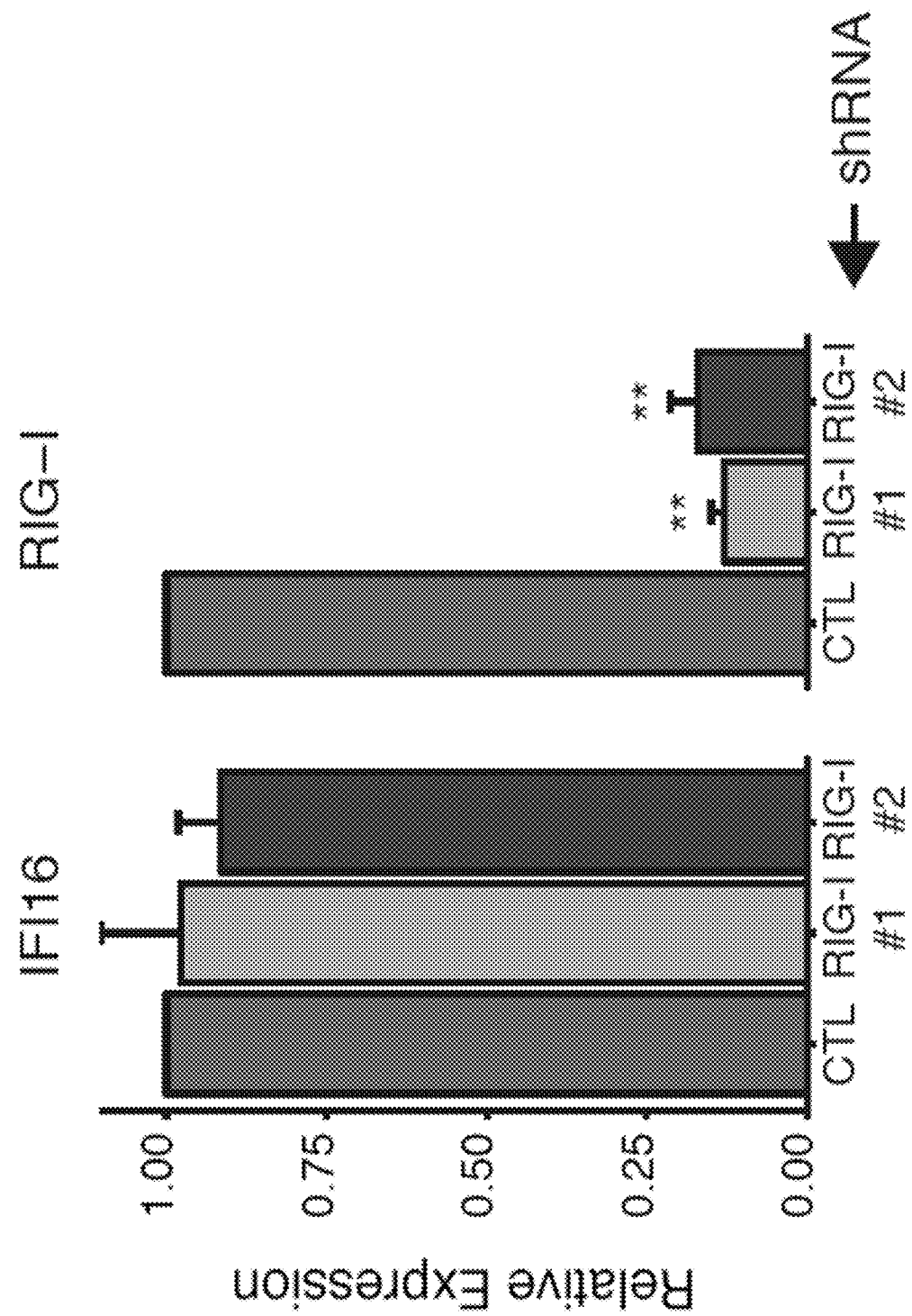
FIG. 13 is a bar graph illustrating gene expression in 1833 breast cancer cells after transduction of control shRNA (CTL) or two independent RIG-I targeting shRNA (RIG-I #1 and RIG-I #2) (n=3). Error bars are SEM of biological replicates and ** p<0.01.

To study whether metastatic progression is associated with breast cancer RIG-I signaling and unshielded RN7SL1 exoRNA from stromal cells, 4175 human breast cancer cells were utilized, which are an ISG-R lung metastatic derivative of MDA-MB-231. Inhibiting RIG-I expression in 4175 cells using two independent shRNAs (FIG. 13) resulted in a significant defect in lung metastatic colonization, indicating the importance of RIG-I signaling in breast cancer cells (FIG. 6D). Compared to non-tumor bearing mice, interrogation of exoRNA from serum of mice with wild-type 4175 lung metastases revealed more unshielding of mouse RN7SL 1 but not 18S rRNA as measured using mouse-specific primers (FIG. 6E). These data suggest that lung metastases from human breast cancer cells can result in greater amounts of circulating unshielded RN7SL1 in exosomes originating from mouse stromal cells. To corroborate these findings, exoRNA from the serum of a small cohort of cancer patients was also examined (FIG. 23). To the extent possible, the analysis in mice was mimicked by examining RN7SL1 in patients after tumor resection. This facilitated assessment of RN7SL1 exoRNA from stromal cells and allowed better comparison to normal controls without cancer. ExoRNA-seq from two patients confirmed that RN7SL1 and POL3 transcripts are present at high levels and among the predominant non-rRNA transcripts in exosomes from cancer patients (FIG. 6F). Compared to healthy controls, this RN7SL1 exoRNA was significantly less shielded in cancer patients having had tumor resection, suggesting that RN7SL1 from remaining cancerized stroma is more unshielded than from normal cells (FIG. 6G). Although cellular origin could not be determined, RN7SL1 exoRNA from two available patients with gross tumors prior to any therapy also showed similar results, arguing that RN7SL1 unshielding was not solely due to confounding factors related to tumor resection. Together, these findings demonstrate that unshielded stromal RN7SL1 in exosomes can propagate anti-viral signaling in the tumor microenvironment to enhance breast cancer progression or metastasis.

Figure 7:
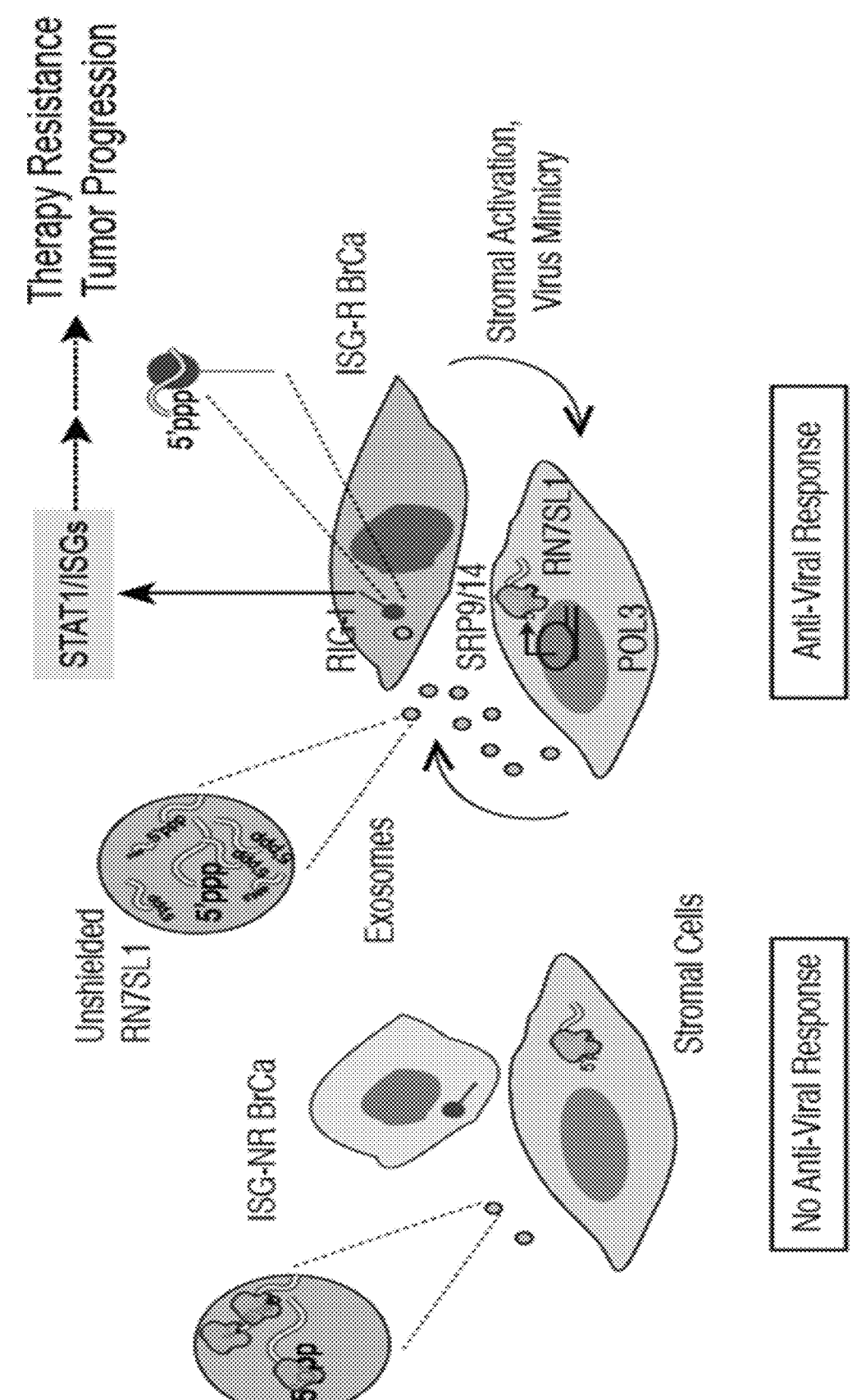
FIG. 7 displays a model of virus mimicry and unshielding of stromal RN7SL1 to activate breast cancer RIG-I through exosome transfer.

In the present study, a phenomenon of virus mimicry was discovered whereby the interaction between breast cancer cells and stromal fibroblasts share several similarities with how virus infected cells relay anti-viral signals to surrounding cells. First, upon encounter with breast cancer cells, stromal cells mount an anti-viral response analogous to virally infected cells by upregulating ISGs and other genes associated with anti-viral signaling. In fact, interferon and anti-viral signaling are dominant pathways induced among hundreds of upregulated transcripts. Second, like virally infected cells that can package viral 5'ppp RNA into exosomes to function as pathogen-associated molecular patterns (PAMPs), stromal cells that have encountered breast cancer cells increase the abundance of endogenous POL3-derived and RBP-devoid 5'ppp RN7SL1 in exosomes to function as DAMPs. Moreover, after interaction between stromal cells and ISG-R breast cancer cells, production of DAMP-laden exosomes can increase ten-fold (Boelens et al. (2014). Cell 159, 499-513). After paracrine transfer, the PAMP/DAMPs stimulate PRRs to propagate the anti-viral response. In the case of cancer, RIG-I activation in breast cancer cells by stromal RN7SL1 can result in STAT1-mediated amplification of the NOTCH3 pathway, as previously described (Boelens et al. (2014). Cell 159, 499-513). Consequently, this interaction favors tumor progression, resistance to therapy, and tumor-initiation capacity. In total, these data demonstrate how cancers can employ virus mimicry in the tumor microenvironment to coerce stromal cells to disseminate anti-viral signals that amplify oncogenic signaling pathways (FIG. 7).

Viral PAMPs are under selective pressure to avoid immune recognition, while endogenous RNA DAMPs must avoid recognition by PRRs under non-pathological conditions. Thus, the discovery presented herein that RN7SL1 is a cancer-associated DAMP presented a conceptual problem. Specifically, given its abundance in the cytoplasm, it was unclear how RN7SL1 could both function as a DAMP in exosomes but at the same time avoid recognition by RIG-I while in the cytoplasm. Indeed, it has long been recognized that RNA modification and subcellular localization may be insufficient to prevent inappropriate activation by endogenous and abundant POL3 5'ppp transcripts, arguing that unknown mechanisms must exist. The findings presented herein on how differential RBP shielding of endogenous RN7SL1 can control DAMP activity and PRR activation provide an explanation for how this discrimination can be achieved. In the cytoplasm, RN7SL1 is nearly completely shielded by RBPs, presumably SRP proteins. In particular, SRP9 and SRP14 are known to interact with the 5' end of RN7SL1 and it was shown herein that these RBPs interfere with RIG-I recognition and activation. In exosomes generated from stromal activation by ISG-R breast cancer cells, SRP9/14 are absent and results in unshielding of RN7SL1 and recognition by RIG-I in recipient cells. These data also indicate that the stimulatory effects of high affinity RNA ligands for RIG-I measured in vitro, may be superseded in vivo by RBP shielding. Thus, control of RBP shielding may be a critical regulatory layer that prevents inappropriate PRR activation, especially of abundant RNAs, while concurrently allowing for a readily available and rapidly deployable DAMP.

When stromal cells encounter breast cancer cells, the initiating event that mimics viral infection and leads to the deployment of RN7SL1 as a DAMP is currently unknown. Cell-cell contact between stromal and breast cancer cells is required as conditioned media from breast cancer cells does not induce ISGs in stromal cells. Indeed, abnormal cell-cell contact between epithelial cells and fibroblasts, which are often separated by a basement membrane, typically occurs under pathological situations such as wounding or with invasive carcinoma. Thus, one possibility is that this heterotypic interaction itself may represent a "damage" signal that initiates DAMP release by the stromal compartment. Although the mechanism for this potential damage signal is unknown, recent evidence demonstrates that oncogenic signals involved in cell-cell regulation such as the Hippo pathway can lead to the secretion of extracellular vesicles containing RNA DAMPs. Consistent with a role for oncogenic signaling, it was shown herein that there is a pronounced transcriptional upregulation characteristic of cellular activation in stromal cells after contact with ISG-R breast cancer cells, as well as an increase in hallmark genes associated with MYC and RAS activation. Interestingly, POL3 activity is augmented by MYC (White, 2011) and by nearby RNA polymerase II (POL2) occupancy (Oler et al., 2010). This suggests that high MYC and POL2 transcriptional output resulting from interaction with ISG-R breast cancer cells may enhance POL3-driven RN7SL1 levels in stromal cells. If binding by RBPs such as SRP9/14 are limiting, an ensuing increase in unshielded RN7SL1 may lead to its export into exosomes. Thus, unshielded RN7SL1 may be a consequence of stromal activation after inappropriate interaction with epithelial cells. This aberrant stromal activation may be a trigger for virus mimicry.

Besides transferring viral RNA, the ability to horizontally transfer DAMPs may also be an important feature of virus infection, further illustrating how tumor-supporting stromal cells may borrow queues from virally infected cells. Consistent with this, virions have been described to contain not only RN7SL1 in the absence of SRP proteins but multiple other endogenous non-viral RNAs (Eckwahl et al., 2015, 2016; Garcia et al., 2009; Onafuwa-Nuga et al., 2006). The role of these non-viral RNAs in virions has not been well characterized; however, it has been postulated that they might stimulate innate immune signaling. Results of the present study would support this notion and suggest that RN7SL1 in virions may act as a potent activator of RIG-I like it does in exosomes. Alternatively, in addition to containing viral RNA, exosomes secreted by infected cells may also package unshielded RN7SL1 capable of RIG-I activation. Therefore, whether in virions or in exosomes, cells under viral attack may help to ensure a broad anti-viral response by packaging endogenous DAMPs alongside viral RNA PAMPs. In support of this concept, recent studies show that cells infected by viruses can package the nucleoside second-messenger cGAMP into secreted virions to trigger a STING-dependent interferon response in recipient cells. In total, these observations suggest that horizontal transfer of DAMPs to promulgate anti-viral signaling is a key feature of virus mimicry. Moreover, RBP unshielding of endogenous RNAs may have broad implications for innate immune sensing not only for cancer but also during host-virus interactions.

In the context of cancer, this study demonstrates that unshielded RN7SL1 activates RIG-I to amplify NOTCH3 signaling, resulting in expansion of tumor-initiating cells. Accordingly, tumor growth, metastasis, and therapy resistance are augmented. Moreover, of all 5'ppp transcripts identified in exosomes, only RN7SL1 was highly abundant, strongly unshielded, and predicted to have extensive double-stranded folding. Nonetheless, we do not rule out contributions from other exoRNAs as DAMPs in our study or in other cellular contexts. Similar to how defense against different viruses may rely on distinct PRRs to optimally engage different viral PAMPs, diverse forms of virus mimicry in cancer may sense different, altered, or inappropriately expressed endogenous RNAs using various innate immune sensors. The extent to which differential RBP shielding impacts these DAMP-PRR combinations is likely an important determinant for activation.

Example 9

Figure 14A:
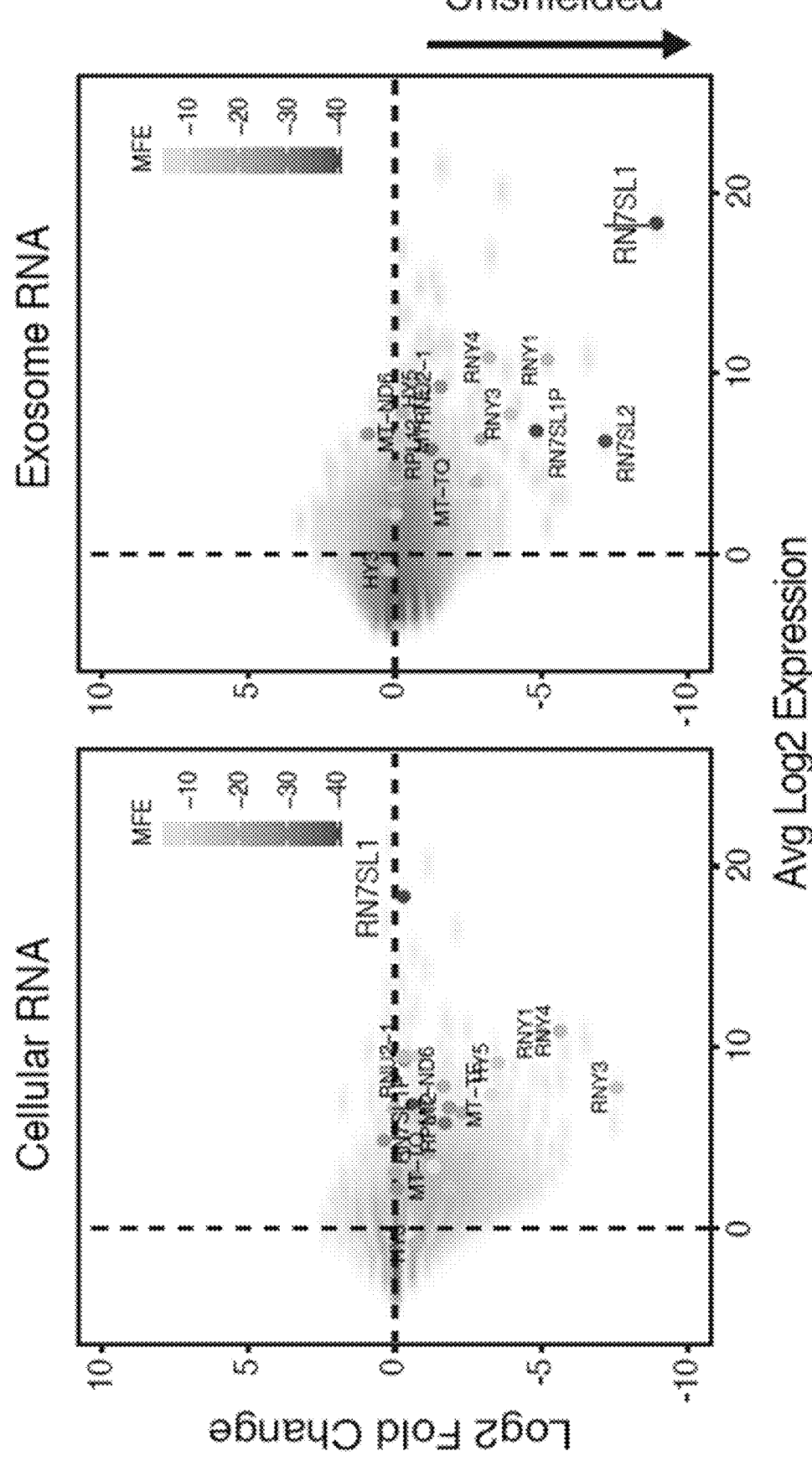

Exosome RNA had a higher amount of unshielded RN7SL1 compared with cellular RNA (FIG. 14A). RN7SL1 ribosomal binding proteins (RBP) SRP9 and SRP14 were absent in exosomes but present in the ctyoplasm of cells (FIG. 14B). Over expression of SRP9/14 in the stromal cells to drive it into the exosomes increased shielding of RN7SL1 in exosomes (FIG. 14C) and interfered with exosomes produced from these stromal cells to stimulate anti-viral activity (FIG. 14D)

Figures 15A, 15B:
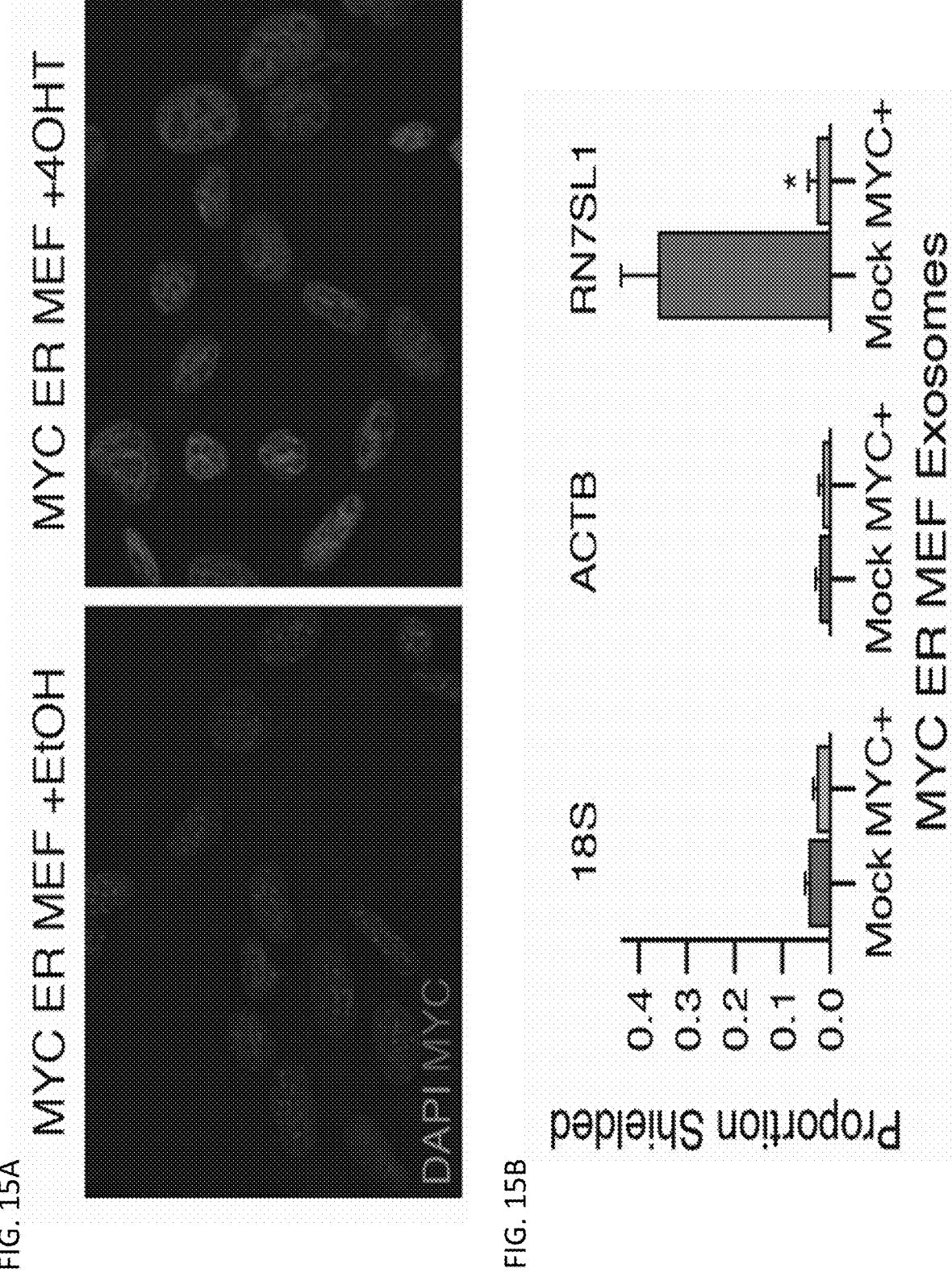
FIGS. 15A-15C are a series of plots and images illustrating how MYC regulates deployment of unshielded RN7SL1 in exosomes.
Figure 15C:
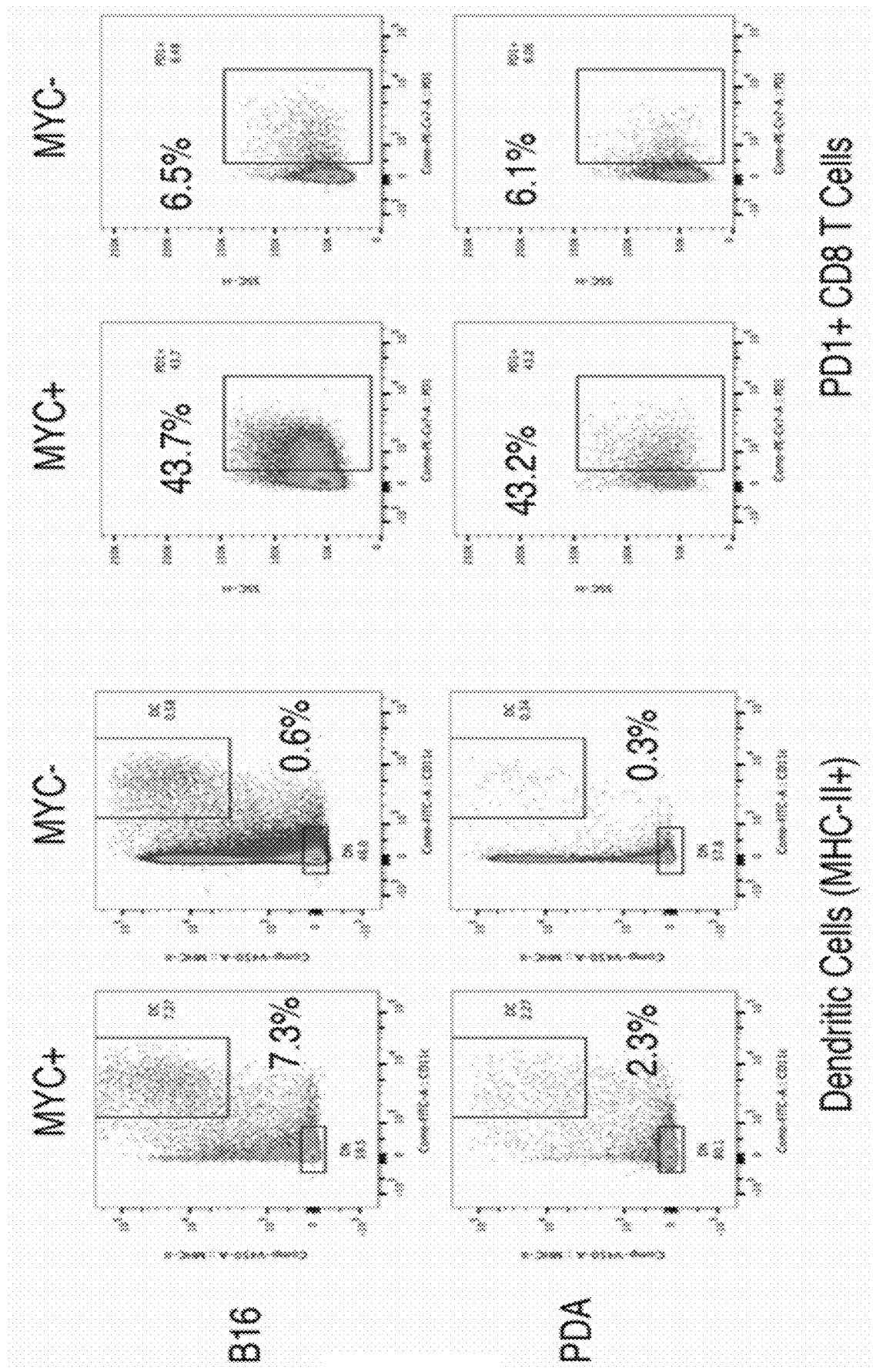
Figures 1, 15C:
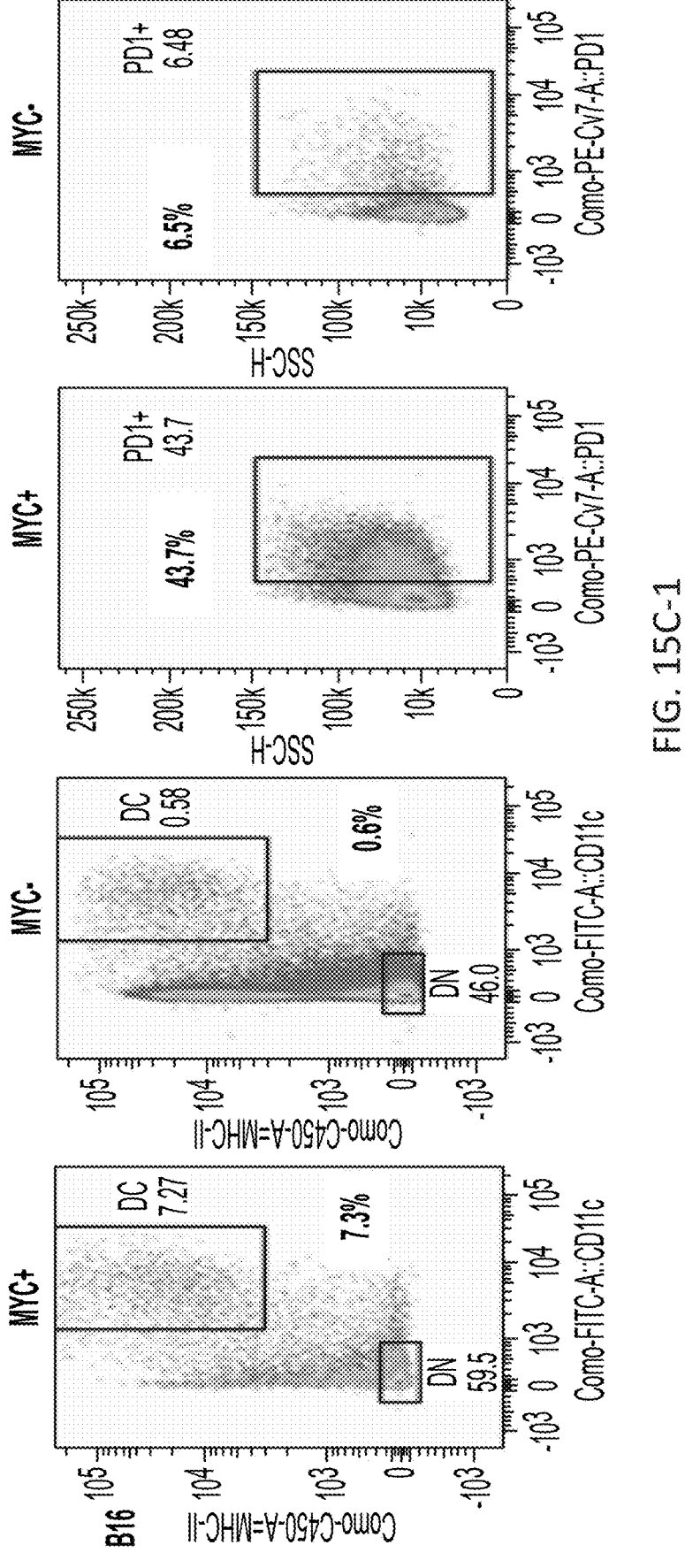
Figures 2, 15C:
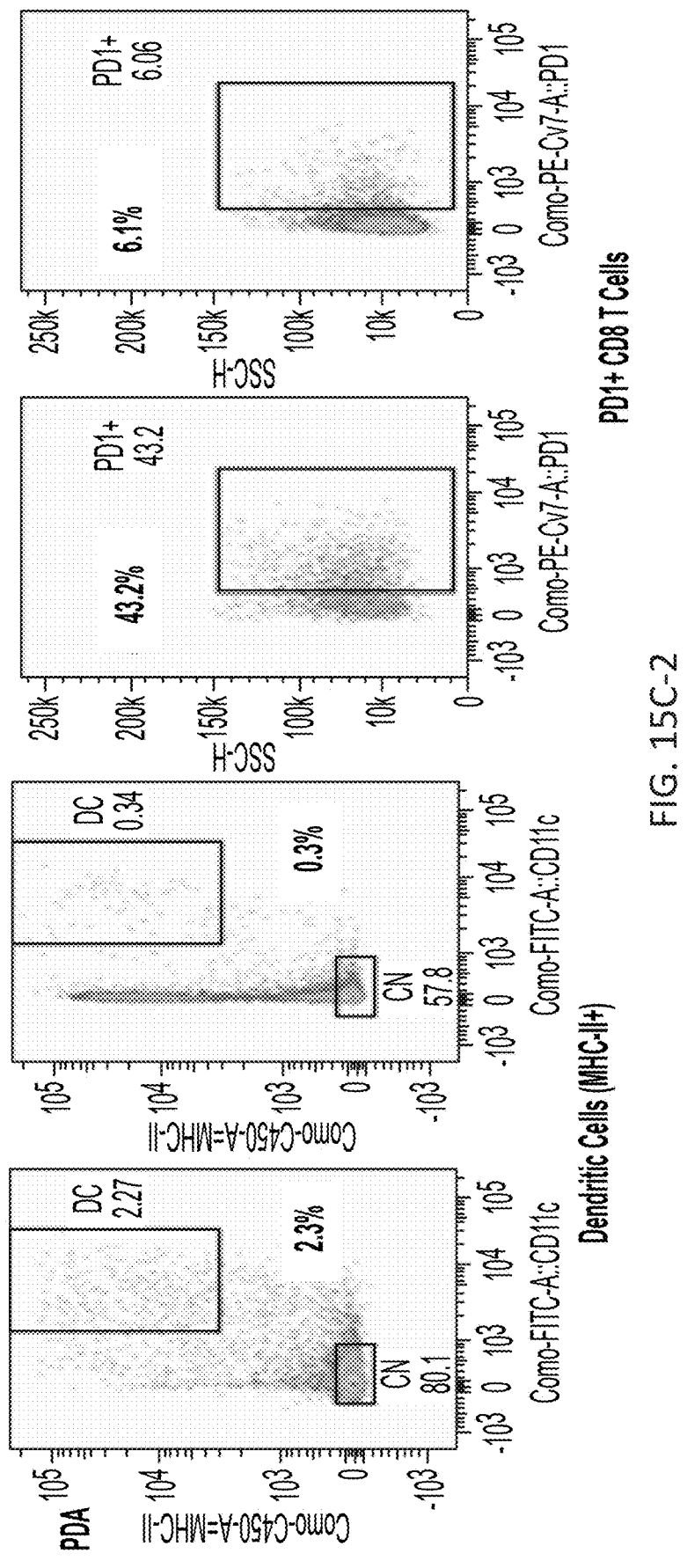

FIGS. 15A-15C show how MYC regulates deployment of unshielded RN7SL1 in exosomes. FIG. 15A shows nuclear translocation of MYC after activation. FIG. 15B shows this unshielded RN7SL1 in exosomes. FIG. 15C shows how these exosomes when injected into mice can then increase intratumoral dendritic cells known to present tumor antigen and activated intratumoral T cells (B16 is melanoma model, and PDA is pancreatic cancer model).

Figures 16A, 16B:
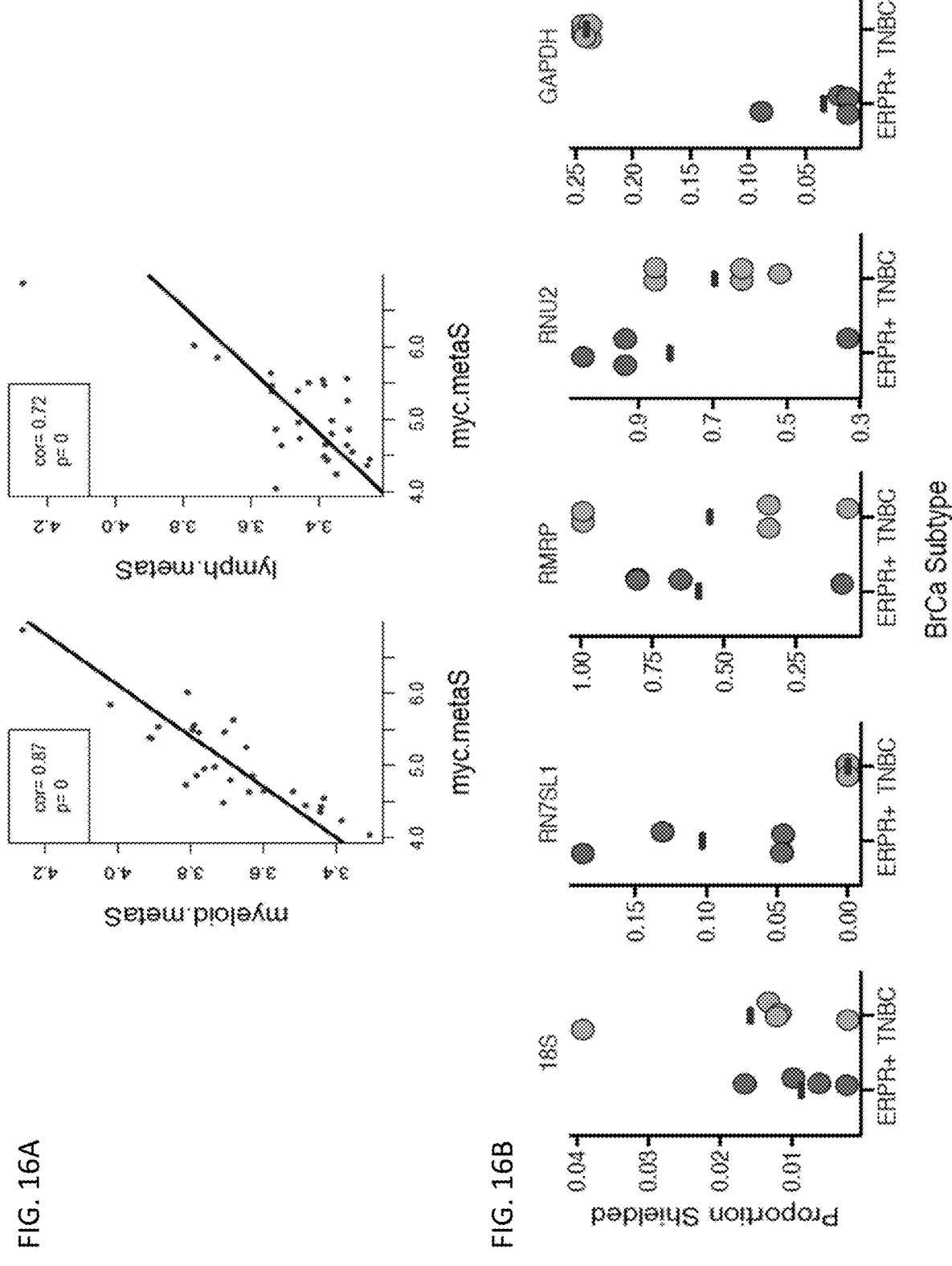
FIGS. 16A-16B are a series of plots illustrating data from breast cancer patients.

Correlations between MYC target genes in stromal cells with myeloid and lymphoid genes (surrogate for the immune cells themselves) in the tumor of breast cancer patients are shown in FIG. 16A. Unshielded RN7SL1 is detected in serum exosomes from triple negative breast cancer (TNBC) patients (FIG. 16B) (n=4 each group). RMRP and RNU2 are MYC regulated as well but are not unshielded because they are not regulated by the RBP SRP9/14.

Figure 17A:
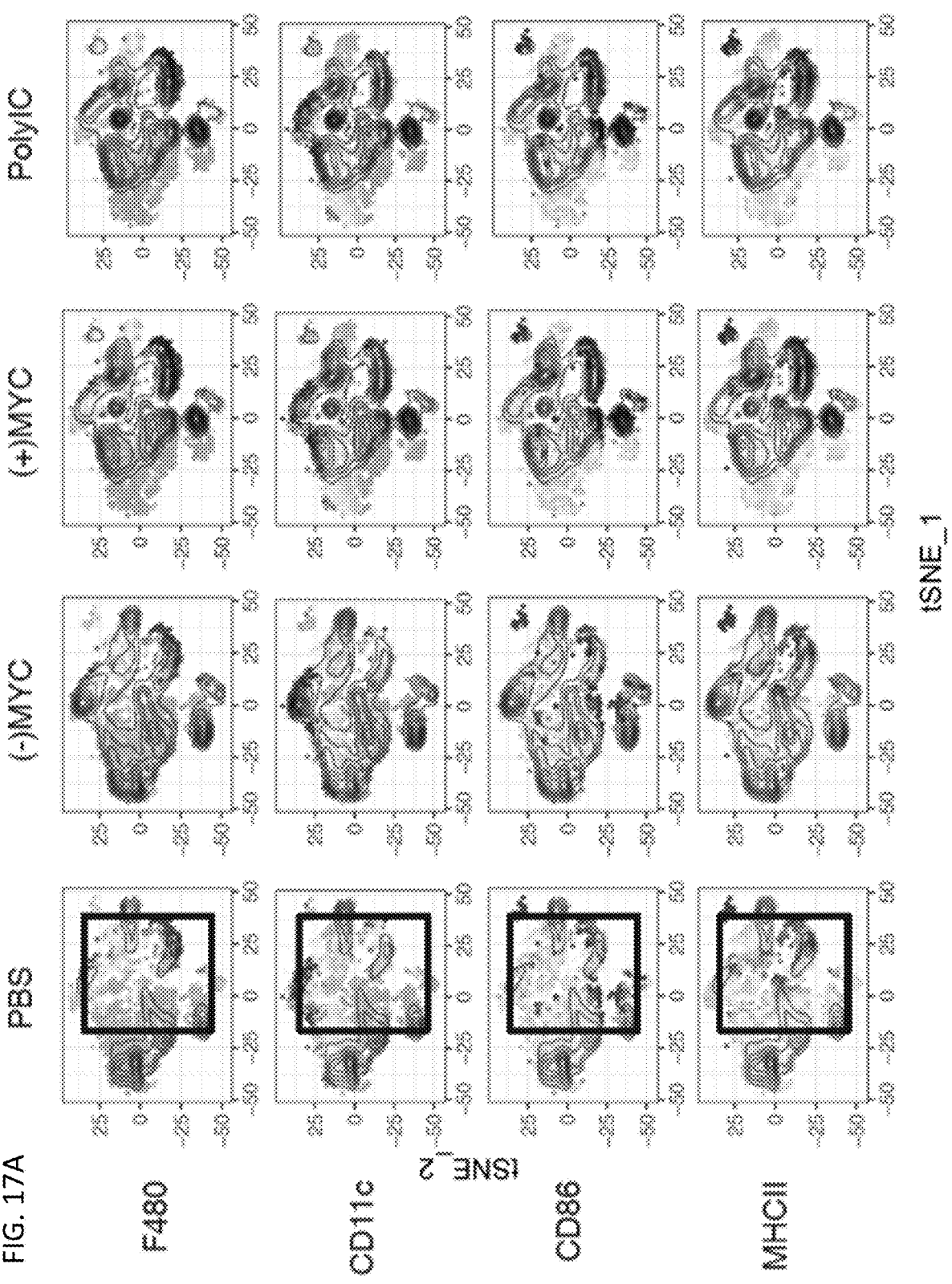
FIGS. 17A-17B are a series of plots illustrating DAMP activity of RN7SL1. Shows how exosomes from MYC-activated stromal cells causes myeloid/dendritic cell maturation and activation in the spleen upon intravenous injection into mice. Note population in the burgundy colored box (MHCII+ and CD86+, which are activation markers). Exosomes from MYC activated stromal cells compare favorably to a synthetic polyIC positive control known to activate myeloid/DC cells. Similar results are seen upon injection of liposome-encapsulated RN7SL1.
Figure 17B:
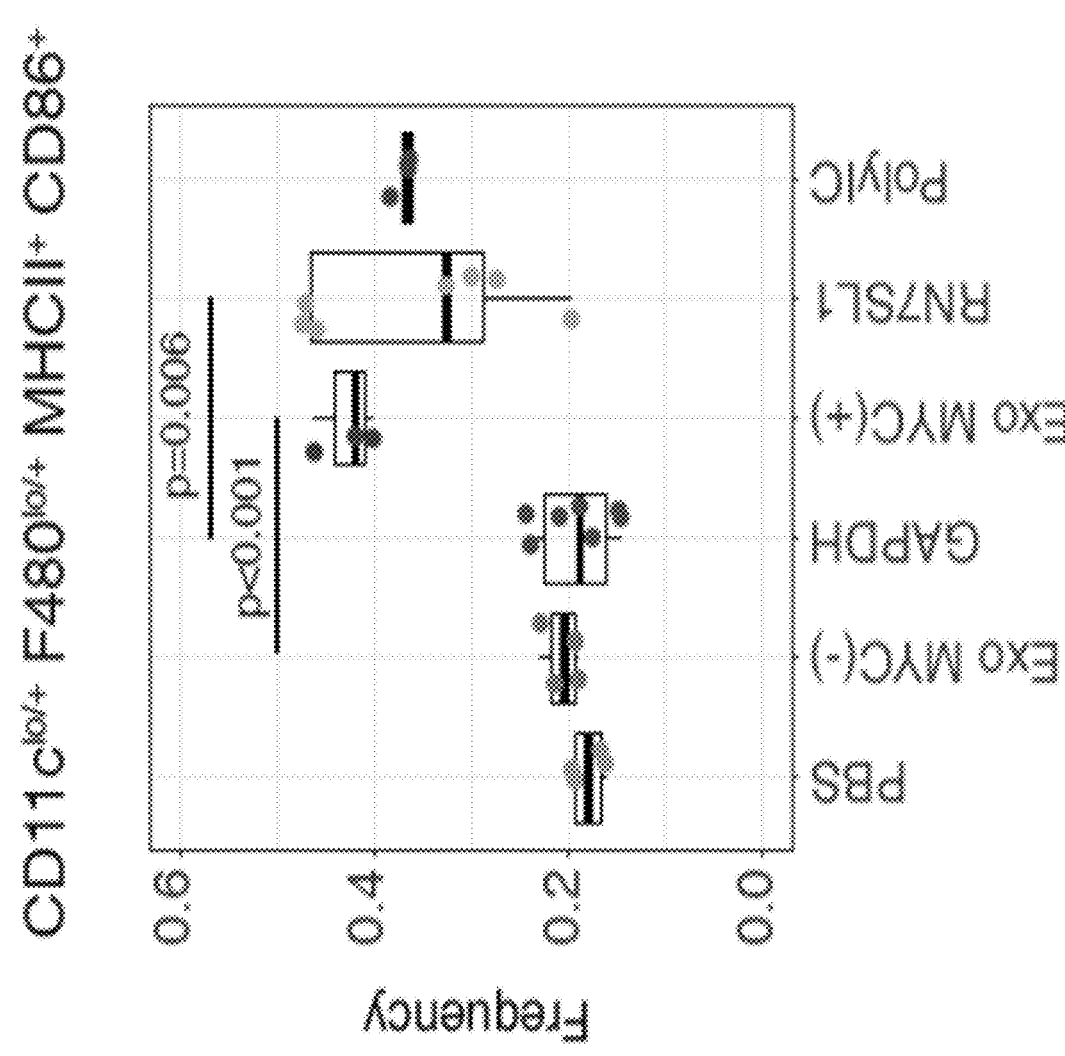

DAMP activity of RN7SL1 is shown in FIGS. 17A-17B. Exosomes from MYC-activated stromal cells causes myeloid/dendritic cell maturation and activation in the spleen upon intravenous injection into mice. Note population in the burgundy colored box (MHCII+ and CD86+, which are activation markers). Exosomes from MYC activated stromal cells compared favorably to a synthetic polyIC positive control known to activate myeloid/DC cells. Similar results are seen upon injection of liposome-encapsulated RN7SL1.

Figure 18A:
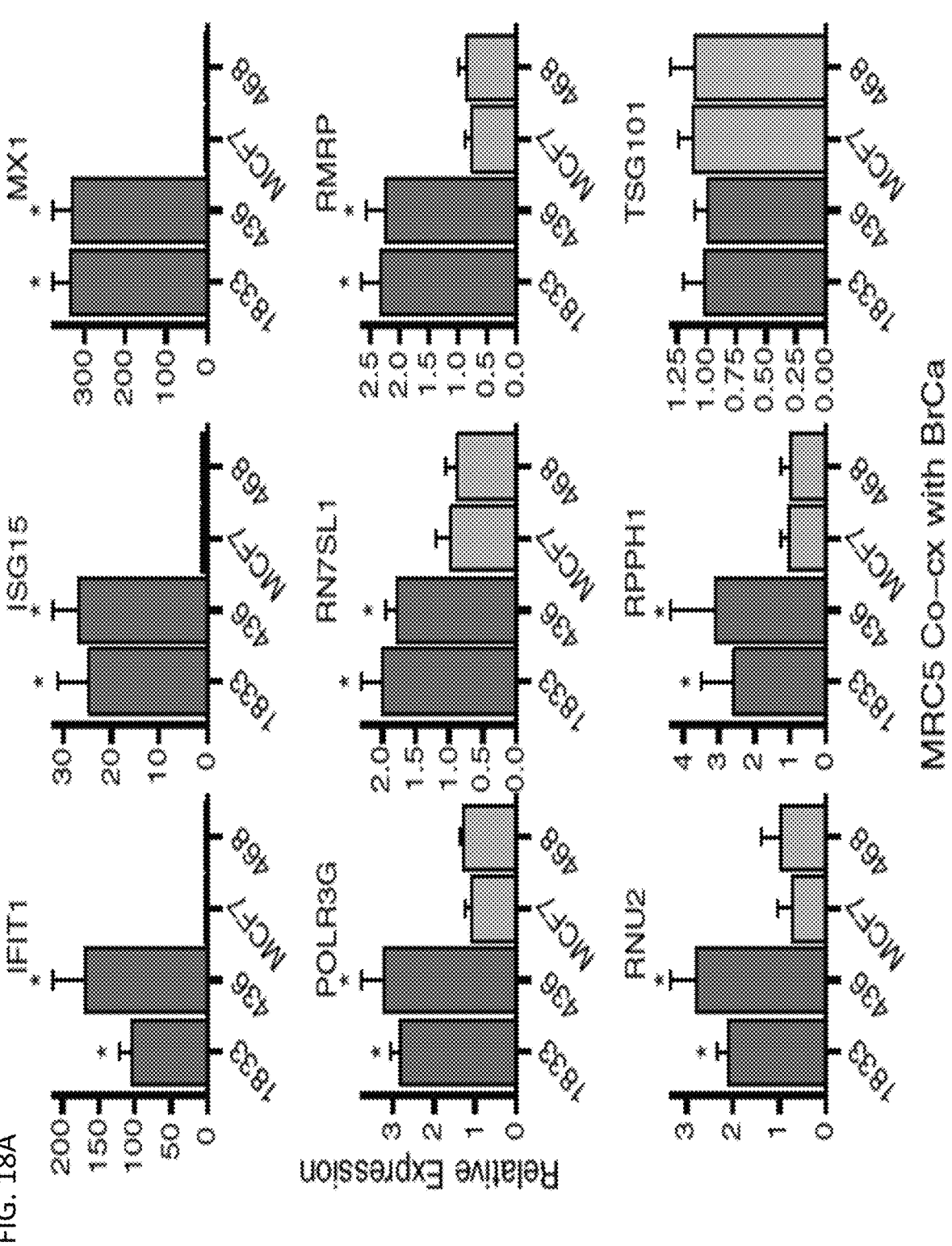
Figures 18E, 18F:
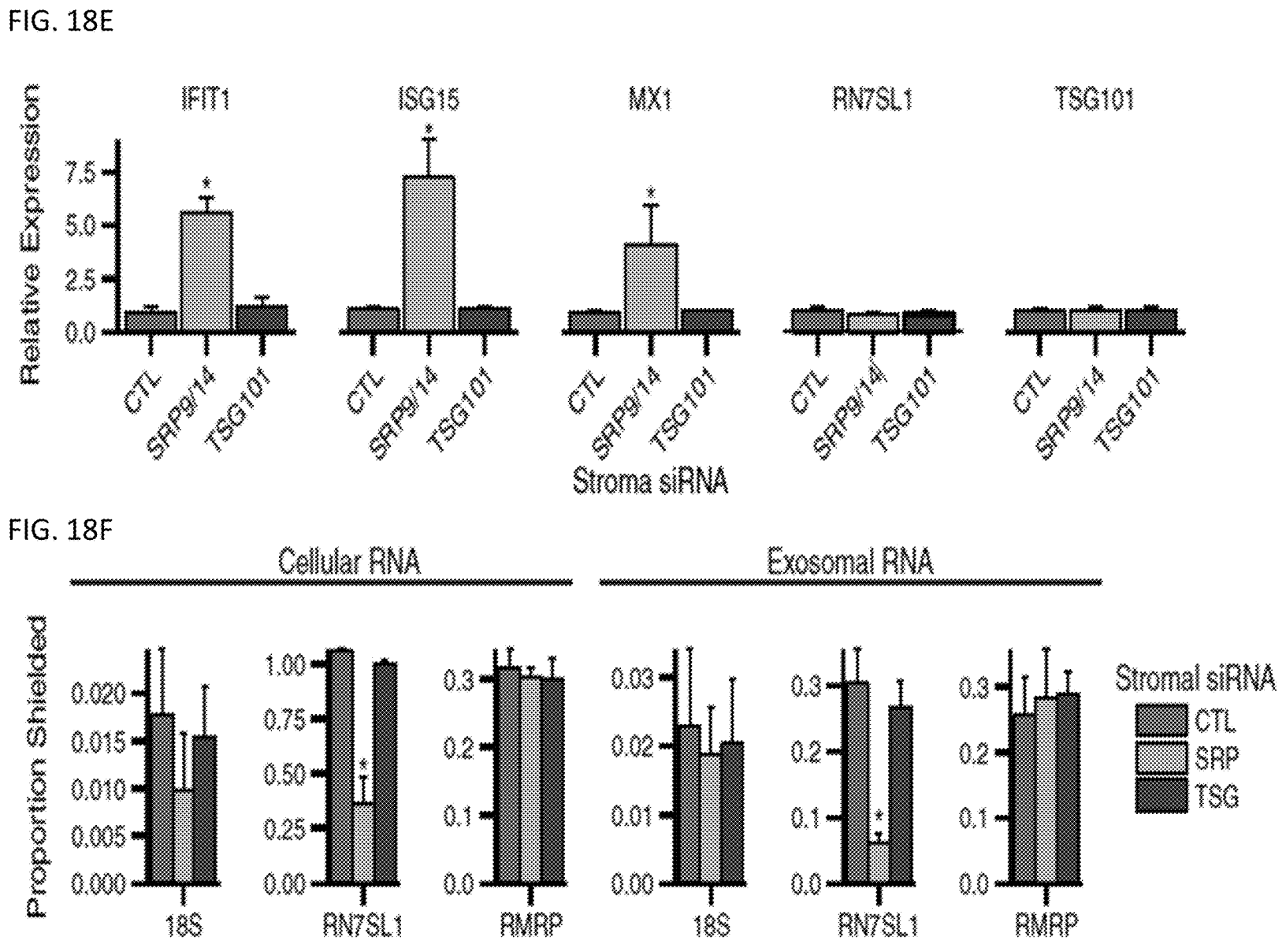

Disruption of the RBP (i.e. SRP9/14) for RN7SL1 in unactivated (mono-cultured) stromal cells (FIG. 18C) leads to increase in stimulatory activity of exosomes (FIG. 18D) and unshielding of RN7SL1 in exosomes (FIG. 18F).

Figures 19E, 19F, 19G:
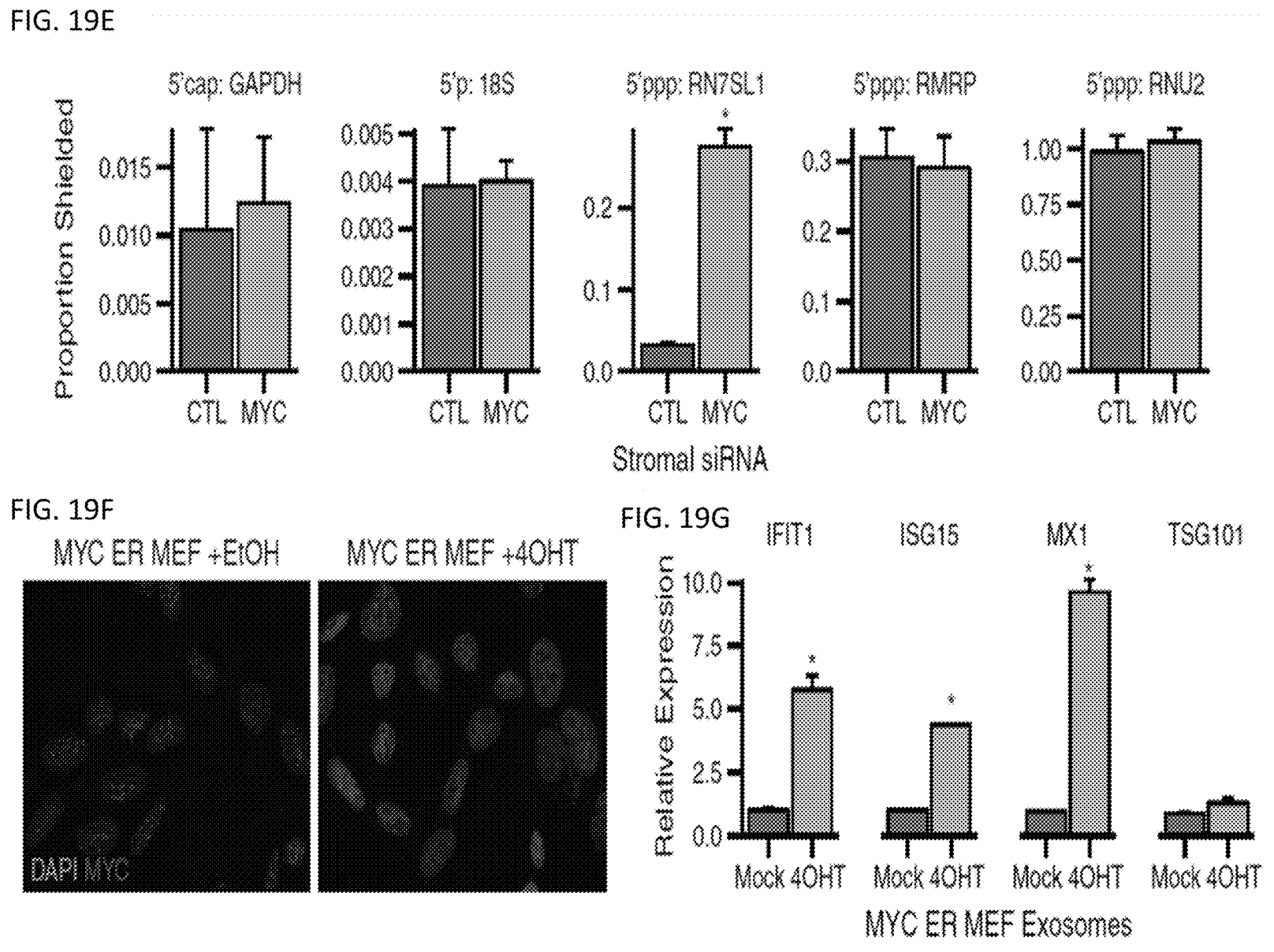

MYC is activated in stromal cells after breast cancer cell interaction (FIGS. 19A-19C) and is necessary to regulate RN7SL1 unshielding in exosomes (FIG. 19E) and subsequent stimulatory activity (FIG. 19D). Conversely, over-expression of MYC in stromal cells (FIG. 19F) is sufficient to unshielded RN7SL1 in exosomes (FIG. 19H) and promote its stimulatory activity (FIG. 19G). This is dependent on RNA POL3 (FIGS. 19I-19J).

Figures 20A, 20B:
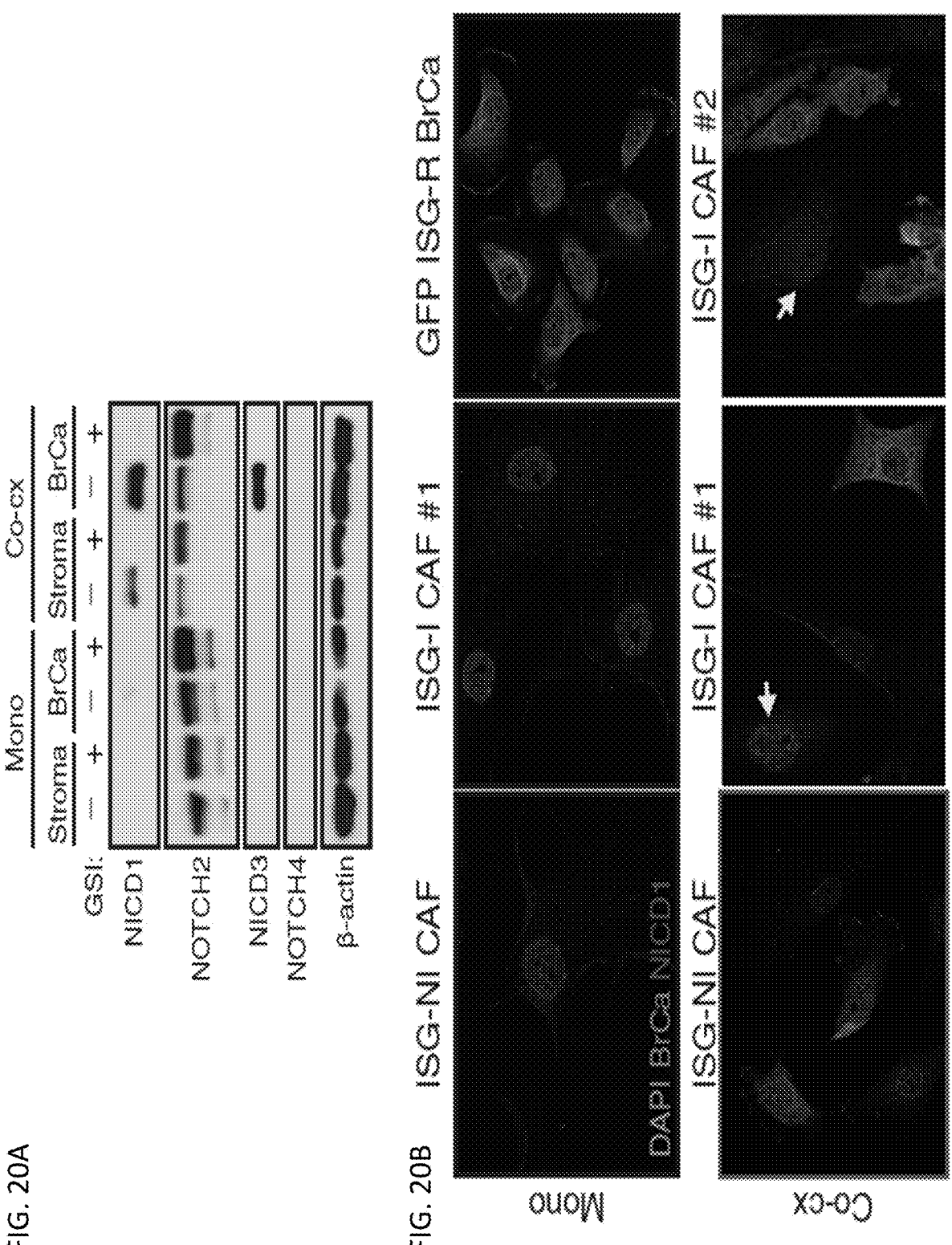
FIGS. 20A-20F series of plots and images illustrating stromal interaction with breast cancer results in stromal NOTCH1 activation (FIGS. 20A-20B), resulting in activated MYC (FIGS. 20C-20D). Anti-viral genes (ISGs), MYC target genes, and NOTCH target genes show co-regulated expression in human breast cancer tumors that have been separated into stromal and cancer cell compartments.
Figure 20C:
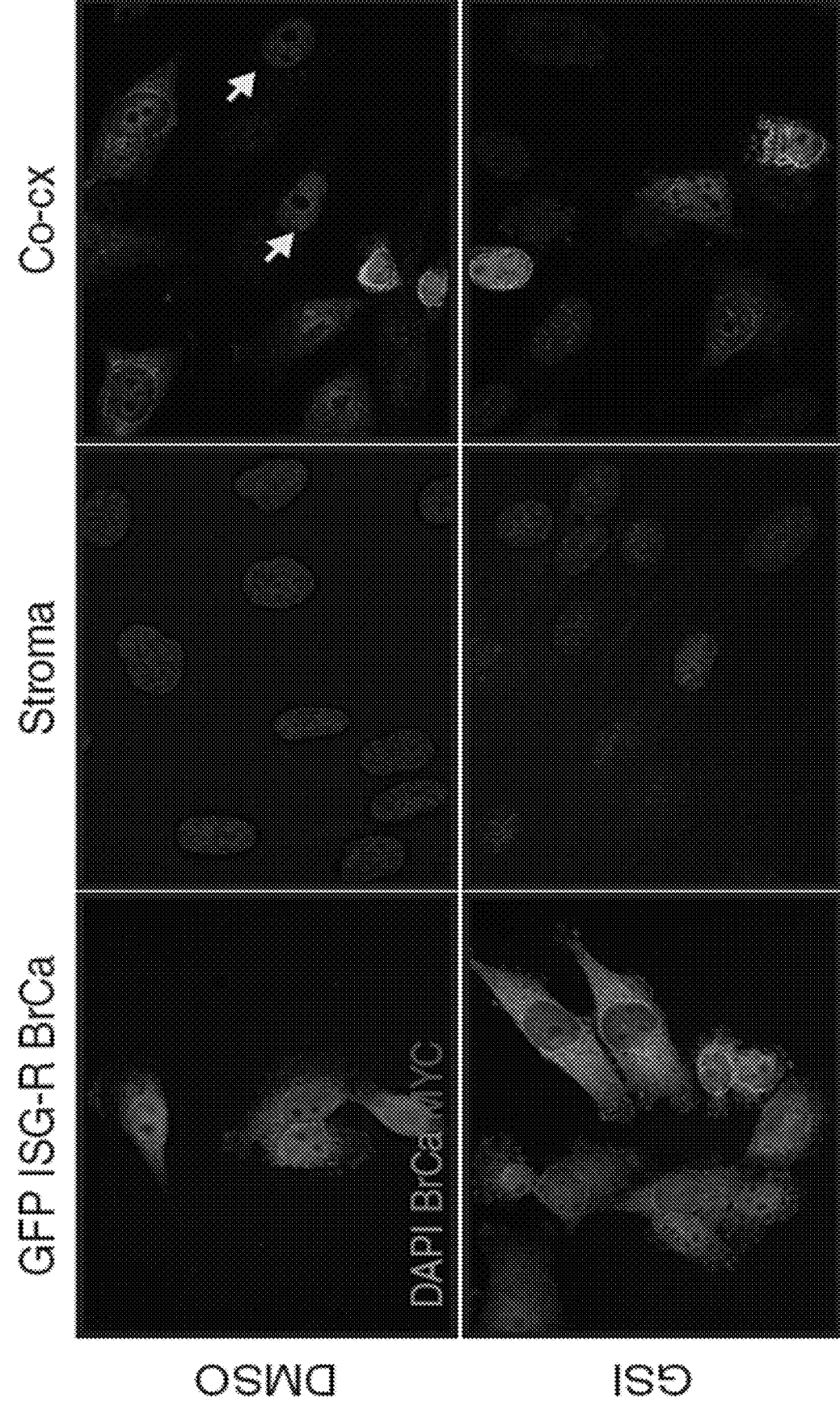
Figures 20D, 20E:
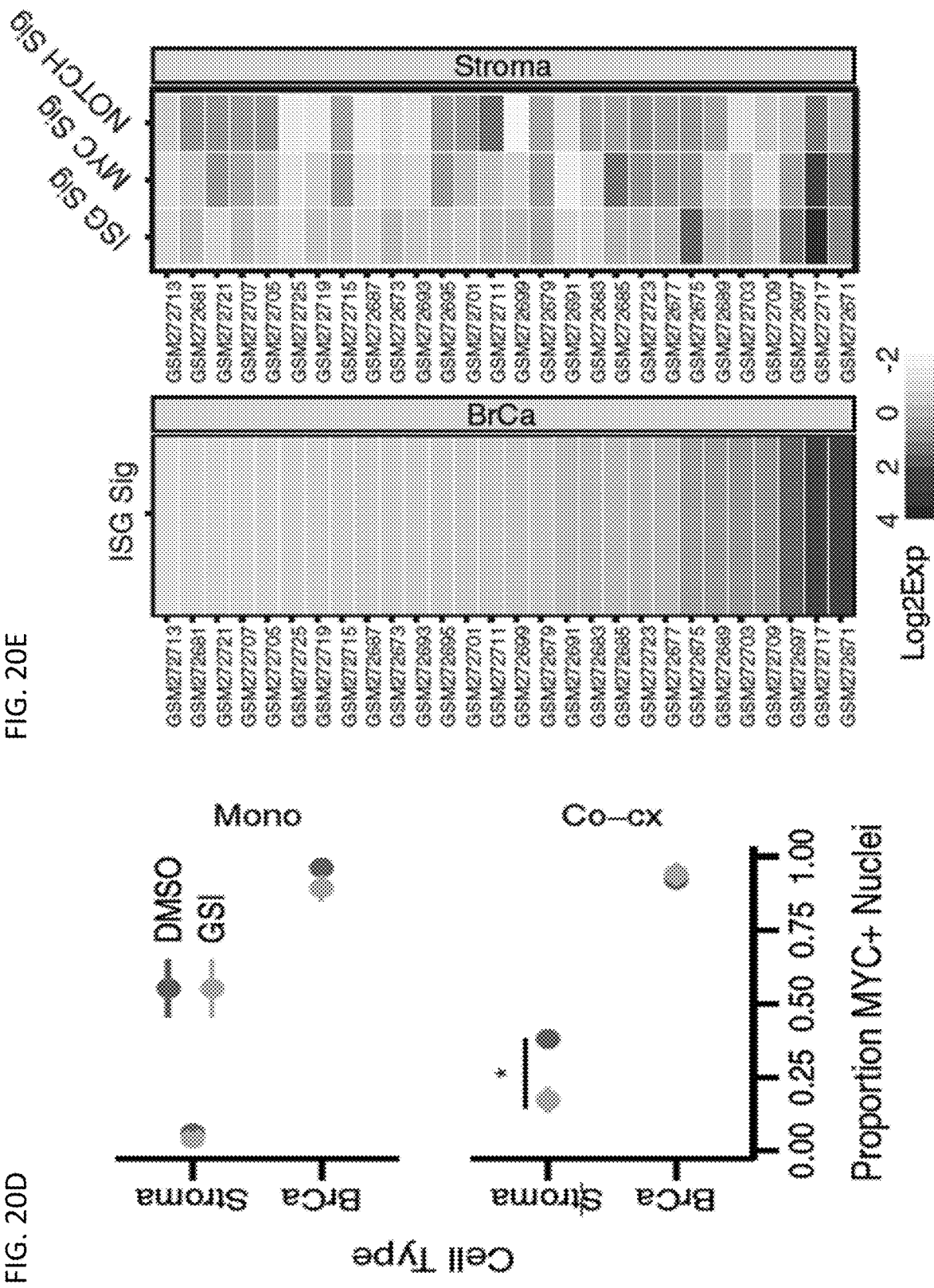
Figure 20F:
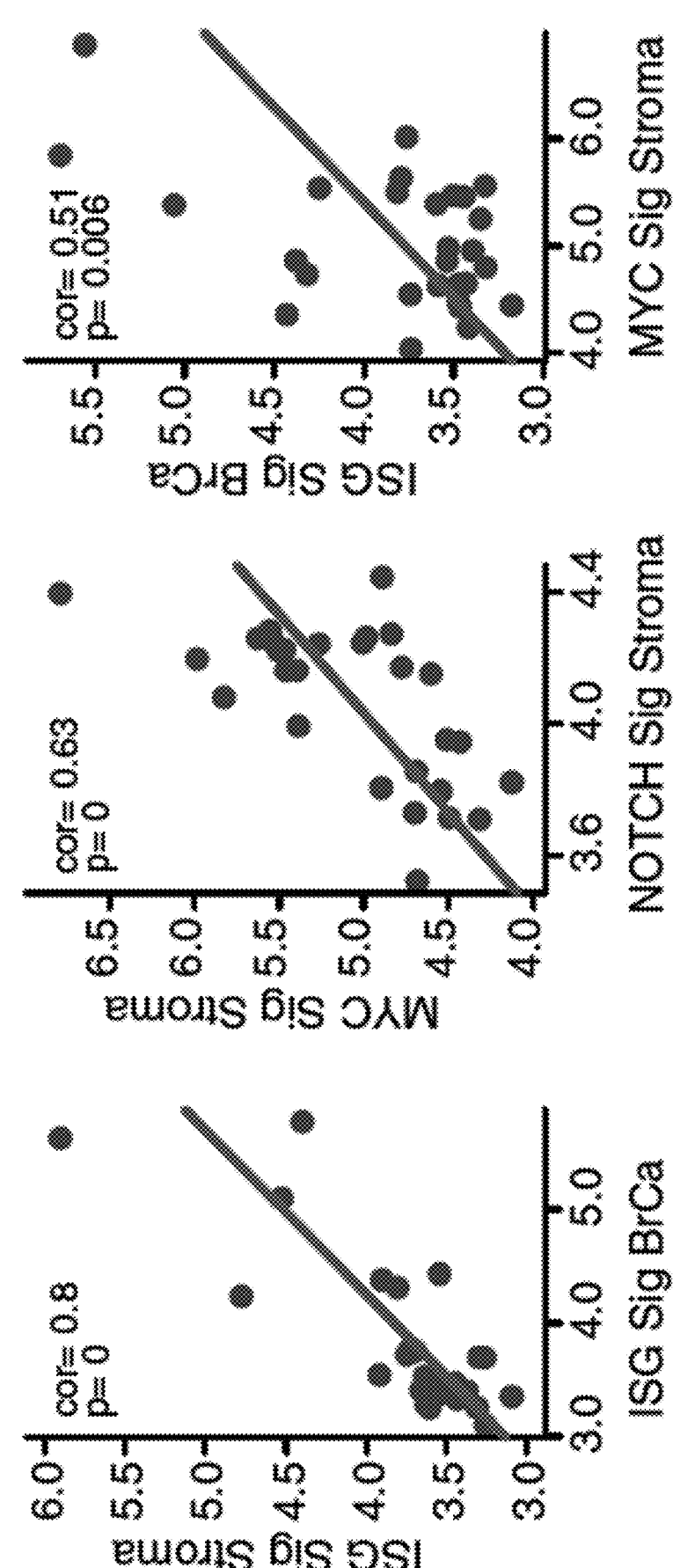

Stromal interaction with breast cancer results in stromal NOTCH1 activation (FIGS. 20A-20B), resulting in activated MYC (FIGS. 20C-20D). Anti-viral genes (ISGs), MYC target genes, and NOTCH target genes show co-regulated expression in human breast cancer tumors that have been separated into stromal and cancer cell compartments.

Example 10: Immunostimulatory RNA in the Tumor Microenvironment

Figures 32A, 32B:
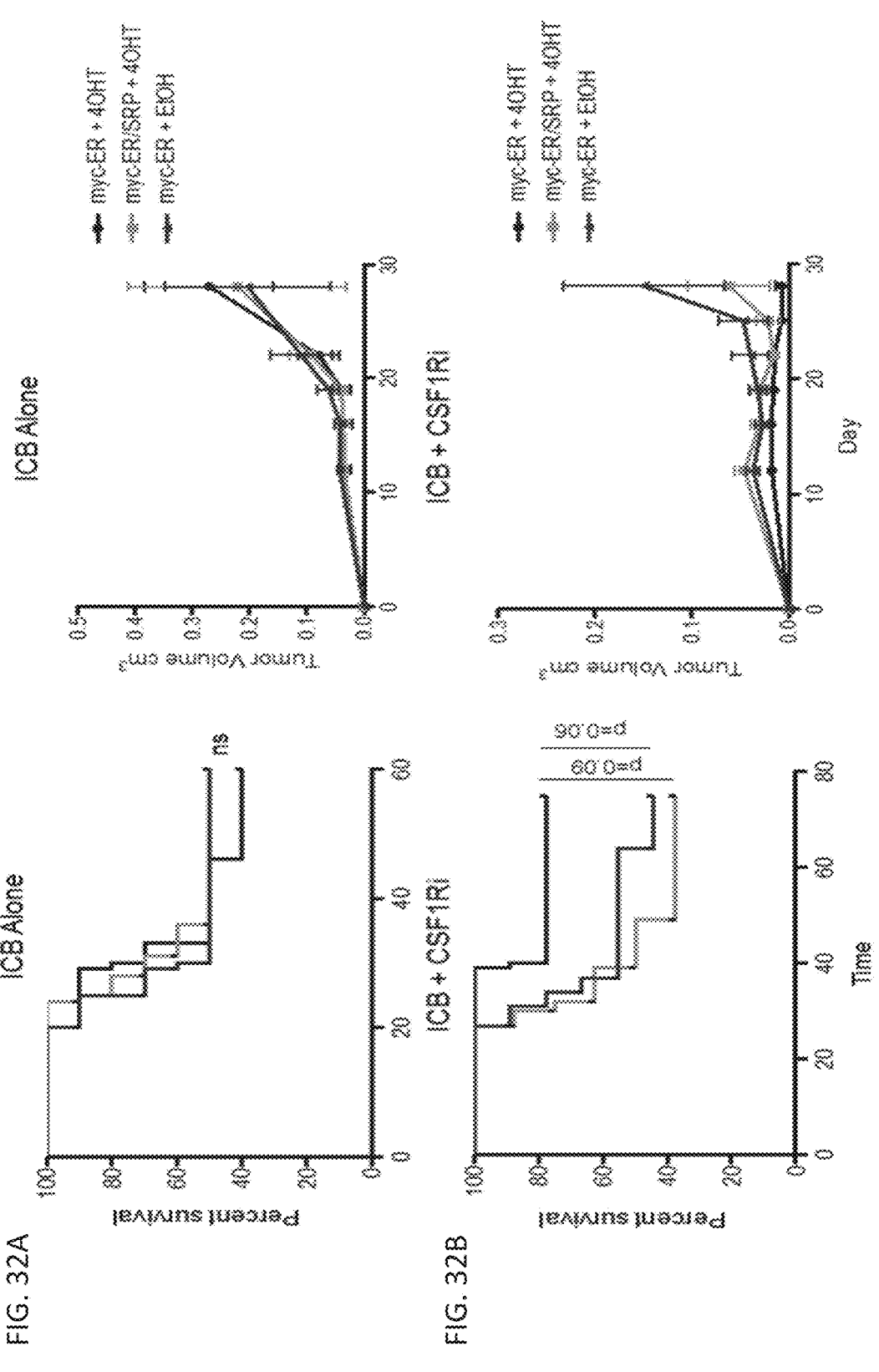
FIGS. 32A-32C are a series of plots illustrating CSF1R inhibition improves response to inhibitory checkpoint blockade in tumors with high levels of unshielded 7SL. Data from mice implanted with tumors as previously described and treated with aCTLA4 and aPD1 blocking antibody (FIG. 32A). CSF1Ri was added to aCTLA4 regimen and tumor growth was monitored (FIG. 32B).

Immune therapies have significantly improved outcomes for patients with poor prognosis in recent years, but are currently restricted to specific cancer types, and do not reach the majority of cancer patients. The highly structured RNA 7SL1 has recently been identified as capable of stimulating immune response genes in tumor cells following secretion by neighboring fibroblasts. Thus, unshielded 7SL1 in the tumor microenvironment may represent a novel intratumoral DAMP and/or an immune stimulus that contributes to immune checkpoint blockade (ICB) responsiveness (FIGS. 24A-24C, FIG. 29, FIG. 30). High levels of unshielded 7SL1 in the tumor microenvironment increased the frequency of DCs in vivo, and was correlated to enhanced T cell activation that is dependent on the signaling molecule MyD88 (FIGS. 31A-31B). MyD88 is downstream of several TLRs, implicating innate immune recognition that leads to adaptive immune activation. Identification of patients with high levels of unshielded RN7SL1 by TCGA RNA sequencing data also correlated to enhanced immune infiltrate and gene signatures that were enriched in responders to anti-PD1 and anti-CTLA4 therapy. However, the presence of 7SL1 also triggered the infiltration of macrophages and MDSCs into the tumor microenvironment in a compensatory manner (FIGS. 26A-26E). Blocking the suppressive polarization of these cells using a small molecule inhibitor of CSF1R revealed the immunostimulatory potential of 7SL1 in the context of immune checkpoint blockade therapy, and led to improved response in tumors with high levels of unshielded 7SL1 (FIGS. 32A-32B). For therapeutic purposes, 7SL1 RNA can be delivered directly to the tumor microenvironment.

Figures 24A, 24B, 24C:
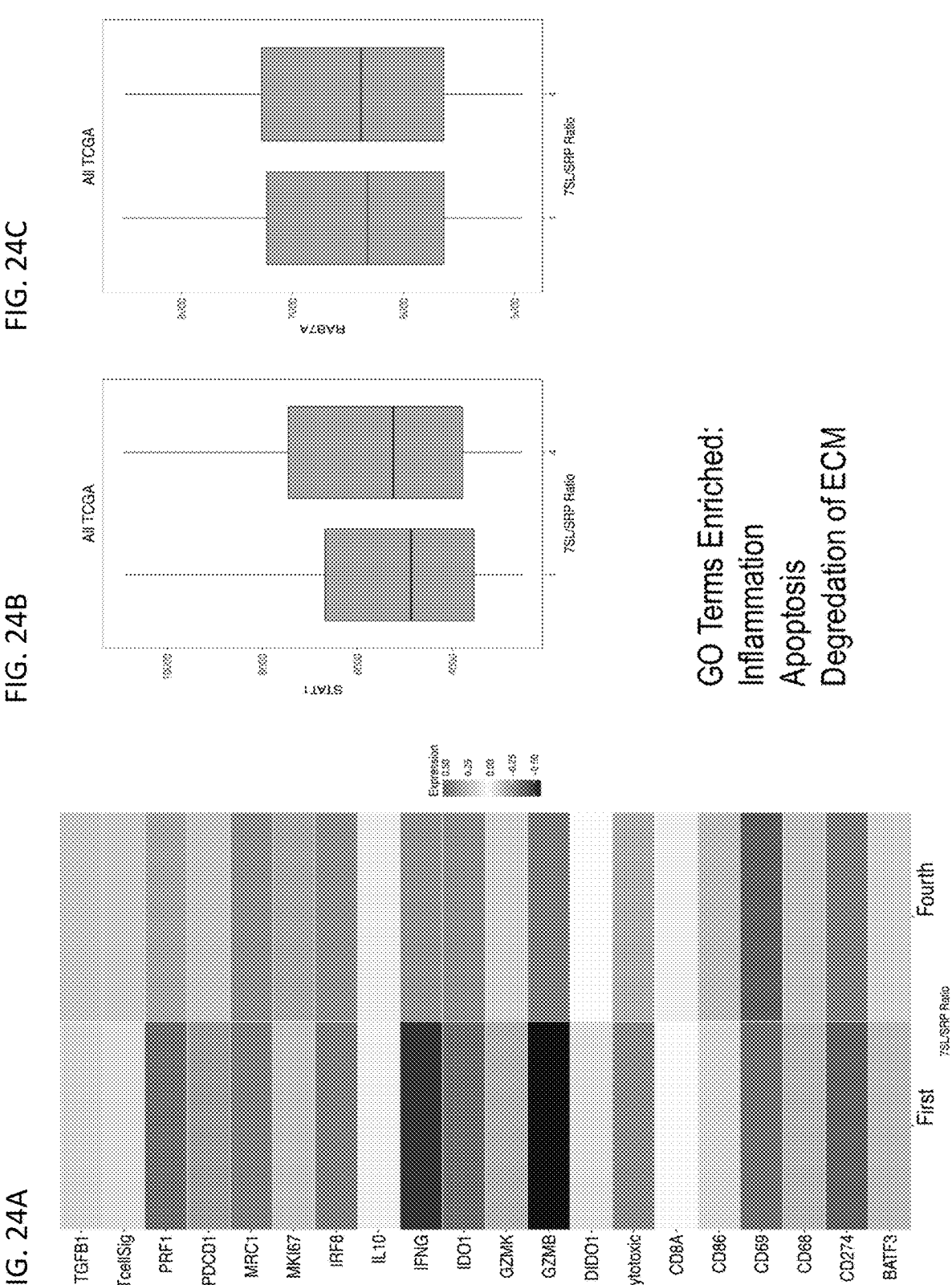
FIGS. 24A-24C are a series of plots showing TCGA data reflects experimental changes observed in murine models. RNA-Seq data from patient samples available in the TCGA data set were assigned to quartiles by level of SRP shielding. This stratification was done by creating a ratio of RN7SL1 reads to SRP9 and SRP14 reads, as these SRP proteins have been experimentally demonstrated to block the immunogenicity of 7SL. Patients were separated into quartiles based on this ratio and then differences in gene expression were assessed between the highest lowest quartiles. False discovery rate was set by randomly sampling p values obtained by two tailed pairwise T test with multiple comparisons using a Holm correction for 1000 genes and allowing genes with p values below the 10th ranked p value in the random list to be considered differentially regulated. Gene ontology analysis was performed on the top 5 percent of differentially regulated genes using the metascape online interface, enriched terms of interest are listed.

TCGA data reflects experimental changes observed in murine models (FIGS. 24A-24C). RNA-Seq data from patient samples available in the TCGA data set were assigned to quartiles by level of SRP shielding. This stratification was done by creating a ratio of RN7SL 1 reads to SRP9 and SRP14 reads, as these SRP proteins have been experimentally demonstrated to block the immunogenicity of 7SL. Patients were separated into quartiles based on this ratio and then differences in gene expression were assessed between the highest and lowest quartiles (FIGS. 24A-24C). False discovery rate was set by randomly sampling p values obtained by two tailed pairwise T test with multiple comparisons using a Holm correction for 1000 genes and allowing genes with p values below the 10th ranked p value in the random list to be considered differentially regulated. Gene ontology analysis was performed on the top 5 percent of differentially regulated genes using the metascape online interface, enriched terms of interest are listed in FIG. 24A.

Figures 25A, 25B:
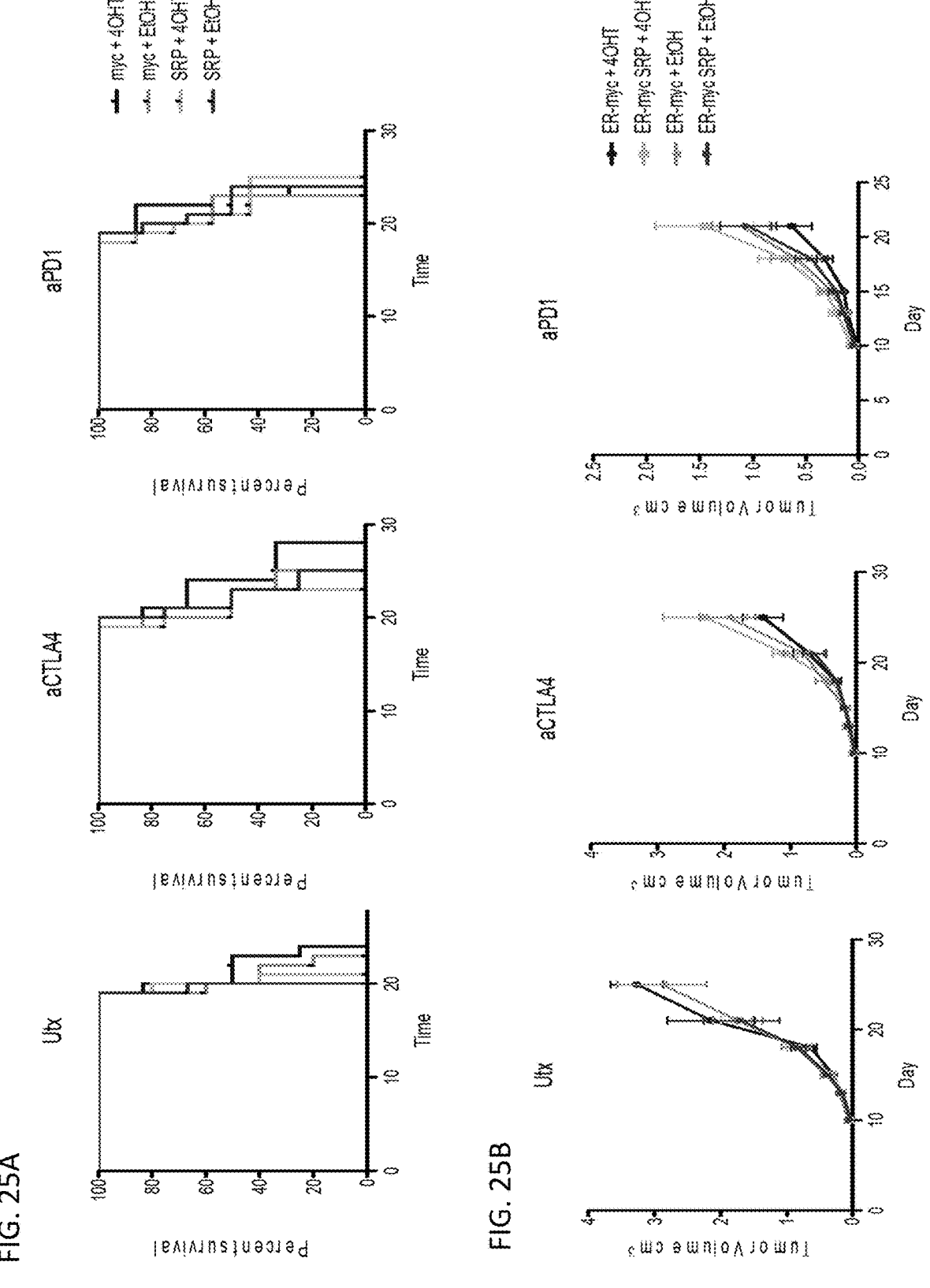
FIGS. 25A-25B are a series of plots illustrating unshielded 7SL does not significantly impact response to inhibitory checkpoint blockade therapy. WT C57BL/6 mice were injected with mixed tumors consisting of $5\times10^4$ B16-F10 tumor cells and $5\times10^4$ MEFs treated as indicated s.c. in the flank. Mice were subsequently treated with the indicated antibody (or not), and then tumor growth was monitored by caliper. Endpoint criteria was considered a tumor measurement of 1.5 cm in any direction.

Unshielded 7SL does not significantly impact response to inhibitory checkpoint blockade therapy (FIGS. 25A-25B). Wild type (WT) C57BL/6 mice were injected with $5 \times 10^4$ B16-F10 tumor cells subcutaneously in the flank with $5 \times 10^4$ MYC activated mouse embryonic fibroblasts (MEFs) or MYC activated MEFs co-expressing SRP9/14. MYC activation is inducible with 4-OHT and results in the secretion of exosomes containing unshielded 7SL1 RNA, while co-expression of SRP9/14 ensures the 7SL1 RNA remains relatively shielded, allowing measurement of the stimulatory capacity specifically of the unshielded form (Nabet B Y, et al. Cell. 2017; 170 (2): 352-366.e13). Mice were subsequently treated with the anti-CTLA-4 or anti-PD-1 antibody (or not), and then tumor growth was monitored by caliper. Endpoint criterion was considered a tumor measurement of 1.5 cm in any direction. As shown in FIGS. 25A and 25B, unshielded 7SL does not significantly impact response to anti-CTLA-4 or anti-PD-1 therapy.

Unshielded 7SL drives myeloid infiltration into the tumor microenvironment (FIGS. 26A-26E). Mice were implanted with tumors as described FIGS. 25A-25B. Tumors were harvested 13 days later and assessed for infiltration of macrophages or myeloid derived suppressor cells (MDSCs). Macrophages are considered Lin-, F4/80+, and CD11b+ cells. MDSCs are considered Lin-, F4/80-, CD11c-, CD11b+, and Ly6C+ cells. Tumors were treated with anti-CTLA4 blocking antibody (FIG. 26D) as described in FIGS. 25A and 25B, and tumors were harvested at d15 to measure M2 polarization of macrophages as marked by CD206. As shown in FIGS. 26A-26D, unshielded 7SL drives myeloid infiltration into the tumor microenvironment.

Figure 26A:
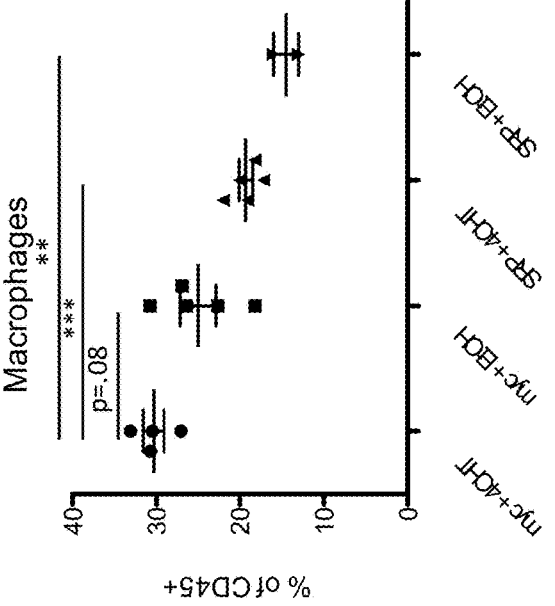
Figure 26B:
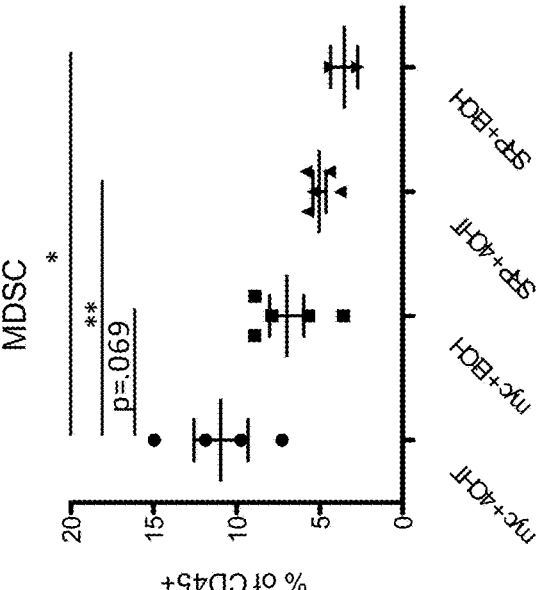
Figure 26C:
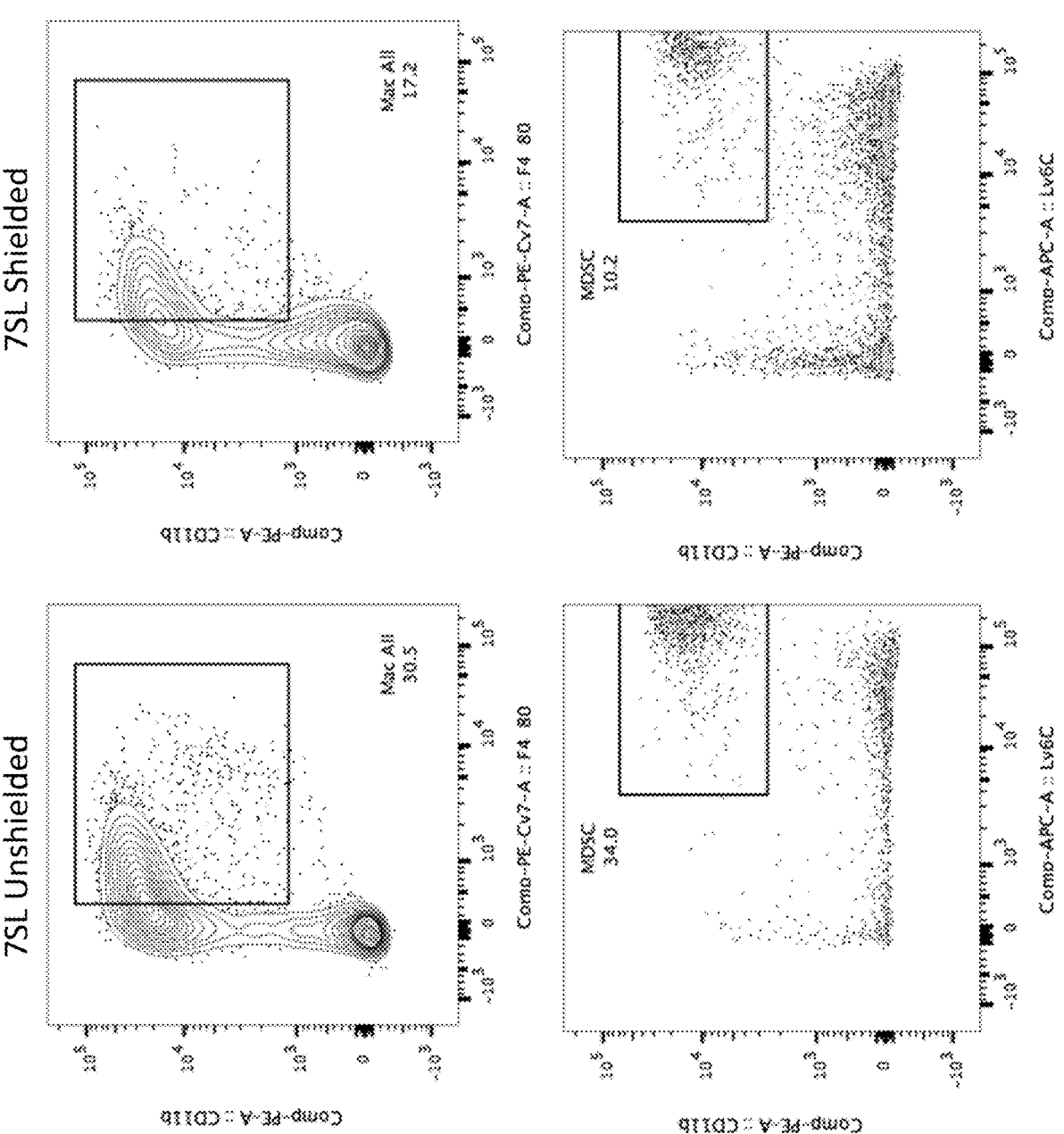
Figure 26D:
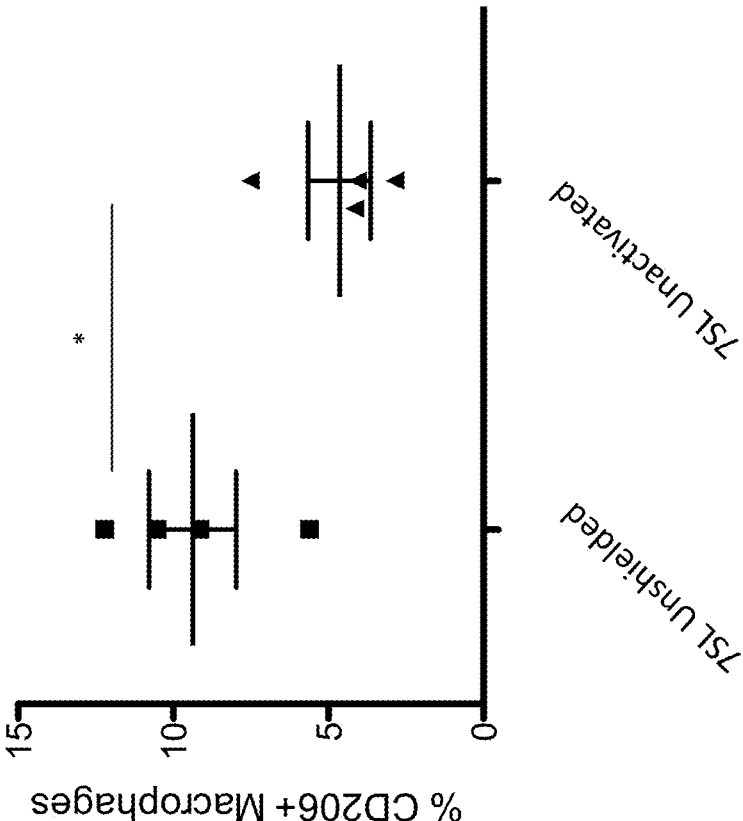
Figure 26E:
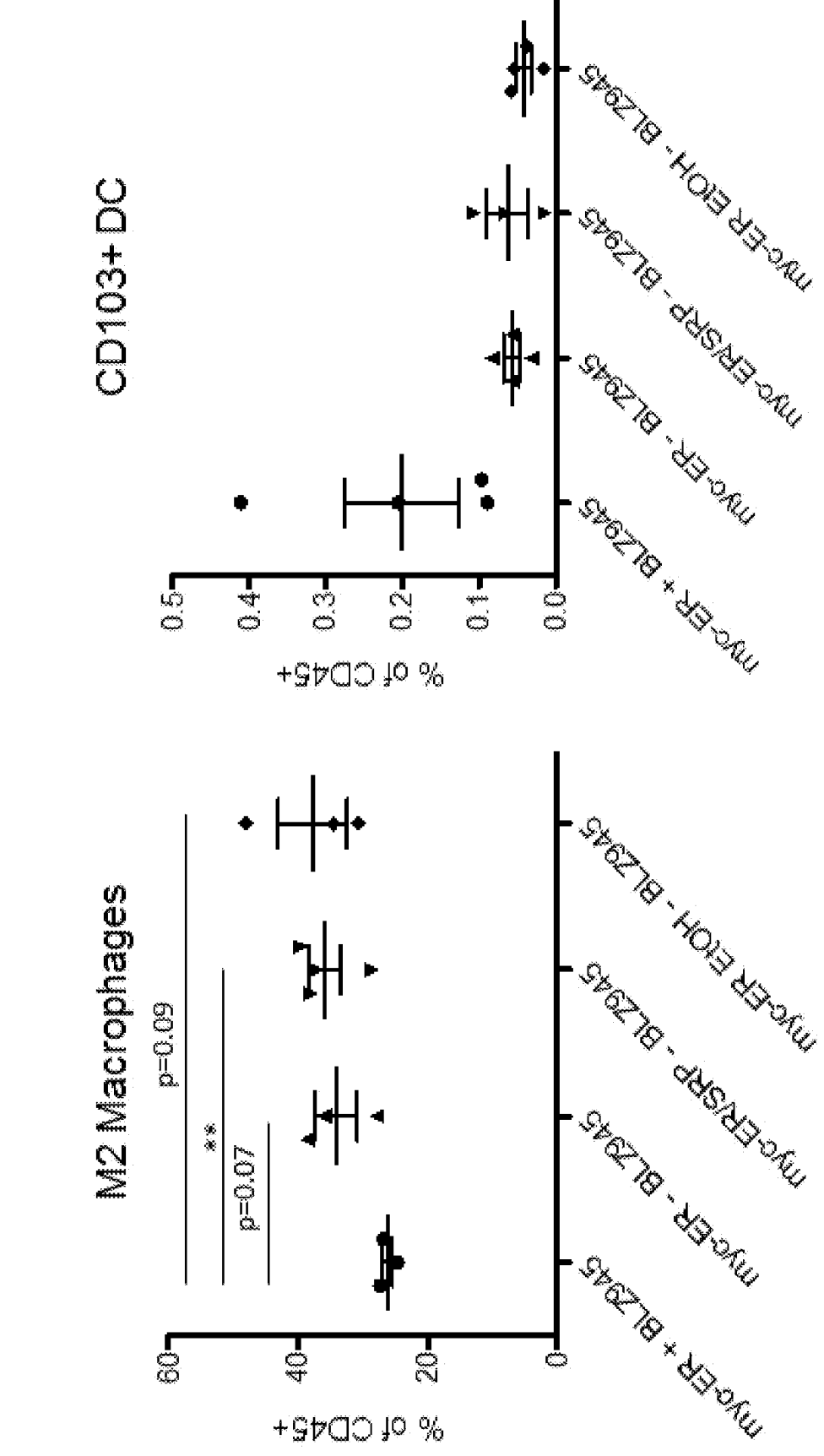

Furthermore, mice were implanted with the same tumors and subsequently treated with the CSF1R inhibitor BLZ945. Polarization of macrophages and frequency of CD103+DCs were tested. Inhibition of CSF1R signaling in the presence of high levels of unshielded 7SL RNA decreased the frequency of M2 macrophages found in the tumor (FIG. 26E) while improving the infiltration of cross-presenting CD103+ DCs (FIG. 26E).

Figures 27A, 27B, 27C:
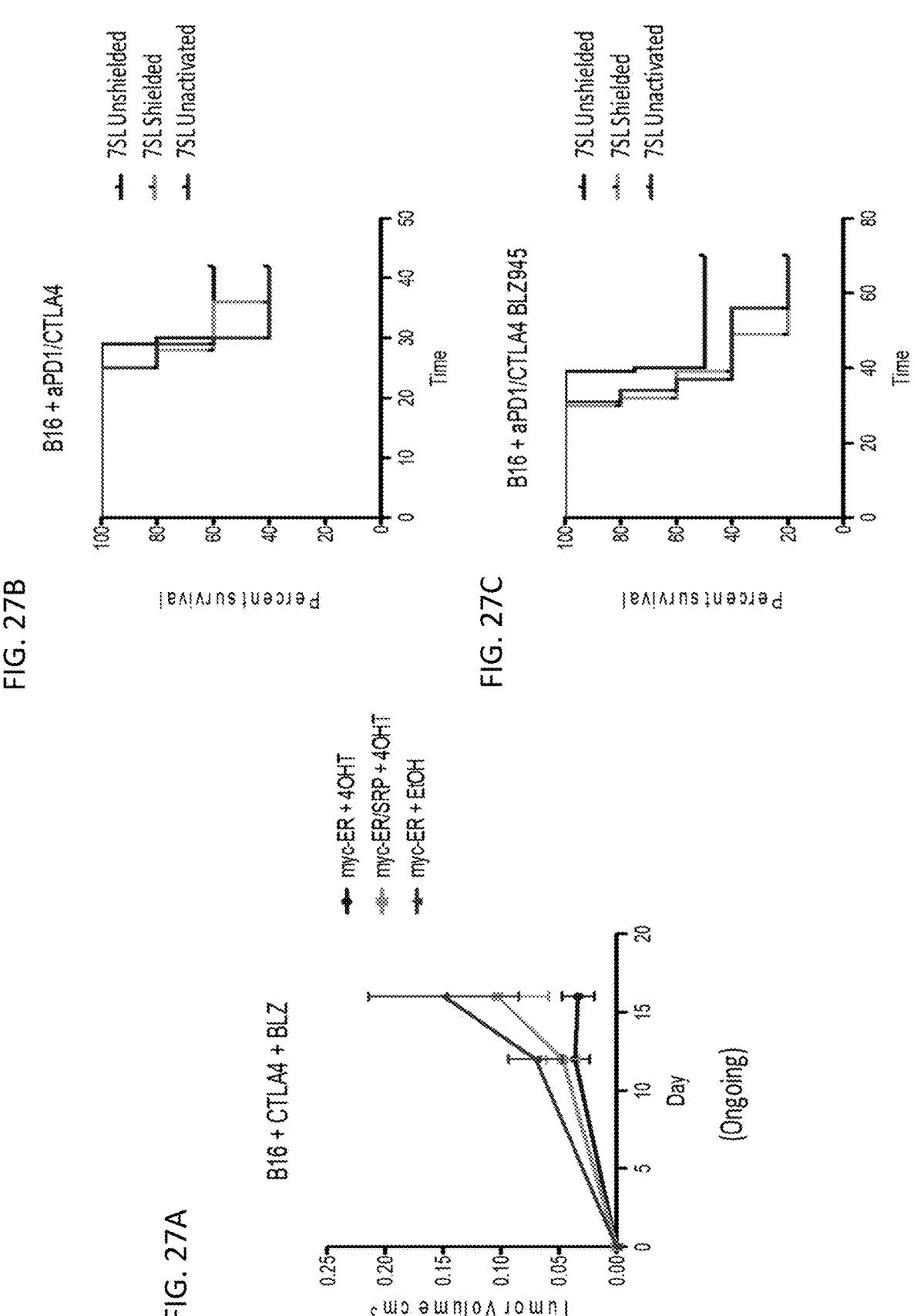
FIGS. 27A-27C are a series of plots illustrating inhibition of M2 polarization allows tumors with high levels of unshielded 7SL to respond more robustly to checkpoint blockade. Mice were implanted with tumors as in FIGS. 25A-25B and treated with CSF1R inhibitor BLZ945 (Novartis) every 2 days for 2 weeks starting at day 0 to prevent M2 polarization of infiltrating myeloid cells. Mice were additionally treated with aCTLA4 (left) or aCTLA4 and aPD1 (right) on day 5, 8, and 11. Tumor growth was monitored by caliper. 7SL Unshielded=myc-ER+4OHT, 7SL Shielded=myc-ER/SRP+4OHT, 7SL Unactivated=myc-ER+ EtOH.

Inhibition of M2 polarization allows tumors with high levels of unshielded 7SL to respond more robustly to checkpoint blockade (FIGS. 27A-27B). Tumors were implanted as described in FIGS. 25A-25B and treated with CSF1R inhibitor BLZ945 (Novartis) every 2 days for 2 weeks starting at day 0 to prevent M2 polarization of infiltrating myeloid cells. Mice were additionally treated with anti-CTLA4 (FIG. 27A) or anti-CTLA4 and anti-PD1 (FIGS. 27B and 27C) on days 5, 8, and 11. Tumor growth was monitored by caliper. As shown in FIGS. 27A and 27C, treatment with CSF1R inhibitor BLZ945 allows tumors with high levels of unshielded 7SL to respond more robustly to checkpoint blockade.

Figure 32C:
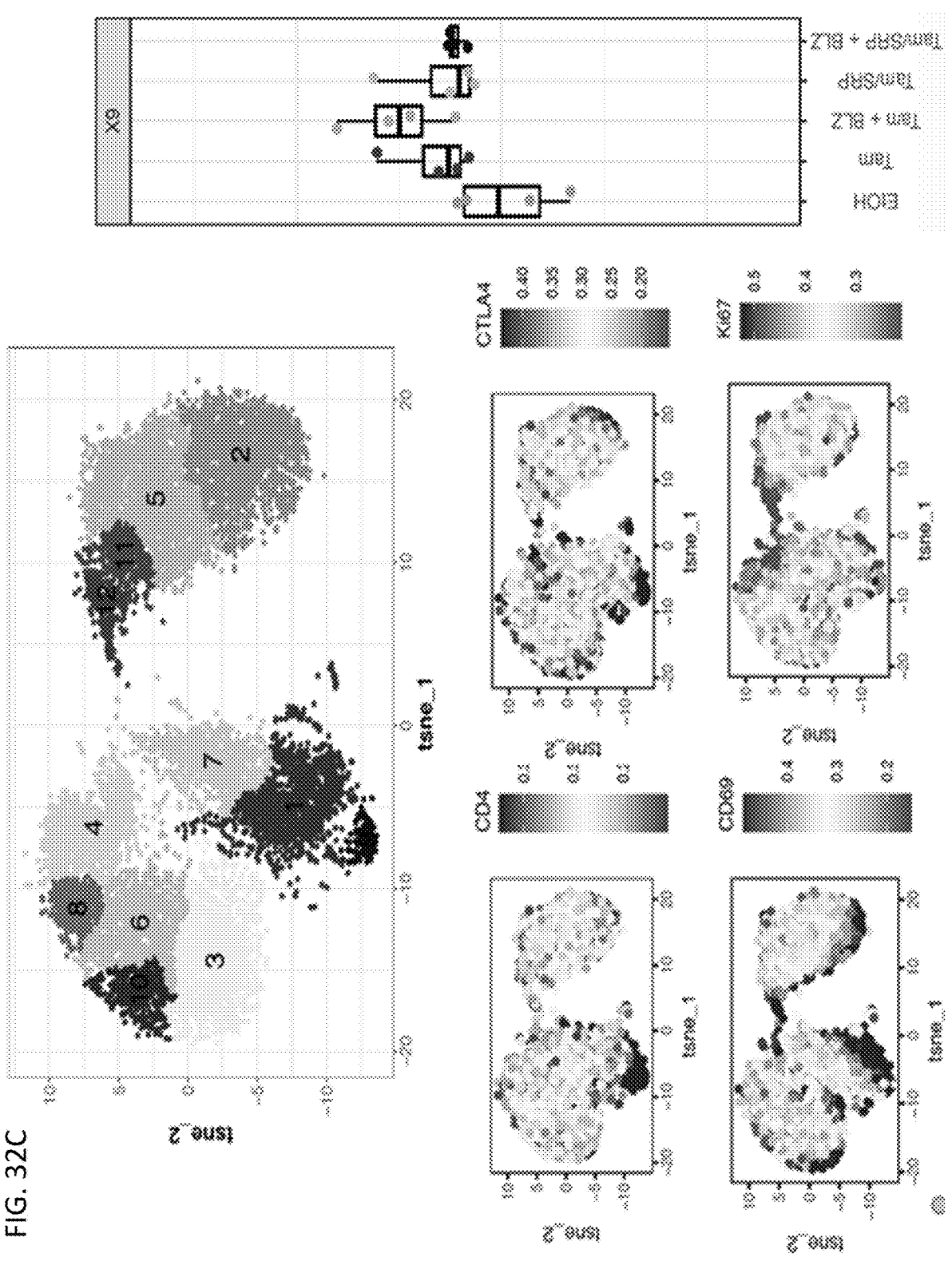

In addition, mice were implanted with tumors and treated with anti-CTLA4+/–CSF1Ri BLZ945. Tumors were harvested 13 days later and immune populations were assessed using an unbiased clustering of flow cytometry data. Activated CD4+ T cells stood out as markedly increased in tumors with high levels of unshielded 7SL that were also treated with CSF1Ri, indicating that CSF1R-driven myeloid polarization prevents optimal CD4+ T cell activation and polarization, and that this activation is important to response to ICB (FIG. 32C).

Figures 28A, 28B:
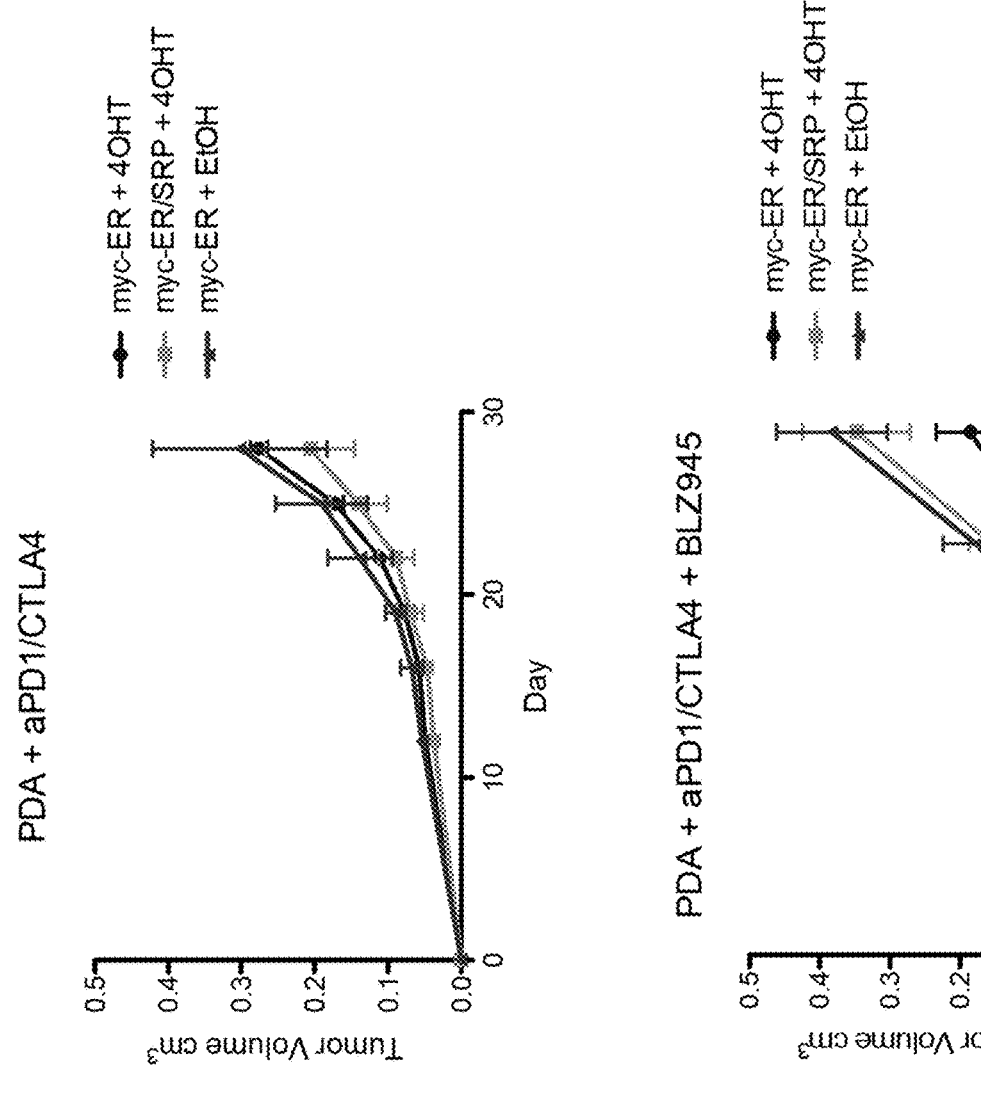
FIGS. 28A-28B are a set of plots illustrating CSF1R inhibition in combination with unshielded 7SL RNA sensitizes PDA tumors to ICB therapy. $1\times10^5$ PDA tumor cells were co-injected with $1\times10^5$ MEFs treated as indicated. Mice were then treated with aCTLA4+aPD1 (left) or aCTLA4+aPD1+BLZ945 (right) using treatment schedules outlined in FIGS. 27A-27C. Tumor growth was monitored by caliper.
Figure 29:
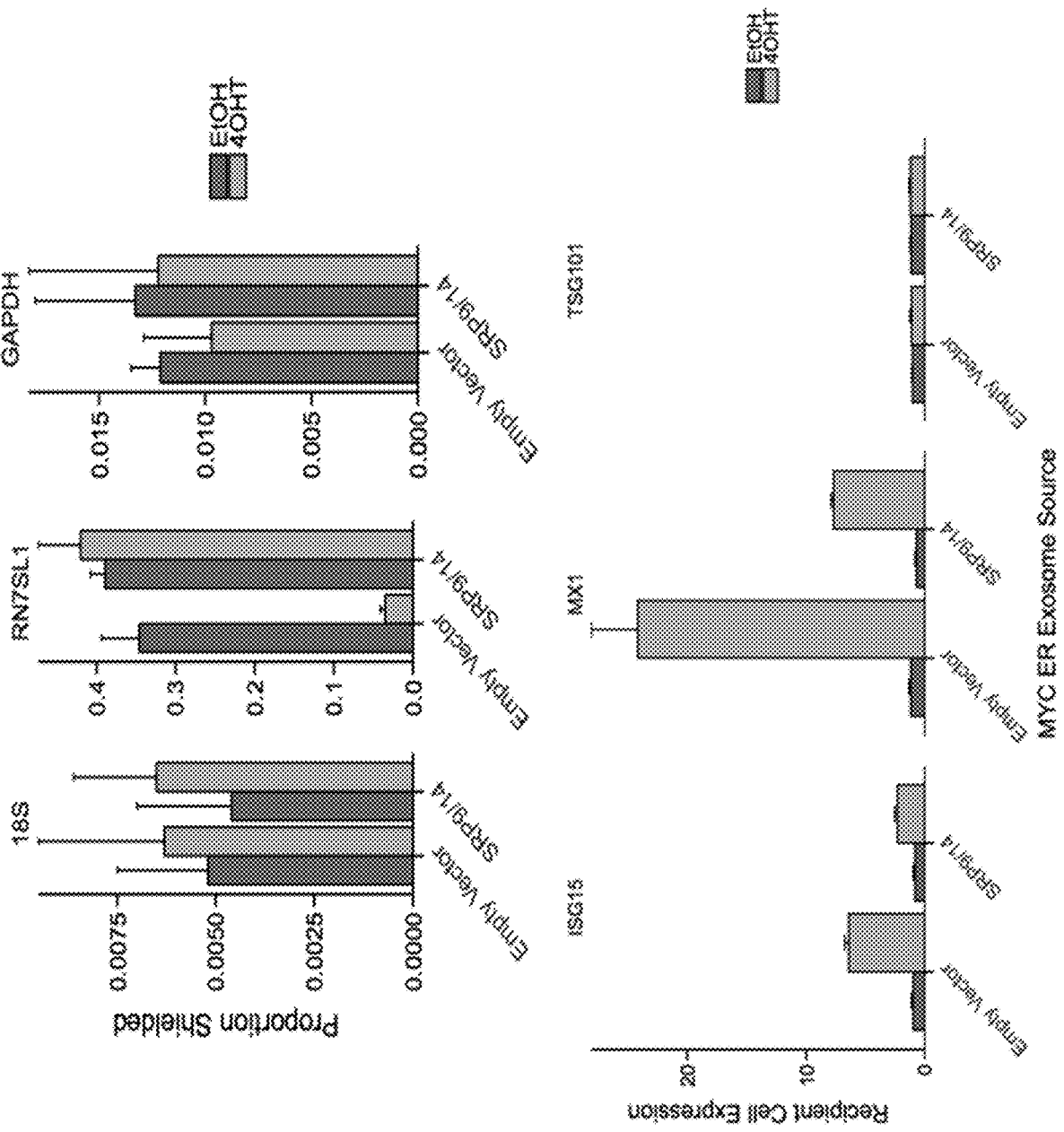
FIG. 29 is a set of graphs illustrating data from exosomes harvested from MEFs and treated with 4OHT in order to drive unshielding of 7SL1 RNA, along with control MEFS. RNA was profiled by MNAse-Seq to assess the proportion of RNA shielded by protein (top panel), and 1833 breast cancer cells were cultured with exosomes and qPCR was performed for indicated genes (bottom panel).

CSF1R inhibition in combination with unshielded 7SL RNA sensitizes PDA tumors to ICB therapy (FIGS. 28A-28B). $1 \times 10^5$ pancreatic ductal adenocarcinoma (PDA) tumor cells were co-injected with $1 \times 10^5$ MEFs ("myc-ER") or MEFs co-expressing SRP9/14 ("myc-ER/SRP") treated with 4OHT or EtOH. Mice were then treated with a combination of anti-CTLA4 and anti-PD1 antibodies (FIG. 28A) or a triple combination of anti-CTLA4, anti-PD1, and BLZ945 (FIG. 28B) using treatment schedules outlined in the study shown in FIGS. 27A-27C. Tumor growth was monitored by caliper. As shown in FIG. 27B, CSF1R inhibitor BLZ945 in combination with unshielded 7SL RNA sensitizes PDA tumors to anti-PD-1 and anti-CTLA-4 antibody therapies.

Figure 33A:
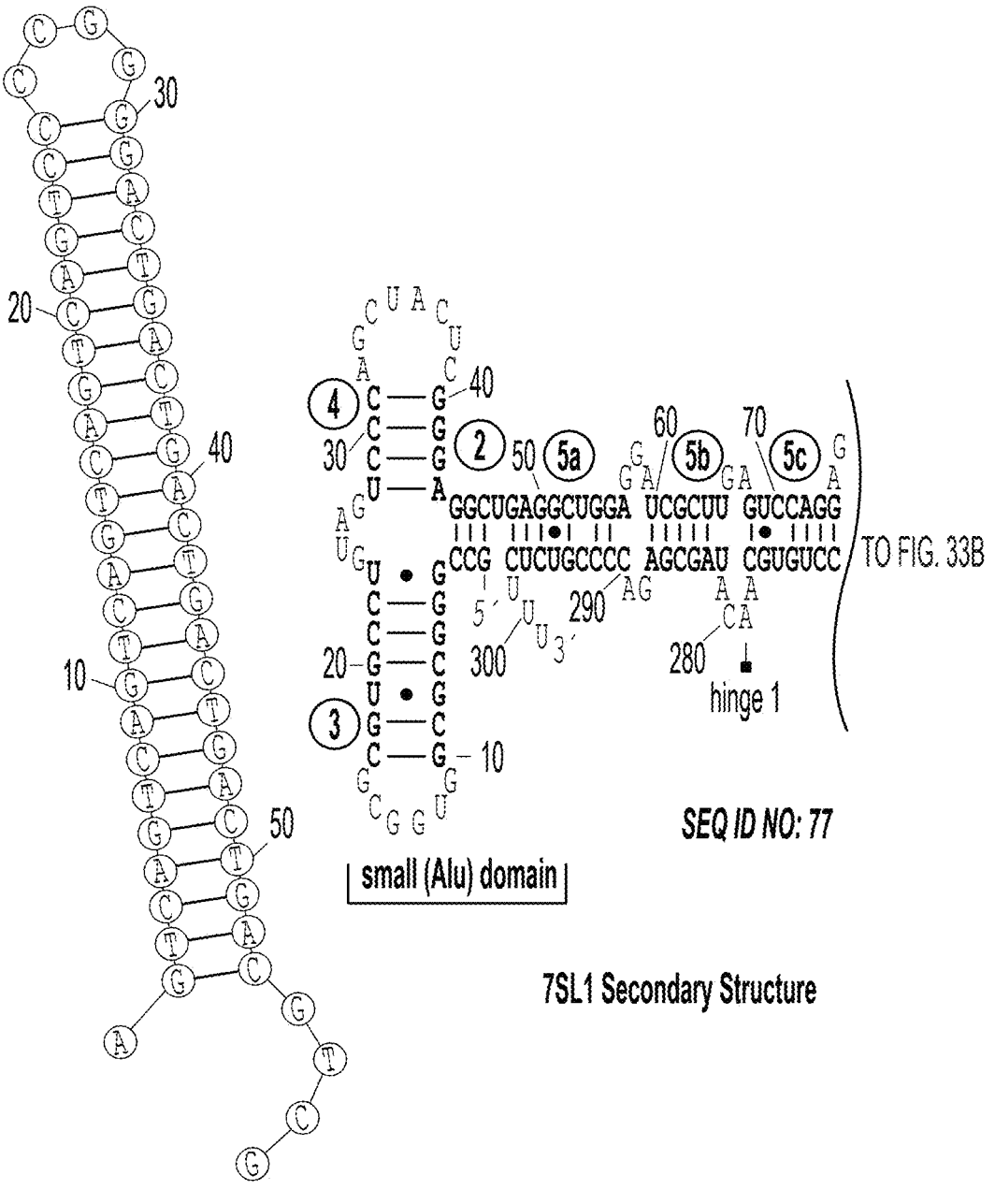
FIG. 33 is a set of images depicting human SRP RNA and 7SL1 secondary structure (SEQ ID NOs: 76-77).
Figure 33B:
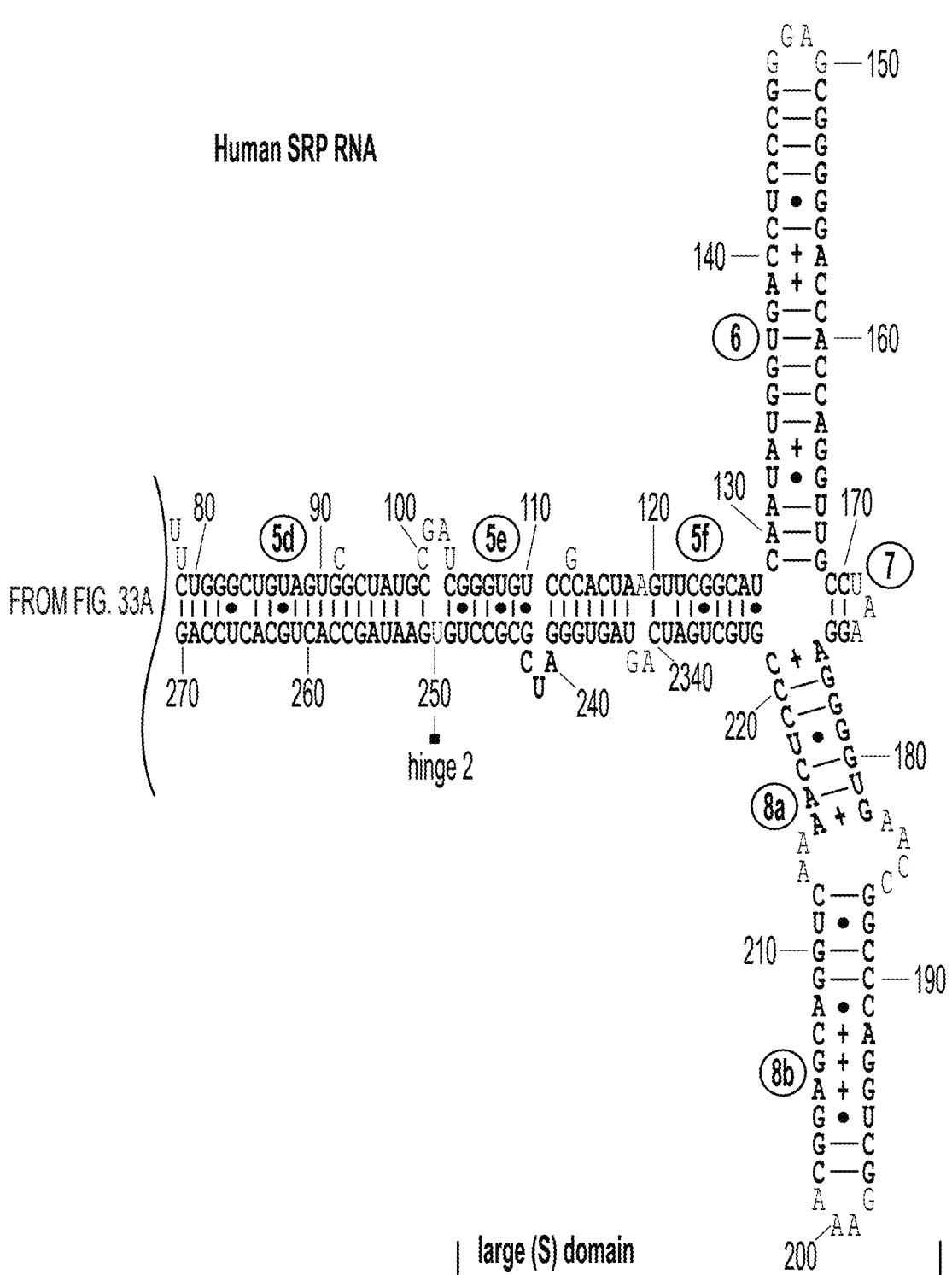
Figure 34:
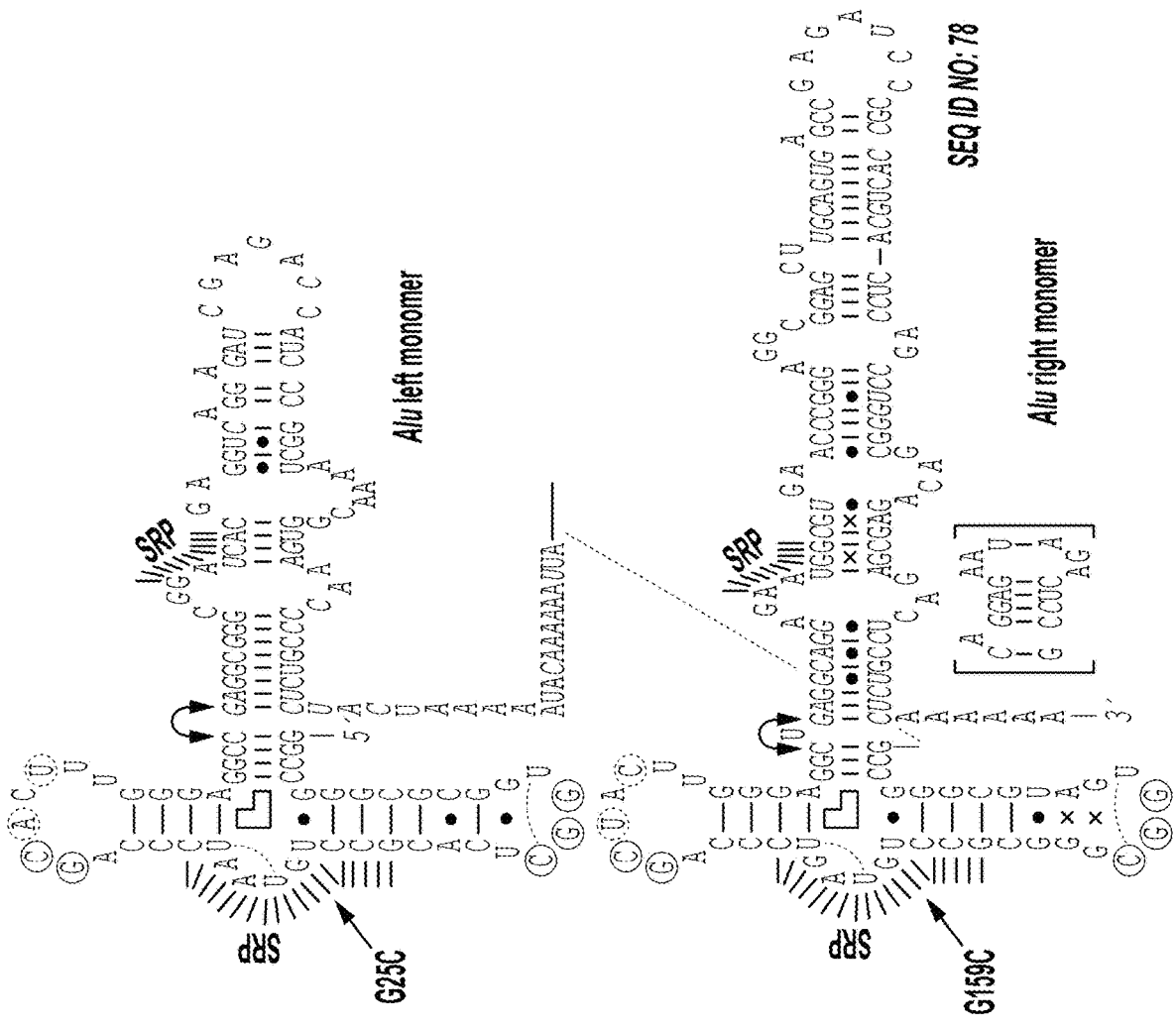
FIG. 34 is a set of images depicting Alu structure and RNA (SEQ ID NO: 78).

Exemplary 7SL RNA and Alu domains are depicted in FIGS. 33-34.

```
RN7SL1 (Homo sapiens RNA, 7SL, cytoplasmic 1 (RN7SL1), NR_002715)
(SEQ ID NO:1):
GCCGGGCGCG GTGGCGCGTG CCTGTAGTCC CAGCTACTCG GGAGGCTGAG

GCTGGAGGAT CGCTTGAGTC CAGGAGTTCT GGGCTGTAGT GCGCTATGCC

GATCGGGTGTCCGCACTAAGTTCGGCATCAATATGGTGACCTCCCGGGAGCGGG

GGACCACCAGGTTGCCTAAGGAGGGGTGAACCGGCCCAGGTCGGAAACGGAGC

AGGTCAAAACTCCCGTGCTGATCAGTAGTGGGATCGCGCCTGTGAATAGCCACT

GCACTCCAGCCTGGGCAACATAGCGAGACCCCGTCTCT
```

Underlined regions designate the Alu domain.

```
Alu (Alu-Ya5 followed by a Poly-A tail to ensure transcription)
(SEQ ID NO: 7):
GCGGCCGCTCTAGAACTAGTGGATCCCCCCCCCCCGCTCCCCAAATGACGTAACT

GTCCCTGCAGCTTCTAGATAGCTTTTCGCAGCGTCTCCGACCGGCCGGGCCGGGC

GCGGTGGCTCACGCCTGTAATCCCAGCACTTTGGGAGGCCGAGGCGGGCGGATC

ACGAGGTCAGGAGATCGAGACCATCCCGGCTAAAACGGTGAAACCCCGTCTCTA

CTAAAAATACAAAAAATTAGCCGGGCGTAGTGGCGGGCGCCTGTAGTCCCAGCT

ACTTGGGAGGCTGAGGCAGGAGAATGGCGTGAACCCGGGAGGCGGAGCTTGCA

GTGAGCCGAGATCCCGCCACTGCACTCCAGCCTGGGCGACAGAGCGAgaCGTCTC

AAATCCCCTCAAAAAAAAAAAAAAAAAAAAAAAAAAAAAAAAAAAAAAAAAAAA

AACATGGGACTCAAAGTTTCAGCATCGCGTCTCTTTTGCCGAATTCGATATCAAG

CTTATCGATACC

Hairpin RNA (as DNA) (SEQ ID NO: 9):
AGTCAGTCAGTCAGTCAGTCAGTCCCCGGGGACTGACTGACTGACTGACTGAC Hairpin RNA (as RNA) (SEQ ID NO: 10):
AGUCAGUCAGUCAGUCAGUCAGUCCCCGGGGACUGACUGACUGACUGACUGAC Hairpin RNA (as RNA Complement Strand) (SEQ ID NO: 11):
UCAGUCAGUCAGUCAGUCAGUCAGGGGCCCCUGACUGACUGACUGACUGACUG
```

FIGS. 35A-37C illustrate the finding that RN7SL1 can favorably activate T cells and critical antigen presenting cells (CD103+ dendritic cells) to promote immune responses. Suppressive effects as demonstrated by an increase in suppressive macrophages or myeloid-derived suppressor cells (MDSCs) may also ensue in response. Without wishing to be bound by specific theory, this could be in direct or indirect response to RN7SL1. However, it is demonstrated herein that RN7SL1 along with blockade of these suppressive events (in this case with a CSF1R inhibitor) can enhance immune checkpoint blockade responses.

Figures 35A, 35B:
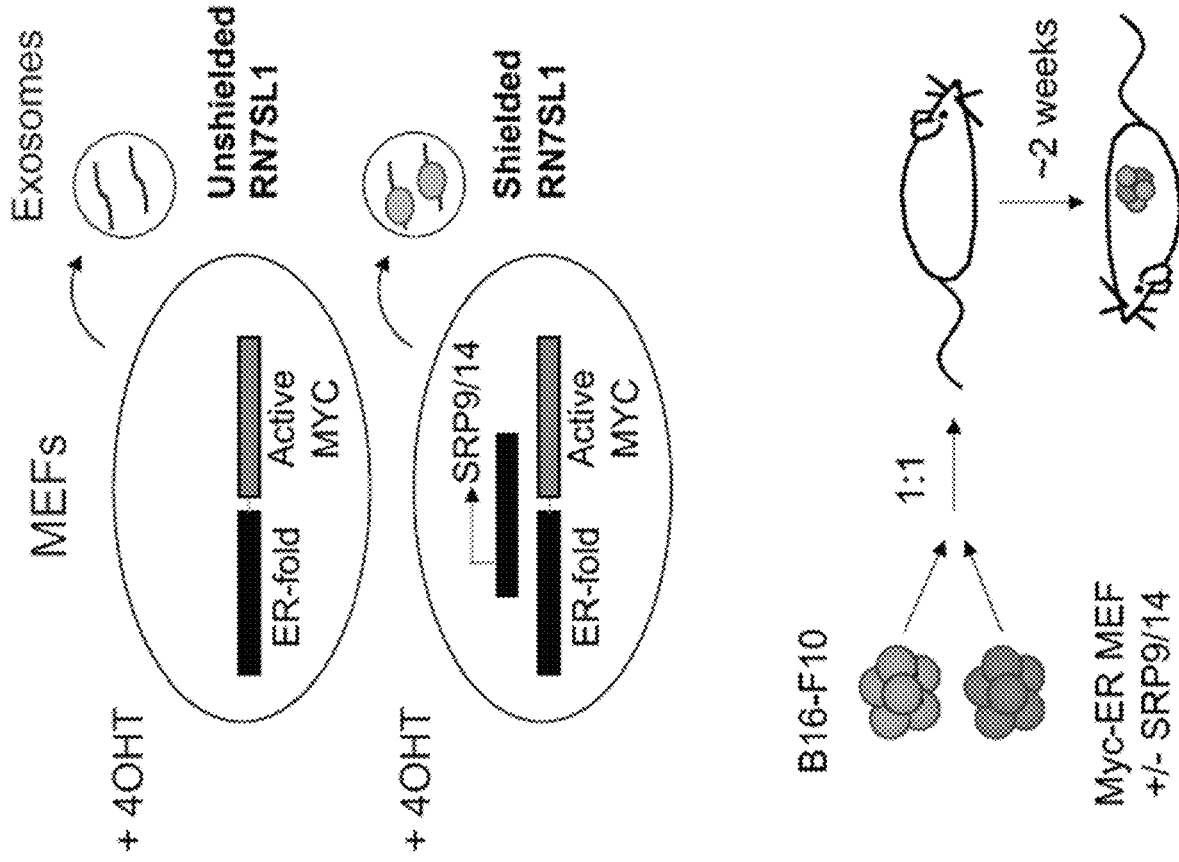
FIGS. 35A-35C are a series of plots and images illustrating unshielded RN7SL1 in the tumor microenvironment enhances DCs and T cell activation.
Figure 35C:
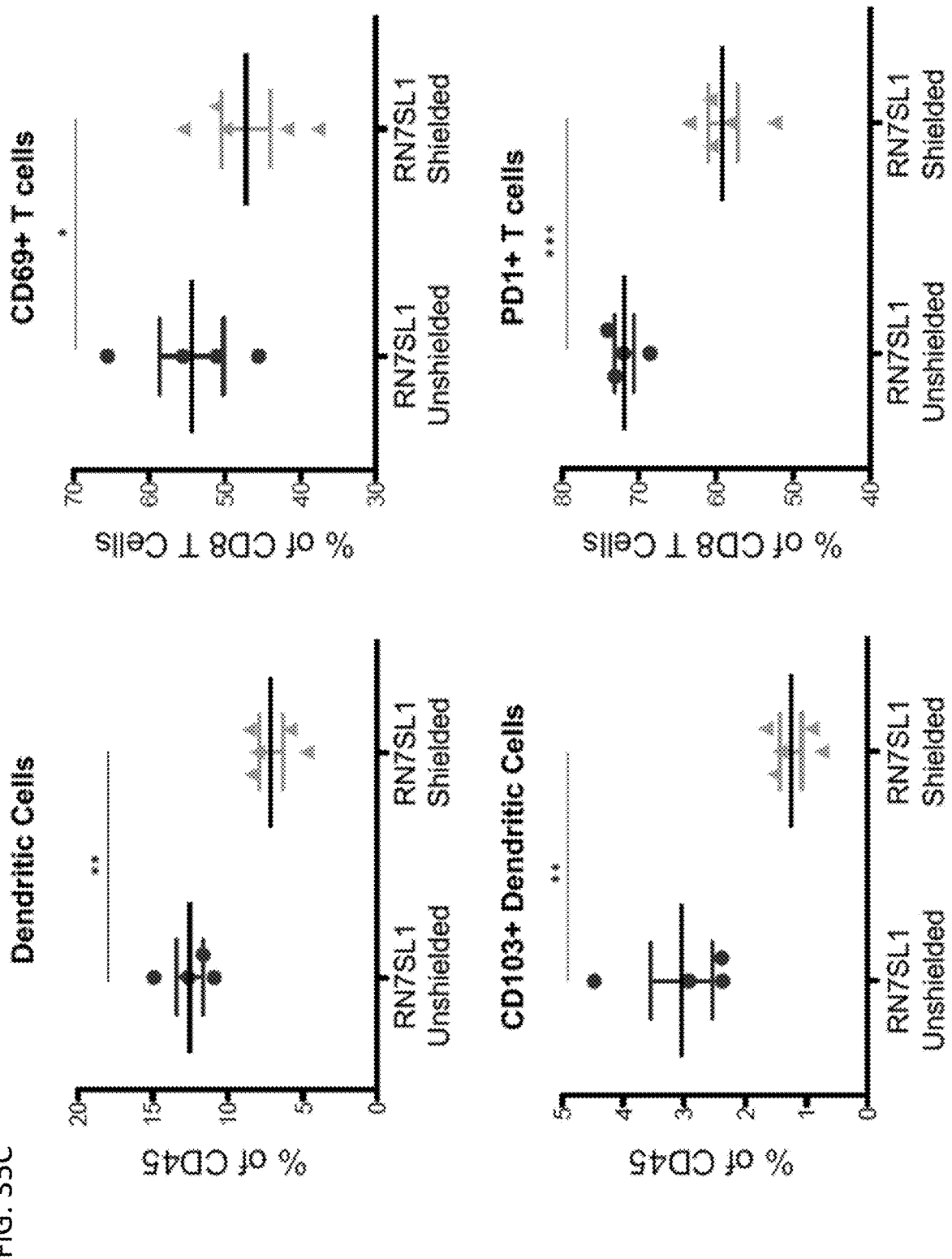
Figure 36B:
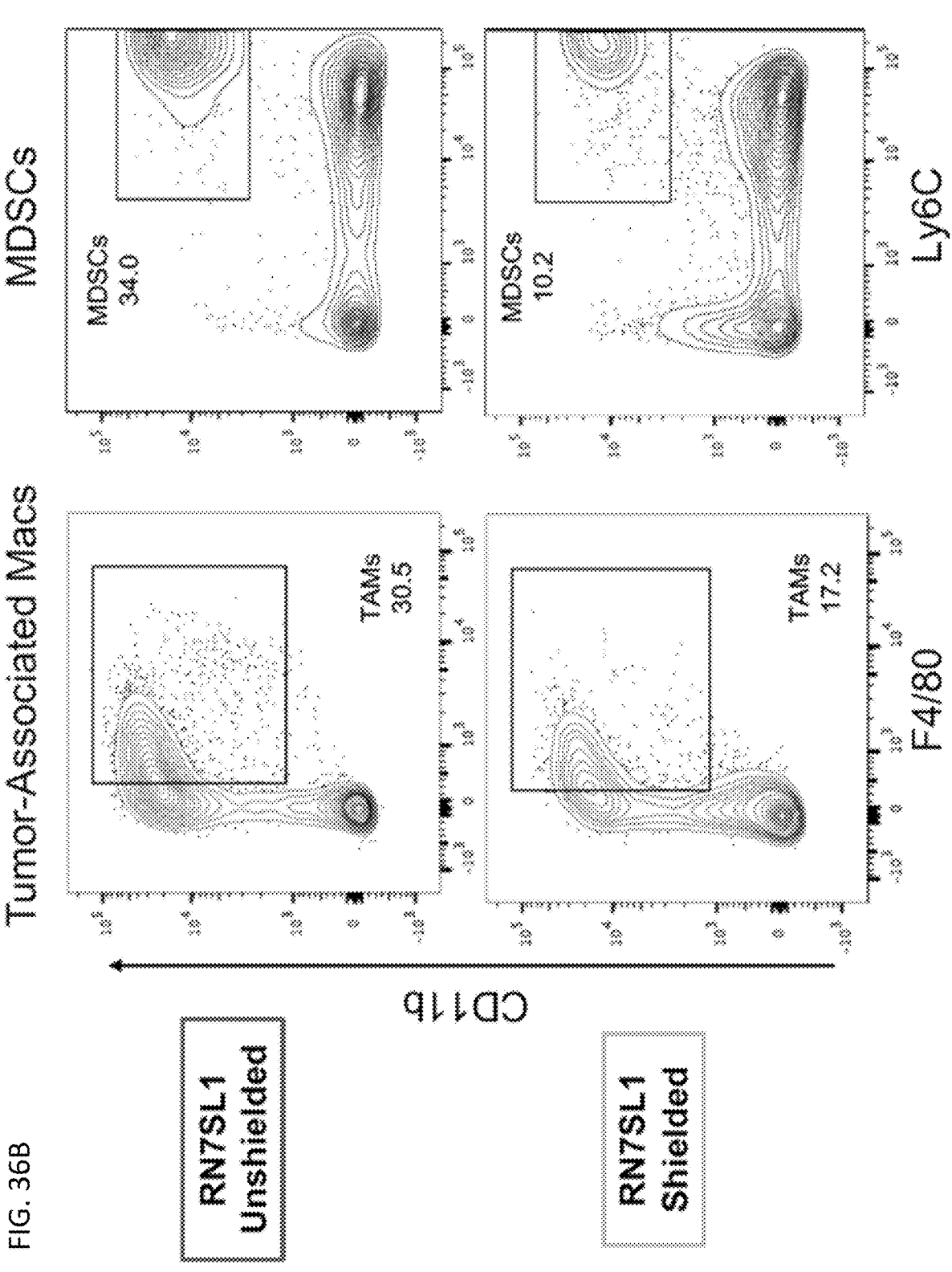
Figure 37A:
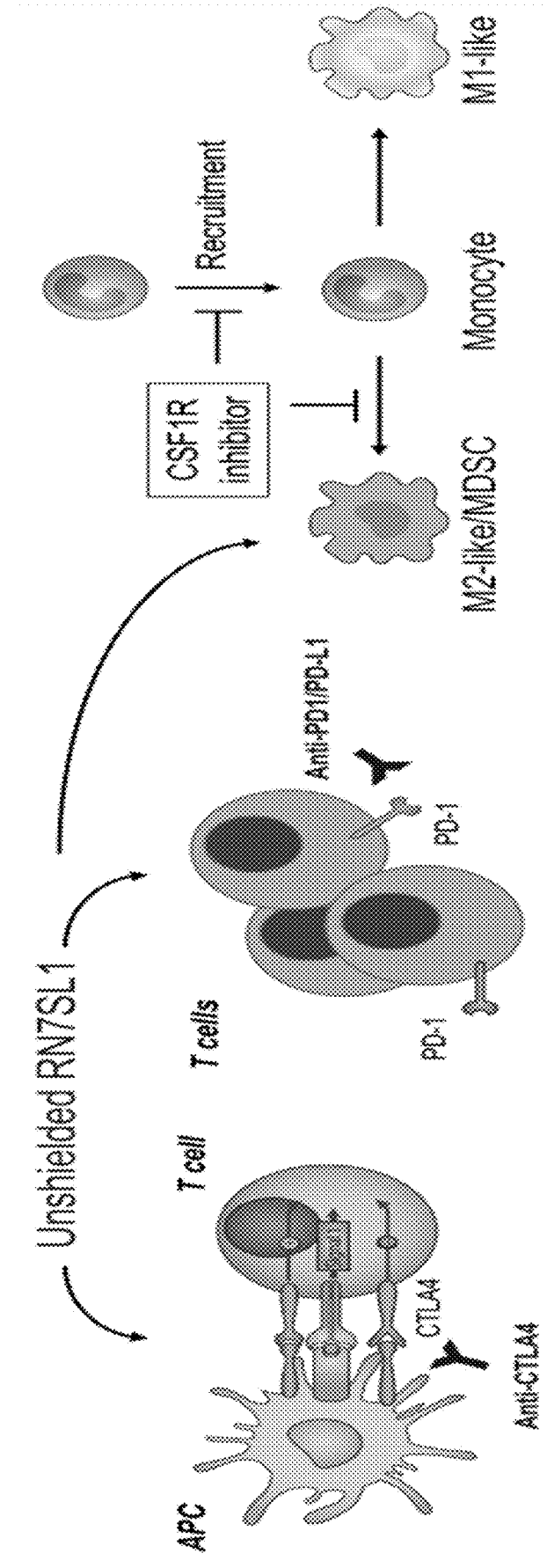
FIGS. 37A-37C are a series of plots and images illustrating inhibition of M2 polarization reveals the immunostimulatory effect of unshielded RN7SL1.
Figures 37B, 37C:
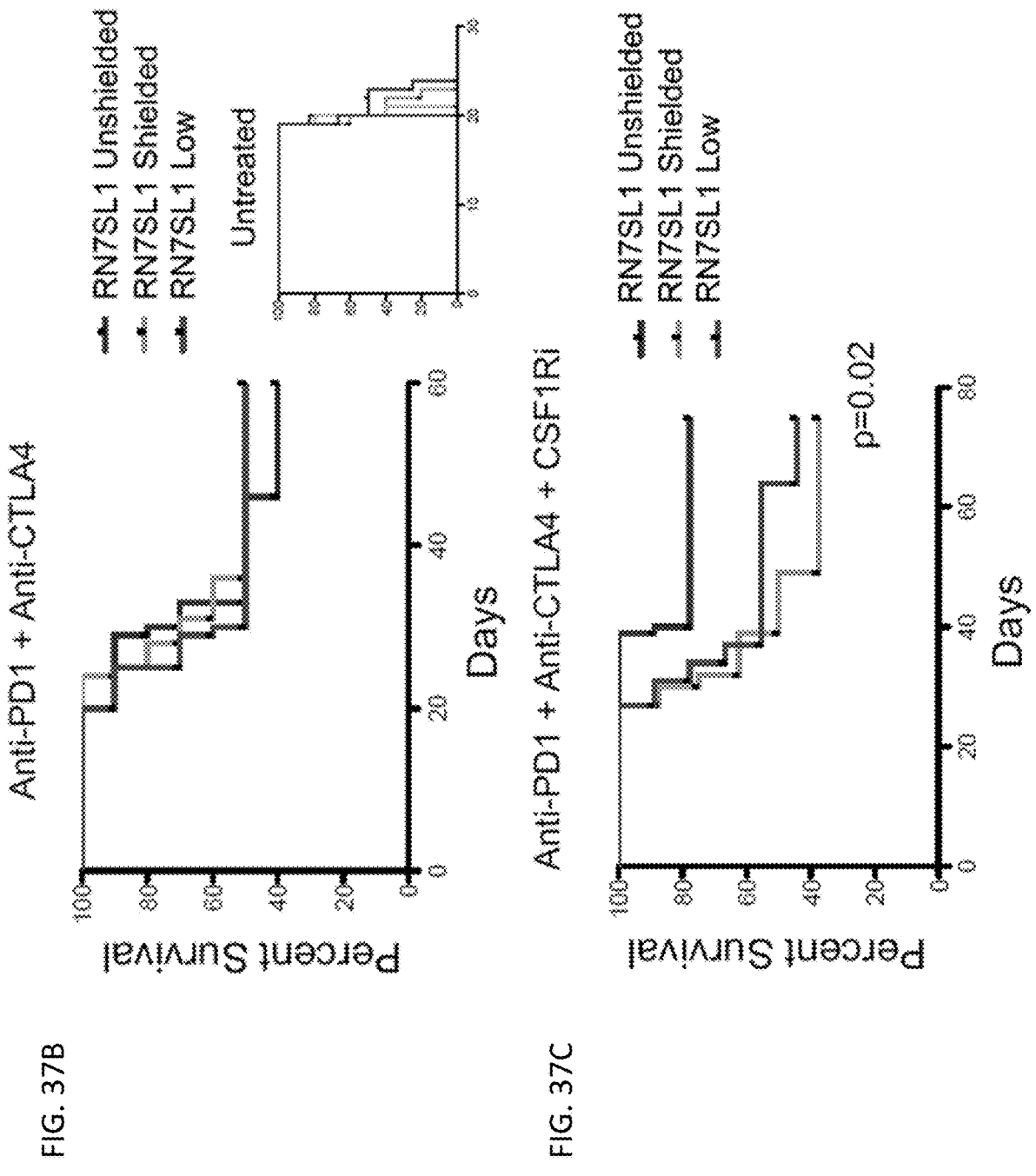

Mice were implanted with B16-F10 tumor cells mixed 1:1 with MEFs or MEFs co-expressing SRP9/14 (FIG. 35B). Tumors were harvested 2 weeks post-injection and analyzed for immune cell populations. Unshielded RN7SL1 increased the frequency of dendritic cells, the percentage of CD103+ dendritic cells, the percentage of CD69+CD8+ T cells, and the percentage of PD1+CD8+ T cells in tumors (FIG. 35C). The percentages of macrophages and MDSCs in CD45+ cells were also increased (FIG. 36A). Without wishing to be bound by theory, a CSF1R inhibitor blocks M2 polarization and may synergize with unshielded RN7SL1. As shown in FIGS. 37B and 37C, combining RN7SL1 with the CSF1R inhibitor BLZ945 enhanced the anti-tumor activity of an anti-PD1 antibody and an anti-CTLA-4 antibody.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a cancer in a subject in need thereof, the method comprising, administering to the subject a therapeutically effective amount of an unshielded RN7SL1 RNA in combination with a CSF1R inhibitor and one or more immune checkpoint blocker(s), wherein the one or more immune checkpoint blocker(s) comprise an anti-PD-1 antibody and/or an anti-CTLA-4 antibody, and wherein the cancer is melanoma or pancreatic adenocarcinoma.

2. The method of claim 1, wherein the CSF1R inhibitor is an anti-CSF1R antibody or a small molecule inhibitor of CSF1R.

3. The method of claim 1, wherein the CSF1R inhibitor is BLZ945.

4. The method of claim 1, wherein the unshielded RN7SL1 RNA is administered to the tumor microenvironment of the subject.

5. The method of claim 1, wherein the RN7SL1 RNA comprises the RNA sequence of SEQ ID NO: 2.

* * * * *

SEQUENCE LISTING

```
<160> NUMBER OF SEQ ID NOS: 78

<210> SEQ ID NO 1
<211> LENGTH: 299
<212> TYPE: DNA
<213> ORGANISM: Homo sapiens

<400> SEQUENCE: 1
gccgggcgcg gtggcgcgtg cctgtagtcc cagctactcg ggaggctgag gctggaggat        60
cgcttgagtc caggagttct gggctgtagt gcgctatgcc gatcgggtgt ccgcactaag       120
ttcggcatca atatggtgac ctcccgggag cggggacca ccaggttgcc taaggagggg       180
tgaaccggcc caggtcggaa acggagcagg tcaaaactcc cgtgctgatc agtagtggga       240
tcgcgcctgt gaatagccac tgcactccag cctgggcaac atagcgagac cccgtctct       299

<210> SEQ ID NO 2
<211> LENGTH: 299
<212> TYPE: RNA
<213> ORGANISM: Homo sapiens

<400> SEQUENCE: 2
gccgggcgcg guggcgcgug ccuguagucc cagcuacucg ggaggcugag gcuggaggau        60
cgcuugaguc caggaguucu gggcuguagu gcgcuaugcc gaucgggugu ccgcacuaag       120
uucggcauca auauggugac cucccgggag cggggacca ccagguugcc uaaggagggg       180
ugaaccggcc caggucggaa acggagcagg ucaaaacucc cgugcugauc aguaguggga       240
ucgcgccugu gaauagccac ugcacuccag ccugggcaac auagcgagac cccgucucu       299

<210> SEQ ID NO 3
<211> LENGTH: 70
<212> TYPE: DNA
<213> ORGANISM: Homo sapiens

<400> SEQUENCE: 3
gccgggcgcg gtggcgcgtg cctgtagtcc cagctactcg ggaggctgag gctggaggat        60
cgcttgagtc                                                              70

<210> SEQ ID NO 4
```

```
<211> LENGTH: 70
<212> TYPE: RNA
<213> ORGANISM: Homo sapiens

<400> SEQUENCE: 4
gccgggcgcg guggcgcgug ccuguagucc cagcuacucg ggaggcugag gcuggaggau      60
cgcuugaguc                                                            70

<210> SEQ ID NO 5
<211> LENGTH: 23
<212> TYPE: DNA
<213> ORGANISM: Homo sapiens

<400> SEQUENCE: 5
caacatagcg agaccccgtc tct                                             23

<210> SEQ ID NO 6
<211> LENGTH: 23
<212> TYPE: RNA
<213> ORGANISM: Homo sapiens

<400> SEQUENCE: 6
caacauagcg agaccccguc ucu                                             23

<210> SEQ ID NO 7
<211> LENGTH: 499
<212> TYPE: DNA
<213> ORGANISM: Homo sapiens

<400> SEQUENCE: 7
gcggccgctc tagaactagt ggatccccct ccccgctcc ccaaatgacg taactgtccc      60
tgcagcttct agatagcttt tcgcagcgtc tccgaccggc cgggccgggc gcggtggctc     120
acgcctgtaa tcccagcact ttgggaggcc gaggcgggcg gatcacgagg tcaggagatc     180
gagaccatcc cggctaaaac ggtgaaaccc cgtctctact aaaaatacaa aaaattagcc     240
gggcgtagtg gcgggcgcct gtagtcccag ctacttggga ggctgaggca ggagaatggc     300
gtgaacccgg gaggcggagc ttgcagtgag ccgagatccc gccactgcac tccagcctgg     360
gcgacagagc gagacgtctc aaatcccctc aaaaaaaaaa aaaaaaaaaa aaaaaaaaaa     420
aaaaaaaaaa aaaacatggg actcaaagtt tcagcatcgc gtctcttttg ccgaattcga     480
tatcaagctt atcgatacc                                                  499

<210> SEQ ID NO 8
<211> LENGTH: 499
<212> TYPE: RNA
<213> ORGANISM: Homo sapiens

<400> SEQUENCE: 8
gcggccgcuc uagaacuagu ggauccccct ccccgcucc ccaaaugacg uaacuguccc      60
ugcagcuucu agauagcuuu ucgcagcguc uccgaccggc cgggccgggc gcgguggcuc     120
acgccuguaa ucccagcacu uugggaggcc gaggcgggcg gaucacgagg ucaggagauc     180
gagaccaucc cggcuaaaac ggugaaaccc cgucucuacu aaaaauacaa aaaauuagcc     240
gggcguagug gcgggcgccu guagucccag cuacuuggga ggcugaggca ggagaauggc     300
gugaacccgg gaggcggagc uugcagugag ccgagauccc gccacugcac uccagccugg     360
gcgacagagc gagacgucuc aaaucccuc aaaaaaaaaa aaaaaaaaaa aaaaaaaaaa      420
aaaaaaaaaa aaaacauggg acucaaaguu ucagcaucgc gucucuuuug ccgaauucga     480
```

-continued

```
uaucaagcuu aucgauacc                                                499

<210> SEQ ID NO 9
<211> LENGTH: 53
<212> TYPE: DNA
<213> ORGANISM: Homo sapiens

<400> SEQUENCE: 9
agtcagtcag tcagtcagtc agtccccggg gactgactga ctgactgact gac        53

<210> SEQ ID NO 10
<211> LENGTH: 53
<212> TYPE: RNA
<213> ORGANISM: Homo sapiens

<400> SEQUENCE: 10
agucagucag ucagucaguc aguccccggg gacugacuga cugacugacu gac        53

<210> SEQ ID NO 11
<211> LENGTH: 53
<212> TYPE: RNA
<213> ORGANISM: Homo sapiens

<400> SEQUENCE: 11
ucagucaguc agucagucag ucaggggccc cugacugacu gacugacuga cug        53

<210> SEQ ID NO 12
<211> LENGTH: 19
<212> TYPE: DNA
<213> ORGANISM: Artificial sequence
<220> FEATURE:
<223> OTHER INFORMATION: shRNA

<400> SEQUENCE: 12
ttaaatttgt cgctaatcc                                                19

<210> SEQ ID NO 13
<211> LENGTH: 19
<212> TYPE: DNA
<213> ORGANISM: Artificial sequence
<220> FEATURE:
<223> OTHER INFORMATION: shRNA

<400> SEQUENCE: 13
taaagtccag aataacctg                                                19

<210> SEQ ID NO 14
<211> LENGTH: 20
<212> TYPE: DNA
<213> ORGANISM: Artificial sequence
<220> FEATURE:
<223> OTHER INFORMATION: gRNA

<400> SEQUENCE: 14
gggtcttccg gatataatcc                                               20

<210> SEQ ID NO 15
<211> LENGTH: 20
<212> TYPE: DNA
<213> ORGANISM: Artificial sequence
<220> FEATURE:
<223> OTHER INFORMATION: gRNA

<400> SEQUENCE: 15
```

-continued ggattatatc cggaagaccc                                                        20

<210> SEQ ID NO 16
<211> LENGTH: 33
<212> TYPE: RNA
<213> ORGANISM: Artificial sequence
<220> FEATURE:
<223> OTHER INFORMATION: adaptor

<400> SEQUENCE: 16
acacucuuuc ccuacacgac gcucuuccga ucu                                         33

<210> SEQ ID NO 17
<211> LENGTH: 43
<212> TYPE: DNA
<213> ORGANISM: Artificial sequence
<220> FEATURE:
<223> OTHER INFORMATION: adaptor
<220> FEATURE:
<221> NAME/KEY: misc_feature
<222> LOCATION: (35)..(43)
<223> OTHER INFORMATION: n is a, c, g, or t

<400> SEQUENCE: 17
gtgactggag ttcagacgtg tgctcttccg atctnnnnnn nnn                              43

<210> SEQ ID NO 18
<211> LENGTH: 21
<212> TYPE: DNA
<213> ORGANISM: Artificial sequence
<220> FEATURE:
<223> OTHER INFORMATION: primer

<400> SEQUENCE: 18
gctcagacac catggggaag g                                                      21

<210> SEQ ID NO 19
<211> LENGTH: 20
<212> TYPE: DNA
<213> ORGANISM: Artificial sequence
<220> FEATURE:
<223> OTHER INFORMATION: primer

<400> SEQUENCE: 19
ttcccgttct cagccttgac                                                        20

<210> SEQ ID NO 20
<211> LENGTH: 20
<212> TYPE: DNA
<213> ORGANISM: Artificial sequence
<220> FEATURE:
<223> OTHER INFORMATION: primer

<400> SEQUENCE: 20
gttcagccac ccgagattga                                                        20

<210> SEQ ID NO 21
<211> LENGTH: 20
<212> TYPE: DNA
<213> ORGANISM: Artificial sequence
<220> FEATURE:
<223> OTHER INFORMATION: primer

<400> SEQUENCE: 21
cccatcacga atggggttca                                                        20

-continued

```
<210> SEQ ID NO 22
<211> LENGTH: 19
<212> TYPE: DNA
<213> ORGANISM: Artificial sequence
<220> FEATURE:
<223> OTHER INFORMATION: primer

<400> SEQUENCE: 22
gccctgaggc actcttcca                                                    19

<210> SEQ ID NO 23
<211> LENGTH: 21
<212> TYPE: DNA
<213> ORGANISM: Artificial sequence
<220> FEATURE:
<223> OTHER INFORMATION: primer

<400> SEQUENCE: 23
cggatgtcca cgtcacactt c                                                 21

<210> SEQ ID NO 24
<211> LENGTH: 22
<212> TYPE: DNA
<213> ORGANISM: Artificial sequence
<220> FEATURE:
<223> OTHER INFORMATION: primer

<400> SEQUENCE: 24
ggctgcctaa tttacagcaa cc                                                22

<210> SEQ ID NO 25
<211> LENGTH: 22
<212> TYPE: DNA
<213> ORGANISM: Artificial sequence
<220> FEATURE:
<223> OTHER INFORMATION: primer

<400> SEQUENCE: 25
ggcatttcat cgtcatcaat gg                                                22

<210> SEQ ID NO 26
<211> LENGTH: 20
<212> TYPE: DNA
<213> ORGANISM: Artificial sequence
<220> FEATURE:
<223> OTHER INFORMATION: primer

<400> SEQUENCE: 26
cgacacgagt tccacaaatg                                                   20

<210> SEQ ID NO 27
<211> LENGTH: 20
<212> TYPE: DNA
<213> ORGANISM: Artificial sequence
<220> FEATURE:
<223> OTHER INFORMATION: primer

<400> SEQUENCE: 27
aagcctggca gctctctacc                                                   20

<210> SEQ ID NO 28
<211> LENGTH: 20
<212> TYPE: DNA
<213> ORGANISM: Artificial sequence
<220> FEATURE:
<223> OTHER INFORMATION: primer
```

-continued

```
<400> SEQUENCE: 28
gagaggcagc gaactcatct                                                    20

<210> SEQ ID NO 29
<211> LENGTH: 20
<212> TYPE: DNA
<213> ORGANISM: Artificial sequence
<220> FEATURE:
<223> OTHER INFORMATION: primer

<400> SEQUENCE: 29
cttcagctct gacaccgaca                                                    20

<210> SEQ ID NO 30
<211> LENGTH: 22
<212> TYPE: DNA
<213> ORGANISM: Artificial sequence
<220> FEATURE:
<223> OTHER INFORMATION: primer

<400> SEQUENCE: 30
cacctcagtt gctgatgaag gc                                                 22

<210> SEQ ID NO 31
<211> LENGTH: 23
<212> TYPE: DNA
<213> ORGANISM: Artificial sequence
<220> FEATURE:
<223> OTHER INFORMATION: primer

<400> SEQUENCE: 31
gtcagaagga agcacttgct acc                                                23

<210> SEQ ID NO 32
<211> LENGTH: 20
<212> TYPE: DNA
<213> ORGANISM: Artificial sequence
<220> FEATURE:
<223> OTHER INFORMATION: primer

<400> SEQUENCE: 32
gatgacgatg atgccgcaga                                                    20

<210> SEQ ID NO 33
<211> LENGTH: 20
<212> TYPE: DNA
<213> ORGANISM: Artificial sequence
<220> FEATURE:
<223> OTHER INFORMATION: primer

<400> SEQUENCE: 33
ggttgcctca tccatgttgt                                                    20

<210> SEQ ID NO 34
<211> LENGTH: 20
<212> TYPE: DNA
<213> ORGANISM: Artificial sequence
<220> FEATURE:
<223> OTHER INFORMATION: primer

<400> SEQUENCE: 34
aggctccacc agtcacagac                                                    20

<210> SEQ ID NO 35
<211> LENGTH: 23
```

```
<212> TYPE: DNA
<213> ORGANISM: Artificial sequence
<220> FEATURE:
<223> OTHER INFORMATION: primer

<400> SEQUENCE: 35
tgccattaac agaaatcaac aaa                                              23

<210> SEQ ID NO 36
<211> LENGTH: 20
<212> TYPE: DNA
<213> ORGANISM: Artificial sequence
<220> FEATURE:
<223> OTHER INFORMATION: primer

<400> SEQUENCE: 36
ttactccagg ccaaaggaag                                                 20

<210> SEQ ID NO 37
<211> LENGTH: 20
<212> TYPE: DNA
<213> ORGANISM: Artificial sequence
<220> FEATURE:
<223> OTHER INFORMATION: primer

<400> SEQUENCE: 37
ttcagctgtg atggcgatag                                                 20

<210> SEQ ID NO 38
<211> LENGTH: 19
<212> TYPE: DNA
<213> ORGANISM: Artificial sequence
<220> FEATURE:
<223> OTHER INFORMATION: primer

<400> SEQUENCE: 38
gggttgattc ggctgatct                                                  19

<210> SEQ ID NO 39
<211> LENGTH: 18
<212> TYPE: DNA
<213> ORGANISM: Artificial sequence
<220> FEATURE:
<223> OTHER INFORMATION: primer

<400> SEQUENCE: 39
ggggatggtc gtcctctt                                                   18

<210> SEQ ID NO 40
<211> LENGTH: 19
<212> TYPE: DNA
<213> ORGANISM: Artificial sequence
<220> FEATURE:
<223> OTHER INFORMATION: primer

<400> SEQUENCE: 40
gtgtccgcac taagttcgg                                                  19

<210> SEQ ID NO 41
<211> LENGTH: 18
<212> TYPE: DNA
<213> ORGANISM: Artificial sequence
<220> FEATURE:
<223> OTHER INFORMATION: primer

<400> SEQUENCE: 41
```
tattcacagg cgcgatcc                                                              18

<210> SEQ ID NO 42
<211> LENGTH: 21
<212> TYPE: DNA
<213> ORGANISM: Artificial sequence
<220> FEATURE:
<223> OTHER INFORMATION: primer

<400> SEQUENCE: 42
gctactcggg aggctgaggc t                                                          21

<210> SEQ ID NO 43
<211> LENGTH: 18
<212> TYPE: DNA
<213> ORGANISM: Artificial sequence
<220> FEATURE:
<223> OTHER INFORMATION: primer

<400> SEQUENCE: 43
tattcacagg cgcgatcc                                                              18

<210> SEQ ID NO 44
<211> LENGTH: 20
<212> TYPE: DNA
<213> ORGANISM: Artificial sequence
<220> FEATURE:
<223> OTHER INFORMATION: primer

<400> SEQUENCE: 44
aaagtccgcc aagaagcgta                                                            20

<210> SEQ ID NO 45
<211> LENGTH: 20
<212> TYPE: DNA
<213> ORGANISM: Artificial sequence
<220> FEATURE:
<223> OTHER INFORMATION: primer

<400> SEQUENCE: 45
ctgcctgcgt aactagaggg                                                            20

<210> SEQ ID NO 46
<211> LENGTH: 20
<212> TYPE: DNA
<213> ORGANISM: Artificial sequence
<220> FEATURE:
<223> OTHER INFORMATION: primer

<400> SEQUENCE: 46
agcttggaac agactcacgg                                                            20

<210> SEQ ID NO 47
<211> LENGTH: 20
<212> TYPE: DNA
<213> ORGANISM: Artificial sequence
<220> FEATURE:
<223> OTHER INFORMATION: primer

<400> SEQUENCE: 47
aatgggcgga ggagagtagt                                                            20

<210> SEQ ID NO 48
<211> LENGTH: 21
<212> TYPE: DNA
<213> ORGANISM: Artificial sequence -continued

```
<220> FEATURE:
<223> OTHER INFORMATION: primer

<400> SEQUENCE: 48
cgtcctctat ccgaggacaa t                                                21

<210> SEQ ID NO 49
<211> LENGTH: 20
<212> TYPE: DNA
<213> ORGANISM: Artificial sequence
<220> FEATURE:
<223> OTHER INFORMATION: primer

<400> SEQUENCE: 49
cggagcaagc tcctattcca                                                  20

<210> SEQ ID NO 50
<211> LENGTH: 20
<212> TYPE: DNA
<213> ORGANISM: Artificial sequence
<220> FEATURE:
<223> OTHER INFORMATION: primer

<400> SEQUENCE: 50
agaaggggcg tgatagacct                                                  20

<210> SEQ ID NO 51
<211> LENGTH: 20
<212> TYPE: DNA
<213> ORGANISM: Artificial sequence
<220> FEATURE:
<223> OTHER INFORMATION: primer

<400> SEQUENCE: 51
cactgagacc ggcagtcttt                                                  20

<210> SEQ ID NO 52
<211> LENGTH: 20
<212> TYPE: DNA
<213> ORGANISM: Artificial sequence
<220> FEATURE:
<223> OTHER INFORMATION: primer

<400> SEQUENCE: 52
tgtggtgtct cacagcttcc                                                  20

<210> SEQ ID NO 53
<211> LENGTH: 20
<212> TYPE: DNA
<213> ORGANISM: Artificial sequence
<220> FEATURE:
<223> OTHER INFORMATION: primer

<400> SEQUENCE: 53
ttttcaactt gcctcccatc                                                  20

<210> SEQ ID NO 54
<211> LENGTH: 21
<212> TYPE: DNA
<213> ORGANISM: Artificial sequence
<220> FEATURE:
<223> OTHER INFORMATION: primer

<400> SEQUENCE: 54
aggtcggtgt gaacggattt g                                                21
```

```
<210> SEQ ID NO 55
<211> LENGTH: 23
<212> TYPE: DNA
<213> ORGANISM: Artificial sequence
<220> FEATURE:
<223> OTHER INFORMATION: primer

<400> SEQUENCE: 55
tgtagaccat gtagttgagg tca                                              23

<210> SEQ ID NO 56
<211> LENGTH: 19
<212> TYPE: DNA
<213> ORGANISM: Artificial sequence
<220> FEATURE:
<223> OTHER INFORMATION: primer

<400> SEQUENCE: 56
ccccatgaac gagggaatt                                                   19

<210> SEQ ID NO 57
<211> LENGTH: 22
<212> TYPE: DNA
<213> ORGANISM: Artificial sequence
<220> FEATURE:
<223> OTHER INFORMATION: primer

<400> SEQUENCE: 57
gggacttaat caagcgaagc tt                                               22

<210> SEQ ID NO 58
<211> LENGTH: 22
<212> TYPE: DNA
<213> ORGANISM: Artificial sequence
<220> FEATURE:
<223> OTHER INFORMATION: primer

<400> SEQUENCE: 58
acaacatgct ggtgacagag cc                                               22

<210> SEQ ID NO 59
<211> LENGTH: 24
<212> TYPE: DNA
<213> ORGANISM: Artificial sequence
<220> FEATURE:
<223> OTHER INFORMATION: primer

<400> SEQUENCE: 59
tgaaaactgc caactcaaca cctc                                             24

<210> SEQ ID NO 60
<211> LENGTH: 21
<212> TYPE: DNA
<213> ORGANISM: Artificial sequence
<220> FEATURE:
<223> OTHER INFORMATION: primer

<400> SEQUENCE: 60
ccagtctctg actgtgagag c                                                21

<210> SEQ ID NO 61
<211> LENGTH: 21
<212> TYPE: DNA
<213> ORGANISM: Artificial sequence
<220> FEATURE:
<223> OTHER INFORMATION: primer
```

<400> SEQUENCE: 61
gcatcactgt gctgctggga c                                        21

<210> SEQ ID NO 62
<211> LENGTH: 21
<212> TYPE: DNA
<213> ORGANISM: Artificial sequence
<220> FEATURE:
<223> OTHER INFORMATION: primer

<400> SEQUENCE: 62
gaccataggg gtcttgacca a                                        21

<210> SEQ ID NO 63
<211> LENGTH: 23
<212> TYPE: DNA
<213> ORGANISM: Artificial sequence
<220> FEATURE:
<223> OTHER INFORMATION: primer

<400> SEQUENCE: 63
agacttgctc tttctgaaaa gcc                                      23

<210> SEQ ID NO 64
<211> LENGTH: 21
<212> TYPE: DNA
<213> ORGANISM: Artificial sequence
<220> FEATURE:
<223> OTHER INFORMATION: primer

<400> SEQUENCE: 64
gctactcggg aggctgagac a                                        21

<210> SEQ ID NO 65
<211> LENGTH: 18
<212> TYPE: DNA
<213> ORGANISM: Artificial sequence
<220> FEATURE:
<223> OTHER INFORMATION: primer

<400> SEQUENCE: 65
tattcacagg cgcgatcc                                            18

<210> SEQ ID NO 66
<211> LENGTH: 20
<212> TYPE: DNA
<213> ORGANISM: Artificial sequence
<220> FEATURE:
<223> OTHER INFORMATION: primer

<400> SEQUENCE: 66
actgggtcat tccctgacca                                          20

<210> SEQ ID NO 67
<211> LENGTH: 21
<212> TYPE: DNA
<213> ORGANISM: Artificial sequence
<220> FEATURE:
<223> OTHER INFORMATION: primer

<400> SEQUENCE: 67
ccctcaggtt cctgatctca c                                        21

<210> SEQ ID NO 68

```
<211> LENGTH: 20
<212> TYPE: DNA
<213> ORGANISM: Artificial sequence
<220> FEATURE:
<223> OTHER INFORMATION: primer

<400> SEQUENCE: 68
tggggcgagt attcccaatg                                            20

<210> SEQ ID NO 69
<211> LENGTH: 21
<212> TYPE: DNA
<213> ORGANISM: Artificial sequence
<220> FEATURE:
<223> OTHER INFORMATION: primer

<400> SEQUENCE: 69
tggggaaatt tgggaagcag t                                          21

<210> SEQ ID NO 70
<211> LENGTH: 20
<212> TYPE: DNA
<213> ORGANISM: Artificial sequence
<220> FEATURE:
<223> OTHER INFORMATION: primer

<400> SEQUENCE: 70
cttgcctgct gcatgttgtg                                            20

<210> SEQ ID NO 71
<211> LENGTH: 20
<212> TYPE: DNA
<213> ORGANISM: Artificial sequence
<220> FEATURE:
<223> OTHER INFORMATION: primer

<400> SEQUENCE: 71
gagcgatagc ggttaagcca                                            20

<210> SEQ ID NO 72
<211> LENGTH: 20
<212> TYPE: DNA
<213> ORGANISM: Artificial sequence
<220> FEATURE:
<223> OTHER INFORMATION: primer

<400> SEQUENCE: 72
gccgctgttg cgtaaatcaa                                            20

<210> SEQ ID NO 73
<211> LENGTH: 20
<212> TYPE: DNA
<213> ORGANISM: Artificial sequence
<220> FEATURE:
<223> OTHER INFORMATION: primer

<400> SEQUENCE: 73
agccgactgc tgctcatatc                                            20

<210> SEQ ID NO 74
<211> LENGTH: 20
<212> TYPE: DNA
<213> ORGANISM: Artificial sequence
<220> FEATURE:
<223> OTHER INFORMATION: primer

<400> SEQUENCE: 74
```

-continued

```
gtactgacca gcgtcacaca                                              20

<210> SEQ ID NO 75
<211> LENGTH: 20
<212> TYPE: DNA
<213> ORGANISM: Artificial sequence
<220> FEATURE:
<223> OTHER INFORMATION: primer

<400> SEQUENCE: 75
gcgtgcggtc aatcatcttc                                              20

<210> SEQ ID NO 76
<211> LENGTH: 301
<212> TYPE: RNA
<213> ORGANISM: Homo sapiens

<400> SEQUENCE: 76
gccgggcgcg guggcgcgug ccuguagucc cagcuacucg ggaggcugag gcuggaggau     60
cgcuugaguc caggaguucu gggcuguagu gcgcuaugcc gaucgggugu ccgcacuaag    120
uucggcauca auauggugac cucccgggag cggggggacca ccagguugcc uaaggagggg    180
ugaaccggcc caggucggaa acggagcagg ucaaaacucc cgugcugauc aguaguggga    240
ucgcgccugu gaauagccac ugcacuccag ccugugcaac auagcgagac cccgucucuu    300
u                                                                  301

<210> SEQ ID NO 77
<211> LENGTH: 57
<212> TYPE: DNA
<213> ORGANISM: Homo sapiens
<220> FEATURE:
<221> NAME/KEY: misc_feature
<222> LOCATION: (1)..(57)
<223> OTHER INFORMATION: Due to limitation of ST.25, hairpin structure
      is RNA.

<400> SEQUENCE: 77
agtcagtcag tcagtcagtc agtccccggg gactgactga ctgactgact gacgtcg        57

<210> SEQ ID NO 78
<211> LENGTH: 287
<212> TYPE: RNA
<213> ORGANISM: Homo sapiens

<400> SEQUENCE: 78
ggccgggcgc gguggcucac gccuguaauc ccagcacuuu gggaggccga ggcgggcgga     60
ucacgagguc aggagaucga gaccaucccg gcuaaaacgg ugaaaccccg ucucuacuaa    120
aaauacaaaa aauuagccgg gcguaguggc gggcgccugu agucccagcu acuugggagg    180
cugaggcagg agaauggcgu gaacccggga ggcggagcuu gcagugagcc gagaucccgc    240
cacugcacuc cagccugggc gacagagcga gacuccgucu caaaaaa                  287
```